(12) United States Patent
Hicks et al.

(10) Patent No.: US 8,188,033 B2
(45) Date of Patent: May 29, 2012

(54) ANTI-MICROBIAL PEPTIDOMIMETIC COMPOUNDS AND METHODS TO CALCULATE ANTI-MICROBIAL ACTIVITY

(76) Inventors: Rickey P. Hicks, Greenville, NC (US); Diva Karamenon Venugopal, Gaithersburg, MD (US); Jayendra Bhonsle, Germantown, MD (US)

(*) Notice: Subject to any disclaimer, the term of this patent is extended or adjusted under 35 U.S.C. 154(b) by 1165 days.

(21) Appl. No.: 12/004,397

(22) Filed: Dec. 20, 2007

(65) Prior Publication Data

US 2009/0291898 A1    Nov. 26, 2009

Related U.S. Application Data

(60) Provisional application No. 60/876,377, filed on Dec. 21, 2006.

(51) Int. Cl.
| | | |
|---|---|---|
| A61K 38/00 | (2006.01) | |
| C07K 5/00 | (2006.01) | |
| C07K 7/00 | (2006.01) | |
| C07K 16/00 | (2006.01) | |
| C07K 17/00 | (2006.01) | |

(52) U.S. Cl. .................................. 514/1.1; 530/326
(58) Field of Classification Search .................... None
See application file for complete search history.

(56) References Cited

U.S. PATENT DOCUMENTS 6,730,326 B2   5/2004   Beyer et al. .................... 424/489

OTHER PUBLICATIONS

Thurieau et al. Design and Synthesis of New Linear and Cyclic Bradykinin Antagonists. J. Med. Chem. 1996, vol. 39, pp. 2095-2101.*
Yeaman, et al., Mechanisms of antimicrobial pepitde action and resistance. Pharmacological Reviews 2003, 55, (1), 27-55.
Dennison, S. R.; Wallace, J.; Harris, F.; Phoenix, D. A., Amphiphilic a-helical antimicrobial peptides and their structure/function relationships. Protein and Peptide Letters, 2005, 12, 31-39.
Toke, 0.,"Antimicrobial peptides; new candidates in the fight against bacterial infections." Biopolymers (2005) 80, pp. 717-735.
Ganz, T., "Defensins: antimicrobial peptides of innate immunity." Nature reviews, Immunology 2003, 3, pp. 710-720.
Simmaco, M.; Mignogna, G.; Barra, D., "Antimicrobial peptides from amphibian skin: what do they tell us? " Biopolymers 1998, 47, pp. 435-450.
Hancock, R. E. W.; Lehrer, R., "Cationic peptides: a new source of antibiotics."Trends Biotechnol 1998, 16, pp. 82-88.
Zasloff, M., "Antimicrobial peptides of multicellular organisms."Nature 2002, 415, pp. 389-395.
Powers, J.-P. S.; Hancock, R. E. W., "The relationship between peptide structure and antibacterial activity." Peptides 2003,24, pp. 1681-1691.
Blondelle, S. E.; Lohner, K.; Aguilar, M.-I., "Lipid-induced conformation and lipid-binding properties of cytolytic and antimicrobial peptide: determination and biological specificity." Biochimica et Blophysica Acta 1999,1462, pp. 89-108.

Brogden, K. A., "Antimicrobial peptides: pore formers or metabolic inhibitors of bacteria." Nature Reviews Microbiol 2005, 3, pp. 238-250.
Pouny, Y.; Rapaport, D.; Mor, A.; Nicolas, P.; Shai, Y., "Interaction of antimicrobial dermaseptin and its fluorescently labeled analogues with phospholipid membranes." Biochemistry 1992, 31, pp. 12416-12423.
Papo, N.; Shai, Y., "Can we predict biological activity of antimicrobial peptides from their interaction with model phospholipid membranes?" Peptides 2003, 24, pp. 1693-1703.
Bechinger, B., "The structure, dynamics and orientation of antimicrobial peptides in membranes by multidimensional solid-state NMR spectroscopy." Biochim.et Biophys. Acta 1999, 1462, pp. 157-183.
Lee, M. T.; Chen, F. Y.; Haung, H. W., "Energetics of pore formation induced by membrane active peptides."Biochemistry 2004, 43, pp. 3590-3599.
Bechinger, B., "Solid-state NMR investigations of the interaction contributions that determine the alignment of helical polypeptides in biological membranes." FEBS Lett. 2001,504, pp. 161-165.
Song, Y. M.; Park, Y.; Lim, S. S.; Yang, S.-T.; Woo, E.-R.; Park, S.; Lee, J. S.; Kim, J. I.; Hahm, K.-S.; Kim, Y.; Shin, S. Y., "Cell selectivity and mechanism of action of antimicrobial model peptides containing peptoid residues." Biochemistry 2005,44 ,pp. 12094-12106.
Giangaspero, A.; Sandri, L; Tossi, A., "Amphipathic a-helical antimicrobial peptides."Eur. J. Biochem. 2001,268, pp. 5589-5600.
Glukhov, E.: Stark, M.; Burrows, L. L.; Deber, C. M., "Basis for selectivity of cationic antimicrobial peptides for bacterial versus mammalian membranes." J. Biol. Chem. 2005, vol. 280, No. 40, pp. 33960-33967.
White, S. H.; Wimley, W. C, "Hydrophobic interactions of peptides with membrane interfaces." Biochim. Biophys. Ada 1998,1376, pp. 339-352.
Situ, H.; Wei, G.; Smith, C. J.; Mashhoon, S.; Bobek, L. A., "Human salivary MUC7 mucin peptides: effect of size, charge and cysteine residues on antifungal activity." Biochem. J. 2003,375, pp. 175-182.
Moerman, L.; Bosteels, S.; Noppe, W.; Willems, J.; Clynen, E.; Schoofs, L.; Thevissen, K.; Tytgat, J.; Van Elder, J.; van der Walt, J.; Verdonck, F., "Antibacterial and antifungal properties of helical cationic peptides in the venom of scorpions from southern Africa." Eur. J. Biochem. 2002, 269, pp. 4799-4810.
Deslouches, B.; Phadke, S. M.; Lazarevic, V.; Cascio, M.; Islam, K..; Montelaro, R. C; Mietzner, T. A. "De novo generation of cationic antimicrobial peptides: influence of length and tryptophan substitution on antimicrobial activity." Antimicrobial Agents and Chemotherapy 2005,vol. 49, No. 1, pp. 316-322.
Wareham, D. W.; Bean, D. C, "In vitro activity of polymyxin B in combination with imipenem, rifampicin and azithromycin versus multidrug resistant strains of Acinetobacter baumannii producing OXA-23 carbapenemases." Ann. Clin. Microbiol. Antimicrob. 2006, 5 (10), pp. 1-5.
Zasloff, M., "Antimicrobial peptides of multicellular organisms."Nature 2002,415, pp. 389-395.
Wenk, M. R.; Seelig, J., "Magainin-2-amide interaction with lipid membranes: calorimetric detection of peptide binding and pore formation." Biochemistry 1998, 37, pp. 3909-3916.

(Continued)

Primary Examiner — Marcela M Cordero Garcia

(57) ABSTRACT

This invention encompasses synthetic antimicrobial peptide analogs having certain un-natural amino acids, including the un-natural amino acids hydrophobic tetrahydroisoquinolinecarboxylic acid (Tic) and octahydroindolecarboxylic acid (Oic), incorporated into the polypeptide backbone. These antimicrobial peptides (AMPs) are useful to treat infection in humans and other mammals of such bacteria as Gram positive bacteria, Gram negative bacteria and *Mycobacterium*. Many of the AMPs also exhibit the property of reduced hemolytic activity. The invention also entails 3D-QSAR models and mathematical equations that calculate the biological activity of any peptide sequence against *Staphylococcus aureus* or *Mycobacterium ranae*.

16 Claims, 22 Drawing Sheets
(14 of 22 Drawing Sheet(s) Filed in Color)

OTHER PUBLICATIONS

Yang, L.; Weiss, T. M.; Lehrer, R. I.; Huang, H. W., "Crystallization of antimicrobial pores in membranes: magainin and protegrin." Biochemical J. 2000,79, pp. 2002-2009.

Hicks, R. P.; Mones, E.; Kim, H.; Koser, B. W.; Nichols, D. A.; Bhattacharjee, A. K., "Comparison of the conformation and electrostatic surface properties of magainin peptides bound to SDS and DPC micelles," Biopolymers 2003, 68, 459-470.

Rozek, A.; Friedrich, C. L.; Hancock, R. E., "Structure of the bovine antimicrobial peptide indolicidin bound to dodecylphosphocholine and sodium dodecyl sulfate micelles." Biochemistry 2000, 39, pp. 15765-15774.

Whitehead, T. L.; Jones, L. M.; Hicks, R. P., "Effects of the incorporation of CHAPS into SDS micelles on neuropeptide-micelle binding: separation of the role of electrostatic interactions from hydrophobic interactions." Biopolymers 2001, 58, (7), pp. 593-605.

Whitehead, T. L.; Jones, L. M.; Hicks, R. P., "PFG-NMR investigations of the binding of cationic neuropeptides to anionic and zwitterionic micelles." J Biomol Struct Dyn 2004, 21, (4), pp. 567-576.

Kyle, D. J.; Blake, P. R.; Smithwick, D.; Green, L. M.; Martin, J. A.; Sinsko, J. A.; Summers, M. F., "NMR and computational evidence that high-affinity bradykinin receptor antagonists adopt C-terminal beta-turns." JMedChem 1993, 36, (10), pp. 1450-1460.

Hicks, R. P.; Bhonsle, J. B.; Venugopal, D.; Koser, B. W.; Magill, A. J., "De Novo Design of Selective Antibiotic Peptides by Incorporation of Un-natural Amino Acids."J. Med. Chem. 2007, 50, (13), pp. 3026-3036.

Giacometti, A.; Cirioni, 0.; Del Prete, M. S.; Paggi, A. M.; D'Errico, M. M.; Scalise, G., "Combination studies between polycationic peptides and clinically used antibiotics against Gram-positive and Gram-negative bacteria." Peptides 2000,21, pp. 1155-1160.

Grgurina, I.; Bensaci, M.; Pocsfalvi, G.; Mannina, L.; Cruciani, O.; Fiore, A.; Fogliano, V.; Sorensen, K. N.; Takemoto, J. Y., "Novel cyclic lipodepsipeptide from Pseudomonas syringae pv. lachrymans strain 508 and Syringopeptin antimicrobial activities." Antimicrobial Agents and Chemotherapy 2005, 49, (12), pp. 5037-5045.

Lockwood, N. A.; Haseman, J. R.; Tirrell, M. V.; Mayo, K. H., "Acylation of SC4 dodecapeptide increases bactericidal potency against Gram-positive bacteria, including drug-resistant strains." Biochem. J. 2004,378, pp. 93-103.

Giacometti, A.; Cirioni, O.; Del Prete, M. S.; Barchiesi, F.; Paggi, A. M.; Petrelli, E.; Scalise, G., "Comparative activities of polycationic peptides and clinically used antimicrobial agents against multidrug-resistant nosocomial isolates of Acinetobacter baumannii." J. Antimicrobial Chemotherapy 2000, 46, pp. 807-810.

Sklenar, M.; Piotto, M.; Leppik, R.; Saudek, V., "Gradient-tailored water suppression for 1H-15N HSQS experiments optimized to retain full sensitivity." J. Magn. Res. Series A 1993, 102, pp. 241-245.

Di Modugno, E.; Erbetti, I.; Ferrari, L.; Galassi, G.; Hammond, S. M.; Xerri, L., "In vitro activity of the tribactam GV 104326 against Gram-Positive, Gram-Negative and anaerobic bacteria." Antimicrobial Agents and Chemotherapy 1994, vol. 38, No. 10, pp. 2362-2368.

Misiek, M.; Pursiano, T. A.; Leitner, F.; Price, K. E., "Microbiological properties of a new cephalosporin, BL-S 339: 7-(phenylacetyimidoyl-aminoacetamido)-3-(2-methyl-1,3,4-thiadiazol-5-ylthlomethyl)ceph-3-em-4-carboxylic acid." Antimicrobial Agents and Chemotherapy, 1973, vol. 3, No. 1,pp. 40-48.

Edwards, J. R.. Turner, P. J.; Withnell, E. S.; Grindy, A. J.; Narin, K..., "In vitro antibacterial activity of SM-7338, a carbapenem antibiotic with stability to dehydropeptidase I." Antimicrobial Agents and Chemotherapy 1989,33, (2), pp. 215-222.

Montesinos, M. C; Gadangi, P.; Longaker, M.; Sung, J.; Levine, J.; Nilsen, D.; Reibman, J.; Li, M.; Jiang, C.-K.; Hirschhorn, R.; Recht, P. A.; Ostad, E.; Levin, R. I.; Cronstein, B. N., "Wound healing is accelerated by agonists of adenosine A2 (Galpha-s-linked) receptors." J. Exp. Med. 1997, vol. 186, No. 9, pp. 1615-1620.

Grant, G. A., Synthetic Peptides, A user's guide. 2nd ed.; Oxford University Press: New York, NY, 2002, Chap. 3, "Principles and Practice of Solid-Phase Peptide Synthesis", pp. 93-171.

Benoiton, N. L., Chemistry ofPeptide Synthesis. Taylor and Francis (CRC Press): Boca-Raton, FL, 2006, Chapters 5.5-5.14, pp. 131-142.

Schmidt, J. J.; Stafford, R. G.; Millard, C. B., "High-throughput assays for botulinum neurotoxin proteolytic activity: serotypes A, B, D, and F." Anal Biochem 2001,296, (1), pp. 130-137.

Ghose, A. K.; Crippen, G. M., "Atomic physicochemical parameters for three-dimensional structure-directed quantitative structure-activity relationships. 2. Modeling dispersive and hydrophobic interactions." Chem. Inf. Comput. Sci. 1987, 27, pp. 21-35.

Ghose, A. K.; Crippen, G. M., "Atomic physicochemical parameters for three-dimensional structure-directed quantitative structure-activity relationships. 1. PArtition coefficients as a measure of hydrophobicity." J. Comput. Chem. 1986, vol. 7, No. 4, pp. 565-577.

Hansch, C, "A quantitative approach to biochemical structure-activity relationships", Accounts of Chemical Research 1969, 2, pp. 232-239.

Cramer, R. D. I.; E., P. D.; Bunce, J. D., "Comparative Molecular Field Analysis (CoMFA). 1. Effect of Shape on Binding of Steroids to Carrier Proteins", J. Am. Chem. Soc. 1988,110, pp. 5959-5967.

Hopfinger, A. J.; Burke, B. J., Chapter 7, Concepts and Applications of Molecular Similarity. "Molecular shape analysis: a formation to quantitatively establish spatial molecular similarity." Wiley: New York, 1990; pp. 173-209.

Klebe, G., "Comparative Molecular Similarity Indices Analysis: CoMSIA", Perspectives in Drug Discovery and Design 1998, 12/13/14, pp. 87-104.

Jain, A. N.; Dietterich, T. G.; Lathrop, R. H.; Chapman, D.; Critchlow, R. E. J., "Compass: A Shape-Based Maching Learning Tool for Drug Design", J. Computer-Aided Mol. Design 1994, 8, pp. 635-652.

Doweyko, A. M., "The hypothetical active site lattice . . . ", Math. Chem. 1991, 7, pp. 273-285.

Wiener, H., "Structural Determination of Paraffin Bioling Points," J. Am. Chem. Soc. 1947, 69, pp. 17-20.

Bonchev, D., Information theoretic indices for characterization of chemical structures. 1983; Research Studies Press, John Wiley & Sons, Ltd., New York, pp. 66-67.

Hosoya, H. "Topological Index. A Newly Proposed Quantity Characterizing the Topological Nature . . . ", Bulletin of the Chemical Society of Japan, 1971, vol. 44, No. 9, pp. 2332-2339.

Kier, L. B.; Hall, L. H., Molecular connectivity in chemistry and drug research. Academic Press: NewYork. 1976; vol. 14, pp. 40-80.

Kier. L. B., "A Shape Index from Molecular Graphs", Quantitative Structure-Activity Relationships 1985, 4, pp. 109-116.

Kier. L. B., Hall, L H., Frazer, J.W., "An Index of Electrotopological State for Atoms in Molecules," J. Math. Chem. 1991, 7, pp. 229-241.

Balaban. A. T., "Highly Discriminating Distance-based Topological Index", Chem. Phys. Letts 1982, vol. 89, No. 5, pp. 399-404.

Bonchev. D., Mekenyan, 0., Trinajstic, N.J., "Isomer Discrimination by Topological Information Approach", J. Computational Chem. 1981, vol. 2, No. 2, pp. 127-148.

Marsili, M., Gasteiger. J., "Fast calculation of atomic charges from molecular topology and orbital electronegativies." Studies in Physical and Theoretical Chemistry 1981, 16, pp. 56-67.

Rohrbaugh, R.H., Jurs. P. C, "Descriptions of Molecular Shape Applied in Studies of Structure . . . ", Analytica Chimica Acta 1987, 199, pp. 99-109.

Hasan, M.N., "Prediction of gas and liquid chromatographic tetention indices of polyhalogenated byphenyls", Jurs. P. C. Anal. C 'hem. 1990, 62, pp. 2323-2329.

Kharkar. P. S.: Desai. B.: Gaveria. II.: Varu. B.: Loriva. R., "Three-dimensional quantitative structure-activity relationship of 1,4-dihydropyridines as antituber cular agents" J. Med. Chem. 2002, 45, pp. 4858-4867.

Drew. M. G. B.: Wilden, G. R. H.; Spillanc. W. J.: Walsh. R. M.; Ryder. C. A."Quantitative structure-activity relationsip studies of sulfamates RNHSO4Na: distinction between sweet, sweet-bitter, and bitter molecules", J. Argicultural and Food Chem. 1998, 46, pp. 3016-3026.

Hirashima, A.: Rafaeli, A.: Gileadi. C; Kuwano. E., "Three-dimensional quantitative structure-activity studies of octopaninergic agonists responsible for the inhibition of sex-pheromone production in Hercoverpa armigera", Bioorg. &Med. Chem. 1999, 7, pp. 2621-2628.

Hasegawa, K.; Arakawa. M.; Funatsu, K., "Rational choice of bioactive conformations through use of conformation analysis and 3-way partial least squares modeling." Chemometrics and Intelligent Lab. Sys. 2000, 50, (2), pp. 252-261.

Hopfinger. A. J.: Wang. S.: Tokarski. J. S.: Jin, B.; Albuquerque. M., "Construction of 3D-QSAR Models using the 4D-QSAR analysis formalism", J. Am. Chem. Soc., 1997, 119, pp. 10509-10524.

Hasegawa, K.; Arakawa, M.; Funatsu, K.. "Simultaneous determination of bioactive conformations and alignment rules by multi-way PLS modeling", Comput. Biol. &Chem. 2003, 27, pp. 211-216.

Vedani, A.: McMasters. D. R.; Dobler. M.. "Multi-conformational ligand representation in 4D-QSAR: reducing the bias associates with ligand alignment", Quantitative Structure-Activity Relationships 2000, 19, pp. 149-161.

Appell. M., Dunn. W. J.; Rcith. M. E. A.; Miller. L.; Flippen-Anderson. J. L., "An analysis of the binding of cocaine analogues to the monoamind transporters using tensor decomposition 3D QSAR", Bioorganic & Med Chem. 2002, 10, pp. 1197-1206.

Klucik; Xiao, Y.D.; Hammond. P. S.: Harris. R.: Schmitt, J. D., "Targacept active conformation search: a new method for predicting the conformation of a ligand bound to its protein target", J.Med Chem. 2004, 47, pp. 6831-6839.

Sulea, T., Kurunczi, L., Oprea, T. L., Simon, Z., "MTD-ADJ: A multiconformational minimal topologic difference for determining bioactive conformers using adjusted biological activities", J. Computer-Aided Mol. Design 1998, 12, pp. 133-146.

Bhonsle, J. B,: Wang. Z. W.: Tamamura, H.: Fujii. N. Peiper. S. C: Trent, J. O., "A simple, automated quasi-4D-QSAR, quasi-multi way PLS approach to develop highly predictive QSAR models for highly flexible CXCR4 inhibitor cyclic pentapeptide ligands using scripted common molecular modeling tools." QSAR & Combinatorial Science 2005, 24, (5), pp. 620-630.

Bhonsle, J. B.; Bhattacharjee, A. K.; Gupta, R., "Novel semi-automated methodology for developing highly predictive QSAR models: application for development of QSAR models for insect repellent amides." J. Molecular Modeling 2007, 13(1), pp. 179-208.

Mayo, S. L.; Olafson, B. D.; Goddard. W. A. I. ,"DREIDING:generic force field."J. Phys. Chem. 1990, 94, pp. 8897-8909.

Levitt, M.; Lifson, S., "Refinement of protein conformations using a macromolecular energy minimization procedure." J. Mol. Biol 1969, 46, (2), pp. 269-279.

Chang, G.; Guida. W. C; Still. W. C, "An internal-coordinate Monte Carlo method for searching conformational space." J. Am. Chem. Soc. 1989, 111, pp. 4379-4386.

Bro, R., "Multiway Calibration. Multilinear PLS", J. Chemometrics 1996, 10, pp. 47-61.

Hasegawa, K.; Arakawa, M.; Funatsu, K., "3D-QSAR study of insecticidal neonicotinoid compounds based on 3-way partial least squares model." Chemometrics and Intelligent Lab. Sys. 1999, 47, pp. 33-40.

Dewar, M. J. S.; Thiel, W. J., "Ground states of molecules. 39. MNDO results for molecules containing hydrogen, carbon, nitrogen, and oxygen," J. Am. Chem. Soc. 1977, 99 (15), pp. 4907-4917.

Richon, A. B.; Young. S. S.. "An introduction to QSAR Methodology. "Network Science Corporation Saluda NC 1991, pp. 1-26. (www.netsci.org/science/Compchem/feature19.html).

Yao, S. W.; Lopes, V. Fl. C; Fernandez. F.; Garcia-Mera, X.; Morales, M.; Rodriqucz-Borges, J. E.: Corderio, M. N. D. S., "Synthesis and QSAR study of the anticancer activity of some novel indane carbocyclic nucleosides." Bioorganic & Med. Chem. 2003, 11, pp. 4999-5006.

Meroueh. S. O.; Beneze, K. Z.; Hesek, D.; Lee, M.; Fisher, J. F.; T Stemmler, T. L.; Mobashery, S., "Three-dimensional structures of bacterial cell wall peptidoglycan." PNAS 2006, 103, (12), pp. 4404-4409.

Hancock. R. E., "Cationic antimicrobial peptides: toward clinical applications." Expert Opin. Investig. Drugs 2000, 9 (8), pp. 1723-1729.

Atrih, A.: Zollner, P.: Allmaicr. G.; Williamson, M. P.; Foster, S. J., "Peptidoglycan structural dynamics during germination of *Bacillus subtilis* 168 Endospores." J. Bacteriology 1998, 180, (17), pp. 4603-4612.

White, et al., "Experimentally Determined Hydrophic Scales", from the Stephen White laboratory at UC Irvine, at website http://blanco.biomol.uci.edu/hydrophobicity_scales.html , pp. 1-5, 1998 | contains the data referred to in reference White et al., "Hydrophobic interactions of peptides with membrane Interfaces."Biochim. Biophys. Ada 1998,1376, pp. 339-352, also submitted with this IDS|.

* cited by examiner

Non-Polar Face

Polar Face

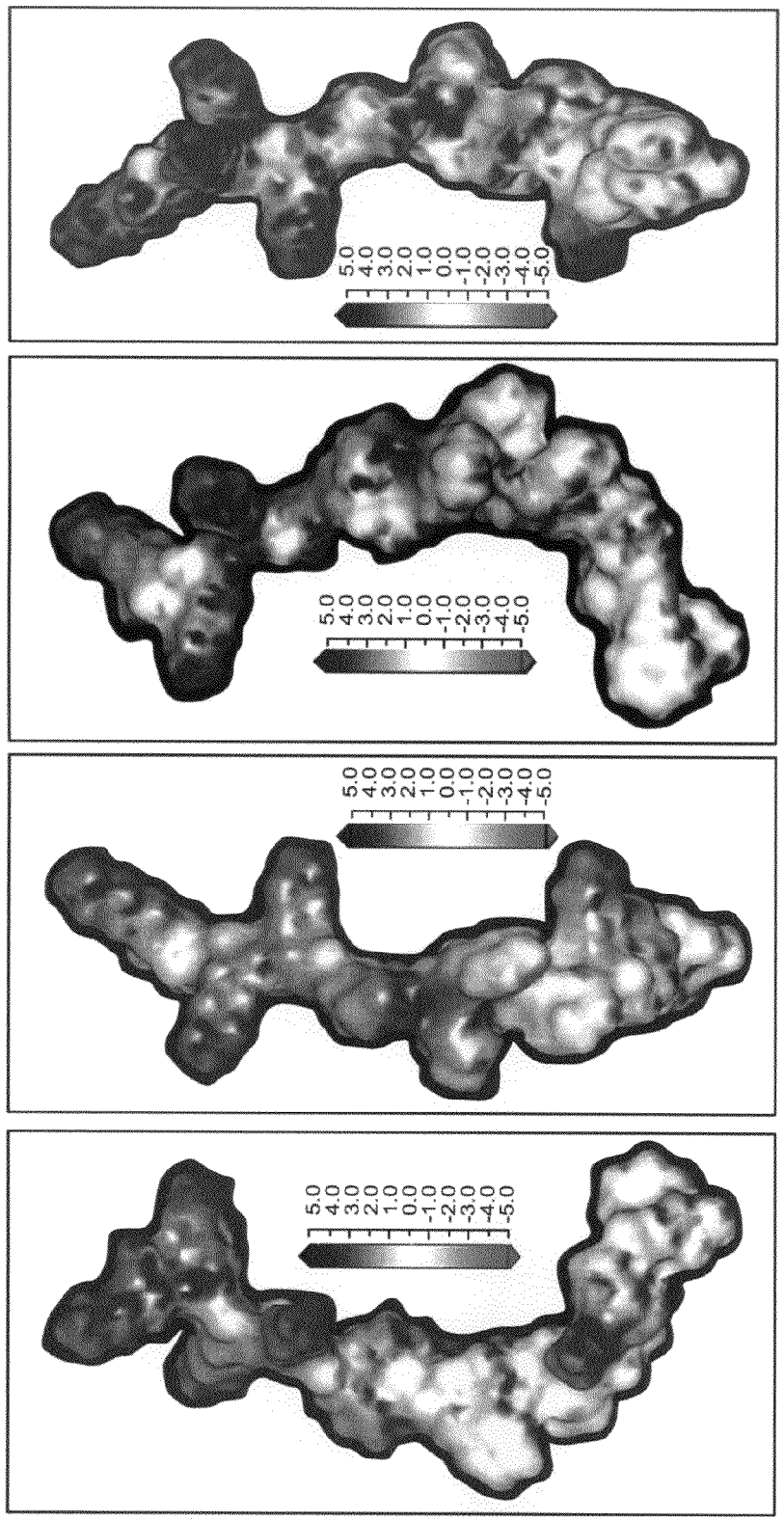

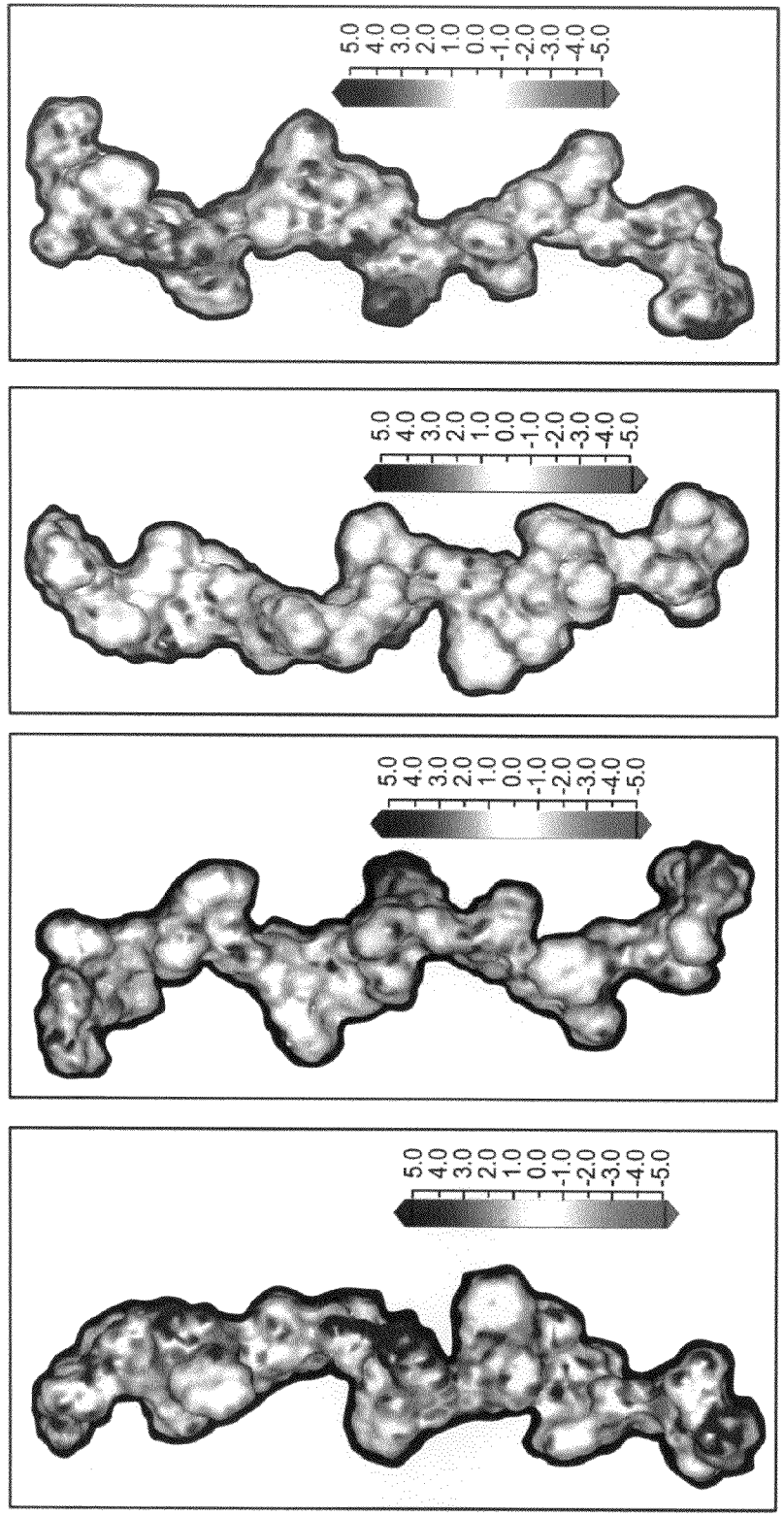

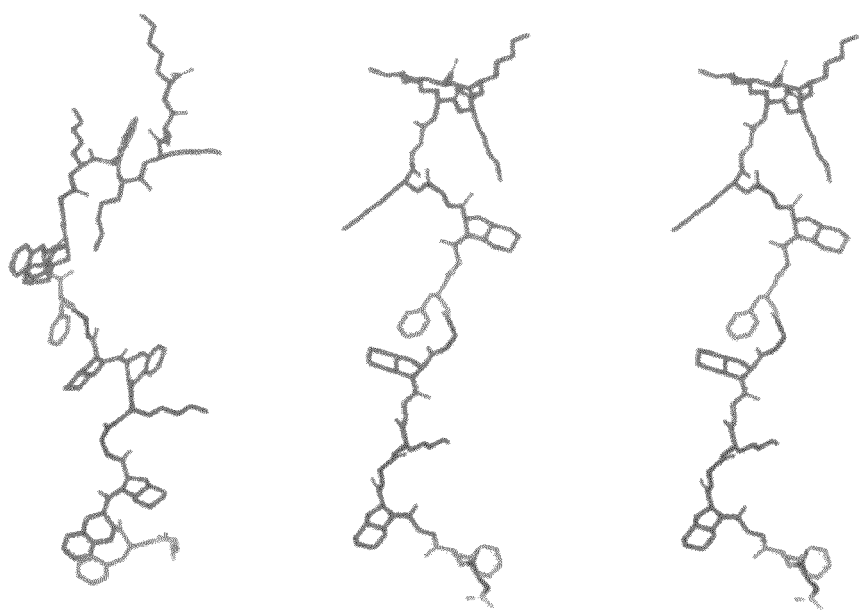
Compound 25    Compound 33    Compound 36
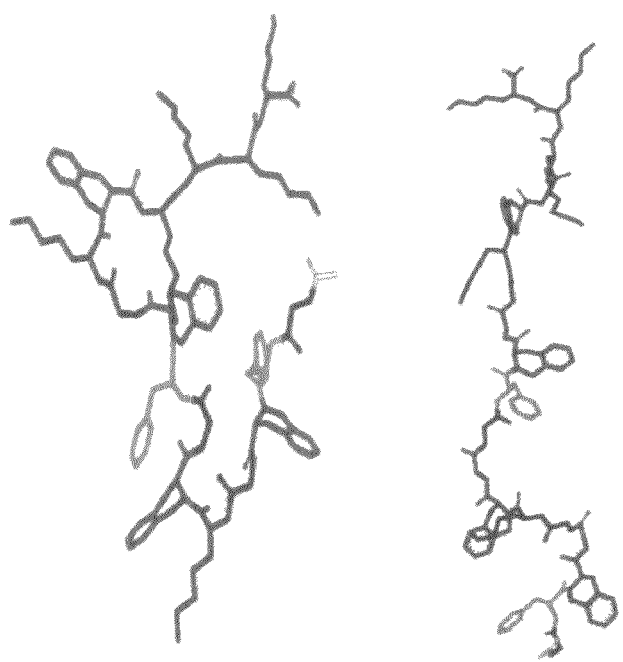
Compound 34    Compound 35
Fig. 17

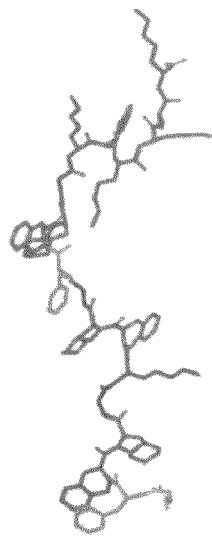
Compound 25
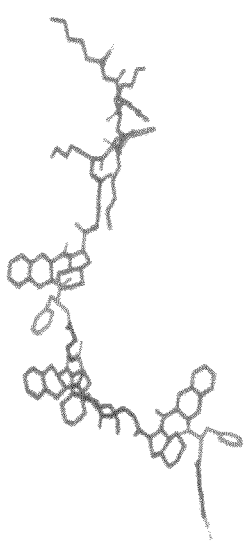
Compound 31
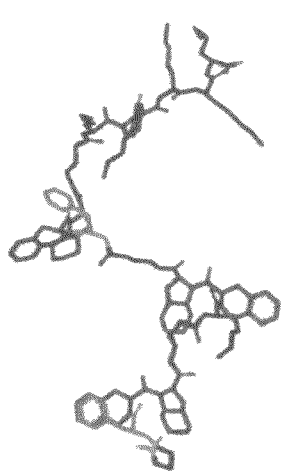
Compound 38
Compound 39
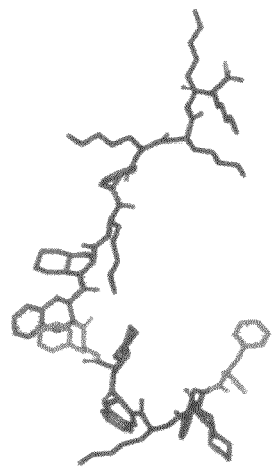
Compound 32
Fig. 18

ANTI-MICROBIAL PEPTIDOMIMETIC COMPOUNDS AND METHODS TO CALCULATE ANTI-MICROBIAL ACTIVITY

This application claims priority from U.S. provisional application 60/876,377, filed Dec. 21, 2006, the entire contents of which are incorporated herein by reference.

FIELD OF THE INVENTION

The focus of this application is novel membrane disruptive antimicrobial peptides (AMPs) with increased selectivity and potency against specific bacterial strains. As described below, this invention encompasses synthetic antimicrobial peptide analogs having certain formulas, including the un-natural hydrophobic amino acids tetrahydroisoquinolinecarboxylic acid (Tic) and octahydroindolecarboxylic acid (Oic). These antimicrobial peptides (AMPs) are useful to treat infection in humans and other mammals caused by such bacteria as Gram positive bacteria, Gram negative bacteria and *Mycobacteria*. Many of the AMPs also exhibit the property of reduced hemolytic activity.

BACKGROUND OF THE INVENTION

Antimicrobial peptides (AMP) have evolved in almost every class of living organism as a defense mechanism against invading micro-organisms including bacteria, fungi, protozoa and parasites.[1, 2] As of 2004,[3] over 800 antimicrobial peptides had been isolated and characterized from various organisms including humans,[4] amphibians,[5] insects, mammals, birds, fish and plants.[2] AMPs are generally small (10-50 amino acid residues) highly positively charged (+3 to +9)[6] amphipathic molecules with well defined hydrophobic and hydrophilic regions.[3, 7]

The exact mechanism of membrane-induced cyclotoxicity of these peptides is currently a topic of debate in the literature.[8] AMPs are broadly divided into two major classes 1) membrane disruptive and 2) non-membrane disruptive. [Powers, 2003 #3][8] All membrane-disrupters follow specific steps in the process of interacting with their target cells.[9] The first step is the attraction (or movement of the AMP through bulk solution to an area near the surface) of the AMP to the surface of the membrane.[10] The driving force for this attraction is the electrostatic interaction between the positively charged basic amino acids on the AMP and the negatively charged acidic phospholipids found in the targets cell's membrane.[11, 12, 13] The second step is binding of the AMP to the surface of the membrane.[10, 14], In this step the AMP attaches to the surface of the membrane by locating the positively charged side chains relatively close to the negatively charged polar head groups of the phospholipids followed by insertion of the hydrophobic side chains of the AMP into the hydrophobic core of the membrane. During this process conformational changes occur on the AMP that stabilizes the attractive electrostatic and hydrophobic interactions while concurrently minimizing the repulsive interactions between the AMP and the membrane. At lower concentrations the long axis of the AMP is oriented parallel to the surface of the membrane, and is called the S-state.[15] As the concentration of the AMPs increases on the surface of the membrane a critical concentration is reached where aggregation occurs forming complexes of 4-6 AMPs. This induces a change in the orientation of the long axis of the AMPs from parallel to perpendicular relative to the membrane surface resulting in the insertion of the aggregate AMPs in to the membrane forming a transmembrane pore, and this is called the I-state.[14, 10]

The membrane-disrupters can be further divided into two sub-classifications; 1) cell selective (i.e. magainins and cecropins), 2) non-selective (i.e. melittin and pardaxin).[16] As the name implies, cell selective AMPs exhibit potent activity against bacterial cells while being inactive against mammalian cells. Non-selective AMPs are active against both bacterial and mammalian cells. The selectivity of AMPs for bacterial vs. mammalian cells is believed to be based on the differences in the chemical composition of the two cell membranes.[2, 3] Bacterial cells contain a high percentage of negatively charged phospholipids while mammalian cells contain a much higher concentration of zwitterionic phospholipids.[12] Other differences also exist between the two including; membrane composition (sterols, lipopolysaccharide, peptidoglycan etc.)[1], structure, transmembrane potential, and membrane polarizability. In addition to the differences between eukaryotic and prokaryotic cells the membranes surrounding different types of bacterial cells are also different. The lipid bilayer of Gram positive bacteria is covered by a porous layer of peptidoglycan, while the structure of Gram negative bacteria is more complex consisting of two lipid membranes containing lipopolysaccharides and porins.[17, 2] The outer membrane of mycobacterium is the most complex of the three, consisting of an additional very thick mycolate-rich outer coat which is very difficult to penetrate.

It is generally no longer accepted that AMPs are uniform and indiscriminant membrane detergents. As more information becomes available regarding the sophisticated and thematic structure-activity relationships underlying distinct mechanisms of action among AMPs, there will be a greater understanding of their likely multiple roles in antimicrobial host defense.[1] There is growing evidence in the literature that the selectivity and potency of a specific AMP is determined in a large measure by the chemical composition of the target membrane.[8] Thus, it is reasonable to postulate that the membrane's physicochemical surface interactions with the physicochemical surface of the AMP defines the organism specific potency and selectivity.[2, 8, 17, 18]. As pointed out by Toke[3], understanding how the physicochemical interactions between AMPs and the lipid composition of their target cells are important that they define organism potency and selectivity which is critical for the development of AMP derived drugs.

SUMMARY OF THE INVENTION

The evolution of drug resistant bacterial strains is one of the most critical problems facing modern medicine and requires the development of drugs that exhibit anti-bacterial activity via novel mechanism. Antimicrobial peptides (AMPs) interact differently with different bacterial strains (such as Gram positive, Gram negative and *Mycobacterium*) based on the differing chemical composition of their respective cell membranes. The inventors have discovered that small changes in the structure and physicochemical properties of the constituent amino acid residues can lead to major changes in the potency and selectivity of a particular AMP for a particular bacterial strain. Therefore, by selection and placement of natural and/or un-natural amino acid residues with specific physicochemical properties, the inventors have designed a new class of AMPs with increased potency and selectivity for one or more specific strains of bacteria.

As a source of new drugs, the inventors have explored naturally occurring peptides that exhibit antimicrobial activity via membrane disruption. They have designed, synthesized and evaluated a new class of novel antimicrobial peptides containing un-natural amino acids, which AMPs exhibit increased potency and selectivity against Gram positive, Gram negative and *Mycobacterium*—and unexpectedly many of the new AMPs also exhibit reduced hemolytic activity. These new compounds were designed based on the electrostatic surface potential maps derived form the SDS and DPC micelle-bound conformations of (Ala$^{8,13,18}$)magainin-2-amide, as described in more detail below. Un-natural amino acids were incorporated into the polypeptide backbone to control the structural and physicochemical properties of the peptides to introduce organism selectivity and potency. The inventors discovered that un-natural amino acid residues increase the resistance to proteolytic or enzymatic degradation, thus providing improved stability in biological systems over AMPs consisting of only natural amino acids. Such peptides may be referred to as peptidomimetic. The term "peptidomimetic" denotes a small protein-like chain synthetically designed to mimic a natural peptide, as for instance, where a natural peptide is modified to alter the peptide's properties. Typically, changes include those that will not occur naturally (such as altered backbones and the incorporation of non-natural amino acids).

More particularly, the inventors discovered that a synthetic antimicrobial peptide analog having one of the following (referred to hereafter as General Formulae) were effective against at least one of Gram positive, Gram negative and *Mycobacterium*, and preferably (but not necessarily) exhibit reduced hemolytic activity.

Σ-Glycine-O-(Tic-Oic-X-J-Tic-Oic-X—Z)$_n$-Tic-Oic-Π-J-Tic-U$_m$—CONH$_2$

Σ-Glycine-O-(Tic-Oic-X—Z-Tic-Oic-X-J)$_n$-Tic-Oic-Π-Z-Tic-U$_m$—CONH$_2$

Σ-Glycine-B-(Tic-Oic-X—Z-Tic-Oic-X-J)$_n$-Tic-Oic-Π-Z-Tic-U$_m$—CONH$_2$

Σ-Glycine-O-(Tic-Oic-X-J-Tic-Oic-X—Z)$_n$-Tic-Oic-Π-J-Tic-U$_m$—CONH$_2$

Σ-Glycine-O-(Tic-Oic-X—Z-Tic-Oic-X-J)$_n$-Tic-Oic-Π-Z-Tic-U$_m$—CONH$_2$

Σ-Glycine-B-(Tic-Oic-X—Z-Tic-Oic-X-J)$_n$-Tic-Oic-Π-Z-Tic-U$_m$—CONH$_2$,

Σ-Glycine-O-(Tic-Oic-X-J-Tic-Oic-X—Z)$_n$-Tic-Oic-Π-J-Tic-U$_m$—CONH—(CH$_2$)$_k$—NH$_2$ Σ-Glycine-O-(Tic-Oic-X-J-Tic-Oic-X—Z)$_n$-Tic-Π-U$_m$—CONH$_2$ Σ-Glycine-O-(Tic-Oic-X-J-Tic-Oic-X—Z)$_n$-Oic-Π-U$_m$—CONH$_2$ Σ-Glycine-O-(Tic-Oic-X—Z-Tic-Oic-X-J)$_n$-Tic-Π-U$_m$—CONH$_2$ and Σ-Glycine-O-(Tic-Oic-X—Z-Tic-Oic-X-J)$_n$-Oic-Π-U$_m$—CONH$_2$ In addition, one preferred embodiment of the AMPs is encompassed by the following, which are referred to as the "Tic-Tic analogs". As shown below, these analogs exhibit greater selectivity for *Mycobacterium ranae*, compared to Gram positive and Gram negative bacteria.

Σ-Glycine-O-(Tic-Tic-X-J-Tic-Tic-X—Z)$_n$-Tic-Tic-Π-J-Tic-U$_m$—CONH$_2$

Σ-Glycine-O-(Tic-Tic-X—Z-Tic-Tic-X-J)$_n$-Tic-Tic-Π-Z-Tic-U$_m$—CONH$_2$

Σ-Glycine-B-(Tic-Tic-X—Z-Tic-Tic-X-J)$_n$-Tic-Tic-Π-Z-Tic-U$_m$—CONH$_2$

Σ-Glycine-O-(Tic-Tic-X-J-Tic-Tic-X—Z)$_n$-Tic-Tic-Π-J-Tic-U$_m$—CONH$_2$

Σ-Glycine-O-(Tic-Tic-X—Z-Tic-Tic-X-J)$_n$-Tic-Tic-Π-Z-Tic-U$_m$—CONH$_2$

Σ-Glycine-B-(Tic-Tic-X—Z-Tic-Tic-X-J)$_n$-Tic-Tic-Π-Z-Tic-U$_m$—CONH$_2$

Σ-Glycine-O-(Tic-Tic-X-J-Tic-Tic-X—Z)$_n$-Tic-Tic-Π-J-Tic-U$_m$—CONH—(CH$_2$)$_k$—NH$_2$ Σ-Glycine-O-(Tic-Tic-X-J-Tic-Tic-X—Z)$_n$-Tic-Π-U$_m$—CONH$_2$ Σ-Glycine-O-(Tic-Tic-X-J-Tic-Tic-X—Z)$_n$-Tic-Π-U$_m$—CONH$_2$ Σ-Glycine-O-(Tic-Tic-X—Z-Tic-Tic-X-J)$_n$-Tic-Π-U$_m$—CONH$_2$, Σ-Glycine-O-(Tic-Tic-X—Z-Tic-Tic-X-J)$_n$-Tic-Π-U$_m$—CONH$_2$.

Σ-Glycine-O-(Tic-Tic-Z-Tic-Tic-J)$_n$-Tic-Tic-Z-Tic-U$_m$—CONH$_2$ and

Σ-Glycine-B-(Tic-Tic-Z-Tic-tic-J)$_n$-Tic-Tic-Z-Tic-U$_m$—CONH$_2$

An example of a compound that falls within this set of formulae is Compound 59, which is described below.

Another preferred embodiment of the AMPs is encompassed by the following formulae, which are referred to as the "Oic-Tic analogs". As shown below, these analogs exhibit greater selectivity for *Mycobacterium ranae*, compared to Gram positive and Gram negative bacteria.

Σ-Glycine-O-(Oic-Tic-X-J-Oic-Tic-X—Z)$_n$-Oic-Tic-Π-J-Tic-U$_m$—CONH$_2$

Σ-Glycine-O-(Oic-Tic-X—Z-Oic-Tic-X-J)$_n$-Oic-Tic-Π-Z-Tic-U$_m$—CONH$_2$

Σ-Glycine-B-(Oic-Tic-X—Z-Oic-Tic-X-J)$_n$-Oic-Tic-Π-Z-Tic-U$_m$—CONH$_2$

Σ-Glycine-O-(Oic-Tic-X-J-Oic-Tic-X—Z)$_n$-Oic-Tic-Π-J-Tic-U$_m$—CONH$_2$

Σ-Glycine-O-(Oic-Tic-X—Z-Oic-Tic-X-J)$_n$-Oic-Tic-Π-Z-Tic-U$_m$—CONH$_2$

Σ-Glycine-B-(Oic-Tic-X—Z-Oic-Tic-X-J)$_n$-Oic-Tic-Π-Z-Tic-U$_m$—CONH$_2$

Σ-Glycine-O-(Oic-Tic-X-J-Tic-Tic-X—Z)$_n$-Tic-Tic-Π-J-Tic-U$_m$—CONH—(CH$_2$)$_k$—NH$_2$ Σ-Glycine-O-(Oic-Tic-X-J-Oic-Tic-X—Z)$_n$-Tic-Π-U$_m$—CONH$_2$ Σ-Glycine-O-(Oic-Tic-X-J-Oic-Tic-X—Z)$_n$-Tic-Π-U$_m$—CONH$_2$ Σ-Glycine-O-(Oic-Tic-X—Z-Oic-Tic-X-J)$_n$-Tic-Π-U$_m$—CONH$_2$, Σ-Glycine-O-(Oic-Tic-X—Z-Oic-Tic-X-J)$_n$-Tic-Π-U$_m$—CONH$_2$.

Σ-Glycine-O-(Oic-Tic-Z-Oic-Tic-J)$_n$-Oic-Tic-Z-Tic-U$_m$—CONH$_2$ and

Σ-Glycine-B-(Oic-Tic-Z-Oic-tic-J)$_n$-Oic-Tic-Z-Tic-U$_m$—CONH$_2$

An example of a compound that falls within this set of formulae is Compound 61, which is described below.

Another embodiment of the AMPs is encompassed by the following formulae, which are referred to as the "Oic-Oic analogs". These analogs may exhibit greater selectivity for *Mycobacterium ranae*, compared to Gram positive and Gram negative bacteria.

Σ-Glycine-O-(Oic-Oic-X-J-Oic-Oic-X—Z)$_n$-Oic-Oic-Π-J-Tic-U$_m$—CONH$_2$

Σ-Glycine-O-(Oic-Oic-X—Z-Oic-Oic-X-J)$_n$-Oic-Oic-Π-Z-Tic-U$_m$—CONH$_2$

Σ-Glycine-B-(Oic-Oic-X—Z-Oic-Oic-X-J)$_n$-Oic-Oic-Π-Z-Tic-U$_m$—CONH$_2$

Σ-Glycine-O-(Oic-Oic-X-J-Oic-Oic-X—Z)$_n$-Oic-Oic-Π-J-Tic-U$_m$—CONH$_2$

Σ-Glycine-O-(Oic-Oic-X—Z-Oic-Oic-X-J)$_n$-Oic-Oic-Π-Z-Tic-U$_m$—CONH$_2$

Σ-Glycine-B-(Oic-Oic-X—Z-Oic-Oic-X-J)$_n$-Oic-Oic-Π-Z-Tic-U$_m$—CONH$_2$

Σ-Glycine-O-(Oic-Oic-X-J-Oic-Oic-X—Z)$_n$-Oic-Oic-Π-J-Tic-U$_m$—CONH—(CH$_2$)$_k$—NH$_2$ Σ-Glycine-O-(Oic-Oic-X-J-Oic-Oic-X—Z)$_n$-Tic-Π-U$_m$—CONH$_2$ Σ-Glycine-O-(Oic-Oic-X-J-Oic-Oic-X—Z)$_n$-Tic-Π-U$_m$—CONH$_2$ Σ-Glycine-O-(Oic-Oic-X—Z-Oic-Oic-X-J)$_n$-Tic-Π-U$_m$—CONH$_2$, Σ-Glycine-O-(Oic-Oic-X—Z-Oic-Oic-X-J)$_n$-Tic-Π-U$_m$—CONH$_2$.

Σ-Glycine-O-(Oic-Oic-Z-Oic-Oic-J)$_n$-Oic-Oic-Z-Tic-U$_m$—CONH$_2$ and

Σ-Glycine-B-(Oic-Oic-Z-Oic-tic-J)$_n$-Oic-Oic-Z-Tic-U$_m$—CONH$_2$

Another embodiment of the AMPs is encompassed by the following set of formulae, which have the positively charge residues (Lys, Arg etc.) at the N-terminus and not the C-terminus. For instance, Compound 63 is as follows: Ac—KKKK-GF-Tic-Oic-GK-Tic-Oic-GF-Tic-Oic-GK-Tic-CONH$_2$ (SEQ ID NO:1), and the "KKKK" (SEQ ID NO:2) in italics at the N-terminus shows the residues with a positive charge.

As shown below, these analogs exhibit greater selectivity for *Mycobacterium* ranae, compared to Gram positive and Gram negative bacteria.

Σ-U$_m$-Glycine-O-(Tic-Oic-X-J-Tic-Oic-X—Z)$_n$-Tic-Oic-Π-J-Tic-CONH$_2$

Σ-U$_m$-Glycine-O-(Tic-Oic-X—Z-Tic-Oic-X-J)$_n$-Tic-Oic-Π-Z-Tic-CONH$_2$

Σ-U$_m$-Glycine-B-(Tic-Oic-X—Z-Tic-Oic-X-J)$_n$-Tic-Oic-Π-Z-Tic-CONH$_2$

Σ-U$_m$-Glycine-O-(Tic-Oic-X-J-Tic-Oic-X—Z)$_n$-Tic-Oic-Π-J-Tic-CONH$_2$

Σ-U$_m$-Glycine-O-(Tic-Oic-X—Z-Tic-Oic-X-J)$_n$-Tic-Oic-Π-Z-Tic-CONH$_2$

Σ-U$_m$-Glycine-B-(Tic-Oic-X—Z-Tic-Oic-X-J)$_n$-Tic-Oic-Π-Z-Tic-CONH$_2$,

Σ-U$_m$-Glycine-O-(Tic-Oic-X-J-Tic-Oic-X—Z)$_n$-Tic-Oic-Π-J-Tic-CONH—(CH$_2$)$_k$—NH$_2$ Σ-U$_m$-Glycine-O-(Tic-Oic-X-J-Tic-Oic-X—Z)$_n$-Tic-Π-CONH$_2$ Σ-U$_m$-Glycine-O-(Tic-Oic-X-J-Tic-Oic-X—Z)$_n$-Oic-Π-CONH$_2$ Σ-U$_m$-Glycine-O-(Tic-Oic-X—Z-Tic-Oic-X-J)$_n$-Tic-Π-CONH$_2$ and Σ-U$_m$-Glycine-O-(Tic-Oic-X—Z-Tic-Oic-X-J)$_n$-Oic-Π-CONH$_2$ Another embodiment of the AMPs is encompassed by the following set of formulae, which is believed to have an especially high selectivity for *Mycobacterium*.

Σ-U$_m$-Glycine-O-(Tic-Tic-X-J-Tic-Tic-X—Z)$_n$-Tic-Oic-Π-J-Tic-CONH$_2$

Σ-U$_m$-Glycine-O-(Tic-Tic-X—Z-Tic-Tic-X-J)$_n$-Tic-Oic-Π-Z-Tic-CONH$_2$

Σ-U$_m$-Glycine-B-(Tic-Tic-X—Z-Tic-Tic-X-J)$_n$-Tic-Oic-Π-Z-Tic-CONH$_2$

Σ-U$_m$-Glycine-O-(Tic-Tic-X-J-Tic-Tic-X—Z)$_n$-Tic-Oic-Π-J-Tic-CONH$_2$

Σ-U$_m$-Glycine-O-(Tic-Tic-X—Z-Tic-Tic-X-J)$_n$-Tic-Oic-Π-Z-Tic-CONH$_2$

Σ-U$_m$-Glycine-B-(Tic-Tic-X—Z-Tic-Tic-X-J)$_n$-Tic-Oic-Π-Z-Tic-CONH$_2$,

Σ-U$_m$-Glycine-O-(Tic-Tic-X-J-Tic-Tic-X—Z)$_n$-Tic-Oic-Π-J-Tic-CONH—(CH$_2$)$_k$—NH$_2$ Σ-U$_m$-Glycine-O-(Tic-Tic-X-J-Tic-Tic-X—Z)$_n$-Tic-Π-CONH$_2$ Σ-U$_m$-Glycine-O-(Tic-Tic-X-J-Tic-Tic-X—Z)$_n$-Oic-Π-CONH$_2$ Σ-U$_m$-Glycine-O-(Tic-Tic-X—Z-Tic-Tic-X-J)$_n$-Tic-Π-CONH$_2$ and Σ-U$_m$-Glycine-O-(Tic-Tic-X—Z-Tic-Tic-X-J)$_n$-Oic-Π-CONH$_2$ An example of a compound that falls within this set of is Compound 64, which is described below.

The following differ from the above in that they do not contain either spacer 1 or 2. However, as shown below, compounds having these still exhibit good activity against Gram positive, Gram negative, and especially mycobacterium, and may offer organism selectivity (see compounds below labeled, FKAB-1 Ge, FKAB-1Gc and FKAB-1Gc1.) These are included within the General Formulae as this term is intended here.

Σ-Glycine-O-(Tic-Oic-Z-Tic-Oic-J)$_n$-Tic-Oic-Z-Tic-U$_m$—CONH$_2$

Σ-Glycine-B-(Tic-Oic-Z-Tic-Oic-J)$_n$-Tic-Oic-Z-Tic-U$_m$—CONH$_2$

For purposes of clarity, these two formulae which do not contain either spacer 1 or spacer 2 are sometimes referred to herein as "the reduced spacer".

In these, Tic stands for tetrahydroisoquinolinecarboxylic acid, and Oic stands for octahydroindolecarboxylic acid. The Tic residue contains an aromatic ring, and Oic contains a non-aromatic ring which contributes to their hydrophobicity. The symbol "Σ" denotes one of acetyl, NH$_2$, biotin, β-thienylalanine (Thi), cysteine, or Keyhole Limpet Haemocyanin (KLH) or BSA (Bovine Serum Albumin) (where acetyl or NH$_2$ are preferred). "U" is lysine, arginine, histidine, ornithine, 2,3-diaminopropionic acid (Dpr), 2,4-diaminobutanoic acid (Dab), 4-aminopiperidine-4-carboxylic acid (Apc4), or 3-aminopiperidine-3-carboxylic acid (Apc3) (where lysine, arginine, ornithine and 2,3-diaminopropionic acid are preferred). "X" is glycine, alanine, β-alanine, gamma-aminobutyric acid (Gaba), ∈-aminohexanoic acid (Ahx), phenylglycine (Phg), 9-aminooctanoic acid (9-Aoa), 10-aminodecanoic acid (10Ada), 12-aminododecanoic acid (12-Adda), or 16-aminopalmitic acid (16-Apa). "J" is lysine, arginine, histidine, ornithine, 2,3-diaminopropionic acid (Dpr), or 2,4-diaminobutanoic acid (Dab). "Z" is phenylalanine, tyrosine, tryptophan, 4-fluorophenylalanine (Fpa), 4-clorophenylalanine (Cph), 4-nitrophenylalanine (Nph), phenyl glycine (Phg), valine or isoleucine. "O" is phenylalanine, leucine, valine, isoleucine, norvaline, norleucine, norisoleucine, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, N-Ethylglycine, allo-Isoleucine, N-Methylglycine (or sarcosine), N-Methylisoleucine, or N-Methylvaline (where phenylalanine and leucine are preferred). "B" is lysine, arginine, histidine, ornithine, 2,3-diaminopropionic acid (Dpr), 2,4-diaminobutanoic acid (Dab), 4-aminopiperidine-4-carboxylic acid (Apc4), or 3-aminopiperidine-3-carboxylic acid (Apc3). "Π" is glycine, alanine, β-alanine or gamma-aminobutyric acid (Gaba), or ∈-Aminohexanoic acid (Ahx), with glycine or β-alanine preferred. "n" is 1 to 4 repeating units (where 1 or 2 is preferred), "m" is 1 to 5 repeating units (where 3 or 4 is preferred), and "k" is 1 to 5 repeating units (where 2 or 3 is preferred).

All of the analogs described here are active against at least one strain of bacteria. These compounds have certain physicochemical properties that will result when these amino acid residues are combined together in the specified manner. The amino acid residues incorporated into these analogs are selected based on the following criteria. Amino acid residues used as Spacers 1 and 2 should exhibit hydrophobicity between 1.2 and −0.75 on the octanol scale (which scale is reported by Professor Stephen White at the University of California Irvine)[19] The cationic amino acid residues should exhibit a hydrophobicity between 1.5 and 3.0 on the octanol scale. The hydrophobic amino acid residues should exhibit a hydrophobicity between −1.0 and −3.0 on the octanol scale. The general formulae are reasonably considered predictive of the antimicrobial activity, since the testing and results of them (as described below) were obtained from a large number of different peptides synthesized based on the general formulae where most variations were represented by at least one example. Further, these predictions were validated by the excellent results obtained through molecular modeling studies.

In simple terms, what is described and encompassed here are antimicrobial peptides comprising turn-inducing tetrahydroisoquinolinecarboxylic acid and octahydroindolecarboxylic acid (Tic-Oic) unit linked to a first spacer amino acid. (The exception to this is the reduced spacer, which lack the first and second spacers.) The first spacer amino acid is linked via an amide bond to an amino acid having a cationic side chain. (FIG. 1A) The amino acid having a cationic side chain is linked to a second Tic-Oic unit which is linked to a second spacer amino acid, which second spacer amino acid is linked to a hydrophobic amino acid. Or the first spacer amino acid is linked via an amide bond to a hydrophobic amino acid. (FIG. 1B) The hydrophobic amino acid is linked to a second Tic-Oic unit which is linked to a second spacer amino acid, which second spacer amino acid is linked to an amino acid having a cationic side chain. A combination of cationic and hydrophobic amino acid residues are required for activity. The exact number and placement of these residues define the organism selectivity and hemolytic activity.

By "spacer" it is meant an amino acid residue separating a single Tic, or Oic residue or an Tic-Oic, Oic-Tic, Tic-Tic or Oic-Oic dipeptide unit from a cationic or hydrophobic residue. A "spacer" amino acid should not be electronically charged (cationic or anionic) nor should it be highly hydrophobic or highly hydrophilic. The role of the "spacer" is to provide conformational flexibility for the polypeptide backbone. In the General Formulae, "X" denotes the first and second spacers, that is, spacers 1 and 2. Spacer 1 and 2 can be any combination of two of the following amino acids. In addition spacer 1 and 2 can be the same amino acid (e.g. Gly).

List of possible amino acids for spacers 1 and 2
1. Gly
2. Ala
3. β-Ala
4. Gaba
5. ∈-Ahx (6-Ahx, 6-Aminohexanoic acid)
6. Phg (Phenylglycine)
7. 9-Aoa: (9-Aminooctanoic acid)
8. 10Ada: 10-Aminodecanoic acid
9. 12-Adda: 12-Aminododecanoic acid
10. 16-Apa (16-Aminopalmitic acid)

It is preferred that the first and second X have a length between 3.5 and 28.0 angstroms. Spacers 1 and 2 may be the same or different amino acids.

There may of course be additional spacers besides spacers 1 and 2. For instance, a third spacer might be present, as long as it is not electronically charged (cationic or anionic) or highly hydrophobic. It is noted that for spacers other than spacers 1 and 2, these should exhibit hydrophobicity between 1.2 and −0.75, and generally provide conformational flexibility for the backbone.

When the term "linked" is used, it is understood that all amino acids are linked together using amide bonds. This is the normal method of linking two amino acids together by condensing the amine of amino acid with the carboxylic acid of another amino acid to form an amide bond.

The cationic amino acid, designated in the General Formulae as "B" and "U", may include the following.
List of possible cationic amino acids
1. Lys
2. Arg
3. His
4. Orn
5. Dpr (2,3-Diaminopropionic acid)
6. Dab (2,4-Diaminobutanoic acid)
7. Apc3 (3-Aminopiperidine-3-carboxylic acid)
8. Apc4 (4-Aminopiperidine-4-carboxylic acid)

The cationic amino acid residues should exhibit hydrophobicity between 1.5 and 3.0 on the octanol scale.

The hydrophobic amino acid, designated in the General Formulae as "Z", may include the following.
List of possible hydrophobic amino acids
1. Phe
2. Leu
3. Tyr
4. Trp
5. Fpa (Fpa, 4-Fluorophenylalanine)
6. Cph (Cph, 4-Chlorophenylalanine)
7. Nph (Nph, 4-Nitrophenylalanine)
8. Phg (Phenyl Glycine)
9. Val
10. Ile
11. Nva (Norvaline)
12. Nle (Norleucine)
13. Norisoleucine
14. 4Abu (-Aminobutyric acid)
15. Piperidinic acid
16. Acp (6-Aminocaproic acid)
17. Ahe (2-Aminoheptanoic acid)
18. Aib (2-Aminoisobutyric acid)
19. βAib (3-Aminoisobutyric acid)
20. Apm (2-Aminopimelic acid)
21. Dbu (2,4-Diaminobutyric acid)
22. EtGly (N-Ethylglycine)
23. aIle (allo-Isoleucine)
24. MeGly (N-Methylglycine or sarcosine)
25. MeIle (N-Methylisoleucine)
26. MeVal (N-Methylvaline)

The hydrophobic amino acid residues should exhibit hydrophobicity between −1.0 and −3.0 on the octanol scale.

For the reasons described below, it is preferred that the Tic and Oic when linked form a unit which induces a β-turn. As is known in the art, there are three types of β-turns that the Tic-Oic dipeptide can induce depending on the amino acid residues used for spacers 1 and 2. Type I-β-turn exhibits a backbone dihedral angles of −60, −30 for residue i+1 and −90, 0 for residue i+2. Type III-β-turn exhibits a backbone dihedral angles of −60, 120 for residue i+1 and 80, 0 for residue i+2. Type III-β-turn exhibits a backbone dihedral angles of −60, −30 for residue i+1 and −60, −30 for residue i+2. A type III β-turn is the basic single unit of a 3/10 helix. In addition a variation of the individual angles of ±30 degrees is allowed within each structural class. Residues i+1 and i+2 are defined as residues 2 and 3 of the four amino acids composing a β-turn. Thus depending on the amino acids used as spacers 1 and 2 the peptide can either adopt back-to-back β-turns (these β-turns maybe Type I, Type II, Type III or any combination of the three) or it can adopt a 3/10 helical conformation on binding to the cell membrane. Thus, the AMPs described here can have Type I, Type II or Type III β-turns, or any combination of these.

It is further preferred that an antimicrobial peptide of one of these General Formulae in its secondary structure will include, when n=1 or 2, at least three β-turns, and preferably five, and exhibits sufficient conformational flexibility to bind to the membrane of at least one of Gram positive bacteria, Gram negative bacteria or *Mycobacteria*. A minimum of three back-to-back β-turns or three turns of a 3/10 helix are required to provide the amphipathic structure. If the number of β-turns is increased above 6 or 7 there is a higher probability that the analogs will exhibit higher hemolytic activity without a concurrent increase in antibacterial activity. (See results below for the analogs labeled WRFK-1 to WRFK-5.) It is preferred that these antimicrobial peptides exhibit cell-selective, membrane-disruptive antimicrobial activity against at least one of Gram positive bacteria, Gram negative bacteria or *Mycobacteria*—such as, for example, *Salmonella typhimurium, Staphylococcus aureus, Mycobacterium ranae* or *Bacillus subtillis*.

In a preferred embodiment, the antimicrobial peptides will exhibit less hemolytic activity than naturally occurring non-selective antimicrobial peptides. Of course, any decrease in hemolysis is advantageous over naturally occurring AMPs, such as melittin and pardaxin.[3]

It is noted that where the AMPs are used against an infection and are administered intravenously or orally, it is more important that the AMPs have reduced hemolytic activity. However, for topical applications, such as for wound treatment and the like, hemolytic activity is not a concern. Thus, especially where the AMPs are included in compositions to treat infections by topical application, it is not important that the AMPs have any decreased hemolytic activity at all.

This invention also contemplates compositions containing one or more of the antimicrobial peptides defined by the General Formulae. Where a particular bacterium is targeted for treatment, the composition may include at least one AMP that is effective against that bacterium. For instance, a composition to treat infection by Gram positive bacteria would contain at least one AMP that is effective against Gram positive bacteria. The same is true for Gram negative bacteria and mycobacteria, for which treatment antibiotic compositions can be prepared which include at least one AMP that is effective against that type of bacteria. On the other hand, where a broad-based antibiotic is desired, which may be effective to treat two or all three of Gram positive bacteria, Gram negative bacteria or *Mycobacteria*, the composition may include multiple AMPs where each AMP is selected for its particular activity against one of these classes of bacteria—thus, the composition would include at least one AMP that is effective against Gram positive bacteria, at least one AMP that is effective against Gram negative bacteria, and at least one AMP that is effective against *Mycobacteria*.

Along those lines, compositions containing the AMPs defined by the General Formulae may also be useful to treat malaria infection. The inventors have shown anti-malarial activity similar to other antibiotic drugs. (Table 1)

TABLE 1

Anti-malarial activity of selected analogs

| Peptide ID | $IC_{50}$ * W2 (ug/mL) | $IC_{50}$ * D6 (ug/mL) |
|---|---|---|
| WRFK-1 | 5.7 | 7.3 |
| WRFK-2 | 6.9 | 7.2 |

TABLE 1-continued

Anti-malarial activity of selected analogs

| Peptide ID | $IC_{50}$ * W2 (ug/mL) | $IC_{50}$ * D6 (ug/mL) |
|---|---|---|
| WRFK-3 | 7.2 | 5.2 |
| WRFK-4 | 6.5 | 7.8 |
| WRFK-5 | 4.2 | 3.9 |

*Plasmodium falciparum* strains used D6 (CDC Sierra Leone, mefloquine resistant), W2 (CDC Indochina III chloroquine, quinine, pyrimethamine and sulfadoxine-resistant)

In addition, compositions containing the AMPs defined by the General Formulae may also be useful as antifungal agents against, for instance, such fungus as *Candida albicans* (which is the most prevent fungal pathogen in humans) and *Cryptococcus neoformans*[20], *Botrytis cinerea, Fusarium culmorum* and *Neurospora crassa*[21] and literature data supports this.

The compositions may include pharmaceutically acceptable adjuvants, stabilizers or carriers. For instance, the compound may be admixed with lactose, sucrose, starch powder, cellulose esters of alkanoic acids, cellulose alkyl ester, talc, stearic acid, magnesium stearate, magnesium oxide, sodium and calcium salts of phosphoric and sulphuric acids, gelatin, acacia, sodium alginate, polyvinyl-pyrrolidone and/or polyvinyl alcohol, and thus tableted or encapsulated for convenient administration. Alternatively, the compound may be dissolved in water, polyethylene glycol, propylene glycol, ethanol, corn oil, cotton seed oil, peanut oil, sesame oil, benzyl alcohol, sodium chloride and/or various buffers. Appropriate additives for the use as ointments, cremes or gels are for example paraffin, vaseline, natural waxes, starch cellulose, or polyethyleneglycol. Other adjuvants and modes of administration are well and widely known in the pharmaceutical art. See the examples and description of U.S. Pat. No. 6,730,326.

For instance, antibiotic compositions are encompassed here, which might include one or more of the novel AMPs described here, plus combinations of the antimicrobial peptides and other known antibiotic drugs such as ciprofloxacin, carbenicillin, nalidixic acid,[22] amoxicillin, levofloxacin, cefuroxime and erythromycin[21] additionally the use of imipenem, rifampicin and azithromycin[23], and the like.

Antibiotics can take the form of a pill, capsule, liquid (in aqueous solution), intravenous, topical cream or ointment, or any known method of administration, depending on the age, weight, health and life situation of a patient, and the type of bacteria/bacterium sought to be treated and stage of infection. For example, as a topical application the antimicrobial peptides of the General Formulae may be useful for treatment of impetigo, diabetic foot ulcer infections, catheter-related bloodstream infections, wound healing, burn healing, and acne. As examples of application in oral solution, the antimicrobial peptides may be useful to treat Gingivitis and mouth infections. As examples of parenteral use, the antimicrobial peptides may be useful to treat invasive fungal infections, lung infections in cystic fibrosis patients, systemic multi-resistant Gram positive bacterial infections, and pediatrics meningococcemia. Another useful application may be for treatment of biofilm infections associated with bone surgeries or artificial metallic implants. Another use may be for treatment of tuberculosis. These are just examples, not at all meant to be limiting, of the wide range of uses, forms and methods of application of the AMPs. Someone having ordinary skill in the area of antimicrobial peptides and antibiotics in general would readily be able to adapt the AMPs to the particular mode of administration and dosage that is appropriate to treat the ailment or condition desired.

In another embodiment, this invention includes methods for treating humans or mammals infected by at least one of Gram positive bacteria, Gram negative bacteria or *Mycobacterium* (such as, for example, *Salmonella typhimurium, Staphylococcus aureus, Mycobacterium ranae* or *Bacillus subtillis*). In a related embodiment, the invention includes methods for treating humans or mammals infected by certain select agents such as *Bacillus anthracis* and *Yersinia pestis* (the plague). (Generally speaking, to be considered effective to treat one or more of these bacteria, the AMP must have a minimum antimicrobial activity of 100 uM in-vitro. Such methods comprise the step of administering to a mammal suspected of infection by at least one of Gram positive bacteria, Gram negative bacteria or *Mycobacteria* a pharmaceutically effective amount of at least one of a synthetic antimicrobial peptide analog having a formula described above in the General Formulae, and a pharmaceutically acceptable adjuvant or carrier. For instance, an antibiotic composition may be used, such as is described above. The inventors have found that in the case of *Mycobacterium ranae*, antimicrobial peptides that include the Tic-Tic analog (such as for instance, compound 59, FKAB-1Gg2, described below) and the Oic-Tic analog (such as for instance, compound 61, FKAB-1Gg1, described below), are particularly selective and effective. In the case of *Bacillus anthracis* and *Yersinia pestis* (the plague), it is preferred that the synthetic antimicrobial peptide analog be chosen from the group consisting of compounds 24, 34, 38, 44, 45, 52-57, 59, and 60 (as described below). Especially preferred for *Bacillus anthracis* are compounds 24, 34, 38, 44, 45, 53, 57, 59 and 60. Especially preferred for *Yersinia pestis* are compounds 34, 44, 45, 52, 53, 54, 55, 56, 59 and 60.

The antimicrobial peptide may be administered by any appropriate methods, as would be understood by someone having skill in this art—such as topical, intravenous, infusion, and oral administration. Someone skilled in this art would be able to readily determine the appropriate dosage for each patient, depending on the age, weight, health and life situation of the patient, and of course the specific type and stage of the infection. In addition, the choice of adjuvant may influence the effectiveness of a dose, and someone having ordinary skill in this art would be able to determine the type of administration and dosage. Standard dosage amounts and schedules for antibiotics would apply for this invention as well. For example, for intravenous administration, the dosage regimen is preferably 1-25 mg/kg per day; for oral administration, the dosage regimen is preferably 1-25 mg/kg per day.

The results of the inventors' analysis of the success of these antimicrobial peptides as a new class of potent broad spectrum antibacterials with relatively low hemolytic activity are detailed below, but some highlights may be summarized as follows. The inventors' reference compound for the ultimate development of their un-natural AMPs was the naturally occurring antimicrobial peptide magainin I. Magainin I exhibited MIC activity against *Salmonella typhimurium* of 30 µM and was not active in vitro against *Staphylococcus aureus* ME/GM/TC resistant bacteria at concentrations as high as 100 µM. The AMP compounds discovered and described herein exhibited a ten fold increase in potency against *Salmonella typhimurium* and at least a 33 fold increase in potency against *Staphylococcus aureus* ME/GM/TC resistant bacteria. In addition the inventors have discovered that small structural modifications will lead to analogs that will exhibit high organism selectivity. This overall approach represents a paradigm shift from the current drug discovery approaches involving antimicrobial peptides.

For instance, one compound designated FKAB-1Gw exhibited the highest in vitro selectivity for *Salmonella typhimurium* with a 10-fold selectivity over *Staphylococcus aureus* ME/GM/TC resistant bacteria and a 33-fold selectivity over *Mycobacterium ranae*. Compound FKAB-1Gd3 exhibited a 3-fold selectivity over *Salmonella typhimurium* and a 10-fold selectivity over *Staphylococcus aureus* ME/GM/TC resistant while compound FKAB-1Go exhibited a 10-fold selectivity over *Salmonella typhimurium* and a 3-fold selectivity over *Staphylococcus aureus* ME/GM/TC resistant These three compounds were the most selective analogs for *Mycobacterium ranae*. Compounds WRFK-2 and WRFK-4 exhibit 10-fold or greater selectivity for *Staphylococcus aureus* ME/GM/TC resistant bacteria versus *Salmonella typhimurium* and *Mycobacterium ranae* however they exhibit 100% hemolytic activity.

Overall, antimicrobial peptides of the General Formulae were shown to exhibit significant potency and selectivity against Gram positive, Gram negative and/or *Mycobacterium*, and many also exhibited the advantageous property of at least some level of reduced hemolytic activity.

This invention also encompasses a Quantitative Structure Activity Relationship (QSAR) modeling system utilizing mathematical equations that calculate the biological activity of any peptide sequence against *Staphylococcus aureus* (MRSA) and *Mycobacterium ranae*. The inventors developed highly predictive 3D-QSAR models for the antimicrobial peptides described herein containing unnatural amino acids, which models employ specific mathematical equations. In particular, they have discovered a set of 5-15 physicochemical properties that are most important for manifestation of antimicrobial activity against *Staphylococcus aureus* or *Mycobacterium ranae*. Using these equations and the list of physicochemical properties, someone having ordinary skill in this art can use them to guide the design and synthesis of other antimicrobial peptides.

As described herein, these AMPs of the invention exhibit extremely potent activity against *Salmonella typhimurium, Staphylococcus aureus, Mycobacterium ranae*, and *Bacillus subtillis*. Employing the recently reported bioactive conformer mining methodology, the inventors have computed highly predictive models for *Staphylococcus aureus* (SA) and *Mycobacterium ranae* (MR) with non-validated $r^2$ of 0.987 and 0.998 respectively. The value $r^2$ is the correlation coefficient, and the best attainable value is 1.00, so the models with a $r^2$ value of 0.99 indicates an excellent correlation of the predictive value of the model. The SA and MR models performed well on internal validation tests, with leave-one-out correlation $q^2_{LOO}$ of 0.839 and 0.997 and leave-10%-out correlation $q^2_{L10O}$ of 0.875 and 0.537 respectively. As is well known, cross-validation is a standard statistical technique.

Internal validation (cross-validation) tests of the selected QSAR models were performed at two levels. Both of the models showed $q^2_{LOO} > 0.83$ for the leave-one-out (LOO) cross-validation tests. For the leave-10%-out or leave-three-out (L1OO) cross-validation tests, SA model showed $q^2_{L10O}$ of 0.875, whereas MR model showed $q^2_{L10O}$ values of 0.537. The propensity for this chance correlation is assessed by the randomization test where the dependent variables (bioactivity) are randomly reassigned to different compounds and a new regression model is recomputed, with the process being repeated several times. If the statistical data of these randomized models are comparable to the computed QSAR model, then the QSAR model is not predictive and the number of observations is insufficient. The inventors performed randomization tests of ninety-nine trials each at 99% confidence level for SA and MR QSAR models. None of the random r values were found to be larger than the non-random r values for either the SA or the MR models. The mean random r value for the SA model was 0.572 ($r^2$=0.327), and for the MR model was 0.617 ($r^2$=0.380). This indicates that the SA and MR QSAR models are not obtained by chance.

Therefore, this embodiment of the invention entails methods for predicting physicochemical and bioactivity properties (especially antimicrobial activity) of a peptide sequence (especially but not limited to peptides containing non-natural amino acids such as the AMPs described herein) against SA and/or MR.

The equation with four significant digits, for SA is as follows:

$$SA\ predicted\ activity=[(-1.4959\times \text{``Fcharge''})+\\(0.0098\times \text{``dipole-mag''})+(0.0140\times \text{``Jurs-SASA''})+\\(0.0023\times \text{``Jurs-PPSA-1''})+(0.1876\times \text{``Jurs-PNSA-1''})+(0.0022\times \text{``Jurs-PNSA-2''})+(0.00037\times \text{``Jurs-DPSA-2''})+(0.0015\times \text{``Jurs-DPSA-3''})+(438.251\times \text{``Jurs-FPSA-1''})+(267.258\times \text{``Jurs-FPSA-3''})+\\(120.432\times \text{``Jurs-FNSA-3''})-(715.316\times \text{``Jurs-RPCG''})-(12.8649\times \text{``Jurs-RPCS''})-(0.0658\times \text{``Jurs-TASA''})-(125.513\times \text{``Jurs-RPSA''})+\\(125.513\times \text{``Jurs-RASA''})-(183.99\times \text{``density''})+\\(1.0340\times \text{``Hbond\ acceptor''})+(0.0395\times \text{``Hbond\ donor''})-(0.3069\times \text{``Rotlbonds''})+(0.1148\times \text{``A\ log\ P''})-(0.10004\times \text{``RadOfGyration''})-225.589].$$

The equation with five significant digits (more preferred) for SA is as follows:

$$SA\ predicted\ activity=[(-1.49592\times \text{``Fcharge''})+\\(0.00981\times \text{``dipole-mag''})+(0.01399\times \text{``Jurs-SASA''})+(0.00233\times \text{``Jurs-PPSA-1''})+(0.18765\times \text{``Jurs-PNSA-1''})+(0.00217\times \text{``Jurs-PNSA-2''})+\\(0.00037\times \text{``Jurs-DPSA-2''})+(0.00150\times \text{``Jurs-DPSA-3''})+(438.251\times \text{``Jurs-FPSA-1''})+\\(267.258\times \text{``Jurs-FPSA-3''})+(120.432\times \text{``Jurs-FNSA-3''})-(715.316\times \text{``Jurs-RPCG''})-(12.8649\times \text{``Jurs-RPCS''})-(0.06575\times \text{``Jurs-TASA''})-\\(125.513\times \text{``Jurs-RPSA''})+(125.513\times \text{``Jurs-RASA''})-(183.99\times \text{``density''})+(1.03397\times \text{``Hbond\ acceptor''})+0.03947\times \text{``Hbond\ donor''})-\\(0.30686\times \text{``Rotlbonds''})+(0.11481\times \text{``A\ log\ P''})-\\(0.10004\times \text{``RadOfGyration''})-225.589].$$

The most preferred equation for SA is as follows:

$$SA\ predicted\ activity=[(-1.49592\times \text{``Fcharge''})+\\(0.0098147\times \text{``dipole-mag''})+(0.013993\times \text{``Jurs-SASA''})+(0.00233\times \text{``Jurs-PPSA-1''})+(0.187647\times \text{``Jurs-PNSA-1''})+(0.0021686\times \text{``Jurs-PNSA-2''})+\\(0.00036919\times \text{``Jurs-DPSA-2''})+(0.0015025\times \text{``Jurs-DPSA-3''})+(438.251\times \text{``Jurs-FPSA-1''})+\\(267.258\times \text{``Jurs-FPSA-3''})+(120.432\times \text{``Jurs-FNSA-3''})-(715.316\times \text{``Jurs-RPCG''})-12.8649\times \text{``Jurs-RPCS''})-(0.065752\times \text{``Jurs-TASA''})-\\(125.513\times \text{``Jurs-RPSA''})+(125.513\times \text{``Jurs-RASA''})-(183.99\times \text{``density''})+(1.03397\times \text{``Hbond\ acceptor''})+(0.039473\times \text{``Hbond\ donor''})-\\(0.306856\times \text{``Rotlbonds''})+(0.114808\times \text{``A\ log\ P''})-(0.10004\times \text{``RadOfGyration''})-225.589].$$

This embodiment of the invention covers the novel equation, as well as a synthetic peptide with bioactivity against SA satisfying the equation. Preferably, the synthetic peptide satisfies at least four terms of the equation. (A term is defined as the product of the QSAR coefficient (e.g. "438.251") and Descriptor (e.g., "Jurs-FPSA-1") shown in parenthesis e.g. (438.251×"Jurs-FPSA-1").) As another way to define the synthetic peptides of this invention, the synthetic peptide may have at least 4, more preferably at least 5, more preferably at least 6, more preferably at least 7, etc., up to 15, where it is most preferable to have at least 15 of the following physicochemical properties:

Jurs-FPSA-1, with a 29.347 [$Ang^2$] (area units Angstroms$^2$), density—16.010 is grams/cubic centimeters;
Jurs-TASA—14,762 [$Ang^2$];
Jurs-PNSA-1—10.540-[$Ang^2$];
Jurs-RASA—7,886-[$Ang^2$];
Jurs-SASA—4.120[$Ang^2$];
Jurs-DPSA-2—3.093-[$Ang^2$];
Jurs-PNSA-2—2.911[$Ang^2$];
Jurs-RPSA—2.492;
Rotlbonds—2.164;
Hbond acceptor—1.910;
Jurs-FPSA-3—1.709;
Fcharge—0.742;
Jurs-RPCG—0.726;
Jurs-PPSA-1—0.555;
Jurs-FNSA-3—0.426;
Dipole-mag—0.162;
RadOfGyration—0.127;
Jurs-RPCS—0.126;
Hbond donor—0.113;
Jurs-DPSA-3—0.053;
and A log P —0.026.

These numbers represent the respective percentages of each property, indicating the respective contribution toward overall bioactivity. Definitions of the descriptors are given in Table 2 and other portions below. We note that for some of the descriptors (e.g., density, Jurs-PNSA-2, Jurs-RPSA, Rotlbonds, Fcharge, Jurs-RPCG, Jurs-FNSA-3, RadOfGyration, Jurs-RPCS, and A log P) the corresponding percentage numbers may appear as a negative number, with a "−" sign preceding it. This is acceptable and understood in the art of QSAR modeling, and the descriptor may be defined either way.

Further details regarding how these properties were characterized and the data obtained are provided below.

Regarding MR, the equation with four significant digits for MR is as follows:

$$MR\ predicted\ activity=[(-0.0084\times \text{``conformer\ energy''})+(2.0576\times \text{``Fcharge''})+(0.00005\times \text{``Apol''})+(0.0061\times \text{``dipole-mag''})-(0.0239\times \text{``Jurs-PPSA-1''})-(0.0083\times \text{``Jurs-PNSA-1''})+(0.00005\times \text{``Jurs-PPSA-2''})+(0.00019\times \text{``Jurs-PNSA-2''})-\\(18.282\times \text{``Jurs-FPSA-1''})+(13.321*\text{``Jurs-FNSA-3''})-(8.4684\times \text{``Jurs-RPCG''})+(66.6262\times \text{``Jurs-RNCG''})+(0.0529\times \text{``Jurs-TPSA''})-(96.9761\times \text{``Jurs-RPSA''})+(96.9761\times \text{``Jurs-RASA''})-\\(127.577\times \text{``density''})+(0.7687\times \text{``Hbond\ acceptor''})-(0.4983\times \text{``Hbond\ donor''})-(0.0608\times \text{``Rotlbonds''})-(0.0758\times \text{``A\ log\ P''})+(0.3378\times \text{``RadOfGyration''})+110.841].$$

The equation with five significant digits (preferred) for MR is as follows:

$$MR\ predicted\ activity=[(-0.00836\times \text{``conformer\ energy''})+(2.05758\times \text{``Fcharge''})+(0.000053\times \text{``Apol''})+(0.00614\times \text{``dipole-mag''})-(0.02394\times \text{``Jurs-PPSA-1''})-(0.00825\times \text{``Jurs-PNSA-1''})+\\(0.000055\times \text{``Jurs-PPSA-2''})+(0.00019\times \text{``Jurs-PNSA-2''})-(18.282\times \text{``Jurs-FPSA-1''})+\\(13.321*\text{``Jurs-FNSA-3''})-(8.46841\times \text{``Jurs-RPCG''})+(66.6262\times \text{``Jurs-RNCG''})+(0.05289\times \text{``Jurs-TPSA''})-(96.9761\times \text{``Jurs-RPSA''})+\\(96.9761\times \text{``Jurs-RASA''})-(127.577\times \text{``density''})+(0.768698\times \text{``Hbond\ acceptor''})-(0.49828\times \text{``Hbond\ donor''})-(0.06076\times \text{``Rotlbonds''})-\\(0.07576\times \text{``A\ log\ P''})+(0.33784\times \text{``RadOfGyration''})+110.841].$$

The most preferred equation for MR is as follows:

$$MR\ predicted\ activity=[(-0.0083585\times \text{``conformer\ energy''})+(2.05758\times \text{``Fcharge''})+(5.3259e\text{-}05\times \text{``Apol''})+(0.0061422\times \text{``dipole-mag''})-(0.023941\times \text{``Jurs-PPSA-1''})-(0.008252\times \text{``Jurs-PNSA-1''})+\\(5.5381e\text{-}05\times \text{``Jurs-PPSA-2''})+(0.00018566\times \text{``Jurs-PNSA-2''})-(18.282\times \text{``Jurs-FPSA-1''})+\\(13.321*\text{``Jurs-FNSA-3''})-(8.46841\times \text{``Jurs-}$$

RPCG")+(66.6262×"Jurs-RNCG")+(0.052889×
"Jurs-TPSA")−(96.9761×"Jurs-RPSA")+
(96.9761×"Jurs-RASA")−(127.577×"density")+
(0.768698× "Hbond acceptor")−(0.498282×
"Hbond donor")−(0.060764×"Rotlbonds")−
(0.075759× "A log P")+(0.337835×
"RadOfGyration")+110.841].

This embodiment of the invention covers the novel equation, as well as a synthetic peptide with bioactivity against MR satisfying the equation. Preferably, the synthetic peptide satisfies at least four terms of the equation. (A term is defined as the product of the QSAR coefficient and Descriptor shown in parenthesis e.g. (438.251×"Jurs-FPSA-1").) As another way to define the synthetic peptides of this invention, the synthetic peptide may have at least 4, more preferably at least 5, more preferably at least 6, more preferably at least 7, etc., up to 15, where it is most preferable to have at least 15 of the following physicochemical properties:

Density—30.784;
Jurs-RASA—16.827;
Jurs-PPSA-1—15.494;
Jurs-TPSA—10.218;
Jurs-RPSA—5.444;
Hbond donor—3.905;
Hbond acceptor—3.729;
Jurs-FPSA-1—3.409;
Fcharge—2.892:
Jurs-PNSA-1—1.244;
RadOfGyration—1.164;
Rotlbonds—1.156;
Apol—1.148;
Jurs-PPSA-2—−1.016;
Jurs-PNSA-2—−0.632;
Jurs-RNCG—0.400;
Dipole-mag—0.298;
Jurs-FNSA-3—0.127;
A log P —0.051;
Conformer Energy—0.037;
Jurs-RPCG—−0.024; and
Jurs-DPSA-2—0.00.

These numbers represent the respective percentages of each property, indicating the respective contribution toward overall bioactivity. Definitions of the descriptors are given in Table 2 and other portions below. We note that for some of the descriptors (e.g., density, Jurs-PPSA-1, Jurs-RPSA, Jurs-FPSA-1, Jurs-PNSA-1, Rotlbonds, Jurs-PNSA-2, Jurs-FNSA-3, Jurs-RPCG, and Hbond donor) the corresponding percentage numbers may appear as a negative number, with a "−" sign preceding it. This is acceptable and understood in the art of QSAR modeling, and the descriptor may be defined either way.

Further details regarding how these properties were characterized and the data obtained are provided below.

In addition, this embodiment of the invention covers methods for predicting whether a peptide is bioactive against *Staphylococcus aureus* (SA) or *Mycobacterium* ranae, comprising the step of applying the respective mathematical equations described herein. These equations provide the blue print for designing potent antimicrobial peptides. Any peptide may be tested, but it is generally desirable to choose a peptide sequence which is thought to have the major 5 to 12 physicochemical properties. Then the conformational models of these peptides are computed, and then lastly is computed the physicochemical properties of those peptide conformations that fall within 0 to 10 Kcals of the peptide global minimum. Those peptides that have conformations which show potent predicted bioactivity are the ones that are most likely to be potent AMPs.

Put a different way, the invention encompasses methods for determining whether a synthetic peptide has an overall structure such that it is bioactive against either *Staphylococcus aureus* (SA) or *Mycobacterium ranae* (MR). The methods apply the respective mathematical equations described herein, and may employ any standard molecular modeling software. The basic steps in applying the equation are as follows:

i) Build the peptide sequence and minimize it using standard molecular mechanics. As an example of molecular mechanics, see http://en/wikipedia.org/wiki/Molecular_ mechanics.

ii) Compute the conformational model for the peptide using standard Monte Carlo or Molecular Dynamics conformational search algorithms (The conformational model is collection of energy minimized conformations within 20 Kcals/mol of the global minimum conformation. The global minimum conformation is the conformation with the least energy value of all the conformations.) As an example of Monte Carlo algorithm, see http://en/wikipedia.org/wiki/Monte_carlo_algorithm. A pool of comformers includes perhaps thousands of "unique" conformations, which is considered in the art to be an exhaustive conformational search.

iii) From all the conformations select the most "extended shaped" conformation (the extended shaped conformation would have the maximum measurement of its backbone when measured from head to tail) that is within 5 Kcals/mole energy range of the global minimum conformer.

iv) Align all conformers with the extended shaped selected conformer backbone as template structure.

v) Compute all the physicochemical (descriptor) properties for all the aligned conformers. These descriptor values are plugged into the equations of step iv) to calculate predicted bioactivity.

vi) Compute the predicted SA and/or MR bioactivity using the relevant QSAR equations, and the descriptor values calculated in step v).

By minimization, it is meant a well-known procedure using computer software by which the shape of the compound is incrementally changed and potential energy calculated. If the energy is lower than the previous shape then the new shape is accepted, and further incremental changes tried until such time that the potential energy is minimized to the extent possible. In computer simulations of compounds, the compound is represented as atoms and bonds, and then the compound has potential energy associates with it by virtue of motion of matter at any temperature above absolute zero. This potential energy value is what will differ between different shapes or conformations of the compound. For example, if a compound has two hydroxyl O—H moieties and if these are placed such that the two oxygen atoms are very close to each other, then there will be a repelling force between them which will effectively strain the compound—this will be manifested in the high potential energy of that conformer/shape of the compound.

Thus, in one embodiment it may be determined whether a synthetic peptide is bioactive (preferably at least showing activity of 100 microMolar or less) against *Staphylococcus aureus* (SA), using a method comprising the steps of:

i) determining the shape of a peptide that has minimum potential energy of the peptide;

ii) computing the conformational model for the peptide using standard Monte Carlo or molecular dynamics conformational search algorithms, so as to generate a pool of peptide conformations that are within 20Kcals/mol energy range of the global minimum conformation;

iii) selecting from the peptide conformations of step ii) the conformation having the maximum measurement of its backbone when measured from head to tail, which conformation is within five Kcals/mole energy range of the global minimum conformer;

iv) aligning all conformations of step ii) with the selected conformation of step iii), wherein the selected conformation is used as a template structure;

v) determining the physicochemical properties for all the aligned conformations, wherein the physicochemical properties determined are conformer energy, Fcharge, dipole-mag, Jurs-SASA, Jurs-PPSA-1, Jurs-PNSA-1, Jurs-PNSA-2, Jurs-DPSA-2, Jurs-DPSA-3, Jurs-FPSA-1, Jurs-FPSA-3, Jurs-FNSA-3, Jurs-RPCG, Jurs-RPCS, Jurs-TASA, Jurs-RPSA, Jurs-RASA, density, Hbond acceptor, Hbond donor, Rotlbonds, A log P , and RadOfGyration; and vi) applying a mathematical equation to each aligned conformation peptide, to determine whether the synthetic peptide is bioactive against *Mycobacterium ranae* (MR), which mathematical equation is:

SA bioactivity equals satisfaction of at least four of the following terms: [(−1.49592×"Fcharge")+(0.0098147×"dipole-mag")+(0.013993×"Jurs-SASA")+(0.00233×"Jurs-PPSA-1")+(0.187647×"Jurs-PNSA-1")+(0.0021686×"Jurs-PNSA-2")+(0.00036919×"Jurs-DPSA-2")+(0.0015025×"Jurs-DPSA-3")+(438.251×"Jurs-FPSA-1")+(267.258×"Jurs-FPSA-3")+(120.432×"Jurs-FNSA-3")−(715.316×"Jurs-RPCG")−12.8649×"Jurs-RPCS")−(0.065752×"Jurs-TASA")−(125.513×"Jurs-RPSA")+(125.513×"Jurs-RASA")−(183.99×"density")+(1.03397× "Hbond acceptor")+(0.039473× "Hbond donor")−(0.306856×"Rotlbonds")+(0.114808× "A log P")−(0.10004×"RadOfGyration")−225.589.

Similarly, to determine whether a synthetic peptide is bioactive (preferably at least showing activity of 100 microMolar or less) against *Mycobacterium ranae* (MR), a method may comprise the steps of:

i) determining the shape of a peptide that has minimum potential energy of the peptide;

ii) computing the conformational model for the peptide using standard Monte Carlo or molecular dynamics conformational search algorithms, so as to generate a pool of peptide conformations that are within 20Kcals/mol energy range of the global minimum conformation;

iii) selecting from the peptide conformations of step ii) the conformation having the maximum measurement of its backbone when measured from head to tail, which conformation is within five Kcals/mole energy range of the global minimum conformer;

iv) aligning all conformations of step ii) with the selected conformation of step iii), wherein the selected conformation is used as a template structure;

v) determining the physicochemical properties for all the aligned conformations, wherein the physicochemical properties determined are conformer energy, Fcharge, Apol, dipole-mag, Jurs-PPSA-1, Jurs-PNSA-1, Jurs-PPSA-2, Jurs-PNSA-2, Jurs-FPSA-1, Jurs-FNSA-3, Jurs-RPCG, Jurs-RNCG, Jurs-TPSA, Jurs-RPSA, Jurs-RASA, density, Hbond acceptor, Hbond donor, Rotlbonds, A log P , and RadOfGyration; and vi) applying a mathematical equation to each aligned conformation peptide, to determine whether the synthetic peptide is bioactive against *Mycobacterium ranae* (MR), which mathematical equation is: MR bioactivity equals satisfaction of at least four of the following terms:

[(−0.0083585×"conformer energy")+(2.05758×"Fcharge")+(5.3259e-05× "Apol")+(0.0061422×"dipole-mag")−(0.023941×"Jurs-PPSA-1")−(0.008252×"Jurs-PNSA-1")+(5.5381e-05×"Jurs-PPSA-2")+(0.00018566×"Jurs-PNSA-2")−(18.282×"Jurs-FPSA-1")+(13.321*"Jurs-FNSA-3")−(8.46841×"Jurs-RPCG")+(66.6262×"Jurs-RNCG")+(0.052889×"Jurs-TPSA")−(96.9761×"Jurs-RPSA")+(96.9761×"Jurs-RASA")−(127.577×"density").+(0.768698× "Hbond acceptor")−(0.498282× "Hbond donor")−(0.060764×"Rotlbonds")−(0.075759× "A log P")+(0.337835×"RadOfGyration")+110.841].

Further details regarding how these equations are applied and bioactivity determined, and the data obtained, are provided below.

TABLE 2

List of trial descriptors used for the QSAR model.

| Descriptor Symbol | Descriptor definition |
|---|---|
| LogP | n-Octanol/water partition coefficient |
| Fh2o | The desolvation free energy for water |
| Foct | The desolvation free energy for n-octanol |
| AlogP98 | The partition coefficient computed on atom types reported by Ghose et al[35] |
| AlogP | The partition coefficient computed on atom types reported by Ghose et al[34] |
| MR | The molar refractivity is computed based on refractive index molecular weight (MW) |
| MolRef | The molar refractivity is computed based on the atom-types with additive contributions reported by Ghose et al[34,35] |
| The thirty Jurs descriptors based on partial charges mapped on surface area were reported by Stanton et al[36] | |
| Jurs-SASA | The total molecular solvent accessible surface. |
| Jurs-PPSA-1 | The sum of the solvent-accessible surface area of all partially positively charged atoms. |
| Jurs-PNSA-1 | The sum of the solvent-accessible surface area of all partially negatively charged atoms. |
| Jurs-DPSA-1 | The differential positively charged surface area is the difference between Jurs-PPSA-1 and Jurs-PNSA-1. |

TABLE 2-continued

List of trial descriptors used for the QSAR model.

| Descriptor Symbol | Descriptor definition |
| --- | --- |
| Jurs-PPSA-2 | The partial positive solvent-accessible surface area times the total positive charge. |
| Jurs-PNSA-2 | The partial negative solvent-accessible surface area times the total negative charge. |
| Jurs-DPSA-2 | The differential positively charged surface area is the difference between Jurs-PPSA-2 and Jurs-PNSA-2. |
| Jurs-PPSA-3 | The sum of the products of solvent accessible surface area and partial charge for all positively charged atoms. |
| Jurs-PNSA-3 | The sum of the products of solvent accessible surface areas and partial charge for all negatively charged atoms. |
| Jurs-DPSA-3 | The differential positively charged surface area is the difference between Jurs-PPSA-3 and Jurs-PNSA-3. |
| Jurs-FPSA-1 | The fractionally charged surface area is obtained by dividing Jurs-PPSA-1 by total molecular solvent-accessible surface area (Jurs-SASA). |
| Jurs-FNSA-1 | The fractionally charged surface area is obtained by dividing Jurs-PNSA-1 by total molecular solvent-accessible surface area (Jurs-SASA). |
| Jurs-FPSA-2 | The fractionally charged surface area is obtained by dividing Jurs-PPSA-2 by total molecular solvent-accessible surface area (Jurs-SASA). |
| Jurs-FNSA-2 | The fractionally charged surface area is obtained by dividing Jurs-PNSA-2 by total molecular solvent-accessible surface area (Jurs-SASA). |
| Jurs-FPSA-3, | The fractionally charged surface area is obtained by dividing Jurs-PPSA-3 by total molecular solvent-accessible surface area (Jurs-SASA). |
| Jurs-FNSA-3 | The fractionally charged surface area is obtained by dividing Jurs-PNSA-3 by total molecular solvent-accessible surface area (Jurs-SASA). |
| Jurs-WPSA-1 | The surface-weighted charged partial surface area is obtained by multiplying the descriptor Jurs-PPSA-1 by SASA and dividing by 1000. |
| Jurs-WNSA-1 | The surface-weighted charged partial surface area is obtained by multiplying the descriptor Jurs-PNSA-1 by SASA and dividing by 1000. |
| Jurs-WPSA-2 | The surface-weighted charged partial surface area is obtained by multiplying the descriptor Jurs-PPSA-2 by SASA and dividing by 1000. |
| Jurs-WNSA-2 | The surface-weighted charged partial surface area is obtained by multiplying the descriptor Jurs-PNSA-2 by SASA and dividing by 1000. |
| Jurs-WPSA-3 | The surface-weighted charged partial surface area is obtained by multiplying the descriptor Jurs-PPSA-3 by SASA and dividing by 1000. |
| Jurs-WNSA-3 | The surface-weighted charged partial surface area is obtained by multiplying the descriptor Jurs-PNSA-3 by SASA and dividing by 1000. |
| Jurs-RPCG | The relative positive charge is computed by dividing the charge of the most positive atom by the total positive charge. |
| Jurs-RNCG | The relative negative charge computed by dividing the charge of the most negative atom by the total negative charge. |
| Jurs-RPCS | The relative positive charge surface area is computed as the solvent-accessible surface area of the most positive atom divided by RPCG. |
| Jurs-RNCS | The relative negative charge surface area is obtained by dividing the solvent-accessible surface area of the most negative atom divided by RNCG. |
| Jurs-TASA | The total hydrophobic surface area is computed as the sum of the solvent-accessible surface area of atoms with absolute partial charge less than 0.2. |
| Jurs-TPSA | The total polar surface area is the sum of the solvent-accessible surface areas of atom with absolute partial charges greater than or equal 0.2. |
| Jurs-RASA | The relative hydrophobic surface area, is computed by dividing TASA by SASA. |
| Jurs-RPSA | The relative polar surface area is obtained by dividing TPSA by SASA. |
| Density | Density is defined as the ratio of molecular weight to molecular volume |
| Vm | Molecular volume |
| PMI-Mag | The magnitude of the principal moments of inertia about the principal axes of the conformers as described by Hill[37] |
| Dipole-Mag | The magnitude of the molecular dipole moment. |
| Energy | 'Energy' gives the conformational energy |
| Fcharge | The formal charge |

TABLE 2-continued

List of trial descriptors used for the QSAR model.

| Descriptor Symbol | Descriptor definition |
| --- | --- |
| H-bond Acceptor | Number of hydrogen bond acceptors |
| H-bond Donor | Number of hydrogen bond donors |
| Rotlbonds | Number of rotatatable bonds |
| ChiralCenters | Number of chiral centers |
| RadOfGyration | The radius of gyration38 |
| Area | The van der waals surface area |
| Apol | Sum of atomic polarizabilities 39 |

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4. The electrostatic surface potential map for the much less active analog FKAB-1Gf (activity against *Salmonella typhimurium*-100 μM, *Staphylococcus aureus* ME/GM/TC resistant-IN ACTIVE, *Mycobacterium ranae*-100 μM) shows the four sides or faces of FKAB-1Gf, clearly there is an even distribution of charge over the entire surface of the molecule. FIG. 4A shows the east face, FIG. 4B shows the north face, FIG. 4C shows the west face, and FIG. 4D shows the south face. The molecule is therefore not amphipathic. Blue color indicates a positive charge, Red indicates a negative charge and white indicates a neutral electric charge.

FIG. 5. The effect of incorporation of the negatively charged penta-peptide (Glu-Leu-Met-Asn-Ser (SEQ ID NO:3)) found at the C-terminus of the magainins at both the C and N terminus is shown by the electrostatic potential map of the completely inactive analog FKAB-4 is shown. FIG. 4A shows the east face, FIG. 4B shows the north face, FIG. 4C shows the west face, and FIG. 4D shows the south face. This Figure indicates that the in active analogs is neither highly charged or amphipathic. Blue color indicates a positive charge, Red indicates a negative charge and white indicates a neutral electric charge.

FIG. 17 shows calculated "bio-active conformers" for the analogs with the deletion of either the Tic or Oic residue indicate that these analogs are extended and do not include a helical or β-turn structure. The Tic-Oic dipeptide turn inducing unit is shown in green. The cationic residues are shown in dark blue. Hydrophobic residues are shown in red. Spacers A and B are shown in light blue.

FIG. 18 shows the calculated "bio-active" conformers of the analogs containing various length amino acid spacers in position A and B indicate that these compounds adopt a helical or β-turn conformation. The Tic-Oic dipeptide turn inducing unit is shown in green. The cationic residues are shown in dark blue. Hydrophobic residues are shown in red. Spacers A and B are shown in light blue.

FIG. 19B shows a view looking toward the highly charged polar face, while

DETAILED DESCRIPTION OF THE PREFERRED EMBODIMENTS

Antimicrobial Peptides

Figure 1A:
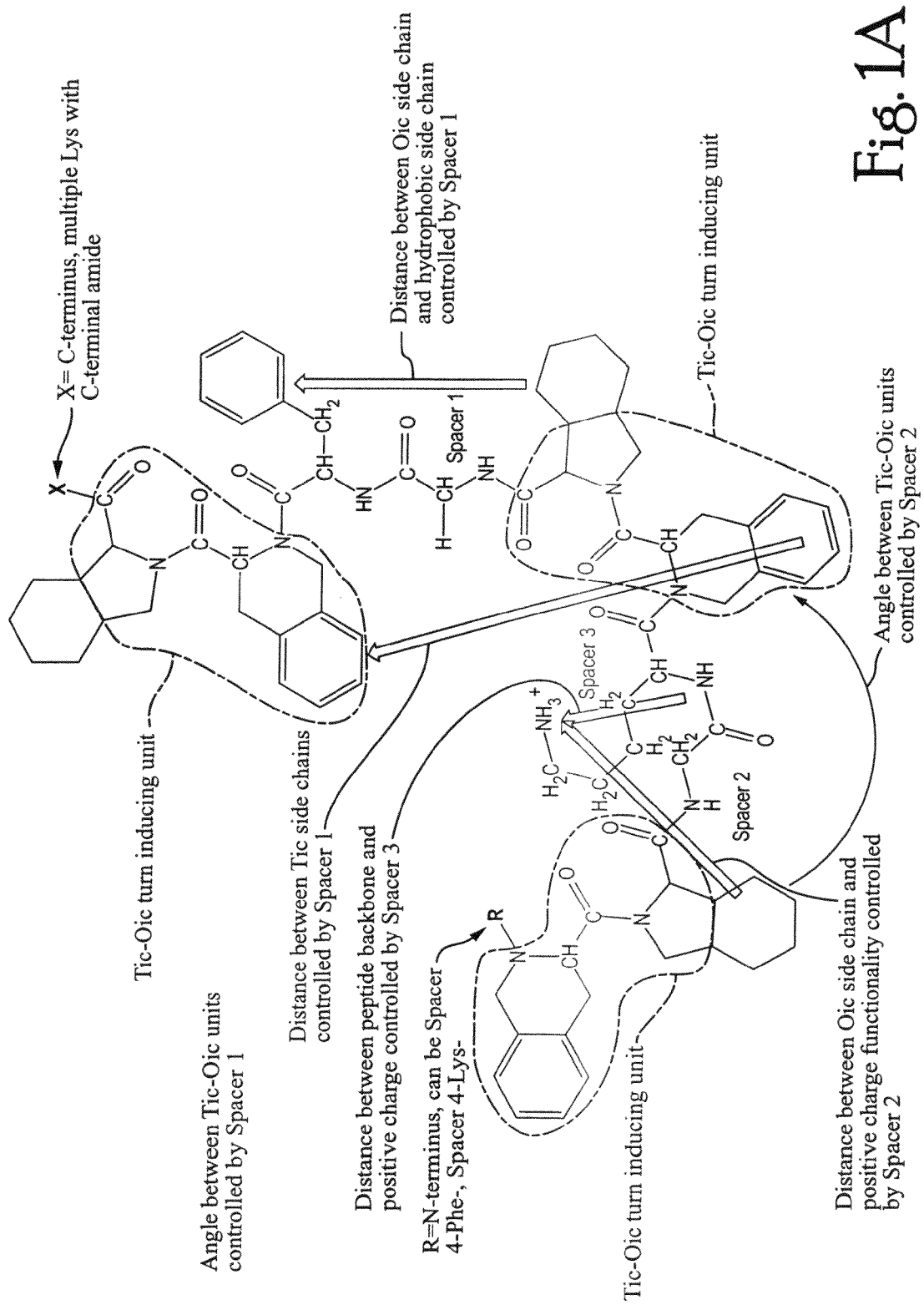
FIGS. 1A and 1B. A diagrammatic representation of the basic skeleton units of AMPs developed in the laboratory. By varying the length of spacer 1 the distance between the turn-inducing Tic-Oic dipeptide unit (enclosed in the dotted line in the figures) and the positive charge as well as the distance and angle (conformational flexibility) between the two turn-inducing units are changed. Varying the length of spacer 2, (spacer 1 and spacer 2 may or may not be the same) the distance between the turn-inducing unit and the hydrophobic residue as well as the distance and angle between the two turn-inducing units are changed. These modifications affect all of the physicochemical properties as well as overall conformational flexibility.

To develop effective synthetic AMPs, the inventors selected analogs of the magainin family of host defense peptides because these peptides are active against Gram positive and negative bacteria, fungi and protozoa while exhibiting little mammalian cell toxicity.[24] The interactions of the magainins[25, 26] with membrane models have been extensively investigated resulting in the characterization of the magainins as well defined α-helical amphipathic cell-selective membrane-disruptors.[16, 18, 19]

The inventors previously reported two-dimensional NMR and molecular modeling.[27] Investigations conducted in their laboratory indicated that (Ala $^{8,13,18}$)magainin-2-amide bound to dodecylphosphocholine (DPC) micelles adopts a α-helical structure involving residues 2 to 16 with the four C-terminal residues converging to a loose β-turn like structure. While (Ala$^{8,13,18}$)magainin-2-amide bound to sodium dodecylsulfate (SDS) micelles adopts a α-helical structure involving residues 7 to 18 with the C- and N-terminal residues exhibiting a great deal of conformational flexibility. The observation of an AMP adopting slightly different conformations on binding to SDS and DPC micelles was also reported by Hancock and co-workers[28] for the antimicrobial peptide indolicidin. The most plausible explanation for this observation is that different non-covalent (electrostatic and hydrophobic) interactions are occurring between the peptide's surface and the two micelle surfaces.

Based on previous research into peptide-micelle interactions, the inventors concluded electrostatic interactions are responsible for peptide-micelle binding while hydrophobic interactions are responsible for inducing a stable secondary structure onto the peptide.[29, 30] The inventors observed that the relative position in three-dimensional space of each of the multiple positive charges on the peptide to the hydrophobic residues controls the allowable conformational changes.[30] Therefore electrostatic interactions between the polar head groups of the micelle and the cationic side chains of the peptides define the positions along the peptide backbone where the helical structures begin and end.

Electrostatic surface potential maps for each conformation were calculated and indicated that the surface electron density of these peptides are highly conformational dependent. This observation lead to the hypothesis that the three-dimensional physicochemical surface properties of the membrane of a bacterial cell interacts with the three-dimensional physicochemical properties of the AMP as it approaches the surface of the cell. This interaction induces a conformational change onto the polypeptide backbone of the AMP in order to maximize attractive interactions and to minimize repulsive interactions between the two moieties. The results of the inventors' investigation indicate that hydrophobic interactions are the major contributors in stabilizing the induced helical structure of the micelle-bound peptides.

The inventors chose (Ala $^{8, 13, 18}$)magainin-2-amide to design a novel class of AMPs since it had different physicochemical surface properties of the SDS and DPC micelle-bound conformations. These synthetic AMP analogs contain both natural and un-natural amino acids that induce a semi-rigid conformation to the peptide backbone thus controlling the three-dimensional physiochemical properties of the peptide. In particular, the two un-natural amino acids Tic (tetrahydroisoquinolinecarboxylic acid) and Oic (octahydroindolecarboxylic acid) are used to induce an amphipathic structure.

It is noted that Kyle et al. reported using NMR and molecular modeling methods that the dipeptide Tic-Oic when placed in positions i+1 and i+2 of a four amino acid sequence induced a β-turn.[31] The work of Kyle et al. was limited to using a single Tic-Oic dipeptide to induce a β-turn conformation exclusively at the C-terminus of bradykinin antagonists which are naturally occurring peptides—quite distinct from the un-natural AMPs described here which are custom tailored synthetic peptides. The logic used by Kyle and co-workers was to force the C-terminus to adopt a conformation favored by the bradykinin $B_1$ receptor. Their work did not involve the use of multiple Tic-Oic dipeptides, spacers or the other well defined and ordered disposition of other key components to interact with cell membranes to induce specific 3D physicochemical parameters onto the polypeptide backbone. Further, as is well known, bradykinin does not exhibit antibacterial activity.

However, the inventors discovered that placement of multiple Tic-Oic units connected via two amino acid spacers with defined properties of charge and hydrophobicity will result in peptides with well defined physiochemical properties and these peptides will still have sufficient conformational flexibility to allow interactions with membranes with different physicochemical properties to induce a "new" stable conformation onto the AMP on binding to the membrane. As noted above, a "spacer" amino acid should not be electronically charged (cationic or anionic) nor should it be highly hydrophobic. Spacers 1 and 2 should exhibit hydrophobicity between 1.2 and −0.75 on the octanol scale reported by Professor Stephen White at the University of California Irvine.[19] The role of "spacer 1 and 2" is to provide conformational flexibility for the polypeptide backbone. The cationic amino acid residues should exhibit hydrophobicity between 1.5 and 3.0 on the octanol scale. The hydrophobic amino acid residues should exhibit hydrophobicity between −1.0 and −3.0 on the octanol scale.

Figure 1B:
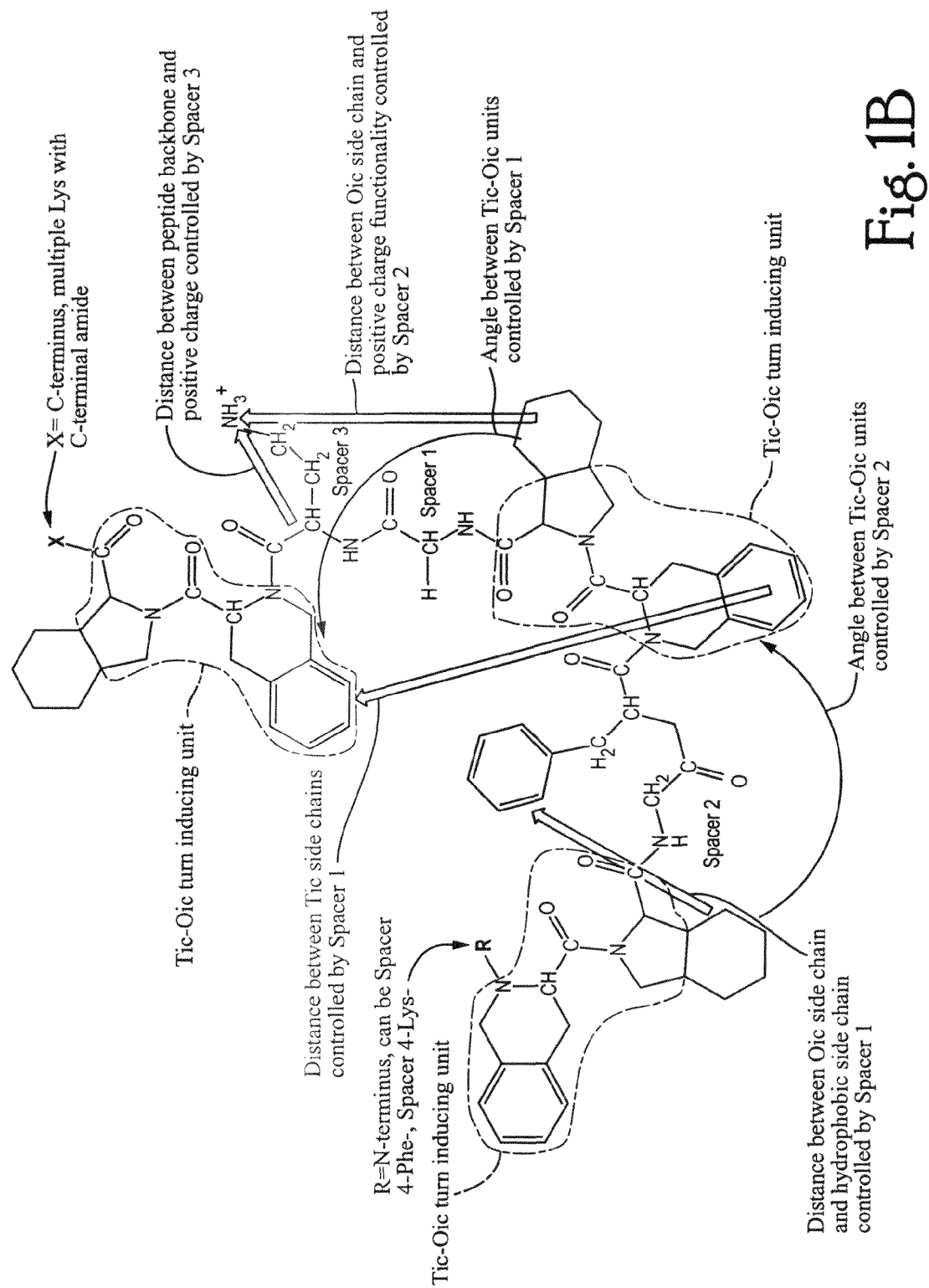
Figure 2A:
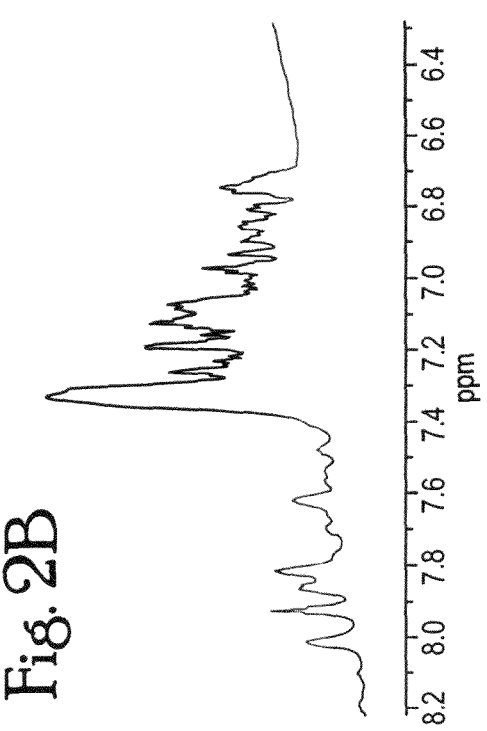
FIG. 2. The amide and aromatic region of the 600 MHz $^1$H spectra of two peptides bound to SDS and DPC micelles. Spectrum A is the anti-bacterial peptide FKAB-1G bound to DPC micelles and spectrum B is the same peptide bound to SDS micelles. Spectrum C is the inactive peptide FKAB-4B bound to DPC micelles and spectrum D is the same peptide bound to SDS micelles. Micelle concentrations 100 mM in 150 mM sodium acetate buffer, pH=4.05.
Figure 2C:
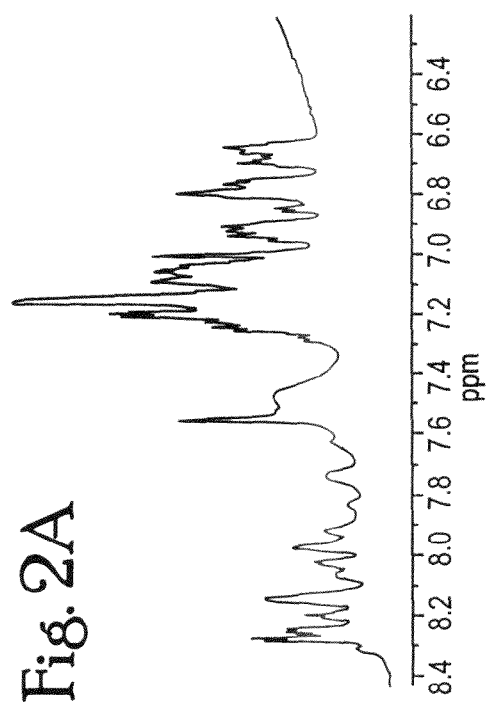
Figure 2B:
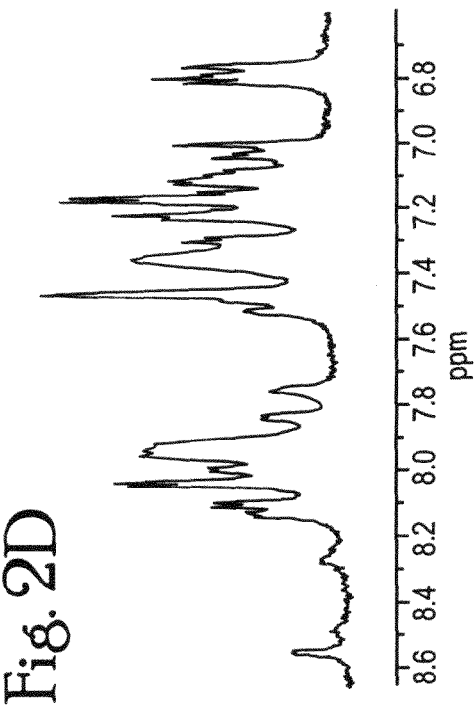
Figure 2D:
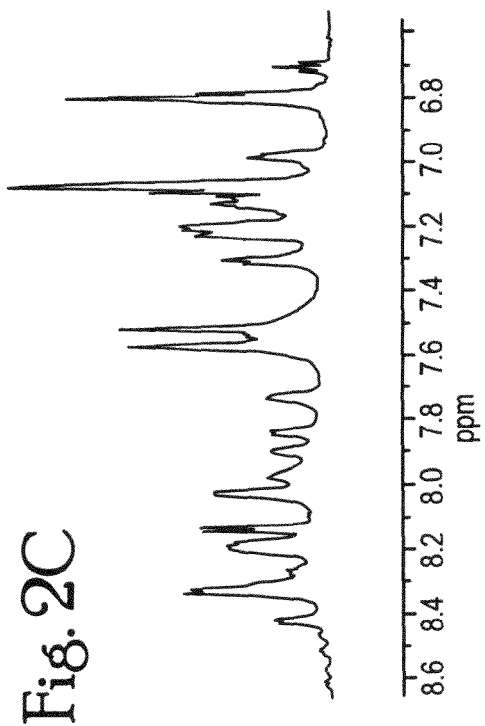

The basic polypeptide skeleton of the new AMPs is given in FIG. 1. This skeleton (FIG. 1A) begins with a turn-inducing Tic-Oic unit coupled to a spacer amino acid followed by an amino acid with a cationic side chain. This is followed with another Tic-Oic unit coupled to a spacer followed by a hydrophobic amino acid residue. Or this skeleton (FIG. 1B) begins with a turn-inducing Tic-Oic unit coupled to a spacer amino acid followed by a hydrophobic amino acid. This is followed with another Tic-Oic unit coupled to a spacer followed by an amino acid residue with a cationic side chain.

FIGS. 1A and 1B also illustrate the inter-relationship between the basic units and the interdependence of distances and angles. This basic unit is repeated to obtain the desired peptide length.[32]

To confirm that these AMPs have sufficient structural flexibility to undergo significant conformational changes on interacting with membranes, their interactions with SDS and DPC micelles was observed by NMR.[32] The effect of binding to DPC and SDS micelles is illustrated in FIG. 2, which shows the amide and aromatic region of the 600 MHz $^1$H spectra of two peptides bound to SDS and DPC micelles. Spectrum A is the anti-bacterial peptide designated as FKAB-1G bound to DPC micelles and spectrum B is the same peptide bound to SDS micelles. Clearly these two spectra are very different and the most likely explanation for this observation is that the peptides exist in two different conformations. The broadening in the resonances of the FKAB-1G bound to SDS micelles, particularly the aromatic resonances indicates restricted motion of the phenyl rings which is consistent with a "tighter" binding to the micelle. At the bottom of FIG. 2 are the spectra of the inactive analog FKAB-4B bound to DPC (spectrum C) and SDS (spectrum D) micelles. Again these spectra are different, indicating that the peptide exists in two different conformations. However the line-widths of both spectra are narrower than those observed for FKAB-1G indicating that even though FKAB-4B binds to both micelles it has a greater degree of molecular flexibility.

A number of new AMPs have been synthesized within the general formulae given above, and the amino acid sequences of some of them are listed in Table 3.

TABLE 3

Amino acid sequences for novel antimicrobial peptides synthesized

| Peptide ID | Peptide # (SEQ ID NO) | Amino acid sequence |
|---|---|---|
| WRFK-1 | 1 (4) | NH$_2$-GKGL-Tic-Oic-GK-Tic-Oic-GF-Tic-Oic-GK-Tic-Oic-GF-Tic-Oic-GK-Tic-Oic-GKR—CONH$_2$ |
| WRFK-2 | 2 (5) | NH$_2$-GKGL-Tic-Oic-GR-Tic-Oic-GF-Tic-Oic-GR-Tic-Oic-GF-Tic-Oic-GR-Tic-Oic-GKR—CONH$_2$ |
| WRFK-3 | 3 (6) | NH$_2$-GKGL-Tic-Oic-GL-Tic-Oic-GK-Tic-Oic-GL-Tic-Oic-GK-Tic-Oic-GL-Tic-Oic-GLR—CONH$_2$ |
| WRFK-4 | 4 (7) | NH$_2$-GKGL-Tic-Oic-GK-Tic-Oic-GL-Tic-Oic-GK-Tic-Oic-GL-Tic-Oic-GK-Tic-Oic-GKR—CONH$_2$ |
| WRFK-5 | 5 (8) | NH$_2$-GKGL-Tic-Oic-FK-Tic-Oic-KF-Tic-Oic-FK-Tic-Oic-KF-Tic-Oic-FK-Tic-Oic-FKR—CONH$_2$ |
| FKAB-1F | 24 (9) | NH$_2$—KL-Tic-Oic-K-Tic-Oic-F-Tic-Oic-K-Tic-Oic-F-Tic-Oic-K-Tic-Oic-KR—CONH$_2$ |
| FKAB-1G | 25 (10) | Ac-GF-Tic-Oic-GK-Tic-Oic-GF-Tic-Oic-GK-Tic-KKKK—CONH$_2$ |
| FKAB-1H | 26 (11) | Ac-GF-Tic-Oic-GK-Tic-Oic-GF-Tic-Oic-GK-Tic-KKKK—CONH—CH$_2$—CH$_2$—NH$_2$ |
| FKAB-1L | 27 (12) | Ac-GF-Tic-Oic-GK-Tic-Oic-GF-Tic-Oic-GK-Tic-KKKK—CONH—CH$_2$—CH$_2$—CH$_2$—NH$_2$ |
| FKAB-1Ga | 28 (13) | NH$_2$--GF-Tic-Oic-GK-Tic-Oic-GF-Tic-Oic-GK-Tic-KKKK—CONH$_2$ |
| FKAB-1Gb | 29 (14) | NH$_2$—KL-Tic-Oic-GK-Tic-Oic-GF-Tic-Oic-GK-Tic-KKKK—CONH$_2$ |
| FKAB-1Gc | 30 (15) | Ac—F-Tic-Oic-K-Tic-Oic-F-Tic-Oic-K-Tic-KKKK—CONH$_2$ |
| FKAB-1Gd | 31 (16) | Ac-Gaba-F-Tic-Oic-Gaba-K-Tic-Oic-Gaba-F-Tic-Oic-Gaba-K-Tic-KKKK—CONH$_2$ |
| FKAB-1Ge | 32 (17) | Ac-G-Tic-Oic-K-Tic-Oic-G-Tic-Oic-K-Tic-KKKK—CONH$_2$ |
| FKAB-1Gf | 33 (18) | Ac-GF-Oic-GK-Oic-GF-Oic-GKKKKK—CONH$_2$ |
| FKAB-1Gg | 34 (19) | Ac-GF-Tic-GK-Tic-GF-Tic-GK-Tic-KKKK—CONH$_2$ |
| FKAB-1Gg1 | 35 (20) | Ac-GF-Tic-G-GK-Tic-G-GF-Tic-G-GK-Tic-KKKK—CONH$_2$ |
| FKAB-1Gf1 | 36 (21) | Ac-GF-G-Oic-GK-G-Oic-GF-G-Oic-GK-G-KKKK—CONH$_2$ |
| FKAB-1Gh | 37 (22) | Ac-GF-F-Oic-GK-F-Oic-GF-F-Oic-GK-F-KKKK—CONH$_2$ |
| FKAB-1Gd1 | 38 (23) | Ac-βAla-F-Tic-Oic-βAla-K-Tic-Oic-βAla-F-Tic-Oic-βAla-K-Tic-KKKK—CONH$_2$ |
| FKAB-1Gd2 | 39 (24) | Ac-Ahx-F-Tic-Oic-Ahx-K-Tic-Oic-Ahx-F-Tic-Oic-Ahx-K-Tic-KKKK—CONH$_2$ |
| FKAB-1Gc1 | 40 (25) | Ac-F-Tic-Oic-K-Tic-Oic-F-Tic-Oic-K-Tic-KKKKKK—CONH$_2$ |
| FKAB-1Gi | 41 (26) | Ac-GF-Tic-Oic-GK-Tic-Oic-GF-Tic-Oic-GK-Tic-KKKKK—CONH$_2$ |
| FKAB-1Gd3 | 42 (27) | Ac-Gaba-F-Tic-Oic-Gaba-K-Tic-Oic-Gaba-F-Tic-Oic-Gaba-K-Tic-KKKKK—CONH$_2$ |
| FKAB-1Gj | 43 (28) | Ac-GF-Tic-Oic-GK-Tic-Oic-GF-Tic-Oic-GK-Tic-Orn-Orn-Orn-Orn-CONH$_2$ |
| FKAB-1Go | 44 (29) | Ac-G-Fpa-Tic-Oic-GK-Tic-Oic-G-Fpa-Tic-Oic-GK-Tic-KKKK—CONH$_2$ |
| FKAB-1Gp | 45 (30) | Ac-GF-Tic-Oic-G-Orn-Tic-Oic-GF-Tic-Oic-G-Orn-Tic-Orn-Orn-Orn-Orn-CONH$_2$ |
| FKAB-1Gl | 46 (31) | Biotin-GF-Tic-Oic-GK-Tic-Oic-GF-Tic-Oic-GK-Tic-KKKK—CONH$_2$ |
| FKAB-1Gs | 47 (32) | Ac-GF-Tic-Oic-G-Dpr-Tic-Oic-GF-Tic-Oic-G-Dpr-Tic-Dpr-DprDpr-Dpr-CONH$_2$ |
| FBAB-1Gw | 48 (33) | Ac-βAla-Fpa-Tic-Oic-βAla-Dpr-Tic-Oic-βAla-Fpa-Tic-Oic-βAla-Dpr-Tic-Dpr-Dpr-Dpr-Dpr-CONH$_2$ |
| FKAB-1G2 | 49 | Ac-G-dF-Tic-Oic-GK-Tic-Oic-G dF-Tic-Oic-GK-Tic-KKKK—CONH$_2$ |

TABLE 3-continued

Amino acid sequences for novel antimicrobial peptides synthesized

| Peptide ID | Peptide # (SEQ ID NO) | Amino acid sequence |
|---|---|---|
| FKAB-1G3 | 50 | Ac-GF-Tic-Oic-G-dK-Tic-Oic-GF-Tic-Oic-G-dK-Tic-KKKK—CONH$_2$ |
| FKAB-1Go2 | 51 (34) | Ac-G-Nph-Tic-Oic-GK-Tic-Oic-G-Nph-Tic-Oic-GK-Tic-KKKK—CONH$_2$ |
| FKAB-1G-βAla | 52 (35) | Ac-GF-Tic-Oic-GK-Tic-Oic-GF-Tic-Oic-GK-Tic-βAla-KKKK-CONH$_2$ |
| FKAB-1G-Gaba | 53 (36) | Ac-GF-Tic-Oic-GK-Tic-Oic-GF-Tic-Oic-GK-Tic-Gaba-KKKK—CONH$_2$ |
| FKAB-1G-Ahx | 54 (37) | Ac-GF-Tic-Oic-GK-Tic-Oic-GF-Tic-Oic-GK-Tic-Ahx-KKKK—CONH$_2$ |
| FKAB-1Gz | 55 (38) | Ac-GF-Tic-Oic-G-Dab-Tic-Oic-GF-Tic-Oic-G-Dab-Tic-Dab-Dab-Dab-Dab-CONH$_2$ |
| FKAB-1G-Thi | 56 (39) | Thi-GF-Tic-Oic-GK-Tic-Oic-GF-Tic-Oic-GK-Tic-KKKK—CONH$_2$ |
| FKAB-1G-Trp | 57 (40) | Ac-GF-Tic-Oic-GW-Tic-Oic-GF-Tic-Oic-GW-Tic-KKKK—CONH$_2$ |
| FKAB-1Gx-R2 | 58 (41) | Ac-GF-Tic-Oic-GR-Tic-Oic-GF-Tic-Oic-GR-Tic-RRRR—CONH$_2$ |
| FKAB-1Gg2 | 59 (42) | Ac-GF-Tic-Tic-GK-Tic-Tic-GF-Tic-Tic-GK-Tic-KKKK—CONH$_2$ |
| FKAB-1Go1 | 60 (43) | Ac-G-Cph-Tic-Oic-GK-Tic-Oic-G-Cph-Tic-Oic-GK-Tic-KKKK—CONH$_2$ |
| FKABB-1G1 | 61 (44) | Ac-GF-Oic-Tic-GK-Oic-Tic-GF-Oic-Tic-GK-Tic-KKKK—CONH$_2$ |
| FKAB-1Gv | 62 (45) | Ac-βAla-Fpa-Tic-Oic-βAla-K-Tic-Oic-βAla-Fpa-Tic-Oic-βAla-K-Tic-Dpr-Dpr-Dpr-Dpr-CONH$_2$ |
| FBAB-1Gq | 63 (1) | Ac—KKKK-GF-Tic-Oic-GK-Tic-Oic-GF-Tic-Oic-GK-Tic-CONH$_2$ |

Additional amino acid sequences, exemplary of the general formulae, for novel AMPs include the following:

(SEQ ID NO: 46)
Ac-GF-Tic-Oic-GK-Tic-Oic-GF-Tic-Oic-GK-Tic-Dpr-Dpr-Dpr-Dpr-CONH$_2$ (SEQ ID NO: 47)
(NH$_2$)$_4$—(K)$_2$-K-Tic-Oic-GK-Tic-Oic-GF-Tic-Oic-GK-Tic-Oic-GF-Tic-Oic-GK-Tic-CONH$_2$ (SEQ ID NO: 48)
Ac-G-Fpa-Tic-Oic-G-Dpr-Tic-Oic-G-Fpa-Tic-Oic-G-Dpr-Tic-Dpr-Dpr-Dpr-Dpr-CONH$_2$ (SEQ ID NO: 49)
Ac-GF-Tic-Oic-G-Tic-Oic-GF-Tic-Oic-G-Tic-G-KKKK—CONH$_2$ (SEQ ID NO: 50)
Ac-GF-Tic-Oic-GK-Tic-Oic-GF-Tic-Oic-GK-Tic-Dab-Dab-Dab-Dab-CONH$_2$ (SEQ ID NO: 51)
(NH$_2$)$_4$-(Orn)$_2$-Orn-Tic-Oic-G-Orn-Tic-Oic-GF-Tic-Oic-G-Orn-Tic-Oic-GF-Tic-Oic-G-Orn-Tic-CONH$_2$ (SEQ ID NO: 52)
Thi-GF-Tic-Oic-GK-Tic-Oic-GF-Tic-Oic-GK-Tic-G-KKKK—CONH$_2$ (SEQ ID NO: 53)
Ac-GF-Oic-Oic-GK-Oic-Oic-GF-Oic-Oic-GK-Oic-KKKK—CONH$_2$, (SEQ ID NO: 54)
Cys-GF-Tic-Oic-GK-Tic-Oic-GF-Tic-Oic-GK-Tic-G-KKKK—CONH$_2$ (SEQ ID NO: 55)
(NH$_2$)$_4$-(Dpr)$_2$-Dpr-Tic-Oic-G-Dpr-Tic-Oic-GF-Tic-Oic-G-Dpr-Tic-Oic-GF-Tic-Oic-G-Dpr-Tic-CONH$_2$, (SEQ ID NO: 56)
(NH$_2$)$_4$-(Dab)$_2$-Dab-Tic-Oic-G-Dab-Tic-Oic-GF-Tic-Oic-G-Dab-Tic-Oic-GF-Tic-Oic-G-Dab-Tic-CONH$_2$
and (SEQ ID NO: 57)
Ac—KKKK-GF-Tic-Tic-GK-Tic-Tic-GF-Tic-Tic-GK-Tic-CONH$_2$.

As noted above, in the General Formulae the term "X" denotes the first and second spacers, that is, spacers 1 and 2, which may or may not be the same amino acid. The Table 4 below shows molecular modeling that relates the length of spacer 1 and spacer 2 to anti-bacterial activity. The data are summarized below.

TABLE 4

Spacer 1 and 2 inter-residue distance data

| AMP | SPACER 1 | SPACER 2 | Distance from Oic to J | Distance from Oic to Z | Salmonella typhimurium | Staphylococcus aureus ME/GM/TC resistant | Mycobacterium ranae | Bacillus subtillis | % hemolysis |
|---|---|---|---|---|---|---|---|---|---|
| FKAB-1G | Gly | Gly | 5.86 | 5.96 | 10 μM | 3 μM | 10 μM | 1 μM | 14% |
| FKAB-1Gc | no spacer | no spacer | 3.96 | 3.89 | 10 μM | 3 μM | 30 μM | 1 μM | 86.80% |
| FKAB-1Gd | Gaba | Gaba | 7.74 | 9.5 | 10 μM | 100 μM | 10 μM | 1 μM | 10.80% |

TABLE 4-continued

Spacer 1 and 2 inter-residue distance data

| AMP | SPACER 1 | SPACER 2 | Distance from Oic to J | Distance from Oic to Z | *Salmonella typhimurium* | *Staphylococcus aureus* ME/GM/TC resistant | *Mycobacterium ranae* | *Bacillus subtillis* | % hemolysis |
|---|---|---|---|---|---|---|---|---|---|
| FKAB-1Gd1 | β-Ala | β-Ala | 8.13 | 7.66 | 10 µM | 10 µM | 1 µM | 1 µM | 24.40% |
| FKAB-1Gd2 | Ahx | Ahx | 9.26 | 8.9 | 10 µM | 10 µM | 3 µM | 1 µM | 44.70% |

Spacers 1 and 2 in FKAB-1G are both Gly residues. Thus there is only one carbon atom between the amide nitrogen atom and the carbonyl carbon atom of the amino acid residue. Compound FKAB-1Gd1 spacers 1 and 2 are both β-Ala residues containing a two carbon spacer. This modification had little or no effect on the activity against all four bacterial strains; however, hemolytic activity increased to 25%. Compound FKAB-1Gd spacers 1 and 2 are both the amino acid Gaba containing a three carbon spacer. This modification had no effect *Salmonella typhimurium*, or *Mycobacterium ranae*. However, the activity against *Staphylococcus aureus* ME/GM/TC resistant bacteria was dramatically reduced from 3 to 100 µM. Hemolytic activity was approximately equal to compound FKAB-1G. Compound FKAB-1Gd2 spacers 1 and 2 are both 6-aminohexonic acid (an un-natural amino acid) containing a five carbon spacer. This modification had little or no effect on the activity against *Salmonella typhimurium* or *Staphylococcus aureus* ME/GM/TC resistant bacteria or *Mycobacterium ranae*. However the hemolytic activity increased to 45%.

The final modification to spacers 1 and 2 was to delete this residue all together in compound FKAB-1Gc. The deletion of both spacers 1 and 2 resulted in no change in the activity against *Salmonella typhimurium* and *Staphylococcus aureus* ME/GM/TC resistant bacteria with a very small increase in the activity against *Mycobacterium ranae*. The hemolytic activity however dramatically increased to 87%, making this compound the most toxic to red blood cells of the series tested.

This data is indicative that spacers 1 and 2 play a role in determining the conformational flexibility of these compounds and the resulting type of β-turn adopted by the Tic-Oic dipeptide unit. Based on the observation that compound FKAB-1Gc exhibits the highest hemolytic activity, coupled with the observation in the literature that helical character favors hemolytic activity, the inventors believe that the absence of spacers 1 and 2 reduces the conformational freedom of the peptide and induces a 3/10 helical conformation on to the peptide facilitating the binding to the membrane of red blood cells. The other spacers seem to exhibit, as one would expect, greater conformational freedom allowing the peptide to adopt different conformations on interaction with red blood cells.

As far as anti-bacterial activity is concerned, none of the spacers had a great effect except for Gaba, (FKAB-1Gd) which had a dramatic effect by reducing the activity 33 fold against *Staphylococcus aureus* ME/GM/TC resistant bacteria. This result implies that this spacer makes it more difficult for compound FKAB-1Gd to adapt under the influence of the physicochemical properties of the *Staphylococcus aureus* cell membrane a favorable binding conformation. From this data, it is believed that the length of spacers 1 and 2 play a significant role in defining hemolytic activity and thus these two distances (spacer lengths) are important for selectivity against bacterial cells versus mammalian cells. The preferred length of the spacers 1 and 2 should be between 5-15 angstroms to reduce hemolytic activity and the spacers may be as long as 50 angstroms.

In this invention, the two un-natural amino acids Tic (tetrahydroisoquinolinecarboxylic acid) and Oic (octahydroindolecarboxylic acid) are used to induce an amphipathic structure. It has been shown using NMR and molecular modeling methods that the dipeptide Tic-Oic when placed in positions i+1 and i+2 of a four amino acid sequence induced a β-turn. The inventors discovered that multiple Tic-Oic dipeptide units will induce back-to-back β-turns onto the polypeptide backbone. It was found that placement of multiple Tic-Oic units connected via two amino acid spacers induces a helical-like or cork-screw like conformation onto the peptide with defined properties of charge and hydrophobicity. Yet, and unexpectedly, the peptide backbone still exhibited sufficient conformational flexibility to allow interactions with membranes with different physicochemical properties to induce a "new" stable conformation onto the peptide.

The importance of the "Tic-Oic" β-turn inducing unit to the invention is illustrated by the following test and results. In order to systemically investigate the effects of varying the spacer and functional groups on selectivity and potency for the three different bacterial strains, compound FKAB-1G was selected based on its broad spectrum activity (activity against *Salmonella typhimurium*: (10 µM), *Staphylococcus aureus* ME/GM/TC resistant: (3 µM) *Mycobacterium ranae*: (10 µM), and *Bacillus* subtillis (1 µM), coupled with relatively low hemolytic activity (14%) as the reference. The first hypothesis to be evaluated was the importance of the Tic-Oic dipeptide turn inducing unit to antibacterial and hemolytic activity. In the compound FKAB-1Gf the Tic residue was completely deleted from the sequence resulting in loss of activity against *Staphylococcus aureus* ME/GM/TC resistant and dramatic reduction in activity against *Salmonella typhimurium* from 10 to 100 µM, and *Mycobacterium ranae*—from 10 to 100 µM. Hemolytic activity was reduced to 6%. It is of interest to point out that FKAB-1 Gf was still very active (3 µM) against the Gram positive strain *Bacillus subtillis*. To determine whether dramatic reduction in activity was due to the reduction of the overall amino acid sequence length from 19 to 15. Compound FKAB-1Gf1 was prepared where all the Tic residues were replaced with Gly residues thus maintaining the overall amino acid sequence length of 19. This resulted in the loss activity against both *Salmonella typhimurium* and *Staphylococcus aureus* ME/GM/TC resistant bacteria while the activity against *Mycobacterium ranae* remained at 100 µM. Again FKAB-1Gf1 was still relatively active against (30 µM) *Bacillus subtillis*. A reduction in hemolytic activity (3%) was also observed for this analog. Two similar analogs were prepared completely deleting the Oic residue in FKAB-1Gg or in FKAB-1Gg1 replacing it with a Gly residue resulted in loss of activity against *Staphy-*

*lococcus aureus* ME/GM/TC resistant and dramatic reduction in activity against *Salmonella typhimurium* (100 μM) while still maintaining relatively good activity against *Bacillus subtillis*. A reduction of hemolytic activity of (6%) was also observed. However it is interesting to note that in both cases activity against *Mycobacterium ranae* was reduced only from 10 to 30 μM. This observation provides critical insight into the conformational and hydrophobic requirements for selective binding to the membranes of mycobacterium vs. Gram positive and Gram negative bacteria. The final analog prepared in the series was compound FBAK-1Gh where the Tic residue was replaced by the non-conformationally restrained aromatic residue Phe, resulting in an analog exhibiting similar anti-bacterial activity to compound FKAB-1G; however a two fold increase in hemolytic activity (28%) was observed. This indicates that in addition to playing a major role of inducing a turn conformation, the hydrophobicity of the Tic residue is also important for anti-bacterial activity and reducing hemolytic activity. To that end, the hydrophobic amino acid residues should exhibit hydrophobicity between −1.0 and −3.0 or higher on the octanol scale.

The following is a list of all un-natural amino residues that may be incorporated in one or more of the General Formulae.

The list includes the three-letter designation and full name.
Dpr 2,3-diaminopropionic acid
Dab 2,4-diaminobutanoic acid
βAla Beta Alanine
Gaba Gama Aminobutyric acid
6-Ahx 6-Aminohexanoic acid
Nav Norvaline
Nle Norleucine
Apc4 4-Aminopiperidine-4-carboxylic acid
Apc3 3-Aminopiperidine-3-carboxylic acid
Tic Tetrahydroisoquinoline-3-carboxylic acid
Oic Octahydroindole-3-carboxylic acid
Thi 2-Thienylalanine
9-Aoa 9-Aminooctanoic acid
10-Ada 10-Aminodecanoic acid
12-Adda 12-Aminododecanoic acid
16-Apa 16-Aminopalmitic acid
Fpa 4-Fluorophenylalanine
Cph 4-Chlorophenylalanine
Nph 4-Nitrophenylalanine
Phg Phenylglycine Regarding hemolytic activity, the data below shows a comparison of maximum tolerated dose study on six of the AMPs. From this data it appears that at possible therapeutic doses of 1, 5, and 25 mg/kg there is no correlation between toxicity and hemolytic activity (Table 5). Only at the higher dose of 125 mg/kg is there a clear toxicity problem. The toxicity will most likely be observed in the dose range of 50-125 mg/mg which at least 8 times higher dosage than the estimated therapeutic dose. As a point of reference, for a maximum tolerated dose study, Deslouches synthesized a series of AMPs composed of repeating Arg and Val residues to induce an idealized amphipathic α-helix secondary structure with substitution of Trp on the hydrophobic face of the helix to increase the over all hydrophobicity of the peptides. These peptides exhibited potent in-vitro antibacterial activity, however these analogs cause death of the treated mice at a dose of 16 mg/kg within 60 minutes.[22]

TABLE 5

Maximum Tolerated Dose/Toxicity and Hemolytic activity

| Peptide ID | 1 mg/kg | 5 mg/kg | 25 mg/kg | 125 mg/kg | Hemolytic activity |
|---|---|---|---|---|---|
| FKAB-1Gc | minor weight loss/no observed toxicity | minor weight loss/no observed toxicity | minor weight loss/no observed toxicity | not tested | 86% |
| FKAB-1Gd | minor weight loss/no observed toxicity | minor weight loss/no observed toxicity | minor weight loss/no observed toxicity | not tested | 10% |
| FKAB-1Gb | no observed toxicity | no observed toxicity | no observed toxicity | not tested | 43% |
| FKAB-1Ge | no observed toxicity | no observed toxicity | no observed toxicity | not tested | 27% |
| FKAB-1G | not tested | no observed toxicity | no observed toxicity | minor weight loss in 4 or of 5 animals/1 death | 14% |
| FKAB-1Gd1 | not tested | no observed toxicity | minor weight loss/no observed toxicity | 5 out of 5 animals died | 25% |

To evaluate the antibacterial activity of compounds within the general formula above, the following four bacterial strains were selected. 1) *Salmonella typhimurium*—because of its clinical relevance to evaluate activity against Gram-negative bacteria. 2) *Staphylococcus aureus* ME/GM/TC resistant-because of its clinical relevance to evaluate activity against drug resistant Gram positive bacteria. 3) *Mycobacterium ranae*—this is a commercially available screen for mycobacterium that hopefully will provide insight into activity against tuberculosis. 4) *Bacillus* subtillis was selected as a commercially available screen that will hopefully provide insight into activity against *Bacillus anthraces*. The results of obtained from these assays are given in Table 6.

TABLE 6

Minimum Inhibitory Concentration for Antimicrobial Activity and Hemolytic Activity (100 and 25 µM) for all active analogs.

| Peptide ID | Salmonella typhimurium | Staphylococcus aureus ME/GM/TC resistant | Mycobacterium ranae | Bacillus subtillis | % hemolysis 100/25 µM | cmpnd # |
|---|---|---|---|---|---|---|
| WRFK-1 | not active | 10 µM | not tested | not tested | | 1 |
| WRFK-2 | 100 µM | 10 µM | not active | 1 µM | 100% | 2 |
| WRFK-3 | not active | 100 µM | not tested | not tested | 100% | 3 |
| WRFK-4 | 100 µM | 10 µM | not tested | not tested | 100% | 4 |
| WRFK-5 | 100 µM | 30 µM | not active | 3 µM | 100% | 5 |
| FKAB-1F | not active | 10 µM | 30 µM | 1 µM | 63% | 24 |
| FKAB-1G | 10 µM | 3 µM | 10 µM | 1 µM | 14% | 25 |
| FKAB-1H | 10 µM | 3 µM | 10 µM | 1 µM | | 26 |
| FKAB-1L | 30 µM | 10 µM | 10 µM | 3 µM | | 27 |
| FKAB-1Ga | 3 µM | 10 µM | 10 µM | 1 µM | 33.4%/14.3% | 28 |
| FKAB-1Gb | 3 µM | 30 µM | 3 µM | 1 µM | 43.6%/24.9% | 29 |
| FKAB-1Gc | 10 µM | 3 µM | 30 µM | 1 µM | 86.8%/50% | 30 |
| FKAB-1Gd | 10 µM | 100 µM | 10 µM | 1 µM | 10.8%/1.0% | 31 |
| FKAB-1Ge | 10 µM | 10 µM | 3 µM | 1 µM | 26.7%/9.2% | 32 |
| FKAB-1Gf | 100 µM | not active | 100 µM | 3 µM | 5.9%/3.2% | 33 |
| FKAB-1Gg | 100 µM | not active | 30 µM | 10 µM | 6%/4.9% | 34 |
| FKAB-1Gg1 | 100 µM | not active | 30 µM | 10 µM | 5.70%/3.80% | 35 |
| FKAB-1Gf1 | not active | not active | 100 µM | 30 µM | 3.30%/3.3% | 36 |
| FKAB-1Gh | 10 µM | 10 µM | 10 µM | 1 µM | 27.30%/8.9% | 37 |
| FKAB-1Gd1 | 10 µM | 10 µM | 1 µM | 1 µM | 24.4%/7.4% | 38 |
| FKAB-1Gd2 | 10 µM | 10 µM | 3 µM | 1 µM | 44.7%/26.6% | 39 |
| FKAB-1Gc1 | 10 µM | 3 µM | 3 µM | 1 µM | 41.3%/33.5% | 40 |
| FKAB-1Gi | 10 µM | 3 µM | 3 µM | 1 µM | 24.9%/18.9% | 41 |
| FKAB-1Gd3 | 10 µM | 30 µM | 3 µM | 1 µM | 29.7%/10.5% | 42 |
| FKAB-1Gj | 10 µM | 10 µM | 10 µM | 1 µM | not tested | 43 |
| FKAB-1Go | 30 µM | 10 µM | 3 µM | 0.3 µM | not tested | 44 |
| FKAB-1Gp | 3 µM | 3 µM | 10 µM | 0.3 µM | not tested | 45 |
| FKAB-1Gl | 30 µM | 3 µM | 10 µM | 1 µM | not tested | 46 |
| FKAB-1Gs | 3 µM | 10 µM | 100 µM | 1 µM | not tested | 47 |
| FBAB-1Gw | 3 µM | 30 µM | 100 µM | 0.3 µM | not tested | 48 |
| FKAB-1G2 | 10 µM | 3 µM | 10 µM | not tested | not tested | 49 |
| FKAB-1G3 | 10 µM | 10 µM | 10 µM | not tested | not tested | 50 |
| FKAB-1Go2 | 30 µM | 30 µM | 10 µM | not tested | not tested | 51 |
| FKAB-1G-βA | 30 µM | 30 µM | 10 µM | not tested | not tested | 52 |
| FKAB-1G-Gaba | 30 µM | 10 µM | 3 µM | not tested | not tested | 53 |
| FKAB-1G-Ahx | 30 µM | 30 µM | 10 µM | not tested | not tested | 54 |
| FKAB-1Gz | 3 µM | 10 µM | 10 µM | not tested | not tested | 55 |
| FKAB-1G-Thi | 30 µM | 10 µM | 30 µM | not tested | not tested | 56 |
| FKAB-1G-Trp | not active | 30 µM | 100 µM | not tested | not tested | 57 |
| FKAB-1Gx-R2 | not tested | not tested | not tested | not tested | not tested | 58 |
| FKAB-1Gg2 | 100 µM | 100 µM | 10 µM | not tested | not tested | 59 |
| FKAB-1Go1 | not active | 10 µM | 10 µM | not tested | not tested | 60 |
| FKABB-1G1 | 100 µM | 100 µM | 30 µM | not tested | not tested | 61 |
| FKAB-1Gv | 10 µM | 100 µM | 30 µM | not tested | not tested | 62 |
| FBAB-1Gq | 100 µM | 30 µM | 3 µM | not tested | not tested | 63 |

As seen in Table 6 these compounds exhibit a broad spectrum of anti-bacterial and hemolytic activity. For the purposes of this study bioactivity is defined as an in vitro MIC of 100 µM or less against a specific bacteria. The observed minimum inhibitory concentrations (MIC) for many of these analogs are as low or lower than those reported for other AMPs against Staphylococcus aureus strains[33, 34 35], Gram negative strains,[36] and mycobacterium strains[34].

Figure 3A:
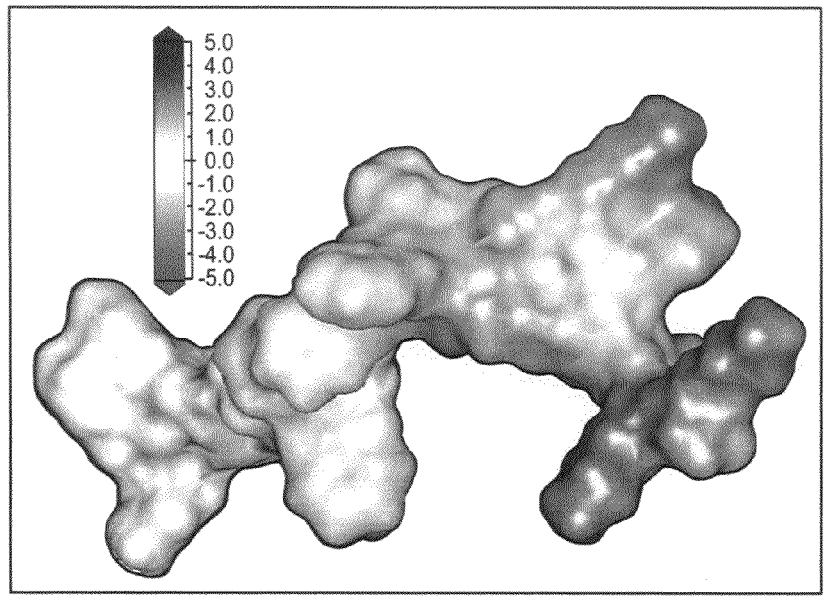
FIG. 3. The electrostatic surface potential map of the active analogs FKAB-1G (activity against *Salmonella typhimurium*-10 μM, *Staphylococcus aureus* ME/GM/TC resistant-3 μM *Mycobacterium ranae*-10 μM) clearly shows that the electrostatic surface potential is located on one face of the molecule (FIG. 3B) while the other face is electrostatically neutral (FIG. 3A). Thus the compound is highly amphipathic. Blue color indicates a positive charge, Red indicates a negative charge and white indicates a neutral electric charge.
Figure 3B:
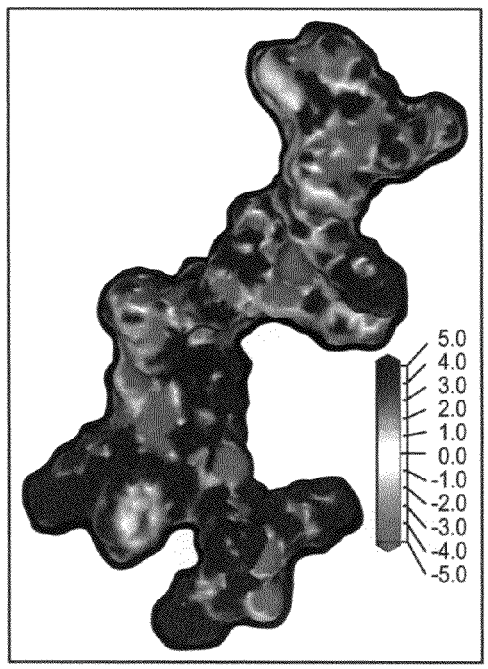

As stated previously these compounds were engineered to mimic the electrostatic surface potential of (Ala [8,13,18])magainin-2-amide. In FIG. 3 the electrostatic surface potential map for one of the most active analogs FKAB-1G (activity against Salmonella typhimurium –10 µM, Staphylococcus aureus ME/GM/TC resistant-3 µM and Mycobacterium ranae-10 µM) is shown which clearly indicates that the compound is highly charged and amphipathic. By contrast, the electrostatic surface potential map for the much less active analog FKAB-1Gf (activity against *Salmonella typhimurium*-100 μM, *Staphylococcus aureus* ME/GM/TC resistant-INACTIVE, *Mycobacterium ranae*-100 μM) shown in FIG. 4, clearly indicates that the compound is highly charged, but the charge is not localized onto any one face of the molecule and therefore the molecule is not amphipathic. It is interesting to note that incorporation of the negatively charged pentapeptide (Glu-Leu-Met-Asn-Ser (SEQ ID NO:3)) found at the C-terminus of the magainins at either the C-terminus, or the N-terminus, or both, of these analogs not only dramatically reduced the hemolytic activity, but also eliminated the antibacterial activity. The effect of incorporation of this pentapeptide sequence at both the C and N terminus is shown by the electrostatic potential map of the completely inactive analog FKAB-4 is shown in FIG. 5. This Figure suggests that the inactive analog is neither highly charged nor amphipathic.

Figure 6:
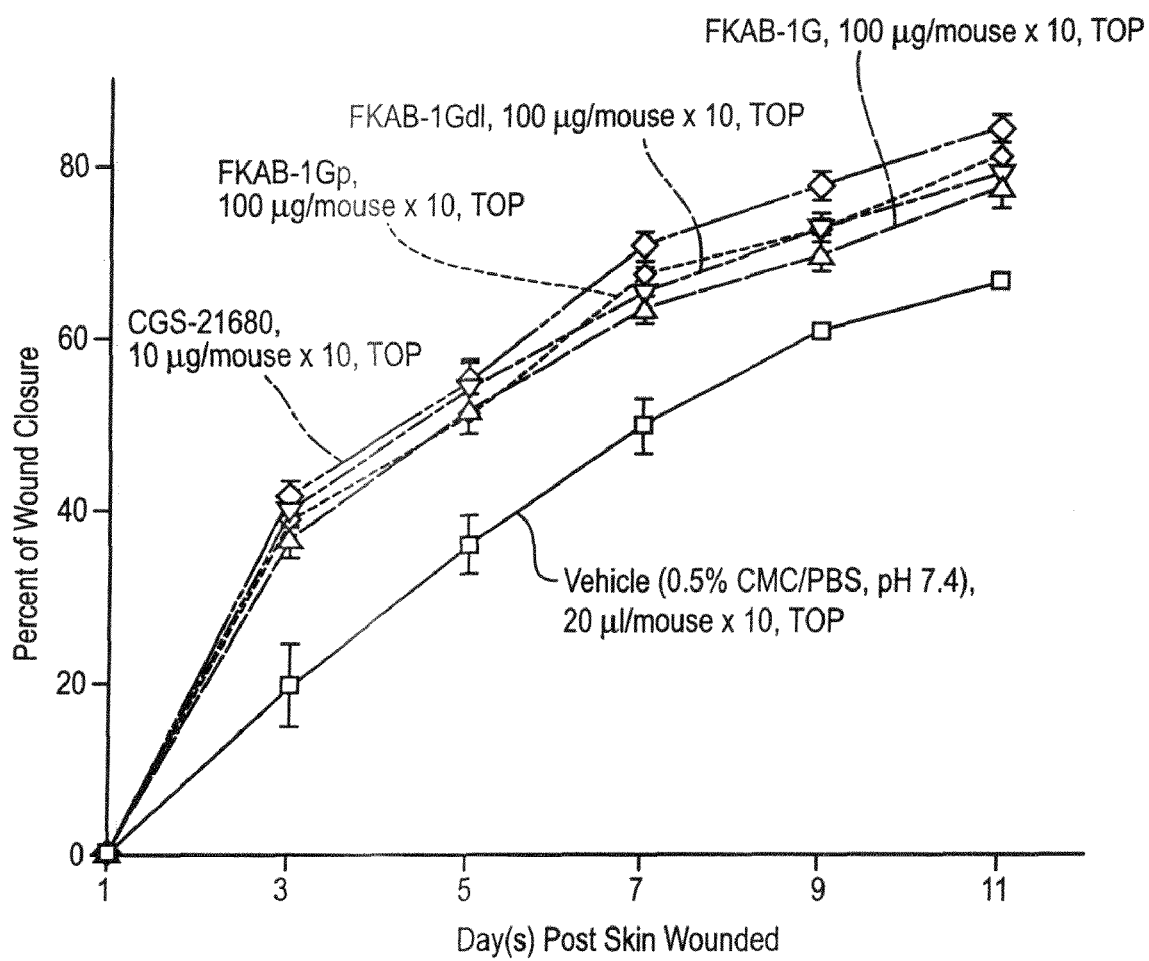
FIG. 6. Time course of the wound healing in mouse cutaneous injury model. Test substances were administered topically once daily for ten consecutive days. The would closure (%) and the would half-closure time (CT50) were determined and One-way ANOVA followed by Dunnett's test was applied for comparison between treated and its corresponding vehicle groups on days 3, 5, 7, 9 and 11. Data provided by MDS Pharma Services.

In addition to exhibiting activity against a broad spectrum of bacteria in-vitro these compounds have also shown activity in the in-vivo mouse wound healing model. (Table 7) As seen in FIG. 6, the three compounds evaluated exhibited activity very similar to the reference compound. In preparation of in-vivo anti-bacterial challenge studies six of the more active analogs were selected to determine the in-vivo maximum tolerated dose in a mouse model. The first four compounds were evaluated at doses of 1/5/25 mg/kg for 6 days—and none of these compounds exhibited any indications of major toxicity problems. (Table 5). Two other compounds were evaluated at 5/25/125 mg/kg and in both cases dosing at 125 mg/kg toxicity was observed. In the cases of compound FKAB-1G all animals lost weight and one animal died, while compound FKAB-1Gd1 exhibited much greater toxicity where 5 out 5 animals died.

FKAB-1Gj where only the C-terminal Lys residues were replaced with Orn, and compound FKAB-1Gs containing Dpr residues with one methylene group in the side chain. (That is, in FKAB-1Gp all of the Lysine residues are replaced with Orn, while in compound FKAB-1Gj only the C-terminal Lysine residues are replaced with Orn residues the other two Lysines are not replaced. This compound is a mixed Lys Orn analog.)

The net result of this study was that these modifications had very little effect on activity in vitro against *Salmonella typhimurium* and *Staphylococcus aureus* ME/GM/TC resistant bacteria; however the activity against *Mycobacterium ranae* was dramatically reduced by 10 fold from 10 to 100 μM. This result indicates that inclusion of Dpr residues will increase selectivity for Gram positive and Gram negative bacteria versus mycobacterium with a 33-fold selectivity for Gram negative and a 10-fold selectivity for Gram positive bacteria verse mycobacterium.

It is known that the Phe residues participate in hydrophobic interactions with the hydrophobic core of cell membrane. In an effort to determine whether changes in the electrostatic properties of Phe's aromatic ring will affect membrane binding the 4-Fluorophenylalanine (4FPhe or Fpa) analog FKAB-1Go was prepared. The net result was a small decrease in activity against *Salmonella typhimurium* and *Staphylococcus aureus* ME/GM/TC resistant bacteria and similar small increase in the activity against *Mycobacterium ranae*. This is a very interesting observation indicating that the hydrophobic interactions between these peptides and the membranes of mycobacterium are different from the hydrophobic interactions with Gram positive and Gram negative membranes.

TABLE 7

Mouse wound healing model results[32]

| Compound | Dose | Day 3 | Day 5 | Day 7 | Day 9 | Day 11 | $CT_{50}$ |
|---|---|---|---|---|---|---|---|
| Vehicle | 20 μl/mouse | 19.7% | 35.8% | 49.6% | 60.6% | 66.4% | 7.7 days |
| FKAB-1G | 100 μg/mouse | 36.3% | 51.5% | 63.3% | 69.8% | 77.5% | 6.1 days |
| FKAB-1Gd | 100 μg/mouse | 39.7% | 54.1% | 64.9% | 72.7% | 79.0% | 5.7 days |
| FKAB-1Gp | 100 μg/mouse | 38.8% | 51.2% | 67.2% | 72.8% | 81.1% | 5.7 days |
| Control[a] | 10 μg/mouse | 41.1% | 54.6% | 70.6% | 77.6% | 84.3% | 5.4 days |

[a]CGS-21680, denoting 2-p-[2-carboxyethyl]phenethyl-amino-5'-N-ethylcarboxamide-adenosine. This compound is a potent adenosine $A_2a$ receptor agonists that promotes wound healing and was used as the reference standard in this study.

Spacers 1 and 2 are defined above. Additional spacers may be present, although as is self-evident from the general formulae, there can be only one spacer between an Oic residue and the cationic or hydrophobic residue. As noted previously, other spacers may exhibit greater conformational freedom allowing the peptide to adopt different conformations on interactions with red blood cells. It is noted that Gaba may be a spacer 1 and 2, but it cannot be a spacer 3.

Spacer 3 is defined as a cationic amino acid residue with a quaternary (protonated) terminal amine group, or similar positively charged nitrogen containing functionality at the end of the residues' side chain. (Generally speaking, there will not be a spacer 4.) Spacer 3 defines the distance from the side chain terminal amine group to the polypeptide backbone and the resulting conformational flexibility of the side chain charge. To determine whether or not this distance has any affect on antibacterial activity, analogs with three different side chain lengths were investigated: compound FKAB-1G containing Lys residues with four methylene groups in the side chain, compound FKAB-1Gp containing Orn residues with three methylene groups in the side chain, compound Therefore, it is preferred that for methods of treating mycobacterium in particular, the AMPs will include at least one Phe residue, but this is not absolutely required for the AMPs to be effective against mycobacterium. For example, the analog designated FKAB-1 Ge (Ac-G-Tic-Oic-K-Tic-Oic-G-Tic-Oic-K-Tic-KKKK—$CONH_2$ (SEQ ID NO:17)) does not contain a Phe residue nor does it contain spacer 1. However, it is quite active against the four bacterial strains, including mycobacterium.

As seen in Table 6 various other modifications produced only small variations in the observed in vitro anti-bacterial activity. Compound FKAB-1Gw containing β-Ala residues for spacers 1 and 2 and Dpr residues for spacer 3 exhibits the highest selectivity for *Salmonella typhimurium* with a 10-fold selectivity over *Staphylococcus aureus* ME/GM/TC resistant bacteria and a 33-fold selectivity over *Mycobacterium ranae*. Compound FKAB-1Gd3 with a 3-fold selectivity over *Salmonella typhimurium* and a 10-fold selectivity over *Staphylococcus aureus* ME/GM/TC resistant bacteria and compound FKAB-1Go with a 10-fold selectivity over *Salmonella typhimurium* and a 3-fold selectivity over *Staphylococcus aureus* ME/GM/TC resistant bacteria are the most selective analogs for *Mycobacterium ranae*. Compounds WRFK-2 and WRFK-4 exhibited 10-fold or greater selectivity *Staphylococcus aureus* ME/GM/TC resistant bacteria versus *Salmonella typhimurium* and *Mycobacterium ranae*—however, these compounds exhibit 100% hemolytic activity and are therefore not selective agents. This does not mean that compounds WRFK-2 and WRFK-4 are not useful—they may be used as topical antibiotics since hemolytic activity is not as critical in topical treatments.

As shown by the data below in Table 8, the Tic-Oic dipeptide can be important for antibacterial potency and selectivity. The data supports that the Tic-Oic dipeptide unit is significant for effective broad spectrum in vitro antibacterial activity. Both the Gram Negative bacteria *Salmonella Typhimurium* and the Gram Positive *Staphylococcus Aureus* ME/GM/TC resistant are very sensitive to the Tic-Oic moiety. Complete removal of either the Tic or the Oic amino acid residue or the replacement of either the Tic or Oic amino acid residue with the amino acid Gly results in at least a 10-fold loss in in vitro efficacy. Only replacement of the Tic amino acid with the amino acid Phe leads to significant in vitro activity against *Salmonella Typhimurium* and *Staphylococcus Aureus* ME/GM/TC. (Tic is a bicyclic analog of the amino acid Phe, both having similar hydrophobicity; however, Phe is more conformationally flexible than Tic.) Substitution of a second Tic residue for the Oic residue (the dipeptide Tic-Tic) as well as reversal of the Tic-Oic didpeptide to the Oic-Tic didpeptide results in a 10-fold loss in in vitro activity against *Salmonella Typhimurium* and *Staphylococcus Aureus* ME/GM/TC.

It is significant that the modifications discussed immediately above have very little effect on the in vitro activity against the Gram Positive bacteria *Bacillus Subtillis*. The case with *Mycobacterium Ranae* is very different from the other three strains of bacteria, where a range of in vitro activity form 10 to 100 µM is observed. It is therefore concluded that these modifications can be used to develop analogs with increased organism selectivity for *Mycobacterium* as compared to the Tic-Oic dipeptide containing analogs. The Tic-Tic and Oic-Tic analogs are shown to be particularly effective against mycobacterium. To that end, in another embodiment, this invention encompasses antimicrobial peptides selective against mycobacterium that include the Tic-Tic analog (such as for instance, compound 59, FKAB-1Gg2) and the Oic-Tic analog (such as for instance, compound 61, FKAB-1Gg1), or a combination of these analogs, as well as methods for selecting against mycobacterium using these peptides.

The four possible dipeptide units formed by linking the two un-natural amino acids, Tic and Oic are: Tic-Oic (the major unit used in the formulae of the invention), the reverse analog Oic-Tic, and two single amino acid analogs Tic-Tic and Oic-Oic. All four dipeptides induce a β-turn like structure onto the backbone of the peptide when incorporated into the sequence. Multiple dipeptides can induce a series of back to back β-turns or an β-helical like structure. The exact dihedral angles of these turns will vary depending on the dipeptide and its local chemical environment (i.e. in aqueous solution or bound to a lipid bilayer) the critical physicochemical parameter which is varied in each dipeptide is the distribution of the overall hydrophobicity over the surface of the dipeptide unit. The amino acid Tic is more hydrophobic than the amino acid Oic. The net hydrophobicity for the two dipeptides Tic-Oic and Oic-Tic will be similar, but the overall distribution of the hydrophobicity for these two dipeptides will be opposite, i.e. they will be mirror images of each other. The Tic-Tic dipeptide will have a net increase in hydrophobicity compared to Tic-Oic or Oic-Tic dipeptides, while Oic-Oic dipeptide will have a lower net hydrophobicity compared to the other three dipeptides. By careful use of these four dipeptide units the overall hydrophobicity presented to the bacterial cell membrane can be changed to complement the hydrophobic character of the membrane to result in analogs with greater selectivity and potency for a particular bacterial strain.

These antimicrobial peptides may be administered in the manner discussed elsewhere in this application, e.g., by topical, intravenous, infusion, and oral administration. For instance, the antimicrobial peptide may be administered by intravenous administration in a dosage regimen of 1-25 mg/kg per day.

In addition to the microorganisms described above, the peptides were screened for anti-bacterial activity in the following four select agent assays: *Bacillus anthracis, Yersinia pestis* (plague), *Francisella tularensis* and *Brucella melitensis*. The test substance/vehicle was added to test wells containing the selected microorganisms ($1 \times 10^{-4}$ to $5 \times 10^{-5}$ CFU/mL) in the appropriate culture medium under controlled conditions. Final incubation concentration as determined by reference to standard optical density curve. After 1-4 days, growth of the culture was examined and scored positive (+) for inhibition of growth or turbidity or negative (−) for no effect upon growth or turbidity. Samples were evaluated at concentrations of 100, 30, 10, 3, 1, 0.3 and 0.1 µM in 1% DMSO to determine minimal inhibitory concentration (MIC). See Table 9 for results.

TABLE 8

Tic-Oic Dipeptide and Antibacterial Activity

| Peptide ID | *Salmonella Typhimurium* | *Staphylococcus Aureus* ME/GM/TC resistant | *Mycobacterium Ranae* | *Bacillus Subtillis* | % hemolysis 100/25 µM | Peptide ID | Analog |
|---|---|---|---|---|---|---|---|
| 25 | 10 µM/24 µg/mL | 3 µM/7.2 µg/mL | 10 µM/24 µg/mL | 1 µM/2.4 µg/mL | 14% | FKAB-1G | Tic-Oic |
| 33 | 100 µM/180 µg/mL | not active | 100 µM/180 µg/mL | 3 µM/5.4 µg/mL | 5.9%/3.2% | FKAB-1Gf | No Tic |
| 34 | 100 µM/200 µg/mL | not active | 30 µM/60 µg/mL | 10 µM/20 µg/mL | 6%/4.9% | FKAB-1Gg | No Oic |
| 35 | 100 µM/220 µg/mL | not active | 30 µM/66 µg/mL | 10 µM/22 µg/mL | 5.70%/3.80% | FKAB-1Gg1 | Gly for Oic |
| 36 | not active | not active | 100 µM/200 µg/mL | 30 µM/60 µg/mL | 3.30%/3.3% | FKAB-1Gf1 | Gly for Tic |
| 37 | 10 µM/24 µg/mL | 10 µM/24 µg/mL | 10 µM/24 µg/mL | 3 µM/7.2 µg/mL | 27.30%/8.9% | FKAB-1Gh | Phe for Tic |
| 59 | 100 µM | 100 µM | 10 µM | not tested | not tested | FKAB-1Gg2 | Tic-Tic |
| 61 | 100 µM | 100 µM | 30 µM | not tested | not tested | FKABB-1G1 | Oic-Tic |

TABLE 9

Minimum Inhibitory Concentration for Antimicrobial Activity against Select Agents

| Peptide # | F. tularensis SCHU-S4 µg/mL | Bacillus anthracis Ames µg/mL | B. melitensis 16M µg/mL | Plague CO92 µg/mL |
|---|---|---|---|---|
| 56 | 250 | 1.95 | >500 | 15.6 |
| 55 | 125 | 0.98 | >500 | 15.6 |
| 54 | 250 | 1.95 | >500 | 15.6 |
| 52 | 250 | 1.95 | >500 | 31.25 |
| 24 | >500 | 0.98 | >500 | >500 |
| 34 | 250 | 0.98 | >500 | 31.25 |
| 60 | 500 | 1.95 | >500 | 7.8 |
| 59 | 250 | 3.91 | >500 | 31.25 |
| 45 | 500 | 1.95 | >500 | 31.25 |
| 53 | >500 | 0.98 | >500 | 31.25 |
| 57 | >500 | 0.98 | >500 | >500 |
| 44 | 250 | 0.98 | >500 | 31.25 |
| 38 | 500 | 1.95 | >500 | 125 |

It is concluded that the peptides, especially compounds 24, 34, 38, 44, 45, 52-57, 59 and 60 are effective against *Bacillus anthracis* and *Yersinia pestis* (plague). These compounds exhibit very good to excellent in vitro MIC activity against two biological warfare agents. Both of these agents are difficult to treat using exiting antibiotic drugs. The compounds of this invention has a mechanism of action that is novel and offers protection against genetically modified strains of these two biological warfare agents. Another embodiment of the invention is use and methods of use of certain peptides in the treatment and prevention of infection by *Bacillus anthracis* and *Yersinia pestis* (plague). In addition, compounds 34, 44, 52, 54, 56, and particularly compound 55 may be useful compounds as biactive against *Francisella* tularensis. These antimicrobial peptides may be administered in the manner discussed elsewhere in this application, e.g., by topical, intravenous, infusion, and oral administration. For instance, the antimicrobial peptide may be administered by intravenous administration in a dosage regimen of 1-25 mg/kg per day.

The following provides details regarding the development and testing of the novel AMPs. This information is not intended to limit the invention to the specific AMPs described, but supports the novelty of the AMPs that fall within the General Formulae.

NMR All $^1$H NMR data was collected using a Bruker Avance-600 spectrometer using a $^1$H, $^{13}$C, $^{15}$N z-gradient cyroprobe. The samples of each peptide were prepared in—A) 100 mM SDS micelles and B) 100 mM DPC micelles in 600 µL of 90% H$_2$O/10% D$_2$O buffered with 150 mM sodium acetate to a pH of 4.2. 1D-$^1$H spectra were collected using the WATERGATE (WATER suppression by GrAdient Tailored Excitation) water suppression pulse sequence developed by Sklenar and co-workers[37] Data was collected at a temperature of 300 K. The spectral width was 9090.9 Hz acquired with 128K data points in F$_2$. 16 scans were collected for each spectrum. Spectra was processed using XWINNMR (Bruker) on a Hewlett Packard workstation.

In-vitro assays: All peptides were screened for anti-bacterial activity in the following four in-vitro assays: 1) *Salmonella, typhimurium* (ATCC 13311) Gram negative,[38, 39] 2) *Staphylococcus aureus*-Methicillin/Gentamicin/Tetracycline Resistant (ATCC 33592) Gram positive,[40] 3) *Bacillus subtillis* (ATCC 43223) Gram positive,[38, 39] 4) *Mycobacterium ranae* (ATCC 110)[38, 39] by MDS Pharma Services using the following protocol. The test substance/vehicle was added to test wells containing the selected microorganisms (1×10$^{-4}$ to 5×10$^{-5}$ CFU/mL) in the appropriate culture medium under controlled conditions. Final incubation concentration was determined by reference to standard optical density curve. After 1-4 days, growth of the culture was examined and scored positive (+) for inhibition or growth or turbidity or negative (−) for no effect upon growth or turbidity. Samples were evaluated at concentrations of 100, 30, 10, 3, 1, 0.3 and 0.1 µM in 1% DMSO to determine minimal inhibitory concentration (MIC).

In-vivo assays: Selected compounds were evaluated in an in-vivo mouse skin wound healing model by MDS Pharma Services using the following protocol. Groups of CD-1 derived male mice (n=5) weighting 24±2 g were used. Under hexobarbitol (90 mg/kg, IP) anesthesia, the shoulder and back region of each animal was shaved. A sharp punch (ID 12 mm) was applied to remove the skin including *panniculus carnosus* and adherent tissues. Test substances at 100 µg/mouse were each administered topically immediately following cutaneous injury, once daily for 10 consecutive days. The reference standard for this study 2-p-[2-carboxyethyl]phenethyl-amino-5'-N-ethylcarboxamide-adenosine. The wound area, traced onto clear plastic sheets, was measured by use of an Image-ProPlus (Media Cybernetics, Version 4.5.0.29) on days 1, 3, 5, 7, 9, and 11. The percent closure of the wound (%) was calculated, and wound half-closure time (CT$_{50}$) was analyzed by linear regression using Graph-Prism (Graph Software USA). One-way ANOVA followed by Dunnett's test was applied for comparison between the treated and its corresponding vehicle groups at each measurement time point. Differences are considered statistically significant at $P<0.05$.[41]

Maximum Tolerated Dose: Six compounds were evaluated in an in vivo mouse model to determine the maximum tolerated dose for each compound by BIOCON, Inc. using the following protocol. For each compound 3 dose concentrations (1/5/25 mg/kg or 5/25/125 mg/kg) were administered IP, 1-2 times per day as split doses. Day 0 weigh the animals, day 1-6 dose daily and observe animals, day 7 weigh, euthanasia followed by necrotize to examine abdominal cavity.

Hemolytic Studies: Took 5 mL of whole blood, spun down at 2500 rpm for 5 minutes, decanted supernatant, washed with PBS (20 mL each time, pH 7.4, isotonic) six times or until the supernatant became clear, and re-suspended in 125 mL of PBS to obtain a 4% count. Used 500 µL each for the experiments.

Peptide Synthesis: All of the above mentioned peptides were synthesized at 60 µM scale using an Advanced Chemtech ACT 396 model, multiple peptide synthesizer. Standard Fmoc chemistry was followed for the synthesis.[42-44] Rink Amide MBHA resins [4(2',4'-Dimethoxyphenyl-Fmoc-aminomethyl)-phenoxyacetamido-L-norleucyl-p-methyl benzhydrylamine resin] (purchased from NovaBioChem) was used as the solid phase and DMF (Dimethyl Formamide) was used as the primary transfer and wash solvent. A 20% piperidine solution in DMF' was used for deprotection. A solution of HBTU (O-Benzotriazole-N,N,N', N'-tetramethyluroniumphosphate) in conjunction with HOBT (1-Hydroxy Benzotriazole) in DMF was used as the coupling agent and 5% acetic anhydride in DMF was used for capping. DIPEA (Diisopropylethyl amine, 2 M in N-Methyl-morpholine) was used as the tertiary amine in the coupling step. All amino acids were dissolved in NMM (N-Methylmorpholine) Upon completion of the synthesis, the resin was thoroughly washed with Methanol (5 times), dried overnight under high vacuum (0.05 torr) and cleaved using a cocktail containing TFA (88%), Water (5%), Phenol (5%) and Triisopropylsilane (2%) for 3 hours. This mixture of resin and cleave cocktail was filtered followed by addition to cold (−20°

C.) stabilizer free dry diethyl ether (10 mL). The precipitated peptide was centrifuged and the supernatant was removed. This pellet of peptide was repeatedly washed with dry diethyl ether (20 mL×2) and dried overnight under high vacuum. The crude peptide thus obtained was dissolved in 0.1% TFA (Trifluoroacetic acid) and a 1% aliquot is saved for HPLC and MS analysis. [Hicks, 2007, #19]

Peptide Purification and analyses: All HPLC analyses were carried out using an Agilent 1100 series Analytical instrument (equipped with autosampler and Diode Array Detector) and C18 Narrow Bore Reverse Phase Column (250×2.1 mm, 5 μM particle size, 100 μL per minute flow rate). The mobile phase A consisted of Water (97.5%, containing 0.5 mL TFA) and 2-Propanol (2.5%) while B consisted of MeCN (88.88%), Water (8.88%, containing 0.4 mL of TFA) and 2-Propanol (2.4%). All analyses were carried out under gradient conditions (1-90% B over 60 minutes). All crude peptides were purified to 97% or more for analytical and other experimental purposes. All preparative purifications were carried out using an Agilent 1100 Series Preparative Instrument and C18 Reverse Phase Preparative Column (250×22 mm, 10 μM particle size, 10 mL per minute flow rate) using same mobile phases. All purified peptides were analyzed again by HPLC and Mass-Spec. Mass Spectral analyses were carried out using a Finnigan LTQ ESI-MS instrument running Xcalibur 1.4SR-1 or a Kratos PC Axima CFR Plus instrument (MALDI) running Kompact V2.4.1. ESI-MS showed multiply charged ions and the accurate mass was calculated. MALDI analyses were performed in reflectron mode and hence in most cases $(M+H)^+$ ion corresponding to Monoisotopic mass was observed (Table 10. AMP Mass Data). In the case of compounds showing only $(M+Na)^+$ or $(M+K)^+$ peaks, the mass was confirmed by running the same experiment in negative ion mode. [Hicks, 2007, #19]

TABLE 10

AMP Analytical Mass Spec Data

| Name | Sequence (and SEQ ID NO:) | Average MW Calcd. ($M^+$) | Monoisotope MW Calcd. ($M^+$) | Observed MW $(M + H)^+$ |
|---|---|---|---|---|
| WRFK-1 | $NH_2$-GKGL-Tic-Oic-GK-Tic-Oic-GF-Tic-Oic-GK-Tic-Oic-GF-Tic-Oic-GK-Tic-Oic-GKR—$CONH_2$ (SEQ ID NO: 4) | 3540.43 | 3538 | 3539.80 |
| WRFK-2 | $NH_2$-GKGL-Tic-Oic-GR-Tic-Oic-GF-Tic-Oic-GR-Tic-Oic-GF-Tic-Oic-GR-Tic-Oic-GKR—$CONH_2$ (SEQ ID NO: 5) | 3624.47 | 3622.02 | 3623.60 |
| WRFK-3 | $NH_2$-GKGL-Tic-Oic-GL-Tic-Oic-GK-Tic-Oic-GL-Tic-Oic-GK-Tic-Oic-GL-Tic-Oic-GLR—$CONH_2$ (SEQ ID NO: 6) | 3442.36 | 3440.01 | 3441.90 |
| WRFK-4 | $NH_2$-GKGL-Tic-Oic-GK-Tic-Oic-GL-Tic-Oic-GK-Tic-Oic-GL-Tic-Oic-GK-Tic-Oic-GKR—$CONH_2$ (SEQ ID NO: 7) | 3472.39 | 3470.03 | 3471.80 |
| WRFK-5 | $NH_2$-GKGL-Tic-Oic-FK-Tic-Oic-KF-Tic-Oic-FK-Tic-Oic-KF-Tic-Oic-FK-Tic-Oic-FKR—$CONH_2$ (SEQ ID NO: 8) | 4043.18 | 4040.34 | 4042.00 |
| FKAB-1F | $NH_2$—KL-Tic-Oic-K-Tic-Oic-F-Tic-Oic-K-Tic-Oic-F-Tic-Oic-K-Tic-Oic-KR—$CONH_2$ (SEQ ID NO: 9) | 3084.01 | 3081.83 | 3082.70 |
| FKAB-1G | Ac-GF-Tic-Oic-GK-Tic-Oic-GF-Tic-Oic-GK-Tic-KKKK—$CONH_2$ (SEQ ID NO: 10) | 2441.07 | 2439.40 | 2440.60 |
| FKAB-1H | Ac-GF-Tic-Oic-GK-Tic-Oic-GF-Tic-Oic-GK-Tic-KKKK—$CONH$—$CH_2$—$CH_2$—$NH_2$ (SEQ ID NO: 11) | 2484.14 | 2482.44 | 2483.30 |
| FKAB-1L | Ac-GF-Tic-Oic-GK-Tic-Oic-GF-Tic-Oic-GK-Tic-KKKK—$CONH$—$CH_2$—$CH_2$—$CH_2$—$NH_2$ (SEQ ID NO: 12) | 2498.17 | 2496.46 | 2497.50 |
| FKAB-1Ga | $NH_2$--GF-Tic-Oic-GK-Tic-Oic-GF-Tic-Oic-GK-Tic-KKKK—$CONH_2$ (SEQ ID NO: 13) | 2414.05 | 2412.40 | 2437.5 (M + Na) |
| FKAB-1Gb | $NH_2$—KL-Tic-Oic-GK-Tic-Oic-GF-Tic-Oic-GK-Tic-KKKK—$CONH_2$ (SEQ ID NO: 14) | 2451.16 | 2449.49 | 2450.20 |
| FKAB-1Gc | Ac—F-Tic-Oic-K-Tic-Oic-F-Tic-Oic-K-Tic-KKKK—$CONH_2$ (SEQ ID NO: 15) | 2212.86 | 2211.32 | 2212.90 |
| FKAB-1Gd | Ac-Gaba-F-Tic-Oic-Gaba-K-Tic-Oic-Gaba-F-Tic-Oic-Gaba-K-Tic-KKKK—$CONH_2$ (SEQ ID NO: 16) | 2553.29 | 2551.53 | 2552.60 |

TABLE 10-continued

AMP Analytical Mass Spec Data

| Name | Sequence (and SEQ ID NO:) | Average MW Calcd. (M+) | Monoisotope MW Calcd. (M+) | Observed MW (M + H)+ |
|---|---|---|---|---|
| FKAB-1Ge | Ac-G-Tic-Oic-K-Tic-Oic-G-Tic-Oic-K-Tic-KKKK—CONH$_2$ (SEQ ID NO: 17) | 2032.61 | 2031.22 | 2032.60 |
| FKAB-1Gf | Ac-GF-Oic-GK-Oic-GF-Oic-GKKKKK—CONH$_2$ (SEQ ID NO: 18) | 1804.32 | 1803.13 | 1804.40 |
| FKAB-1Gg | Ac-GF-Tic-GK-Tic-GF-Tic-GK-Tic-KKKK—CONH$_2$ (SEQ ID NO: 19) | 1987.44 | 1986.10 | 1987.50 |
| FKAB-1Gg1 | Ac-GF-Tic-G-GK-Tic-G-GF-Tic-G-GK-Tic-KKKK—CONH$_2$ (SEQ ID NO: 20) | 2158.60 | 2157.17 | 2158.20 |
| FKAB-1Gf1 | Ac-GF-G-Oic-GK-G-Oic-GF-G-Oic-GK-G-KKKK—CONH$_2$ (SEQ ID NO: 21) | 2032.53 | 2031.21 | 2032.60 |
| FKAB-1Gh | Ac-GF-F-Oic-GK-F-Oic-GF-F-Oic-GK-F-KKKK—CONH$_2$ (SEQ ID NO: 22) | 2393.03 | 2391.40 | 2392.20 |
| FKAB-1Gd1 | Ac-βAla-F-Tic-Oic-βAla-K-Tic-Oic-βAla-F-Tic-Oic-βAla-K-Tic-KKKK—CONH$_2$ (SEQ ID NO: 23) | 2497.18 | 2495.46 | 2496.50 |
| FKAB-1Gd2 | Ac-Ahx-F-Tic-Oic-Ahx-K-Tic-Oic-Ahx-F-Tic-Oic-Ahx-K-Tic-KKKK—CONH$_2$ (SEQ ID NO: 24) | 2665.61 | 2663.65 | 2664.30 |
| FKAB-1Gc1 | Ac—F-Tic-Oic-K-Tic-Oic-F-Tic-Oic-K-Tic-KKKKKK—CONH$_2$ (SEQ ID NO: 25) | 2469.21 | 2467.51 | 2468.50 |
| FKAB-1Gi | Ac-GF-Tic-Oic-GK-Tic-Oic-GF-Tic-Oic-GK-Tic-KKKKK—CONH$_2$ (SEQ ID NO: 26) | 2569.25 | 2567.50 | 2568.70 |
| FKAB-1Gd3 | Ac-Gaba-F-Tic-Oic-Gaba-K-Tic-Oic-Gaba-F-Tic-Oic-Gaba-K-Tic-KKKKK—CONH$_2$ (SEQ ID NO: 27) | 2681.47 | 2679.62 | 2680.60 |
| FKAB-1Gj | Ac-GF-Tic-Oic-GK-Tic-Oic-GF-Tic-Oic-GK-Tic-Orn-Orn-Orn-Orn-CONH$_2$ (SEQ ID NO: 28) | 2384.97 | 2383.34 | 2384.30 |
| FKAB-1Go | Ac-G-Fpa-Tic-Oic-GK-Tic-Oic-G-Fpa-Tic-Oic-GK-Tic-KKKK—CONH$_2$ (SEQ ID NO: 29) | 2477.05 | 2475.38 | 2476.30 |
| FKAB-1Gp | Ac-GF-Tic-Oic-G-Orn-Tic-Oic-GF-Tic-Oic-G-Orn-Tic-Orn-Orn-Orn-Orn-CONH$_2$ (SEQ ID NO: 30) | 2356.91 | 2355.31 | 2356.30 |
| FKAB-1G1 | Biotin-GF-Tic-Oic-GK-Tic-Oic-GF-Tic-Oic-GK-Tic-KKKK—CONH$_2$ (SEQ ID NO: 31) | 2625.33 | 2623.47 | 2624.30 |
| FKAB-1Gs | Ac-GF-Tic-Oic-G-Dpr-Tic-Oic-GF-Tic-Oic-G-Dpr-Tic-Dpr-DprDpr-Dpr-CONH$_2$ (SEQ ID NO: 32) | 2188.59 | 2187.12 | 2188.90 |
| FBAB-1Gw | Ac-βAla-Fpa-Tic-Oic-βAla-Dpr-Tic-Oic-βAla-Fpa-Tic-Oic-βAla-Dpr-Tic-Dpr-Dpr-Dpr-Dpr-CONH$_2$ (SEQ ID NO: 33) | 2280.68 | 2279.16 | 2280.90 |
| FKAB-1G2 | Ac-G(dF)-Tic-Oic-GK-Tic-Oic-G(dF)-Tic-Oic-GK-Tic-KKKK—CONH$_2$ | 2441.07 | 2439.40 | 2440.40 |
| FKAB-1G3 | Ac-GF-Tic-Oic-G(dK)-Tic-Oic-GF-Tic-Oic-G(dK)-Tic-KKKK—CONH$_2$ | 2441.07 | 2439.40 | 2440.40 |

TABLE 10-continued

AMP Analytical Mass Spec Data

| Name | Sequence (and SEQ ID NO:) | Average MW Calcd. (M+) | Monoisotope MW Calcd. (M+) | Observed MW (M + H)+ |
|---|---|---|---|---|
| FKAB-1Go2 | Ac-G-Nph-Tic-Oic-GK-Tic-Oic-G-Nph-Tic-Oic-GK-Tic-KKKK—CONH₂ (SEQ ID NO: 34) | 2531.07 | 2529.37 | 2530.80 |

Metabolic Stability

Liver microsomal incubations were performed to obtain preliminary estimates metabolic stability. Selected compounds were incubated in pooled liver microsomes from human, monkey, dog, rat, and mouse, and the test article percent remaining was measured by LC-MS/MS. Test results showed that the compounds exhibited acceptable to excellent metabolic stability in human liver microsomes as well as liver microsomes of four other species. This demonstrates that these compounds should exhibit satisfactory metabolic stability in humans for the treatment of systemic bacterial infections.

As can be seen in Table 11 below, for the results (high, moderate, low and very low) for all metabolic stability testing in the five species at T=60 minutes in the table below, all 20 analogs exhibit very good to excellent first pass metabolic stability in several species—specifically and most importantly in humans. However, as seen from the data below The inventors have the ability to modify the metabolic stability of these compounds which in turn will allow us to control the therapeutic half-life of these compounds. This control will allow for the adjustment of the dosing scheme to be used, for example once a day, once every other day, etc. Please see tables below for additional details.

both phosphate buffer (75 mM, pH 7.4) and the NADPH regenerating system (MgCl$_2$, 3.3 mM; G6P, 3.3 mM; G6PD, 0.4 U/mL; NADP+, 1.3 mM). Positive controls included warfarin, propranolol, and testosterone, incubated as a cocktail.

Results for all metabolic stability testing are also summarized in Table 12.

TABLE 12

Summary of Metabolic Stability Testing

|  | Human Liver | | | Monkey Liver | | |
|---|---|---|---|---|---|---|
| Warfarin | 100% | 97% | 97% | 113% | 109% | 81% |
| Propranolol | 97% | 86% | 72% | 34% | 9% | 0.50% |
| Testosterone | 77% | 53% | 29% | 34% | 11% | 1% |
| 25 | 152% | 145% | 140% | 55% | 73% | 91% |
| 29 | 98% | 97% | 106% | 86% | 87% | 97% |
| 30 | 139% | 134% | 128% | 17% | 24% | 75% |
| 31 | 106% | 94% | 114% | 16% | 25% | 76% |
| 38 | 94% | 99% | 97% | 90% | 87% | 89% |
| 32 | 114% | 116% | 120% | 56% | 73% | 125% |
| 41 | 86% | 95% | 113% | 72% | 75% | 99% |
| 44 | 103% | 119% | 210% | 57% | 65% | 94% |
| 46 | 144% | 136% | 120% | 80% | 77% | 77% |
| 24 | 99% | 224% | 153% | 28% | 29% | 9% |

TABLE 11

Metabolic Stability

| compound # | metabolic stability T = 60 min human | metabolic stability T = 60 min monkey | metabolic stability T = 60 min dog | metabolic stability T = 60 min rat | metabolic stability T = 60 min mouse |
|---|---|---|---|---|---|
| 25 | high | high | Moderate | high | very low |
| 29 | high | high | Moderate | high | moderate |
| 30 | high | high | low | high | very low |
| 31 | high | high | High | high | very low |
| 38 | high | high | Moderate | high | moderate |
| 32 | high | high | Moderate | high | very low |
| 41 | high | high | High | high | very low |
| 43 | high | high | Moderate | high | very low |
| 46 | high | high | High | high | high |
| 24 | high | very low | very low | high | very low |
| 52 | very low | high | High | low | high |
| 53 | very low | high | High | high | moderate |
| 54 | very low | high | High | high | high |
| 56 | high | very low | High | high | very low |
| 57 | high | very low | High | very low | high |
| 55 | very low | high | very low | high | low |
| 26 | very low | very low | No data | No data | moderate |
| 37 | high | high | Moderate | very low | high |

The test articles were incubated in pooled liver microsomes from human, monkey, dog, rat, and mouse. Test article percent remaining was measured by LC-MS/MS. The samples consisted of the test articles at 1 μM, pooled microsomes at 0.5 mg/mL final protein concentration, and an NADPH regenerating system in a final volume of 200 μL. Water was used as the test article solvent. The assay was standardized for TABLE 12-continued Summary of Metabolic Stability Testing

| 52 | 133% | 122% | −1% | 130% | 125% | 181% |
| 53 | 118% | 146% | 21% | 117% | 120% | 153% |
| 54 | 112% | 123% | −13% | 134% | 131% | 183% |

TABLE 12-continued

Summary of Metabolic Stability Testing

| | | | | | | |
|---|---|---|---|---|---|---|
| 56 | 234% | 220% | 253% | 206% | 194% | −40% |
| 57 | 112% | 137% | 108% | 0% | 0% | 0% |
| 55 | 1383% | 800% | −550% | 194% | 119% | 200% |
| 26 | 34% | 151% | 51% | 0% | 0% | 0% |
| 37 | 92% | 105% | 147% | 137% | 146% | 141% |

| | Dog Liver | | |
|---|---|---|---|
| | T = 15 | T = 30 | T = 60 |
| Warfarin | 109% | 104% | 94% |
| Propranolol | 76% | 51% | 24% |
| Testosterone | 85% | 62% | 33% |
| 25 | 54% | 50% | 63% |
| 29 | 100% | 99% | 81% |
| 30 | 22% | 14% | 46% |
| 31 | 35% | 34% | 55% |
| 38 | 84% | 78% | 71% |
| 32 | 43% | 43% | 54% |
| 41 | 68% | 63% | 79% |
| 44 | 63% | 54% | 59% |
| 46 | 96% | 84% | 80% |
| 24 | 54% | 27% | 8% |
| 52 | −6% | 66% | 105% |
| 53 | 67% | 80% | 86% |
| 54 | 83% | 79% | 84% |
| 56 | 66% | 61% | 140% |
| 57 | 58% | 116% | 169% |
| 55 | −84% | −4% | 3% |
| 26 | NC | NC | NC |
| 37 | −27% | 103% | 60% |

| | Rat liver | | | Mouse liver | | |
|---|---|---|---|---|---|---|
| | T = 15 | T = 30 | T = 60 | T = 15 | T = 30 | T = 60 |
| Warfarin | 93% | 97% | 84% | 86% | 111% | 110% |
| Propranolol | 0.10% | 0.10% | 0.10% | 9% | 9% | 4% |
| Testosterone | 0% | 0% | 0% | 3% | 0% | 0% |
| 25 | 71% | 79% | 90% | 80% | 10% | 12% |
| 29 | 84% | 84% | 91% | 87% | 73% | 70% |
| 30 | 73% | 80% | 107% | 86% | 10% | 7% |
| 31 | 67% | 78% | 83% | 90% | 7% | 9% |
| 38 | 82% | 79% | 92% | 90% | 64% | 53% |
| 32 | 69% | 73% | 95% | 85% | 20% | 11% |
| 41 | 76% | 86% | 87% | 77% | 26% | 15% |
| 44 | 74% | 57% | 75% | 81% | 26% | 22% |
| 46 | 73% | 83% | 105% | 96% | 87% | 78% |
| 24 | 113% | 120% | 202% | 124% | 45% | 22% |
| 52 | 118% | 122% | 44% | 11% | 174% | 156% |
| 53 | 113% | 72% | 104% | 88% | 71% | 66% |
| 54 | 120% | 106% | 121% | 97% | 98% | 113% |
| 56 | 107% | 61% | 199% | 41% | 67% | −21% |
| 57 | 131% | 84% | 0% | 54% | 81% | 106% |
| 55 | 21% | 7% | 80% | 74% | 29% | 42% |
| 26 | NC | NC | NC | 0% | 62% | 73% |
| 37 | 313% | 284% | 0% | 36% | 71% | 112% |

Values are shown as % remaining at time T (in minutes)

In Vivo Antimicrobial Efficacy

Five compounds were selected for in vivo challenge against a gram-positive and a gram-negative infection. Each test involved 60 subjects—10 for control and 10 for treatment with five selected compounds each. *Streptococcus pneumoniae* serotype 6B was selected for the gram-positive test, and *Salmonella typhimurium* strain LT2 was selected for the gram-negative test.

Figure 15:
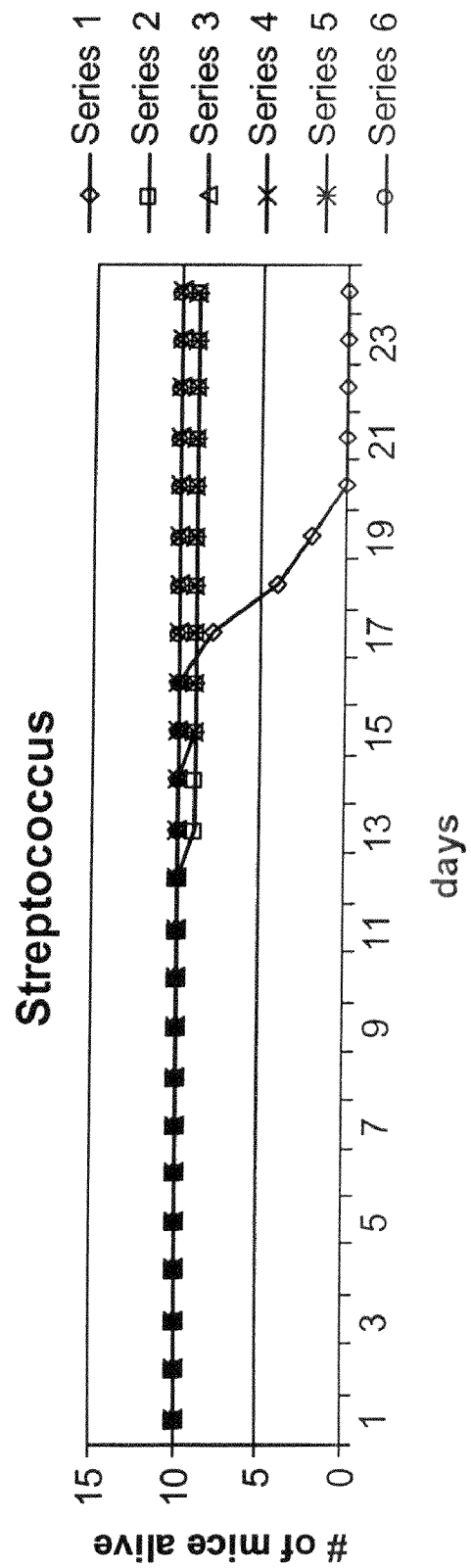
FIG. 15 shows the survival rate of mice against *Streptococcus pneumonia* (gram-positive), when tested with five compounds. Series 1=control group; series 2=compound 25; series 3=compound 38; series 4=compound 44; series 5=compound 46; series 6=compound 24.
Figure 16:
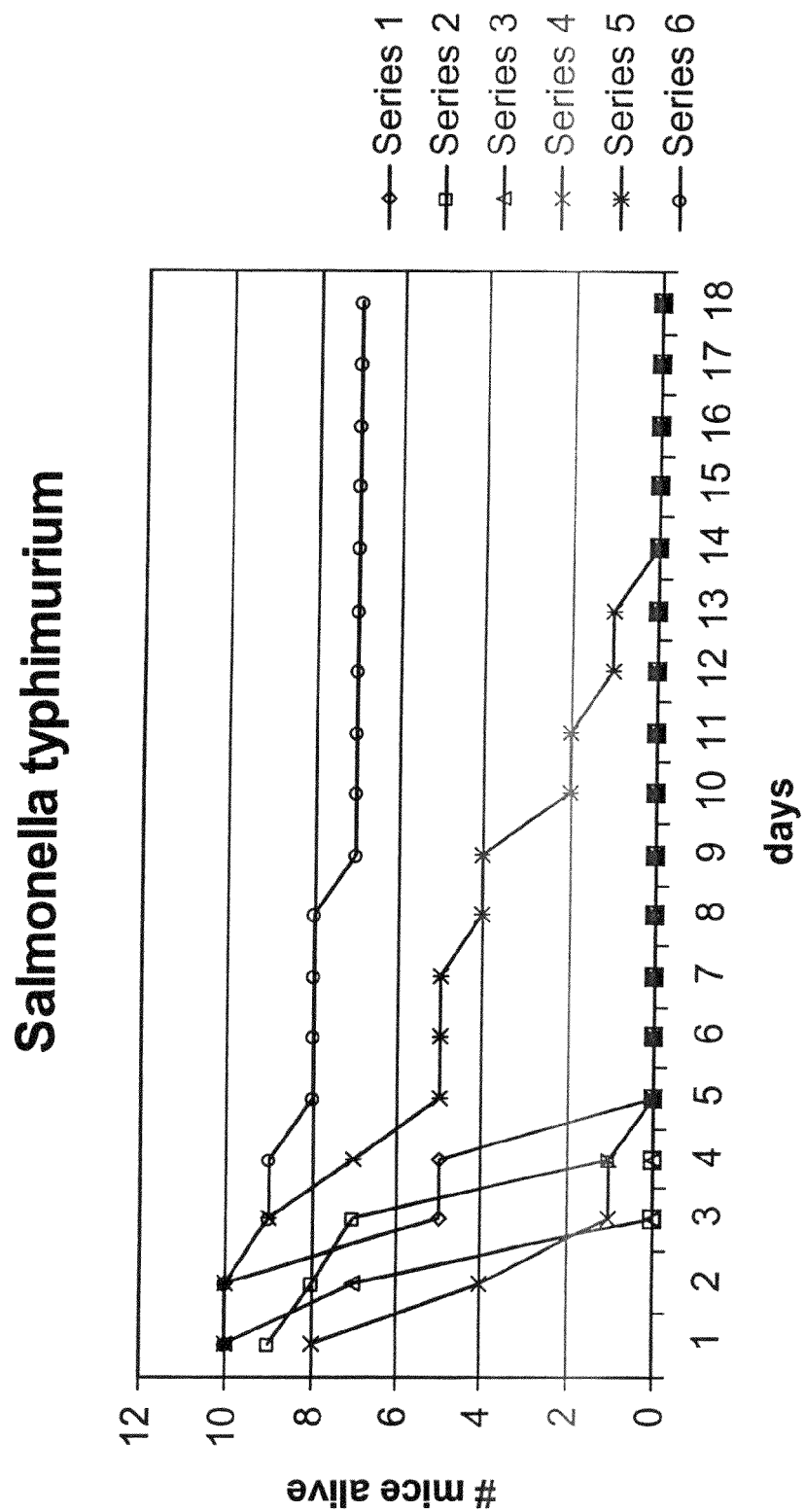
FIG. 16 shows the survival rate of mice against *Salmonella typhimurium* (gram-negative), when tested with five compounds. Series 1=control group; series 2=compound 25; series 3=compound 38; series 4=compound 44; series 5=compound 46; series 6=compound 24.
Figure 19A:
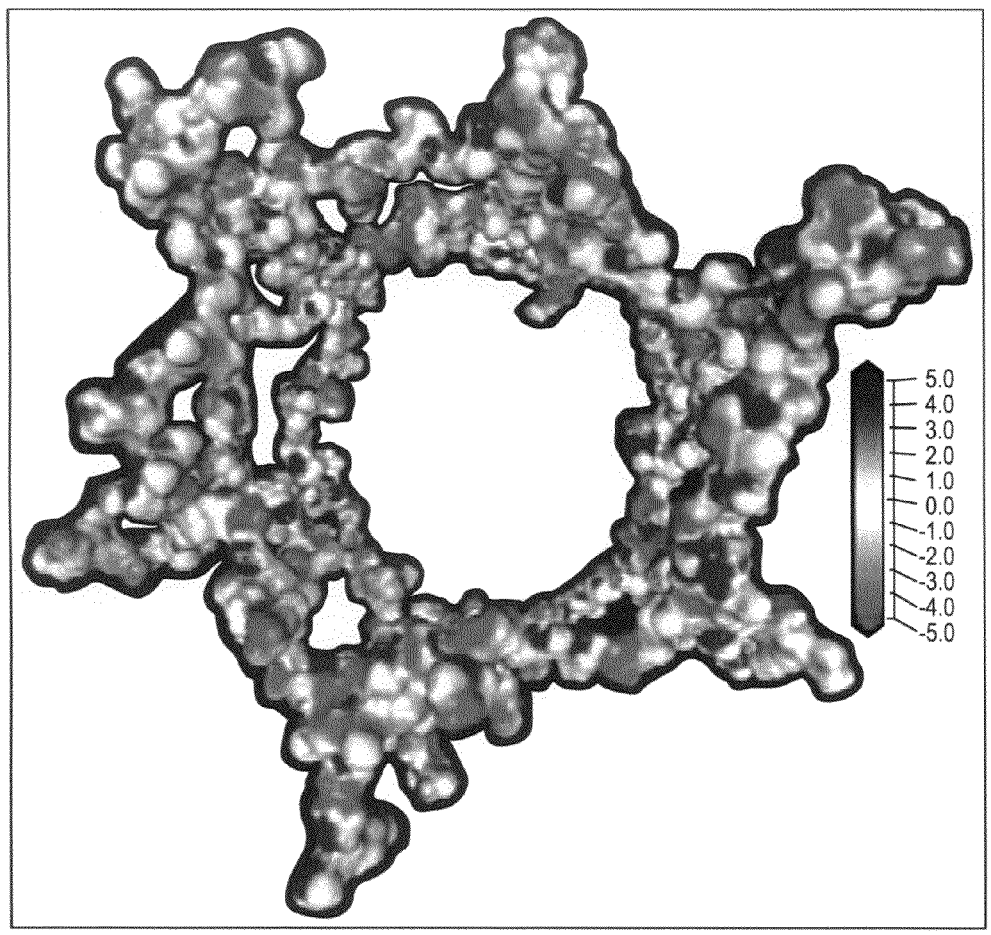
FIG. 19A is a top down view into the hexagonal pore form of SA peptidoglycan outer layer showing a highly charged polar surface. 8B and 8C are views from inside of the pore looking at two internal faces of the pore.
Figure 19B:
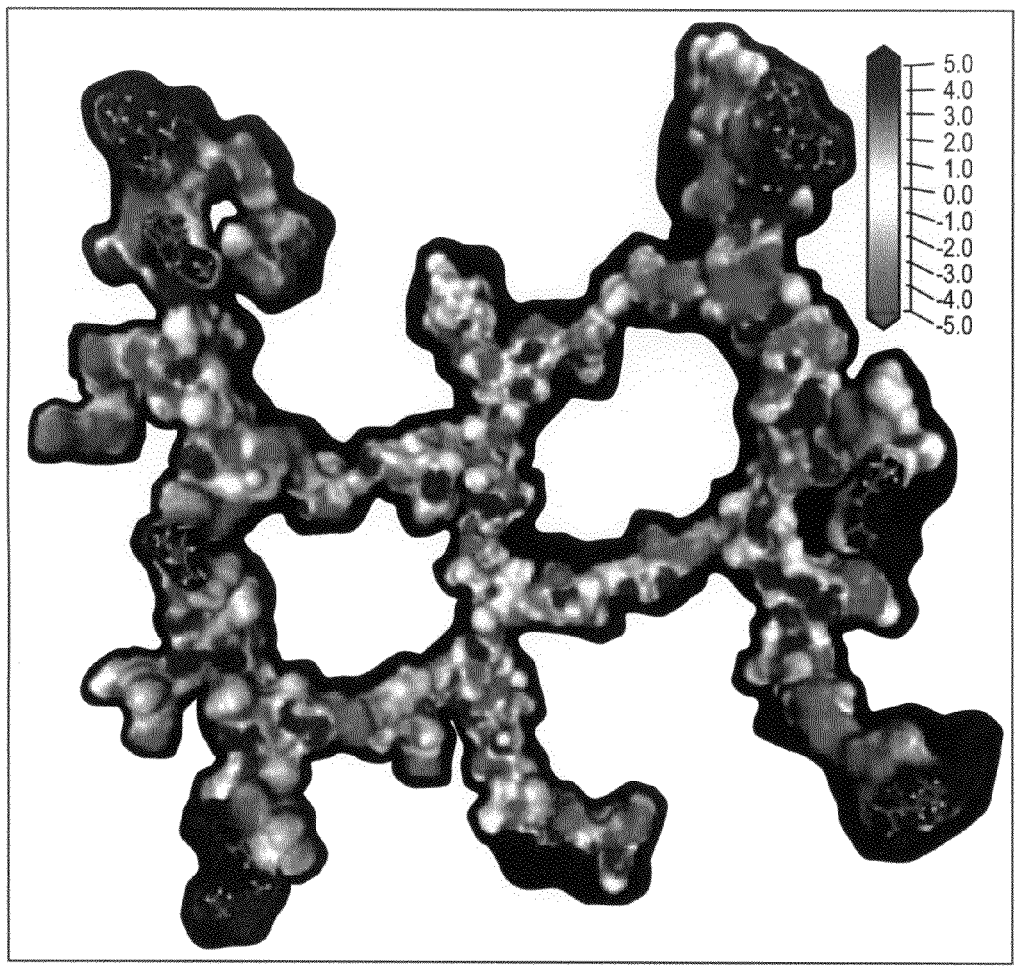
Figure 19C:
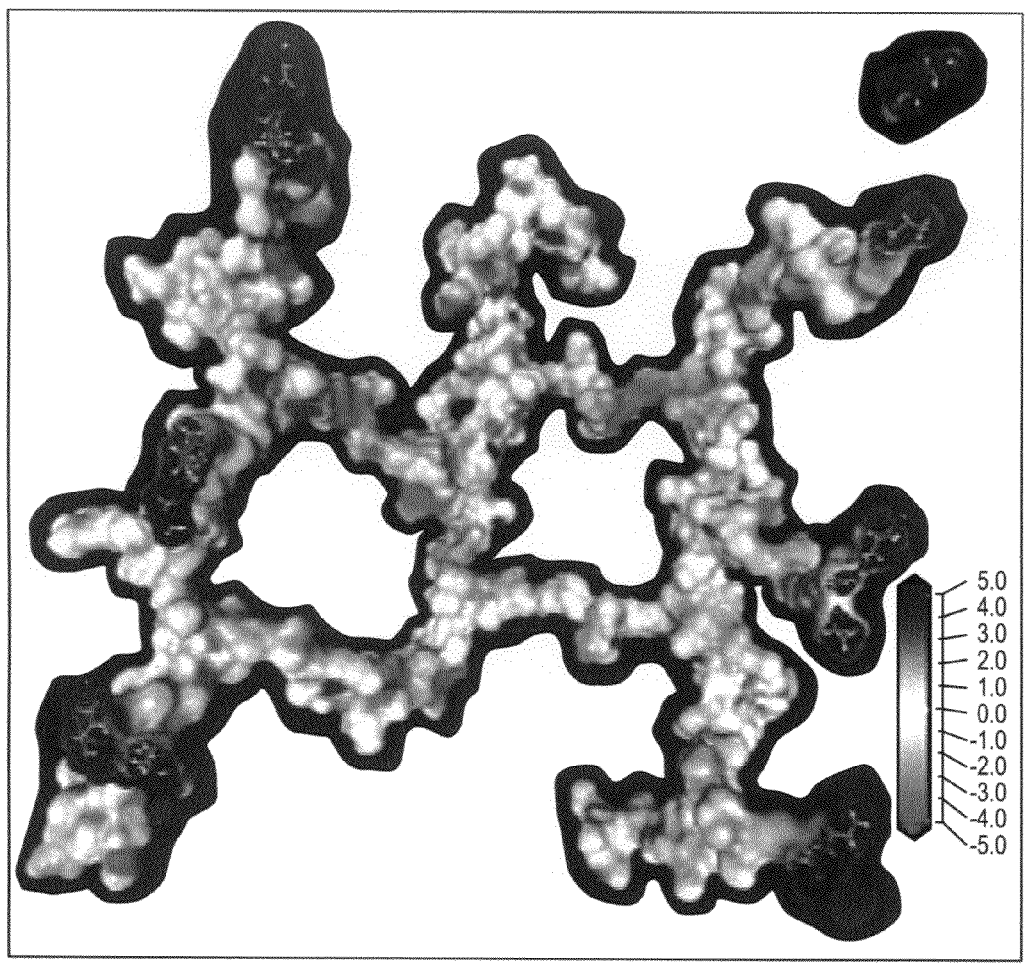
FIG. 19C shows a view looking at the relatively non-polar opposite face. Color Coding: blue indicates positive potential, red indicates negative potential and white indicates neutral potential.

All five compounds used in the *streptococcus* challenge demonstrated significant protection (>90% survival). Prolonged survival (up to 70%) was noted for recipients of two compounds tested against *salmonella* infection. See FIGS. 15 and 16, where Series 1=control group; Series 2=compound 25; Series 3=compound 38; Series 4=compound 44; Series 5=compound 46; Series 6=compound 24.

All treated subjects were given an initial treatment injection of 5 mg/kg in the afternoon of the first day of the challenge, followed by a morning and afternoon injection of 2.5 mg/kg for the remainder of the challenge period.

Sixty ICR mice received 0.1 ml ($5 \times 10^6$) of the challenge bacterium *Streptococcus pneumoniae* serotype 6B, via intraperitoneal injection. All untreated controls died from bacterial infection by day 21. All drug treatments demonstrated significant protection (>90% survival).

Sixty Balb/c mice received 0.1 ml ($2.5 \times 10^6$) of the challenge bacterium *Salmonella typhimurium* strain LT2 via intraperitoneal injection. All Untreated controls died from bacterial infection by day 4. Accelerated morbidity was observed (decreased survival compared to control group) among recipients of FKAB-1Gd1 and FKAB-1Gp. Prolonged survival (up to 70%) was noted among recipients of compounds FKAB-1Go and FKAB-1F. This data demonstrates that these compounds exhibit good to very good in vivo efficacy against a Gram positive and a Gram negative systemic bacterial infections. This data coupled with the maximum tolerated dose studies indicates that these compounds are effective against Gram positive and a Gram negative systemic bacterial infections at concentrations much lower than their lethal dose. Early estimates of their therapeutic index is greater than 20:1.

Quantitative Structure Activity Relationship (QSAR) and Analysis

The inventors have successfully built highly predictive 3D-QSAR models for the above-described novel unnatural amino acids containing antimicrobial peptides. As noted above, these AMPs exhibit extremely potent activity against *Salmonella typhimurium*, *Staphylococcus aureus*, *Mycobacterium ranae*, and *Bacillus subtillis*. For the purposes of this invention, bioactivity is defined as in vitro MIC of 100 µM or less against a specific bacteria. Employing the recently reported bioactive conformer mining methodology, the inventors have computed highly predictive models for *Staphylococcus aureus* (SA) and *Mycobacterium ranae* (MR) with non-validated $r^2$ of 0.987 and 0.998 respectively. The SA and MR models performed well on internal validation tests, with leave-one-out correlation $q^2_{LOO}$ of 0.839 and 0.997 and leave-10%-out correlation $q^2_{L10O}$ of 0.875 and 0.537 respectively.

The QSAR models concur with the reported mechanism of action involving electrostatic physicochemical properties such as polar surface areas and high positive charge. The models also show the importance of shape by demonstrating that physicochemical properties such as density and solvent accessible surface areas correlate with bioactivity. The SA QSAR model indicates that polarity and electrostatics are more significant in bioactivity manifestation for the anionic membrane bearing gram-positive *Staphylococcus aureus*; whereas, the MR QSAR model indicates that hydrophobicity and shape are more important in exhibiting bioactivity for the mycolate rich membrane bearing *Mycobacterium ranae*. Thus, the inventors' findings concur with the reported findings that amphipathicity, high positive charge and specific shape are required for AMP to exhibit bioactivity. Further, effective and efficient use of Tcl-based Cerius2 scripts is demonstrated in development of predictive QSAR models for highly flexible AMPs.

The predictive 3D-QSAR defining the activity of these analogs against *Staphylococcus aureus*; and *Mycobacterium ranae* clearly supports the importance of various physicochemical properties in defining organism potency and selectivity. The sixteen physiochemical properties common to the SA and MR QSAR models are shown in Table 13. See Table 2 for definitions of these properties.

TABLE-13

Common & Different PC properties between the two models

| Commonality of Physico-chemical properties | *Mycobacterium ranae* QSAR_DSP | *Staphylococcus aureus* QSAR_DSP |
|---|---|---|
| Common to both of the models | AlogP<br>Density<br>Dipole-mag<br>Fcharge<br>Hbond acceptor<br>Hbond donor<br>Jurs-FNSA-3<br>Jurs-FPSA-1<br>Jurs-PNSA-1<br>Jurs-PNSA-2<br>Jurs-PPSA-1<br>Jurs-RPCG<br>Jurs-RASA<br>Jurs-RPSA<br>RadOfGyration<br>Rotlbonds | AlogP<br>Density<br>Dipole-mag<br>Fcharge<br>Hbond acceptor<br>Hbond donor<br>Jurs-FNSA-3<br>Jurs-FPSA-1<br>Jurs-PNSA-1<br>Jurs-PNSA-2<br>Jurs-PPSA-1<br>Jurs-RPCG<br>Jurs-RASA<br>Jurs-RPSA<br>RadOfGyration<br>Rotlbonds |
| Specific to single model | Apol<br>Conformer Energy<br>Jurs-PPSA-2<br>Jurs-RNCG<br>Jurs-TPSA | Jurs-FPSA-3<br>Jurs-RPCS<br>Jurs-DPSA-2<br>Jurs-DPSA-3<br>Jurs-SASA<br>Jurs-TASA |

While the five physicochemical properties specific to the MR QSAR model are Apol (partition coefficient computed on atom types), Conformer Energy, Jurs-PPSA-2 (The partial positive solvent-accessible surface area times the total positive charge), Jurs-RNCG (relative negative charge computed by dividing the charge of the most negative atom by the total negative charge), and Jurs-TPSA (the total polar surface area, which is the sum of the solvent-accessible surface areas of atom with absolute partial charges greater than or equal 0.2). The commonality of physicochemical properties show the minimal requirement for activity against SA and MR. The physicochemical properties such as Dipole-mag, (Dipole moment magnitude: The dipole moment descriptor is a 3D electronic descriptor that indicates the strength and orientation behavior of a molecule in an electrostatic field. Both the magnitude and the components (X, Y, Z) of the dipole moment are calculated. It is estimated by utilizing partial atomic charges and atomic coordinates. Partial atomic charges are computed using the charge setup option in the QSAR control panel offering CHARMm charging rules, Gasteiger, CNDO2, and Del Re methods. The descriptor uses Debye units. Dipole properties have been correlated to lon-grange ligand-receptor recognition and subsequent binding. Fcharge (Sum of all formal charges in the molecule), Jurs-FNSA-3 ([the sum of the products of solvent accessible surface area and partial charge for all positively charged atoms]/[total molecular solvent-accessible surface area], Jurs-RPSA (relative polar surface area), Jurs-FPSA-1 [partial positive solvent accessible area]/[total molecular solvent-accessible surface area]), Jurs-PNSA-1 (sum of the solvent-accessible surface area of all partially negatively charged atoms), Jurs-PNSA-2 (partial negative solvent-accessible surface area times the total negative charge), Jurs-PPSA-1 (partial positive solvent accessible area), and Jurs-RPCG (relative positive charge computed by dividing the charge of the most positive atom by the total positive charge) indicate the importance of electrostatic potential for the AMPs bioactivity. This property is controlled by the inter-relationship of Spacers 1 and 2 as well as by Spacer 3 (the distance of the side chain terminal quaternary amine and the peptide backbone.) While the physicochemical properties such as Density (A 3D spatial descriptor that is defined as the ratio of molecular weight to molecular volume. It has the units of g ml-1. The density reflects the types of atoms and how tightly they are packed in a molecule. Density can be related to transport and melt behavior) H-bond acceptor, (Total number of hydrogen-bond acceptors in the molecule), Jurs-RASA {[total hydrophobic surface area, which is computed as the sum of the solvent-accessible surface area of atoms with absolute partial charge less than 0.2.)/(total molecular solvent accessible surface)]}, H-bond donor (Total number of hydrogen-bond donors in the molecule), RadOfGyration, Radius of gyration—The radius of gyration is calculated using the following equation:

$$Rog = \sqrt{\left(\sum \frac{(x_i^2 + y_i^2 + z_i^2)}{N}\right)}$$

where N is the number of atoms and x, y, z are the atomic coordinates relative to the center of mass and Rotlbonds {Counts the number of bonds in the current molecule having rotations that are considered to be meaningful for molecular mechanics. All terminal H atoms are ignored (for example, methyl groups are not considered rotatable)} indicate the significance of the AMP molecular shape (appropriate conformation) for bioactivity. These properties are controlled by the Tic-Oic dipeptide and the inter-relationship between the cationic and hydrophobic residues as defined by Spacers 1 and 2. The importance of amphiphilicity is alluded to by the physicochemical properties such as Jurs-RASA {[total hydrophobic surface area, which is computed as the sum of the solvent-accessible surface area of atoms with absolute partial charge less than 0.2.)/(total molecular solvent accessible surface)}, Jurs-RPSA (relative polar surface area), and A log P (Log of the partition coefficient calculated using the method described by Ghose & Crippen[45, 46]. In this atom-based approach, each atom of the molecule is assigned to a particular class, with additive contributions to the total value of logP) These properties are controlled by Tic-Oic dipeptide and the inter-relationship between Spacers 1 and 2 and the resulting conformational flexibility.

By way of background, it is noted that Quantitative Structure Activity Relationship (QSAR) is among the most widely used techniques in rational drug design. Following the pioneering work of Hansch, et al[47] in 2D-QSAR, several sophisticated techniques like Comparative Molecular Field Analysis (CoMFA)[48], Molecular Shape Analysis (MSA)[49], Comparative Molecular Similarity Index Analysis (COMSIA)[50], Condensed Phase Optimized Molecular Potentials for Atomistic Simulation Studies (COMPASS)[51], and Hypothetical Active Site Lattice (HASL)[52] have been developed for three dimensional QSAR (3D-QSAR). Several novel two-dimensional QSAR (2D-QSAR) descriptors to quantify the topology and information-content of molecules have been recently reported. Among them are the Weiner[53], Zagreb[54], and Hosoya indices[55], the Kier and Hall molecular connectivity indices[56], the Kier and Hall subgraphs count indices[56], the Kier's shape indices[57], molecular flexibility indices[58], and the Balaban indices[59]. The 2D molecular graph based graph-theoretic descriptors recently reported are the information-content-info of atomic composition descriptors[60], information index based on adjacency matrix (A-matrix), distance matrix (D-matrix), Edge matrix (E-matrix), and edge-distance matrix (ED-matrix)[54], the sum of atomic polarizability[61], and the multi-graph information content indices[54]. Several novel 3D descriptors to capture the conformational electronic and spatial information have also been reported. Among the recently reported 3D descriptors are shadow indices[62] and Jurs indices[63]. All of the 2D and 3D descriptors have been widely used in QSAR models. For example, in anti-tubercular agents[64], sulfamates have been used to distinguish sweet, sweet-bitter, and bitter tasting molecules[65], and octopaminergic agonists to inhibit sex-pheromones production in insects[66].

The selection of bioactive conformer is among the most important challenges in QSAR analysis[67]. Numerous sophisticated techniques have been reported to address this challenge, such as by Hopfinger et al[68] using conformational averaging or conformational ensembles; by Hasagewa et al[69] employing several conformers in multi-way data arrays; by Vedani et al[70] using multi-conformational ligand representation; by Appell et al[71] invoking tensor decomposition; by Hasagewa et al[67] employing three-way-PLS analysis; by Xiao et al[72] propounding the Targacept Active Conformational Search algorithm; and by Sulea et al[73] employing the multi-conformational minimal topologic difference (MTD-ADJ) using adjusted biological activities.

1. Material and Methods

The inventors have previously shown that employing several conformers, of highly flexible cyclic pentapeptides, in a CoMFA based QSAR study coupled with several sequential partial least square analyses mimicking the multi-way-Partial Least Square analysis, they could develop highly predictive QSAR models[74]. The inventors extended the method with a semi-automated heuristic using the Cerius2 software package[75] to develop highly predictive 3D-QSAR models for insect repellents.[76]

Cerius2 (C2) version 4.9[75] and InsightII version 2001 running on a Silicon Graphics Octane workstation under IRIX 6.5 operating system were used for all of the modeling work presented here. Gasteiger[77] charges, ClassII force field[78] was used for all of the computations using C2, and Consistent Valence force field (CVFF) was used for all computations using InsightII. Unless otherwise noted, default C2 and InsightII settings were used.

All peptides were screened for antibacterial activity in the following four in-vitro assays: 1) *Salmonella typhimurium* (ATCC 13311) Gram negative, 2) *Staphylococcus aureus* Methicillin/Gentamicin/Tetracycline resistant (ATCC 33592) Gram positive, 3) *Bacillus* subtillis (ATCC 43223) Gram positive, 4) *Mycobacterium ranae* (ATCC 110) by MDS Pharma services using the following protocol. The test substance/vehicle was added to test wells containing the selected microorganisms (1×10-4 to 5×10-5 CFU/ml) in the appropriate culture medium under controlled conditions. Final inoculum concentration was determined by reference to standard optical density curve. After 1-4 days, growth of the culture was examined and stored positive (+) for inhibition or growth or turbidity or negative (−) for no effect upon growth or turbidity. Samples were evaluated at concentration of 100, 30, 10, 3, 1, 0.3 and 0.1 M in 1% DMSO to determine Minimal Inhibitory Concentration (MIC).

The Table 14 summarizes the AMPs and their biological activity sequences data used in this QSAR study.

TABLE 14

Biological activity data

| Peptide ID | *Salmonella typhimurium* | | *Staphylococcus aureus* ME/GM/TC resistant) | | *Mycobacterium ranae* | | *Bacillus Subtillis* | |
|---|---|---|---|---|---|---|---|---|
| | μM | p(MIC) | μM | p(MIC) | μM | p(MIC) | μM | p(MIC) |
| FKAB-1 | 1000000 | 0.00 | not tested | | not tested | | not tested | |
| FKAB-1F | 1000000 | 0.00 | 10.00 | 5.00 | 30.00 | 4.52 | 1.00 | 6.00 |
| FKAB-1G | 10 | 5.00 | 3.00 | 5.52 | 10.00 | 5.00 | 1.00 | 6.00 |
| FKAB-1Ga | 3 | 5.52 | 10.00 | 5.00 | 10.00 | 5.00 | 1.00 | 6.00 |
| FKAB-1Gb | 3 | 5.52 | 30.00 | 4.52 | 3.00 | 5.52 | 1.00 | 6.00 |
| FKAB-1Gc | 10 | 5.00 | 3.00 | 5.52 | 30.00 | 4.52 | 1.00 | 6.00 |
| FKAB-1Gc1 | 10 | 5.00 | 3.00 | 5.52 | 3.00 | 5.52 | 1.00 | 6.00 |
| FKAB-1Gd | 10 | 5.00 | 100.00 | 4.00 | 10.00 | 5.00 | 1.00 | 6.00 |
| FKAB-1Gd1 | 10 | 5.00 | 10.00 | 5.00 | 1.00 | 6.00 | 1.00 | 6.00 |
| FKAB-1Gd2 | 10 | 5.00 | 10.00 | 5.00 | 3.00 | 5.52 | 1.00 | 6.00 |
| FKAB-1Gd3 | 10 | 5.00 | 30.00 | 4.52 | 3.00 | 5.52 | 1.00 | 6.00 |
| FKAB-1Ge | 10 | 5.00 | 10.00 | 5.00 | 3.00 | 5.52 | 1.00 | 6.00 |
| FKAB-1Gf | 100 | 4.00 | 1000000 | 0.00 | 100.00 | 4.00 | 3.00 | 5.52 |
| FKAB-1Gf1 | 1000000 | 0.00 | 1000000 | 0.00 | 100.00 | 4.00 | 30.00 | 4.52 |
| FKAB-1Gg | 100 | 4.00 | 1000000 | 0.00 | 30.00 | 4.52 | 10.00 | 5.00 |
| FKAB-1Gg1 | 100 | 4.00 | 1000000 | 0.00 | 30.00 | 4.52 | 10.00 | 5.00 |
| FKAB-1Gh | 10 | 5.00 | 10.00 | 5.00 | 10.00 | 5.00 | 1.00 | 6.00 |
| FKAB-1Gi | 10 | 5.00 | 3.00 | 5.52 | 3.00 | 5.52 | 1.00 | 6.00 |
| FKAB-1Gj | 10 | 5.00 | 10.00 | 5.00 | 10.00 | 5.00 | 1.00 | 6.00 |
| FKAB-1Go | 30 | 4.52 | 10.00 | 5.00 | 3.00 | 5.52 | 0.30 | 6.52 |
| FKAB-1Gp | 3 | 5.52 | 3.00 | 5.52 | 10.00 | 5.00 | 0.30 | 6.52 |
| FKAB-1H | 10 | 5.00 | 3.00 | 5.52 | 10.00 | 5.00 | 1.00 | 6.00 |
| FKAB-1L | 30 | 4.52 | 10.00 | 5.00 | 10.00 | 5.00 | 3.00 | 5.52 |
| FKAB-4 | 1000000 | 0.00 | 1000000 | 0.00 | 1000000 | 0.00 | 1000000 | 0.00 |
| WRFK-1 | 1000000 | 0.00 | 10.00 | 5.00 | not tested | | not tested | |
| WRFK-2 | 100 | 4.00 | 10.00 | 5.00 | 1000000 | 0.00 | 1.00 | 6.00 |
| WRFK-3 | 1000000 | 0.00 | 100.00 | 4.00 | not tested | | not tested | |
| WRFK-4 | 100 | 4.00 | 10.00 | 5.00 | not tested | | not tested | |
| WRFK-5 | 100 | 4.00 | 30.00 | 4.52 | 1000000 | 0.00 | 3.00 | 5.52 |

Molecular Structure Building, Conformational Search, & Cluster Analyses

Each peptide molecule was built using the Biopolymer module, and minimized using steepest descent algorithm[79] and a brief molecular dynamics run. Conformational searches were performed using the Boltzmann Jump method [80] as implemented in C2. The parameters used were as follows: Torsion window was fixed to 120, temperature was set to 5000K, and number of perturbations was set to 50. The torsion bond is defined as a single bond connecting different groups, which on rotation would give rise to potential local minimum conformer. Tcl-based Cerius2 scripts were developed to automate the repetitive conformational searches.

The inventors performed cluster analysis based on the RMS (root mean squares) differences of the torsion angles between the conformers. The steps in the algorithm are well known,[75] and a general description is as follows: All of the conformers are sorted by energy. The lowest energy conformer is assigned to the first cluster and it becomes the cluster nuclei. Next, all the conformers that have RMS difference below the specified threshold value are placed in the first cluster. The lowest energy conformer of the remaining unclustered conformers is placed in the second cluster as its cluster nuclei. Again, all the conformers that have rms difference below the specified threshold value are placed in the second cluster. The above two steps are repeated until all the conformers are placed into clusters.

Preliminary cluster analysis was performed to generate 10-20, 20-30, 30-40 and 40-50 conformers per cluster. The cluster nuclei of each set were examined for 3D-spatial representation. The cluster nuclei for the 10-20 set showed poor 3D-spatial representation, while cluster nuclei in the 40-50 conformer sets showed crowding in some region. The cluster nuclei of the 20-30 and 30-40 conformers set showed the best 3D sampling for most of the AMPs. Consequently, the inventors selected the best set of conformational clusters, showing the best 3D-spatial representation, between 20-40 for the QSAR analysis.

Descriptor Computation and QSAR Model Building

A total of 50 descriptors were computed for all of the conformers using the default setting in C2. The correlation matrix computed for the all the descriptor values of all the conformers of all peptides. Partial Least Square analysis (PLS) was used to compute the QSAR models with the descriptor column auto scaled and means removed. The number of components to explore was set to six, unless otherwise noted.

Quasi-Multi-Way PLS Analyses

The partial least squares (PLS) method[75] is used when there are far more independent variables (descriptors) than observations and when there is co-linearity in the independent variables. The inventors used the following PLS parameters: 6 components to explore, the column means removed, and the column data auto-scaled. The internal 'regression-only' cross-validation was used during the model building process. The definitions of the statistical terms used in this paper are well known.

The multi-way PLS method, developed by Bro et al[81], was applied to develop the 3D-QSAR models of insecticidal neonicotinoid compounds[82]. Each dimension of the multi-way data corresponds to the compounds in training set, CoMFA field variables, conformations, and alignments. The conformers and alignments that gave the best correlation to observed bioactivities were determined from the multi-way PLS solution. The inventors have mimicked the multi-way-PLS analyses by performing several sequential two-way PLS analyses on the data. The inventors used a Tcl based Cerius2 script[74] to automate the repetitive task of several PLS analyses.

Computation of Electrostatic Potential Surfaces

Electrostatic potential surfaces for the selected AMP conformers were computed as follows. The electrostatic potential were computed employing a grid with origin at its grid points, resolution of 65 points per axis and solute extending to 80 Å. The solute was defined with Gasteiger charges, VDW radii, dielectric constant of 2.0 and point charge distribution. The solvent dielectric constant was set to 80, solvent radii set to 1.4 Å, ionic strength set to 0.145 and the ionic radii was set to 2.0 Å. The molecular surfaces computed were Connolly surfaces with solid display style, using atom radii scale of 1.0, atom radii increment of 0.0 and probe radius of 1.4 Å. The surfaces were colored with Delphi spectrum using electrostatic potential grid as coloring method.

Conformational Search and Cluster Analysis

All peptides were subjected to Boltzmann Jump method of conformational search and a total of 2000 conformers were obtained. The global minimum conformer for each compound was obtained by exhaustive minimization of the least energy conformer. Table 15 summarizes the conformational search and cluster analysis data. The inventors used Tcl-based Cerius2 scripts[74] to automate the repetitive task of conformational searches and cluster analyses.

TABLE 15

Conformational Search & Cluster Analysis Data

| Compd # | Global min Energy Kcals/mol | # Torsion bonds | Highest Energy value of conformer | # Clusters Obtained | Energy Difference between Global minimum and Highest Energy conformer |
|---|---|---|---|---|---|
| FKAB-1 | −160.00 | 98 | 44.16 | 57 | −204.16 |
| FKAB-1F | −127.22 | 79 | −123.53 | 38 | −3.69 |
| FKAB-1G | 87.03 | 78 | 96.28 | 29 | −9.25 |
| FKAB-1Ga | 111.83 | 76 | 136.26 | 22 | −24.43 |
| FKAB-1Gb | 93.33 | 80 | 100.15 | 27 | −6.82 |
| FKAB-1Gc | 38.93 | 66 | 53.26 | 30 | −14.33 |
| FKAB-1Gc1 | 89.01 | 80 | 89.87 | 24 | −0.86 |
| FKAB-1Gd | −141.01 | 86 | −126.59 | 31 | −14.42 |
| FKAB-1Gd1 | −152.67 | 82 | −150.70 | 31 | −1.97 |
| FKAB-1Gd2 | −164.14 | 94 | −155.86 | 29 | −8.28 |
| FKAB-1Gd3 | −157.57 | 93 | −154.66 | 25 | −2.91 |
| FKAB-1Ge | 99.21 | 62 | 100.00 | 26 | −0.79 |
| FKAB-1Gf | 28.86 | 70 | 30.99 | 29 | −2.13 |
| FKAB-1Gf1 | 41.49 | 82 | 42.95 | 26 | −1.46 |
| FKAB-1Gg | 50.76 | 72 | 51.27 | 24 | −0.51 |
| FKAB-1Gg1 | 92.11 | 81 | 93.71 | 29 | −1.60 |

TABLE 15-continued

Conformational Search & Cluster Analysis Data

| Compd # | Global min Energy Kcals/mol | # Torsion bonds | Highest Energy value of conformer | # Clusters Obtained | Energy Difference between Global minimum and Highest Energy conformer |
|---|---|---|---|---|---|
| FKAB-1Gh | −32.71 | 90 | −20.09 | 26 | −12.62 |
| FKAB-1Gi | 78.81 | 85 | 89.36 | 26 | −10.55 |
| FKAB-1Gj | 133.86 | 74 | 140.37 | 25 | −6.51 |
| FKAB-1Go | 74.62 | 78 | 77.57 | 24 | −2.95 |
| FKAB-1Gp | 84.66 | 72 | 92.62 | 25 | −7.96 |
| FKAB-1H | 136.76 | 81 | 138.66 | 24 | −1.90 |
| FKAB-1L | 137.15 | 82 | 143.25 | 24 | −6.10 |
| FKAB-4 | −154.45 | 106 | −149.25 | 39 | −5.20 |
| WRFK-1 | −49.38 | 103 | −48.64 | 32 | −0.74 |
| WRFK-2 | −845.89 | 103 | −842.75 | 25 | −3.14 |
| WRFK-3 | −51.90 | 99 | −46.09 | 25 | −5.81 |
| WRFK-4 | −37.00 | 103 | −35.75 | 24 | −1.25 |
| WRFK-5 | −161.13 | 119 | −140.11 | 24 | −21.02 |

This methodology mines the 3D-encompassing conformations cluster nuclei to identify the conformer that most closely correlate with bioactivity. Further, the use of the gradual, stepwise refinement gives steady enrichment of bioactive conformers in each successive model.

3D-QSAR Model Development

Descriptor Computation

A total of 50 different 2D and 3D descriptors were calculated for all the compounds. The thermodynamic descriptors included are n-octanol/water partition coefficient (LogP), the desolvation free energy for water (Fh2o), the desolvation free energy for n-octanol (Foct), the partition coefficient computed on atom types reported by Ghosh et al[45, 46] (A log P and A log P 98), the molar refractivity (MR) computed based on refractive index, molecular weight, compound density, and the molar refractivity (MolRef) computed based on the atom-types with additive contributions reported by Ghosh et al[45, 46]. The thirty Jurs descriptors based on partial charges mapped on surface area were reported by Stanton et al[63] and are described in Table 2.

The four quantum mechanical descriptors included are HOMO_MOPAC, LUMO_MOPAC, DIPOLE_MOPAC, and HF_MOPAC. These are the HOMO, LUMO, dipole moment and heat of formation calculated by semi-empirical methods, which are generally known to provide more accurate values. The 3D-spatial descriptors are Density, and PMI-mag. The descriptor Density is defined as the ratio of molecular weight to molecular volume. The descriptor PMI-Mag is the magnitude of the principal moments of inertia about the principal axes of the conformers as described by Hill[83]. The descriptor Hf is a thermodynamic descriptor that gives the enthalpy of formation of the conformer as described by Dewar et al[84]. The conformational descriptor 'Energy' gives the energy of the conformer.

Descriptor Selection

The selection of descriptors is an important first step in QSAR study. A good correlation between the selected variables and the bioactivity will entail better bioactivity predictions[85]. The inventors adapted the descriptor selection strategy, reported earlier by Yao et al[86]. First, all descriptors that had very low correlation with bioactivity ($-|r|<~0.01$) were discarded. Next, the highly collinear descriptors ($-|$cross correlation coefficient$|>~0.9$) were identified. Those descriptors with more physical significance to offer mechanistic insight in the QSAR information were retained. For example, given a choice between Jurs-DPSA-2, Molecular weight, and HOMO, the Jurs-DPSA-2 was retained because it provides information about the difference between the positive and negative charged solvent accessible surface areas.

The cross correlation matrix was computed for the two models *Staphylococcus aureus* (SA), and *Mycobacterium ranae* (MR). The descriptors that showed very poor correlation with bioactivity (r<0.01) were removed. Table 16 shows the discarded descriptors and their correlation coefficients with bioactivity for the four models.

The cross correlation matrix showed that, all but 31 descriptors exhibited very high cross correlation ($-|r|>~0.9$). Table 17 summarizes the descriptor types, names and their cross-correlation coefficient values. These descriptors were removed to leave four sets of 23 different final descriptors which are shown in Table 18 for the two models.

TABLE 16

List of Descriptors with correlation of less than 0.01 with Bioactivity (BA)

*Staphylococcus aureus*

| Descriptor | 0.036 | 0.036 |
|---|---|---|
| Foct | −0.035 | 0.035 |
| Fh2o | 0.029 | 0.029 |
| Jurs-RNCS | −0.028 | 0.028 |
| Jurs-WPSA-2 | −0.024 | 0.024 |
| Jurs-TPSA | 0.009 | 0.009 |
| Area | 0.008 | 0.008 |
| MR | −0.008 | 0.008 |
| Jurs-RNCG | −0.005 | 0.005 |
| | 0.039 | |

*Mycobacterium ranae*

| Descriptor | Correlation with BioActivity | Abs(BA) |
|---|---|---|
| Conformer Rank | −0.079 | 0.079 |
| Jurs-RPCS | −0.074 | 0.074 |
| Fh2o | −0.061 | 0.061 |
| Jurs-RNCS | −0.049 | 0.049 |
| MR | 0.049 | 0.049 |

TABLE 17

Highly correlated (|r| > ~0.9) Descriptors and their Cross Correlation coefficients

(Part 1)

Jurs-SASA

| | |
|---|---|
| Jurs-SASA | 1.000 |
| Jurs-WPSA-1 | 0.992 |
| Jurs-PPSA-1 | 0.981 |
| Jurs-TASA | 0.971 |
| Jurs-WNSA-1 | 0.939 |
| PMI-mag | 0.924 |
| Area | 0.910 |

Jurs-PNSA-1

| | |
|---|---|
| Jurs-PNSA-1 | 1.000 |
| Jurs-WNSA-1 | 0.967 |

Jurs-FNSA-3

| | |
|---|---|
| Jurs-FNSA-2 | 0.905 |
| Jurs-PNSA-3 | 0.903 |

Jurs-WPSA-1

| | |
|---|---|
| Jurs-WPSA-1 | 1.000 |
| Jurs-SASA | 0.992 |
| Jurs-PPSA-1 | 0.989 |
| Jurs-TASA | 0.964 |
| PMI-mag | 0.919 |
| Jurs-WNSA-1 | 0.911 |
| Jurs-DPSA-1 | 0.904 |
| Area | 0.899 |

Apol

| | |
|---|---|
| Apol | 1.000 |
| Vm | 0.998 |
| Area | 0.994 |
| Chiral centers | 0.946 |

Jurs-PPSA-1

| | |
|---|---|
| Jurs-PPSA-1 | 1.000 |
| Jurs-WPSA-1 | 0.989 |
| Jurs-SASA | 0.981 |
| Jurs-TASA | 0.951 |
| Jurs-DPSA-1 | 0.950 |

Jurs-DPSA-1

| | |
|---|---|
| Jurs-DPSA-1 | 1.000 |
| Jurs-PPSA-1 | 0.950 |
| Jurs-WPSA-1 | 0.904 |

Jurs-TASA

| | |
|---|---|
| Jurs-TASA | 1.000 |
| Jurs-SASA | 0.971 |
| Jurs-WPSA-1 | 0.964 |
| Jurs-PPSA-1 | 0.951 |
| Jurs-WNSA-1 | 0.910 |
| Area | 0.903 |

Jurs-PPSA-2

| | |
|---|---|
| Jurs-PPSA-2 | 1.000 |
| Jurs-DPSA-2 | 0.995 |
| Jurs-WPSA-2 | 0.982 |
| Jurs-WPSA-3 | 0.971 |
| Jurs-FPSA-2 | 0.942 |
| Jurs-DPSA-3 | 0.935 |
| Jurs-WNSA-2 | −0.924 |
| Jurs-PPSA-3 | 0.911 |

Jurs-PNSA-2

| | |
|---|---|
| Jurs-PNSA-2 | 1.000 |
| Jurs-WNSA-2 | 0.980 |
| Jurs-WNSA-3 | 0.978 |
| Jurs-PNSA-3 | 0.962 |
| Jurs-FNSA-2 | 0.958 |
| Jurs-DPSA-2 | −0.934 |
| Jurs-DPSA-3 | −0.905 |

Jurs-DPSA-2

| | |
|---|---|
| Jurs-DPSA-2 | 1.000 |
| Jurs-PPSA-2 | 0.995 |
| Jurs-WPSA-2 | 0.974 |
| Jurs-WNSA-2 | −0.954 |
| Jurs-WPSA-3 | 0.950 |
| Jurs-DPSA-3 | 0.946 |
| Jurs-FPSA-2 | 0.942 |
| Jurs-PNSA-2 | −0.934 |
| Jurs-WNSA-3 | −0.919 |

(Part 2)

Jurs-WNSA-1

| | |
|---|---|
| Jurs-WNSA-1 | 1.000 |
| Jurs-PNSA-1 | 0.967 |
| Jurs-SASA | 0.939 |
| PMI-mag | 0.933 |
| Jurs-WPSA-1 | 0.911 |
| Jurs-TASA | 0.910 |

Jurs-WPSA-2

| | |
|---|---|
| Jurs-WPSA-2 | 1.000 |
| Jurs-PPSA-2 | 0.982 |
| Jurs-DPSA-2 | 0.974 |
| Jurs-WPSA-3 | 0.970 |
| Jurs-WNSA-2 | −0.927 |

Jurs-WNSA-2

| | |
|---|---|
| Jurs-WNSA-2 | 1.000 |
| Jurs-WNSA-3 | 0.981 |
| Jurs-PNSA-2 | 0.980 |
| Jurs-DPSA-2 | −0.954 |
| Jurs-WPSA-2 | −0.927 |
| Jurs-PPSA-2 | −0.924 |
| Jurs-PNSA-3 | 0.914 |

Jurs-WPSA-3

| | |
|---|---|
| Jurs-WPSA-3 | 1.000 |
| Jurs-PPSA-2 | 0.971 |
| Jurs-WPSA-2 | 0.970 |
| Jurs-DPSA-2 | 0.950 |
| Jurs-PPSA-3 | 0.946 |
| Jurs-DPSA-3 | 0.909 |

Area

| | |
|---|---|
| Area | 1.000 |
| Vm | 0.999 |
| Apol | 0.994 |
| Chiral centers | 0.946 |
| Jurs-SASA | 0.910 |
| Jurs-TASA | 0.903 |

Vm

| | |
|---|---|
| Vm | 1.000 |
| Area | 0.999 |
| Apol | 0.998 |
| Chiral centers | 0.952 |

PMI-mag

| | |
|---|---|
| PMI-mag | 1.000 |
| RadOfGyration | 0.937 |
| Jurs-WNSA-1 | 0.933 |
| Jurs-SASA | 0.924 |
| Jurs-WPSA-1 | 0.919 |

Chiral centers

| | |
|---|---|
| Chiral centers | 1.000 |
| Vm | 0.952 |

TABLE 17-continued

Highly correlated (|r| > ~0.9) Descriptors and their Cross Correlation coefficients

| Apol | 0.946 |
|---|---|
| Area | 0.946 |

Fh2o

| Fh2o | 1.000 |
|---|---|
| Foct | 0.980 |
| MR | −0.918 |

Jurs-PPSA-3

| Jurs-PPSA-3 | 1.000 |
|---|---|
| Jurs-WPSA-3 | 0.946 |
| Jurs-DPSA-3 | 0.933 |
| Jurs-FPSA-2 | 0.921 |
| Jurs-PPSA-2 | 0.911 |

Jurs-PNSA-3

| Jurs-PNSA-3 | 1.000 |
|---|---|
| Jurs-WNSA-3 | 0.962 |
| Jurs-PNSA-2 | 0.962 |
| Jurs-FNSA-2 | 0.959 |
| Jurs-WNSA-2 | 0.914 |
| Jurs-FNSA-3 | 0.903 |
| Jurs-DPSA-3 | −0.902 |

Jurs-DPSA-3

| Jurs-DPSA-3 | 1.000 |
|---|---|
| Jurs-FPSA-2 | 0.950 |
| Jurs-DPSA-2 | 0.946 |
| Jurs-PPSA-2 | 0.935 |
| Jurs-PPSA-3 | 0.933 |
| Jurs-WNSA-3 | −0.912 |
| Jurs-WPSA-3 | 0.909 |
| Jurs-PNSA-2 | −0.905 |
| Jurs-PNSA-3 | −0.902 |

Jurs-FPSA-1

| Jurs-FNSA-1 | −1.000 |
|---|---|
| Jurs-FPSA-1 | 1.000 |

(Part 3)

Jurs-WNSA-3

| Jurs-WNSA-3 | 1.000 |
|---|---|
| Jurs-WNSA-2 | 0.981 |
| Jurs-PNSA-2 | 0.978 |
| Jurs-PNSA-3 | 0.962 |
| Jurs-DPSA-2 | −0.919 |
| Jurs-DPSA-3 | −0.912 |
| Jurs-FNSA-2 | 0.900 |

Foct

| Foct | 1.000 |
|---|---|
| Fh2o | 0.980 |
| MR | −0.930 |

MR

| MR | 1.000 |
|---|---|
| Foct | −0.930 |
| Fh2o | −0.918 |

Jurs-FNSA-2

| Jurs-FNSA-2 | 1.000 |
|---|---|
| Jurs-PNSA-3 | 0.959 |
| Jurs-PNSA-2 | 0.958 |
| Jurs-FNSA-3 | 0.905 |
| Jurs-WNSA-3 | 0.900 |

AlogP

| AlogP | 1.000 |
|---|---|
| AlogP98 | 0.927 |

AlogP98

| AlogP98 | 1.000 |
|---|---|
| AlogP | 0.927 |

Jurs-FNSA-1

| Jurs-FPSA-1 | −1.000 |
|---|---|
| Jurs-FNSA-1 | 1.000 |

Jurs-FPSA-2

| Jurs-FPSA-2 | 1.000 |
|---|---|
| Jurs-DPSA-3 | 0.950 |
| Jurs-DPSA-2 | 0.942 |
| Jurs-PPSA-2 | 0.942 |
| Jurs-PPSA-3 | 0.921 |

RadOfGyration

| RadOfGyration | 1.000 |
|---|---|
| PMI-mag | 0.937 |

TABLE 18

Selected Descriptors for the two QSAR Models

| Staphylococcus aureus | Mycobacterium ranae |
|---|---|
| Fcharge | Conformer Energy |
| Dipole-mag | Fcharge |
| Jurs-SASA | Apol |
| Jurs-PPSA-1 | Dipole-mag |
| Jurs-PNSA-1 | Jurs-PPSA-1 |
| Jurs-PNSA-2 | Jurs-PNSA-1 |
| Jurs-DPSA-2 | Jurs-PPSA-2 |
| Jurs-DPSA-3 | Jurs-PNSA-2 |
| Jurs-FPSA-1 | Jurs-FPSA-1 |
| Jurs-FPSA-3 | Jurs-FNSA-3 |
| Jurs-FNSA-3 | Jurs-RPCG |
| Jurs-RPCG | Jurs-RNCG |
| Jurs-RPCS | Jurs-TPSA |
| Jurs-TASA | Jurs-RPSA |
| Jurs-RPSA | Jurs-RASA |
| Jurs-RASA | Density |
| Density | Hbond acceptor |
| Hbond acceptor | Hbond donor |
| Hbond donor | Rotlbonds |
| Rotlbonds | AlogP |
| AlogP | Foct |
| LogP | LogP |
| RadOfGyration | RadOfGyration |

Quasi-Multi-Way PLS Analyses

Bhonsle et al[74] has reported the use of automated quasi-multi-way PLS analyses for CoMFA based 3D-QSAR of cyclic pentapeptides CXCR4 inhibitors. They have mimicked the multi-way-PLS analyses by employing several automated two-way-PLS analyses using SYBYL[87] software. The PLS analysis procedure in C2 provides for a quick cross-validation of QSAR models. In this cross-validation procedure, only the "regression" part of the model development is cross-validated. This "regression-only" cross-validation was computed for all generation QSAR models. The non-validated $r^2$ and the sum of squares of predicted residual (PRESS) was used to guide the successive generations of model development. Bhonsle et al[74] have demonstrated a successful application of this approach for computation of highly predictive QSAR models for insect repellents.

Staphylococcus aureus (SA) and Mycobacterium ranae (MR) QSAR Model Development

The first generation SA and MR QSAR model were obtained by performing PLS analysis on 820 and 682 conformers of the twenty-nine and twenty-five AMPs respectively. The computed QSAR model showed non-validated $r^2$ of 0.695 and 0.873, and sum of squares of predicted residuals (PRESS) of 1560.52 and 273.96 respectively. The second (IInd) generation SA and MR models of 549 and 454 conformers were obtained as follows. The predicted residual values of several conformers of the same compound in the first generation model showed almost identical values. A closer examination of the descriptor values of all such conformers showed that the descriptor values were also almost identical. Thus, all such 'duplicate' conformers were removed. The computed SA and MR QSAR models showed non-validated $r^2$ of 0.698 and 0.878, and PRESS value of 1081.29 and 185.54 respectively.

For all of the following QSAR models, the inventors eliminated the worst residual value conformer is a stepwise and gradual fashion. The inventors used the non-validated $r^2$ and PRESS as measures to guide the model improvement.

The IIIrd generation SA and MR models of 290 and 250 conformers were obtained by selecting 10 least residual values conformers and it showed non-validated $r^2$ of 0.677 and 0.874, and PRESS value of 502.99 and 100.23. While, the IVth generation SA and MR models of 145 and 125 conformers were constructed with five least residual value conformers from IIIrd generation SA and MR models respectively. These models displayed non-validated $r^2$ of 0.682 and 0.88, and PRESS value of 269.75 and 54.98, respectively for the SA and MR models. The Vth generation SA and MR models of 58 and 50 conformers were obtained with two least residual value conformers, and it exhibited non-validated $r^2$ of 0.687 and 0.879, and PRESS value of 185.75 and 30.12 respectively. The VIth generation SA and MR models of 58 and 50 conformers were obtained by employing 22 components instead of 6 to furnish more complex, but better models, with non-validated $r^2$ of 0.972 and 0.995, and PRESS value of 84.84 and 17.96 respectively. The VIIth generation model for *Staphylococcus aureus* was constructed by eliminating the worst residual value conformers of all AMPs with p(MIC) with p(MIC) {viz. −log(MIC)} less than 4.52. For the remaining 12 AMPs, namely FKAB-1Go, FKAB-1I, FKAB-1F, WRFK-1, WRFK-2, WRFK-4, FKAB-1G, FKAB-1Gc1, FKAB-1Gc, FKAB-1Gi, FKAB-1Gp, and FKAB-1H, two conformers each were retained in the model. This QSAR model with 41 conformers had non-validated $r^2$ of 0.972, and PRESS value of 84.84. Whereas, the VIIth generation model for *Mycobacterium ranae* was constructed by removing the worst residual value conformers of all AMPs with p(MIC) less than 4.52. For the remaining 12 AMPs, namely FKAB-1Gj, FKAB-1I, FKAB-1Gd2, FKAB-1Gd3, FKAB-1Ge, FKAB-1Go, FKAB-1Gb, FKAB-1Gc1, FKAB-1Gd1, FKAB-1Gi, FKAB-1Gp, and FKAB-1H, two conformers each were retained in the model. This QSAR model with 37 conformers had non-validated $r^2$ of 0.993, and PRESS value of 29.19.

At this juncture, there were 24 conformers from which the best set of 12 conformers could be chosen in 4096 ($2^{12}$) ways for both of the SA and MR QSAR models. The inventors used a Tcl-based Cerius2 script[74] to compute these 4096 eighth (VIIth) generation models. The inventors found the best SA and MR models with leave-one-out (regression-only) cross-validated $r^2$ of 0.421 and 0.598 respectively. These VIIth generation SA and MR QSAR model showed non-validated $r^2$ of 0.988 and 0.997, leave-one-out cross-validated $r^2$ of 0.839 and 0.997, and PRESS value of 22.92 and 29.19 respectively.

The statistical data of all the eight-generation models, for the *Salmonella typhimurium, Staphylococcus aureus*, and *Mycobacterium ranae*, obtained during the QSAR model development phases, is presented in Table 19.

TABLE 19

All Generation QSAR Models Statistical data

|  | QSAR Model Generation Number | Number of Conformers in Model | Non-validated r2 | Leave-One-Out Cross-validated (regression only) q2 | PRESS |
| --- | --- | --- | --- | --- | --- |
| *Staphylococcus aureus* | 1 | 820 | 0.695 | 0.687 | 1560.53 |
|  | 2 | 549 | 0.698 | 0.686 | 1081.29 |
|  | 3 | 290 | 0.677 | 0.647 | 502.99 |
|  | 4 | 145 | 0.682 | 0.621 | 269.75 |
|  | 5 | 58 | 0.687 | 0.347 | 185.75 |
|  | 6 | 58 | 0.965 | 0.672 | 93.23 |
|  | 7 | 41 | 0.972 | 0.467 | 84.84 |
|  | 8 | 29 | 0.988 | 0.839 | 22.92 |
| *Mycobacterium ranae* | 1 | 682 | 0.873 | 0.869 | 273.96 |
|  | 2 | 454 | 0.878 | 0.872 | 185.54 |
|  | 3 | 250 | 0.874 | 0.862 | 100.23 |
|  | 4 | 125 | 0.88 | 0.849 | 54.98 |
|  | 5 | 50 | 0.879 | 0.793 | 30.12 |
|  | 6 | 50 | 0.995 | 0.876 | 17.96 |
|  | 7 | 37 | 0.993 | 0.5 | 40.62 |
|  | 8 | 25 | 0.997 | 0.598 | 29.19 |

The QSAR Models/Equations

QSAR Equation Analysis

The *Staphylococcus aureus* QSAR model is described by the following equation:

SA Predicted Activity=−1.49592*"*F*charge"+ 0.0098147*"Dipole-mag"+0.013993*"Jurs-SASA"+0.00233*"Jurs-PPSA-1"+ 0.187647*"Jurs-PNSA-1"+0.0021686*"Jurs-PNSA-2"+0.00036919*"Jurs-DPSA-2"+ 0.0015025*"Jurs-DPSA-3"+438.251*"Jurs-FPSA-1"+267.258*"Jurs-FPSA-3"+ 120.432*"Jurs-FNSA-3"−715.316*"Jurs-RPCG"−12.8649*"Jurs-RPCS"−0.065752*"Jurs-TASA"−125.513*"Jurs-RPSA"+125.513*"Jurs-RASA"−183.99*"Density"+1.03397*"*H*bond acceptor"+0.039473*"*H*bond donor"− 0.306856*"Rotlbonds"+0.114808*"*A* log *P*"−0.10004*"RadOfGyration"−225.589

The *Staphylococcus aureus* QSAR model with the selected conformers, predicted bioactivities, and residual values is presented in Table 20.

TABLE 20

Predictive *Staphylococcus aureus* QSAR Model selected conformers, predicted Bioactivities, and residual prediction errors.

| AMP ID | Conformer # | Actual Bioactivity | Model # A Predicted Bioactivity | Residual of Predicted Bioactivity |
|---|---|---|---|---|
| FKAB-1F | 19 | 5.000 | 5.072 | −0.07 |
| FKAB-1G | 6 | 5.520 | 5.105 | 0.42 |
| FKAB-1Ga | 8 | 5.000 | 4.906 | 0.09 |
| FKAB-1Gb | 10 | 4.520 | 4.335 | 0.19 |
| FKAB-1Gc | 11 | 5.520 | 5.824 | −0.30 |
| FKAB-1Gc1 | 10 | 5.520 | 5.851 | −0.33 |
| FKAB-1Gd | 14 | 4.000 | 4.407 | −0.41 |
| FKAB-1Gd1 | 4 | 5.000 | 4.522 | 0.48 |
| FKAB-1Gd2 | 16 | 5.000 | 5.380 | −0.38 |
| FKAB-1Gd3 | 6 | 4.520 | 3.597 | 0.92 |
| FKAB-1Ge | 13 | 5.000 | 5.006 | −0.01 |
| FKAB-1Gf | 9 | 0.000 | −0.016 | 0.02 |
| FKAB-1Gf1 | 11 | 0.000 | 0.175 | −0.18 |
| FKAB-1Gg | 2 | 0.000 | −0.033 | 0.03 |
| FKAB-1Gg1 | 1 | 0.000 | 0.480 | −0.48 |
| FKAB-1Gh | 1 | 5.000 | 4.675 | 0.32 |
| FKAB-1Gi | 8 | 5.520 | 6.350 | −0.83 |
| FKAB-1Gj | 17 | 5.000 | 4.294 | 0.71 |
| FKAB-1Go | 1 | 5.000 | 4.986 | 0.01 |
| FKAB-1Gp | 5 | 5.520 | 5.450 | 0.07 |
| FKAB-1H | 2 | 5.520 | 5.447 | 0.07 |
| FKAB-1L | 22 | 5.000 | 5.207 | −0.21 |
| FKAB-4 | 1 | 0.000 | 0.003 | 0.00 |
| WRFK-1 | 5 | 5.000 | 5.047 | −0.05 |
| WRFK-2 | 8 | 5.000 | 5.053 | −0.05 |
| WRFK-3 | 1 | 4.000 | 3.939 | 0.06 |
| WRFK-4 | 10 | 5.000 | 5.027 | −0.03 |
| WRFK-5 | 17 | 4.520 | 4.431 | 0.09 |

Figure 7:
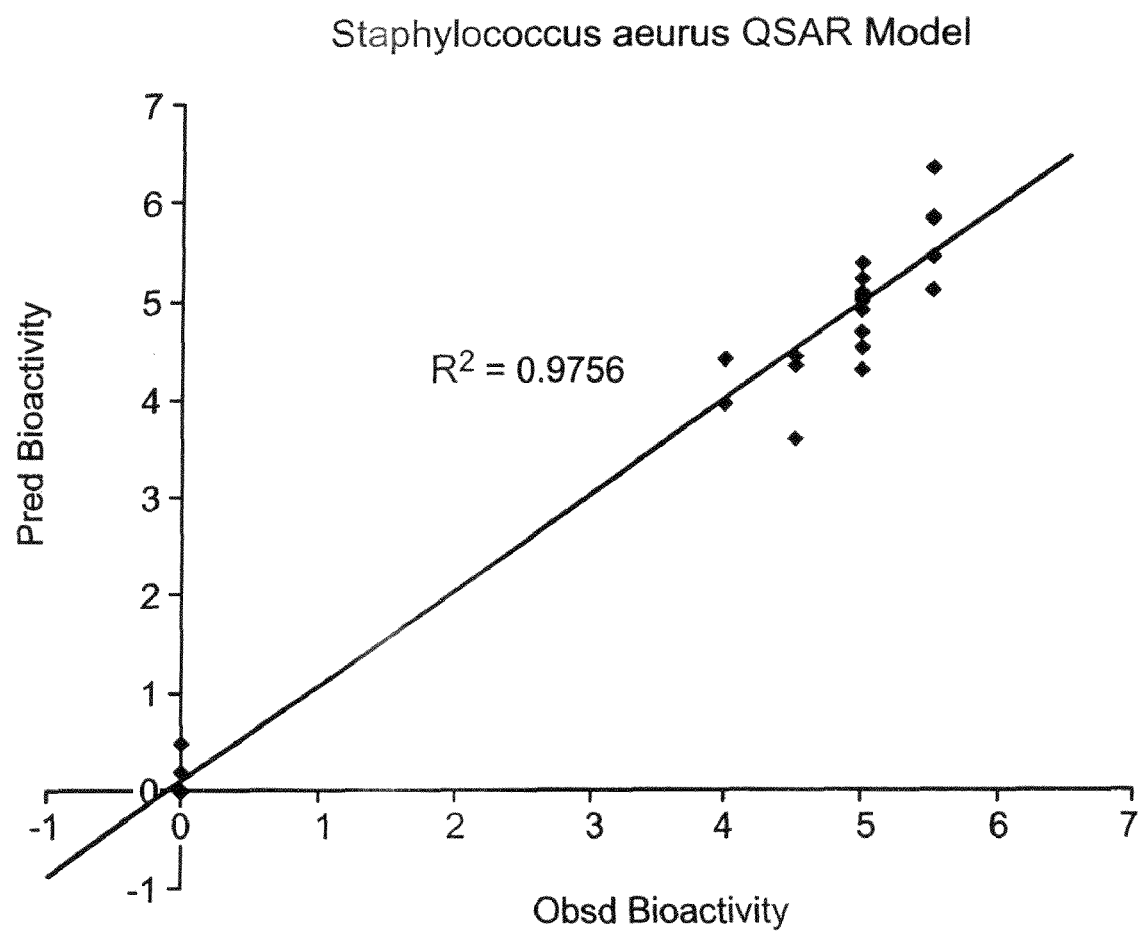
FIG. 7 shows the SA QSAR model with observed bioactivity versus the predicted bioactivity.

FIG. 7 shows the SA QSAR model with observed bioactivity versus the predicted bioactivity.

The *Mycobacterium ranae* QSAR model is described by the following equation:

MR Predicted Activity=−0.0083585*"Conformer Energy"+2.05758*"$F$charge"+5.3259$e$-05*"$A$pol"+0.0061422*"Dipole-mag"−0.023941*"Jurs-PPSA-1"−0.008252*"Jurs-PNSA-1"+5.5381$e$-05*"Jurs-PPSA-2"+0.00018566*"Jurs-PNSA-2"−18.282*"Jurs-FPSA-1"+13.321*"Jurs-FNSA-3"−8.46841*"Jurs-RPCG"+66.6262*"Jurs-RNCG"+0.052889*"Jurs-TPSA"−96.9761*"Jurs-RPSA"+96.9761*"Jurs-RASA"−127.577*"Density"+0.768698*"$H$bond acceptor"−0.498282*"$H$bond donor"−0.060764*"Rotlbonds"−0.075759*"$A$log $P$"+0.337835*"RadOfGyration"+110.841

The final *Mycobacterium ranae* QSAR model with the selected conformers, predicted bioactivities, and residual values is presented in Table 21.

TABLE 21

Predictive *Mycobacterium ranae* QSAR Model selected conformers, predicted Bioactivities, and residual prediction errors

| AMP ID | Conformer # | Actual Bioactivity | Predicted Bioactivity | Residual of Predicted Bioactivity |
|---|---|---|---|---|
| FKAB-1F | 1 | 4.520 | 4.463 | 0.057 |
| FKAB-1G | 9 | 5.000 | 4.883 | 0.117 |
| FKAB-1Ga | 2 | 5.000 | 4.940 | 0.060 |
| FKAB-1Gb | 8 | 5.520 | 5.554 | −0.034 |
| FKAB-1Gc | 10 | 4.520 | 4.552 | −0.032 |
| FKAB-1Gc1 | 1 | 5.520 | 5.528 | −0.008 |
| FKAB-1Gd | 21 | 5.000 | 5.239 | −0.239 |
| FKAB-1Gd1 | 4 | 6.000 | 6.024 | −0.024 |
| FKAB-1Gd2 | 25 | 5.520 | 5.306 | 0.214 |
| FKAB-1Gd3 | 6 | 5.520 | 5.572 | −0.052 |
| FKAB-1Ge | 23 | 5.520 | 5.542 | −0.022 |
| FKAB-1Gf | 13 | 4.000 | 4.081 | −0.081 |
| FKAB-1Gf1 | 22 | 4.000 | 3.907 | 0.093 |
| FKAB-1Gg | 1 | 4.520 | 4.442 | 0.078 |
| FKAB-1Gg1 | 12 | 4.520 | 4.577 | −0.057 |
| FKAB-1Gh | 24 | 5.000 | 5.059 | −0.059 |
| FKAB-1Gi | 7 | 5.520 | 5.346 | 0.174 |
| FKAB-1Gj | 1 | 5.000 | 5.023 | −0.023 |
| FKAB-1Go | 3 | 5.520 | 5.556 | −0.036 |
| FKAB-1Gp | 11 | 5.000 | 5.014 | −0.014 |
| FKAB-1H | 4 | 5.000 | 4.875 | 0.125 |
| FKAB-1L | 5 | 5.000 | 5.201 | −0.201 |
| FKAB-4 | 27 | 0.000 | −0.002 | 0.002 |
| WRFK-2 | 1 | 0.000 | −0.020 | 0.020 |
| WRFK-5 | 9 | 0.000 | 0.058 | −0.058 |

Figure 8:
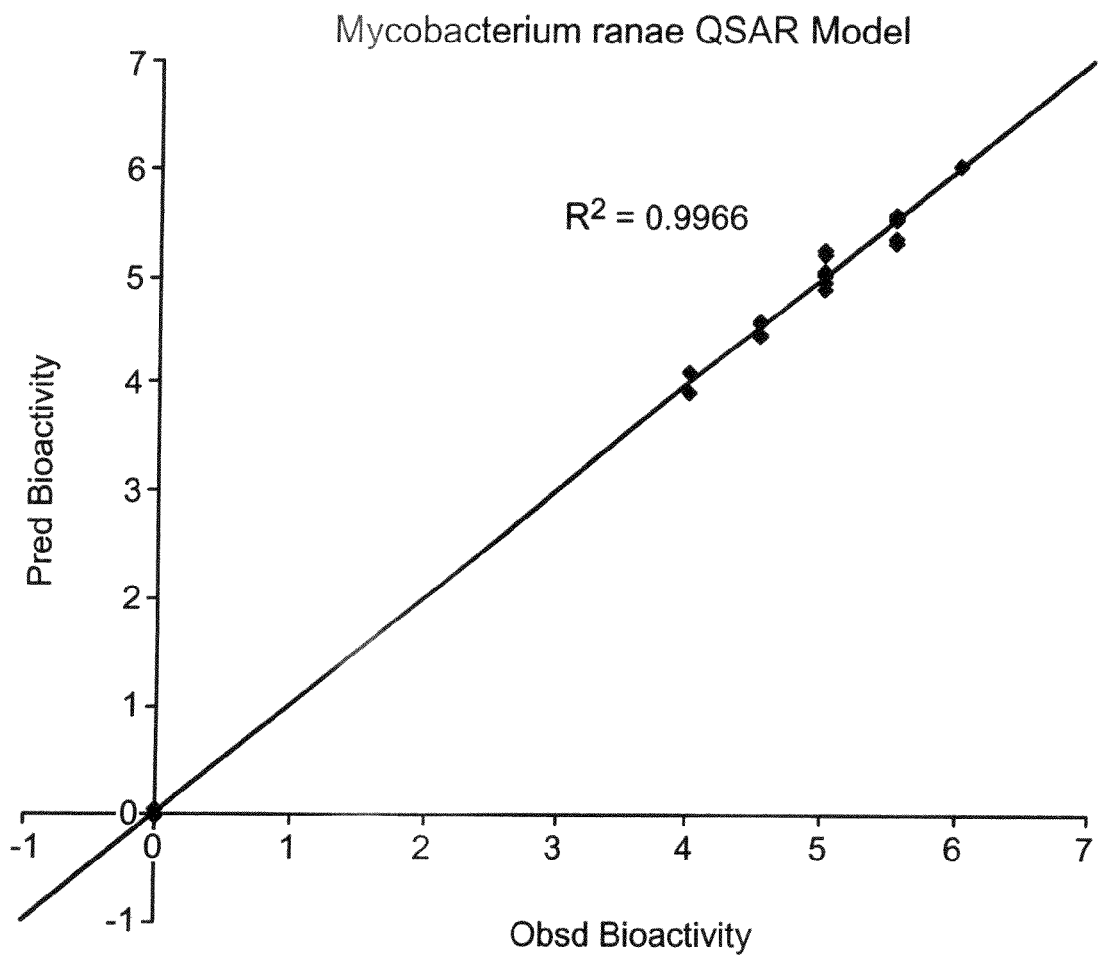
FIG. 8 shows the MR QSAR model with observed bioactivity versus the predicted bioactivity.

FIG. 8 shows the MR QSAR model with observed bioactivity versus the predicted bioactivity.

Computation of Descriptor Significance Percentage (DSP)

The values and sign of the QSAR equation coefficients provide a qualitative insight in the correlation of the physicochemical properties with biological activity. The quantitative contribution of any physicochemical property to the bioactivity of the compound is judged from both the respective QSAR equation coefficient and the value of the descriptor quantifying the property. The product of the QSAR coefficients and the respective descriptor mean value (Descriptor_Mean=ΣDescriptor_values_all_training_set_compounds/30)

would provide the contribution value of that descriptor to the overall bioactivity (Contribution_to_BioActivity—CtoBA).

$CtoBA = QSAR$_Coefficient*Descriptor_mean_value

The significance of CtoBA of any descriptor vis-à-vis the CtoBA of all the other descriptors can be computed by dividing the individual CtoBA by the sum total of all the CtoBA of all descriptors. The percentage value of this quotient is termed as 'Descriptor Significance Percentage—DSP'.

$DSP = (CtoBA*100)/\Sigma abs(CtoBA)$

The DSP values would provide a better insight in the quantitative contributions of the descriptors to the bioactivities of the compounds. The QSAR coefficients for the SA and MR QSAR model, CtoBA, and DSP values are presented in Table 22 and Table 23 respectively.

TABLE 22

Computation of Descriptor Significance Percentage (DSP) for *Staphyloccocus aureus* QSAR Model

| Descriptor Name | *Staphylococcus aureus* QSAR Model Predicted Bioactivity | Mean Values of Descriptors of all compounds (MVD) | Contribution of Descriptor to BioActivity = Coefficient * Descriptors Mean (CtoBA) | Absolute (Coefficient * Mean) | Descriptor Significance Percentage DSP = CtoBA * 100/ Sum_Of_All_CtoBA | Abs(DSP) |
|---|---|---|---|---|---|---|
| AlogP | 0.115 | −2.694 | −0.309 | 0.309 | −0.026 | 0.026 |
| Density | −183.990 | 1.052 | −193.628 | 193.628 | −16.010 | 16.010 |
| Dipole-mag | 0.010 | 199.158 | 1.955 | 1.955 | 0.162 | 0.162 |
| Fcharge | −1.496 | 6.000 | −8.976 | 8.976 | −0.742 | 0.742 |
| Hbond acceptor | 1.034 | 22.345 | 23.104 | 23.104 | 1.910 | 1.910 |
| Hbond donor | 0.039 | 34.517 | 1.362 | 1.362 | 0.113 | 0.113 |
| Jurs-DPSA-2 | 0.00037 | 101316.629 | 37.405 | 37.405 | 3.093 | 3.093 |
| Jurs-DPSA-3 | 0.00150 | 429.447 | 0.645 | 0.645 | 0.053 | 0.053 |
| Jurs-FNSA-3 | 120.432 | −0.043 | −5.157 | 5.157 | −0.426 | 0.426 |
| Jurs-FPSA-1 | 438.251 | 0.810 | 354.927 | 354.927 | 29.347 | 29.347 |
| Jurs-FPSA-3 | 267.258 | 0.077 | 20.664 | 20.664 | 1.709 | 1.709 |
| Jurs-PNSA-1 | 0.188 | 679.305 | 127.469 | 127.469 | 10.540 | 10.540 |
| Jurs-PNSA-2 | 0.00217 | −16233.835 | −35.205 | 35.205 | −2.911 | 2.911 |
| Jurs-PPSA-1 | 0.00233 | 2881.175 | 6.713 | 6.713 | 0.555 | 0.555 |
| Jurs-RASA | 125.513 | 0.760 | 95.372 | 95.372 | 7.886 | 7.886 |
| Jurs-RPCG | −715.316 | 0.012 | −8.784 | 8.784 | −0.726 | 0.726 |
| Jurs-RPCS | −12.865 | 0.118 | −1.522 | 1.522 | −0.126 | 0.126 |
| Jurs-RPSA | −125.513 | 0.240 | −30.141 | 30.141 | −2.492 | 2.492 |
| Jurs-SASA | 0.014 | 3560.480 | 49.822 | 49.822 | 4.120 | 4.120 |
| Jurs-TASA | −0.066 | 2715.292 | −178.536 | 178.536 | −14.762 | 14.762 |
| RadOfGyration | −0.100 | 15.399 | −1.541 | 1.541 | −0.127 | 0.127 |
| Rotlbonds | −0.307 | 85.276 | −26.167 | 26.167 | −2.164 | 2.164 |
| QSAR Coefficient | | −225.589 | | | | |

TABLE 23

Computation of Descriptor Significance Percentage (DSP) for *Mycobacterium ranae* QSAR Model

| Descriptor Name | *Mycobacterium ranae* QSAR Model Predicted Bioactivity | Mean Values of Descriptors of all compounds (MVD) | Contribution of Descriptor to BioActivity = Coefficient * Descriptors Mean (CtoBA) | Absolute (Coefficient * Mean) | DSP = CtoBA * 100/Sum_Of_All_CtoBA | Abs(DSP) |
|---|---|---|---|---|---|---|
| AlogP | −0.076 | −2.951 | 0.224 | 0.224 | 0.051 | 0.051 |
| Apol | 0.000 | 93855.529 | 4.999 | 4.999 | 1.148 | 1.148 |
| Conformer Energy | −0.008 | −19.432 | 0.162 | 0.162 | 0.037 | 0.037 |
| Density | −127.577 | 1.051 | −134.041 | 134.041 | −30.784 | 30.784 |
| Dipole-mag | 0.006 | 211.567 | 1.299 | 1.299 | 0.298 | 0.298 |
| Fcharge | 2.058 | 6.120 | 12.592 | 12.592 | 2.892 | 2.892 |
| Hbond acceptor | 0.769 | 21.120 | 16.235 | 16.235 | 3.729 | 3.729 |
| Hbond donor | −0.498 | 34.120 | −17.001 | 17.001 | −3.905 | 3.905 |
| Jurs-FNSA-3 | 13.321 | −0.042 | −0.555 | 0.555 | −0.127 | 0.127 |
| Jurs-FPSA-1 | −18.282 | 0.812 | −14.844 | 14.844 | −3.409 | 3.409 |
| Jurs-PNSA-1 | −0.008 | 656.338 | −5.416 | 5.416 | −1.244 | 1.244 |
| Jurs-PNSA-2 | 0.000 | −14815.738 | −2.751 | 2.751 | −0.632 | 0.632 |
| Jurs-PPSA-1 | −0.024 | 2818.021 | −67.466 | 67.466 | −15.494 | 15.494 |
| Jurs-PPSA-2 | 0.000 | 79913.288 | 4.426 | 4.426 | 1.016 | 1.016 |
| Jurs-RASA | 96.976 | 0.756 | 73.270 | 73.270 | 16.827 | 16.827 |
| Jurs-RNCG | 66.626 | 0.026 | 1.740 | 1.740 | 0.400 | 0.400 |
| Jurs-RPCG | −8.468 | 0.012 | −0.105 | 0.105 | −0.024 | 0.024 |
| Jurs-RPSA | −96.976 | 0.244 | −23.706 | 23.706 | −5.444 | 5.444 |
| Jurs-TPSA | 0.053 | 841.186 | 44.489 | 44.489 | 10.218 | 10.218 |
| RadOfGyration | 0.338 | 15.003 | 5.068 | 5.068 | 1.164 | 1.164 |
| Rotlbonds | −0.061 | 82.840 | −5.034 | 5.034 | −1.156 | 1.156 |
| QSAR Coefficient | | 110.841 | | | | |

Comparison of SA and MR QSAR Models: Insights in Mechanism of Action

The sixteen physiochemical properties common to the SA and MR QSAR models are shown in Table 24. The six physicochemical properties specific to the SA QSAR model are Jurs-FPSA-3, Jurs-RPCS. Jurs-DPSA-2, Jurs-DPSA-3, Jurs-SASA and Jurs-TASA. While the five physicochemical properties specific to the MR QSAR model are Apol, Conformer Energy, Jurs-PPSA-2, Jurs-RNCG, and Jurs-TPSA. The commonality of physicochemical properties show the minimal requirement for activity against SA and MR. The physicochemical properties such as Dipole-mag, Fcharge, Jurs-FNSA-3, Jurs-RPSA, Jurs-FPSA-1, Jurs-PNSA-1, Jurs-PNSA-2, Jurs-PPSA-1, and Jurs-RPCG indicate the importance of electrostatic potential for the AMPs bioactivity. While the physicochemical properties such as Density, H-bond acceptor, Jurs-RASA, H-bond donor, RadOfGyration, and Rotlbonds indicate the significance of the AMP molecular shape (appropriate conformation) for bioactivity. The importance of amphiphilicity is alluded to by the physicochemical properties such as Jurs-RASA, Jurs-RPSA, and A log P . The magnitude order sorted DSP for the SA QSAR model is presented in Table 25. The top six DSP viz. Jurs-FPSA-1 (29.35), Density (−16.01), Jurs-TASA (−14.76), Jurs-PNSA-1 (10.54), Jurs-RASA (7.89), and Jurs-SASA (4.12) account for 82% of the SA predicted activity.

TABLE 24

A Rank ordering of the Physicochemical Properties defining anti-bacterial activity

| Physico-chemical property | Staphylococcus aureus QSAR_DSP | Physico-chemical property | Mycobacterium ranae QSAR_DSP |
|---|---|---|---|
| Jurs-FPSA-1 | 29.347 | Density | −30.784 |
| Density | −16.01 | Jurs-RASA | 16.827 |
| Jurs-TASA | −14.762 | Jurs-PPSA-1 | −15.494 |
| Jurs-PNSA-1 | 10.54 | Jurs-TPSA | 10.218 |
| Jurs-RASA | 7.886 | Jurs-RPSA | −5.444 |
| Jurs-SASA | 4.12 | Hbond donor | −3.905 |
| Jurs-DPSA-2 | 3.093 | Hbond acceptor | 3.729 |
| Jurs-PNSA-2 | −2.911 | Jurs-FPSA-1 | −3.409 |
| Jurs-RPSA | −2.492 | Fcharge | 2.892 |
| Rotlbonds | −2.164 | Jurs-PNSA-1 | −1.244 |
| Hbond acceptor | 1.91 | RadOfGyration | 1.164 |
| Jurs-FPSA-3 | 1.709 | Rotlbonds | −1.156 |
| Fcharge | −0.742 | Apol | 1.148 |
| Jurs-RPCG | −0.726 | Jurs-PPSA-2 | 1.016 |
| Jurs-PPSA-1 | 0.555 | Jurs-PNSA-2 | −0.632 |
| Jurs-FNSA-3 | −0.426 | Jurs-RNCG | 0.4 |
| Dipole-mag | 0.162 | Dipole-mag | 0.298 |
| RadOfGyration | −0.127 | Jurs-FNSA-3 | −0.127 |
| Jurs-RPCS | −0.126 | AlogP | 0.051 |
| Hbond donor | 0.113 | Conformer | 0.037 |
| Jurs-DPSA-3 | 0.053 | Jurs-RPCG | −0.024 |
| AlogP | −0.026 | Jurs-DPSA-2 | 0 |

Figure 9:
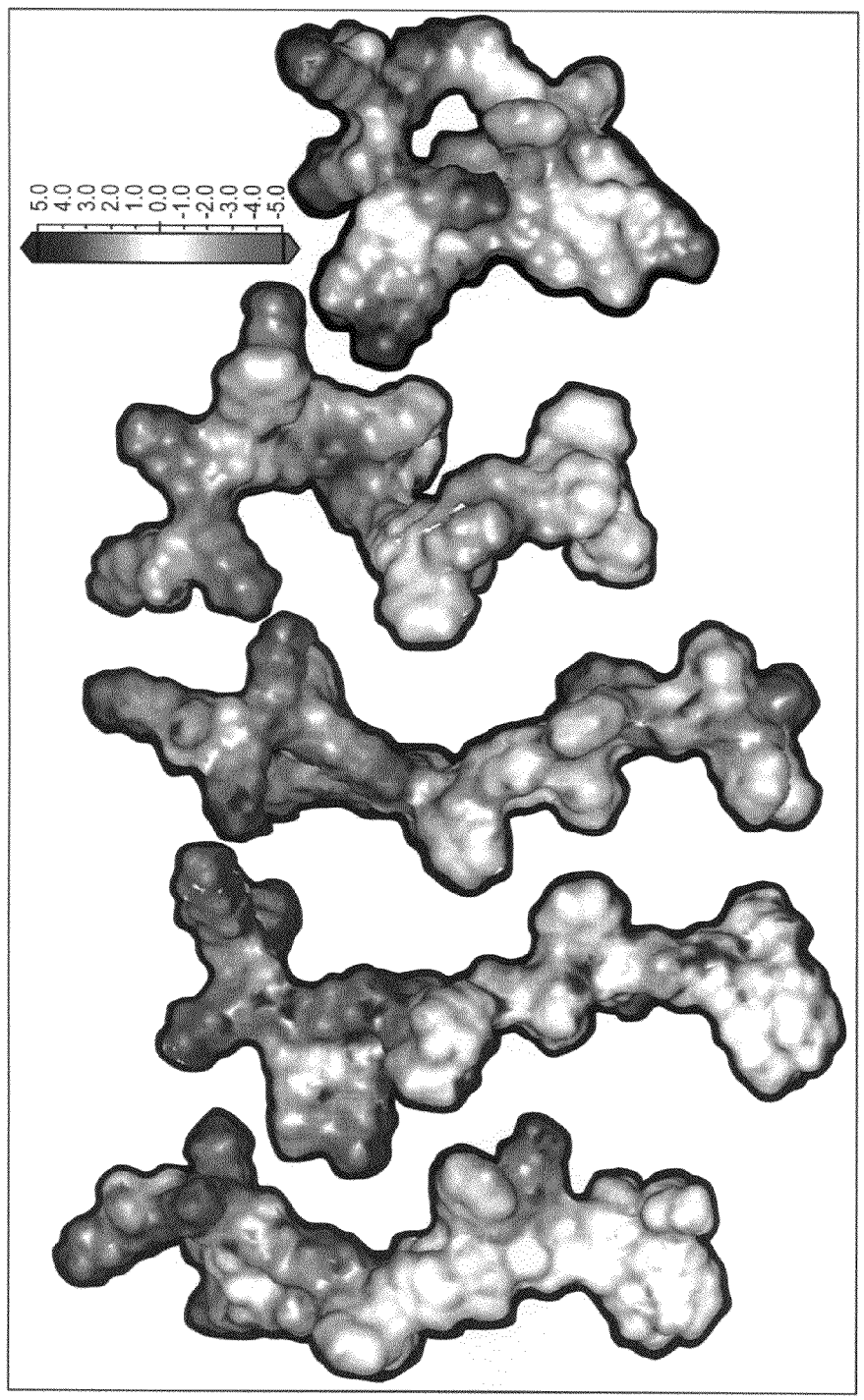
FIG. 9 shows the non-polar face of AMPs *Staphylococcus aureus* FKAB-1G, FKAB-1Go, FKAB-1Gb, FKAB-1Gd, and FKAB-1Gg.
Figure 10:
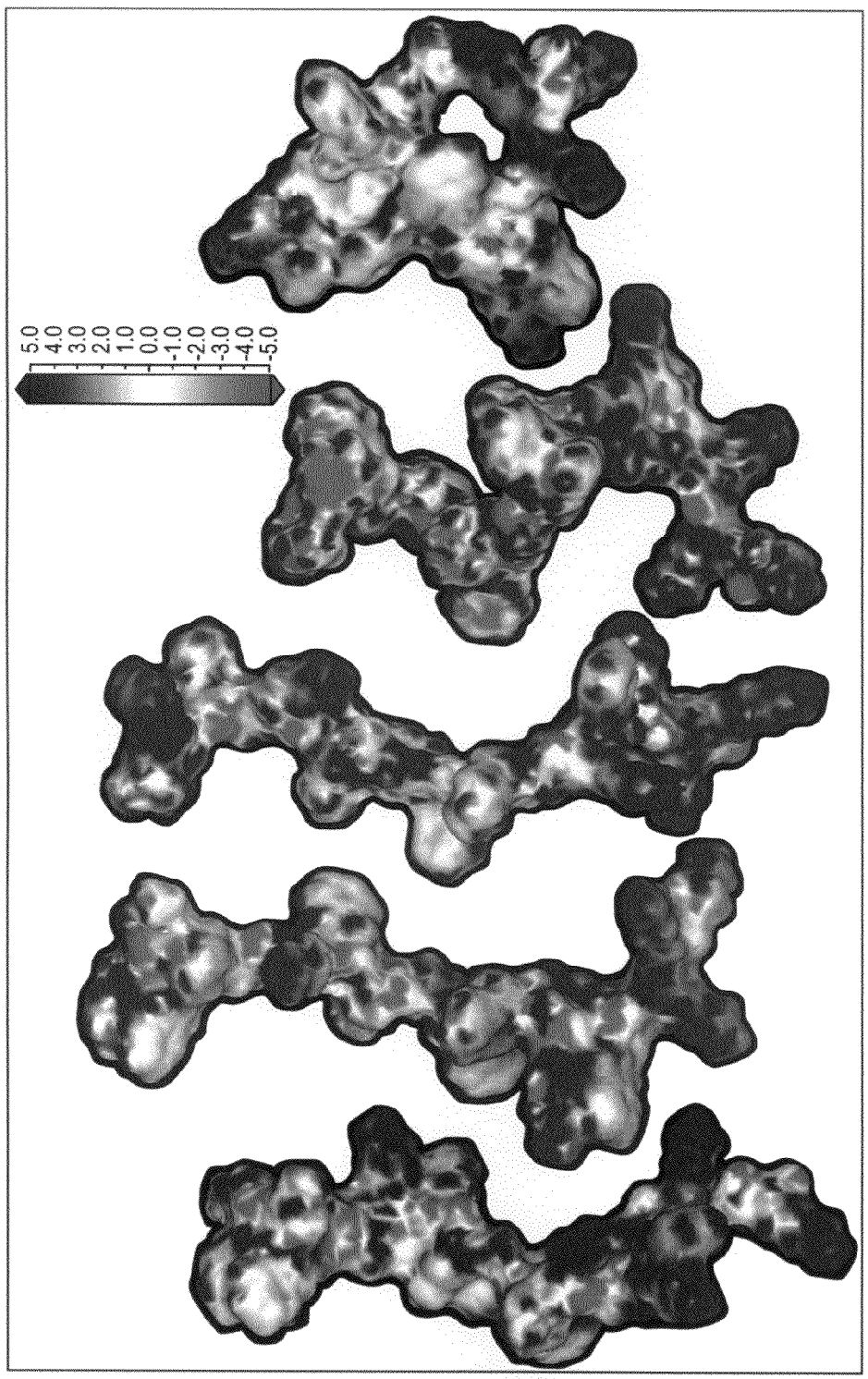
FIG. 10 shows the polar face of AMPs *Staphylococcus aureus* FKAB-1G, FKAB-1Go, FKAB-1Gb, FKAB-1Gd, and FKAB-1Gg.

To study the significance of electrostatics and sterics in the SA activity, the inventors selected five representative AMPs from each activity class as follows. The inventors chose FKAB-1G from 3 μM, FKAB-1Go from 10 μM, FKAB-1Gb from 30 μM, FKAB-1Gd from 100 μM, and FKAB-1Gg from inactive activity classes respectively. The Delphi spectrum electrostatic potential surface of these AMPs shown in FIG. 9 and FIG. 10 indicate that all AMPs have a distinct non-polar face and polar face. The correlation of non-polar surface area to bioactivity is seen from the descriptors Jurs—Total Hydrophobic Surface Area (Jurs-TASA) with −14.76% DSP contribution and Jurs—Relative Hydrophobic Surface Area (Jurs-RASA) with 7.89% DSP contribution. The 180 degrees opposite face of all the AMPs is presented in FIG. 10. The active AMPs (p(MIC)<100) show more polar surface area than the inactive AMP FKAB-1Gg. The high polar surface area correlation with bioactivity is shown by the Jurs—Fractional Positive Surface Area—1 (Jurs-FPSA-1) with 29.4% DSP contribution and Jurs—Partial Negatively charged Surface Area—1 (Jurs-PNSA-1) with 10.5% DSP contribution. The shape of the AMPs is critical for bioactivity as is seen in FIG. 9 and FIG. 10. An open helical shape is required for activity. A globular shape as that of FKAB-1Gg relates to loss of SA bioactivity. The shape correlation to bioactivity is illustrated by the descriptor Density with −16.01% DSP contribution and Jurs—Sum of Solvent Accessible Surface Area (Jurs-SASA) with 4.12% DSP contribution.

Figure 11:
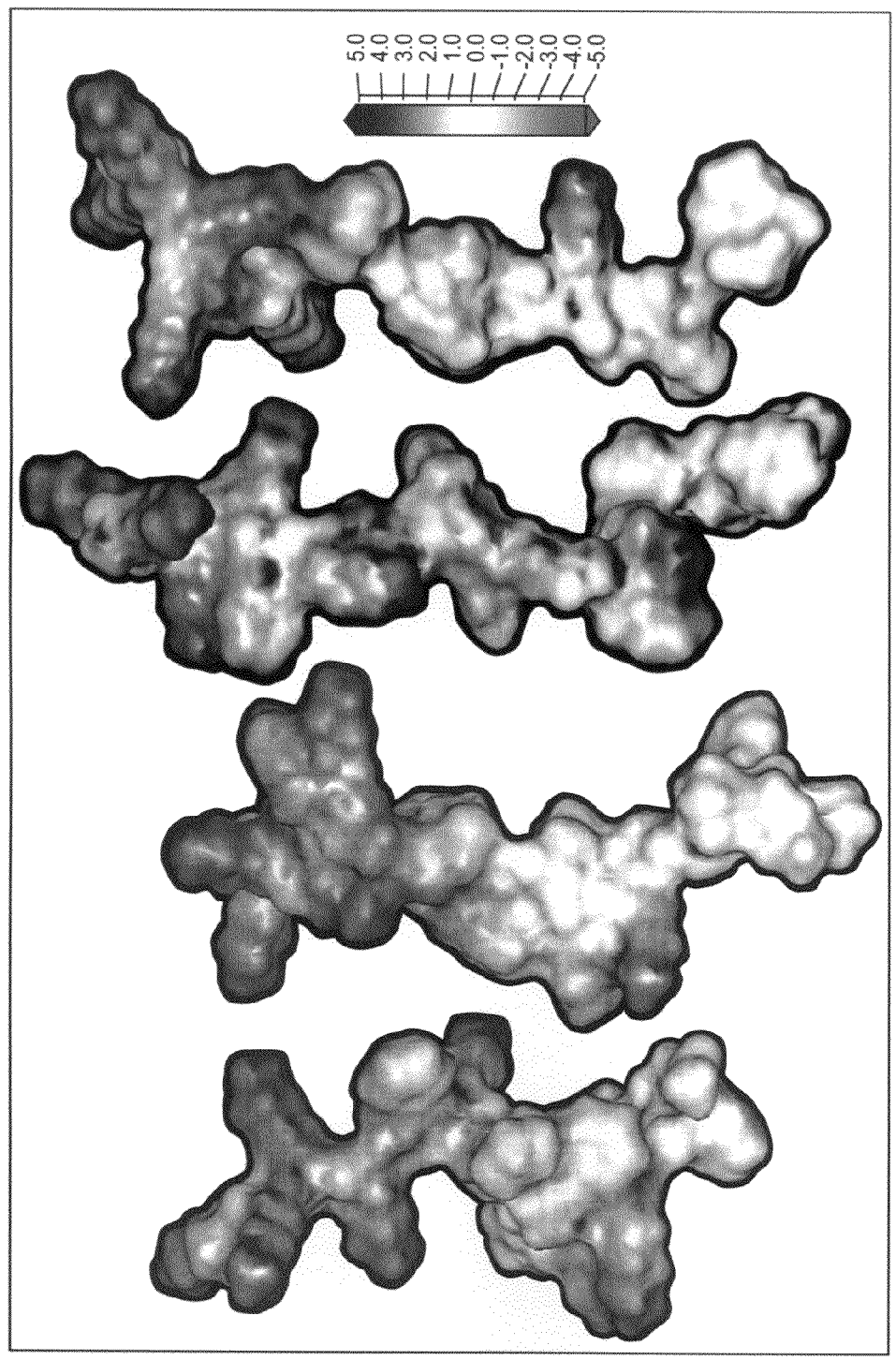
FIG. 11 shows the non-polar face of AMPs *Mycobacterium ranae* FKAB-1Ge, FKAB-1Gj, FKAB-1Gg1, and FKAB-1Gf1.
Figure 12:
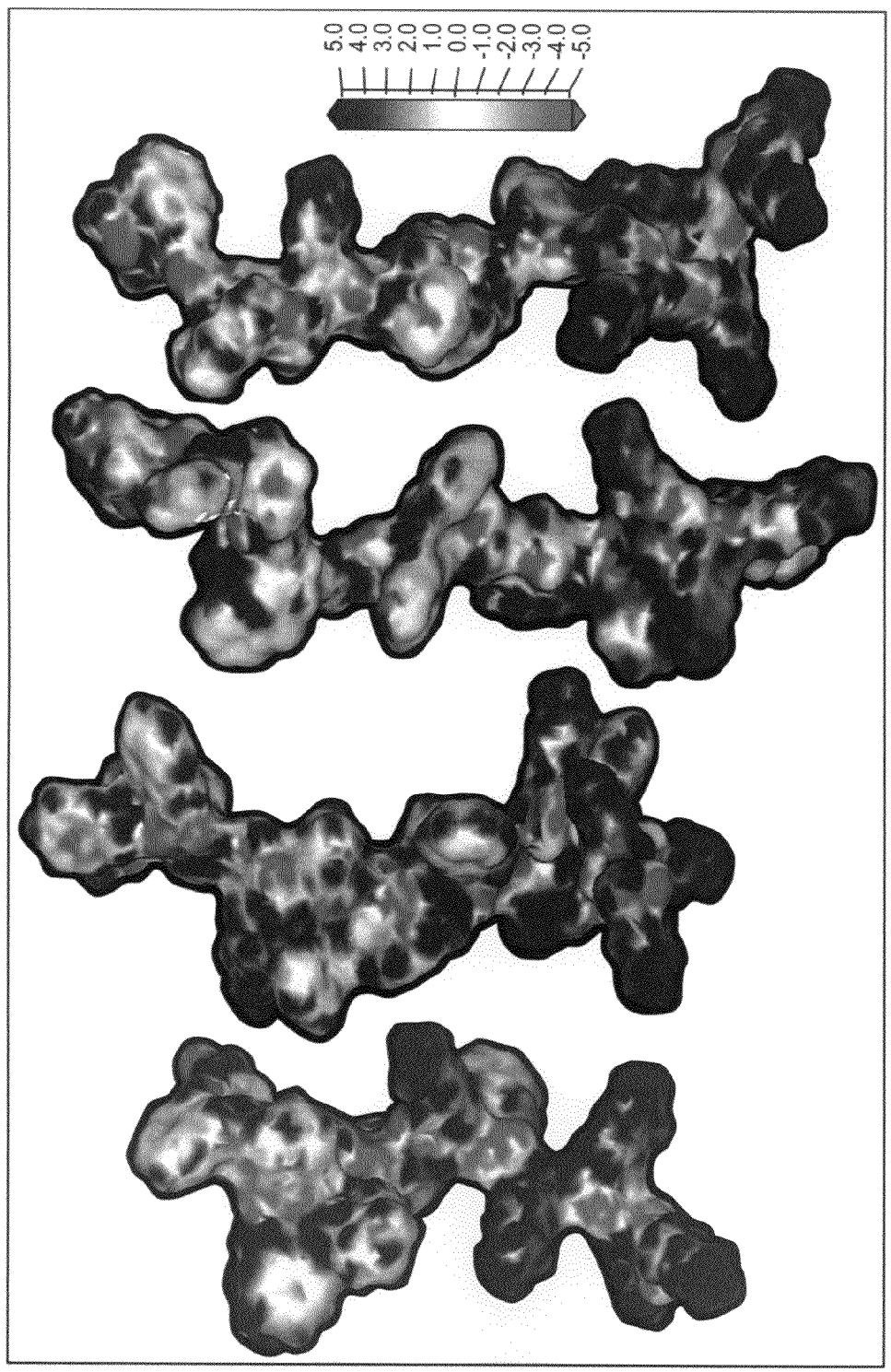
FIG. 12 shows the polar face of AMPs *Mycobacterium ranae* FKAB-1Ge, FKAB-1Gj, FKAB-1Gg1, and FKAB-1Gf1.
Figure 13:
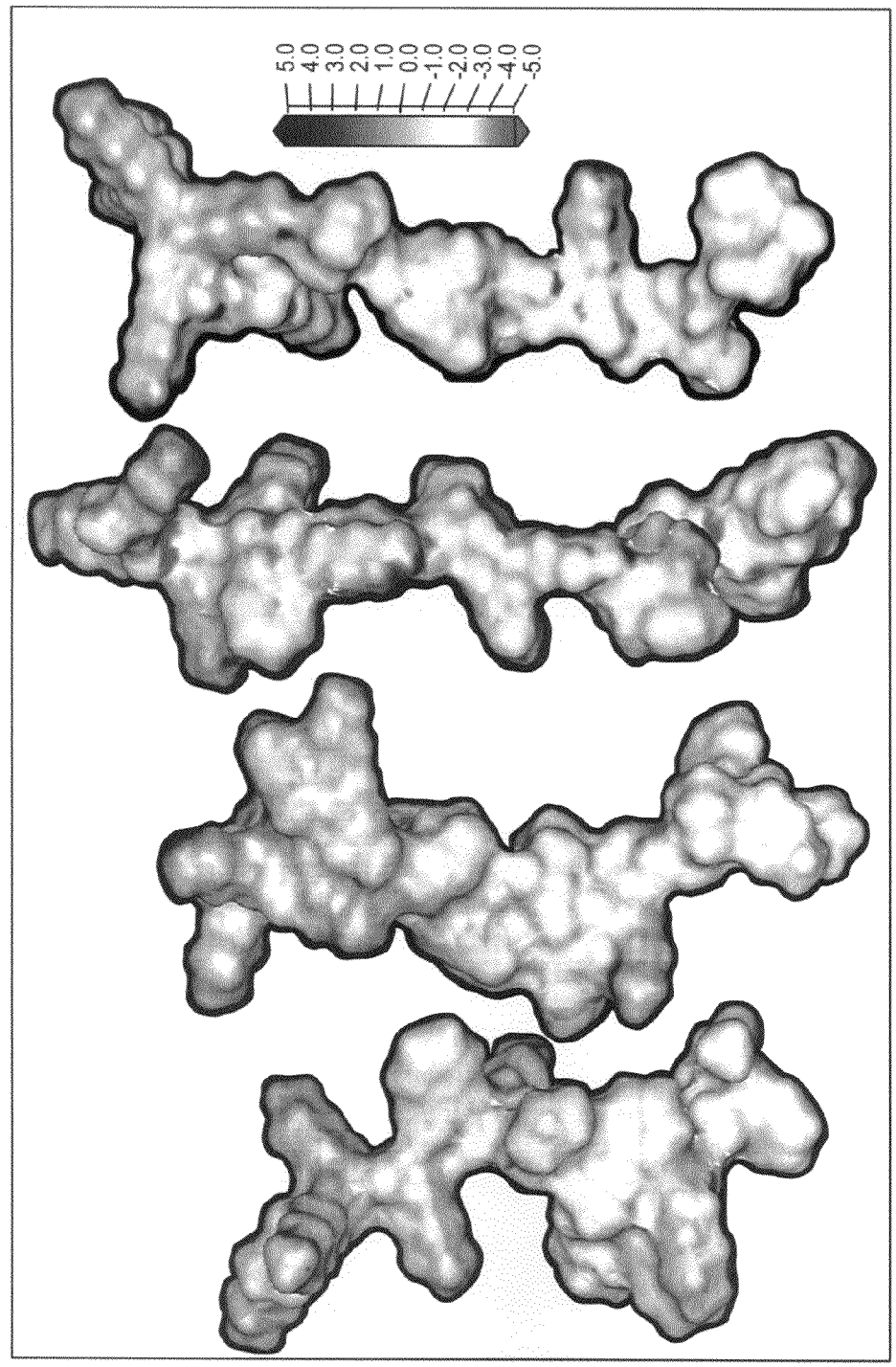
FIG. 13 shows the hydrophobic polar face of AMPs *Mycobacterium ranae* FKAB-1Ge, FKAB-1Gj, FKAB-1Gg1, and FKAB-1Gf1.
Figure 14:
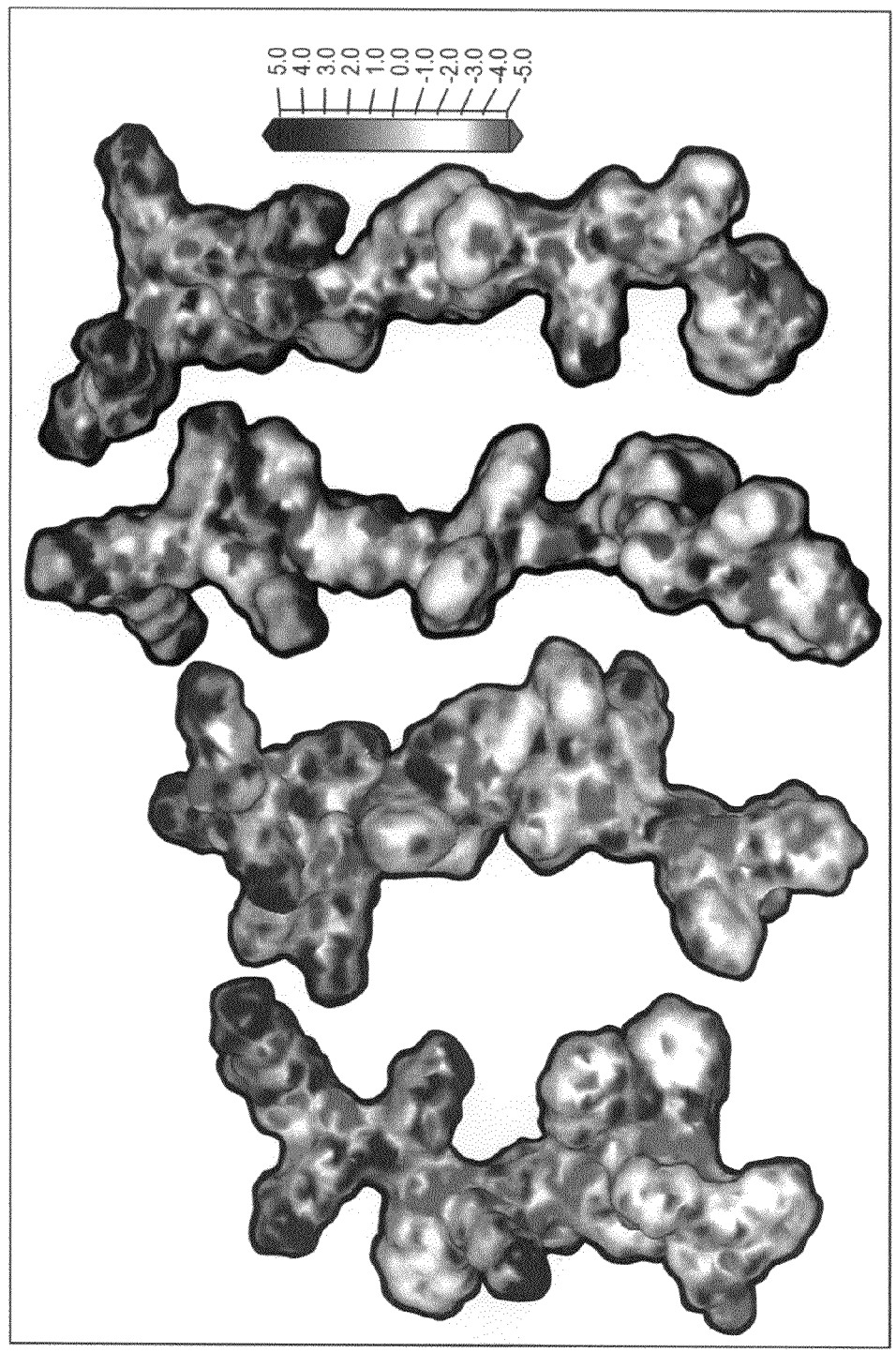
FIG. 14 shows the 180° opposite (from FIG. 13) hydrophobic face of AMPs *Mycobacterium ranae* FKAB-1Ge, FKAB-1Gj, FKAB-1Gg1, and FKAB-1Gf1.

The magnitude order sorted DSP for the MR QSAR model is presented in Table 26. The significant descriptors accounting for 82% of MR predicted activity are Density (−30.78), Jurs-RASA (16.83), Jurs-PPSA-1 (−15.49), Jurs-TPSA (10.22), Jurs-RPSA (−5.44), and H-bond donor (−3.91%). The inventors demonstrate the implication of electrostatics, sterics, hydrophobicity, and hydrophilicity in FIG. 11 to FIG. 14 for four representative AMPs from each activity class. The inventors selected FKAB-1 Ge for 3 μM, FKAB-1Gj for 10 μM, FKAB-1Gg for 30 μM, and FKAB-1Gf1 for 100 μM activity classes respectively. The Delphi electrostatic surface potential maps of the AMPs are presented in FIG. 11 and FIG. 12. All of the AMPs show a fairly good non-polar face and a very polar 180 degrees opposite face giving them the required amphipathic character. The correlation of the polar surface area to the MR bioactivity is evident from the descriptors Jurs-Sum of Solvent Accessible Surface Area of all Partially Positively charged Atoms (Jurs-PPSA-1) with −15.5% DSP contribution, Jurs—Total Polar Surface Area (Jurs-TPSA) with 10.5% DSP contribution and Jurs—Relative Polar Surface Area (Jurs-RPSA) with −5.44% DSP contribution. *Mycobacterium* is reported to be surrounded by a mycolate (thick waxy coat) or lipid layer, which is very hydrophobic in nature. Thus, the membrane disruption of the mycolate layer would necessitate hydrophobic nature for the AMPs. The hydrophobic hydrophilic surface potential map of the selected AMPs is shown in FIG. 13 and FIG. 14. The hydrophobicity, hydrophilicity correlation with the MR bioactivity is shown by the descriptors Jurs-Relative Hydrophobic Surface Area (Jurs-RASA) with 16.8% DSP contribution, and H-bond donor with −3.9% DSP contribution. The contribution of shape to MR predicted bioactivity comes from the descriptor Density with −30.78% DSP contribution.

TABLE 25

*Staphylococcus aureus* Magnitude order descriptor significance percentage (DSP)

| Physico-chemical property | Staphylococcus aureus QSAR_DSP |
|---|---|
| Jurs-FPSA-1 | 29.347 |
| Density | −16.010 |
| Jurs-TASA | −14.762 |
| Jurs-PNSA-1 | 10.540 |
| Jurs-RASA | 7.886 |
| Jurs-SASA | 4.120 |
| Jurs-DPSA-2 | 3.093 |
| Jurs-PNSA-2 | −2.911 |
| Jurs-RPSA | −2.492 |
| Rotlbonds | −2.164 |
| Hbond acceptor | 1.910 |
| Jurs-FPSA-3 | 1.709 |
| Fcharge | −0.742 |
| Jurs-RPCG | −0.726 |
| Jurs-PPSA-1 | 0.555 |
| Jurs-FNSA-3 | −0.426 |
| Dipole-mag | 0.162 |
| RadOfGyration | −0.127 |
| Jurs-RPCS | −0.126 |
| Hbond donor | 0.113 |
| Jurs-DPSA-3 | 0.053 |
| AlogP | −0.026 |
| Apol | 0.000 |
| Conformer|Energy | 0.000 |
| Jurs-PPSA-2 | 0.000 |

TABLE 25-continued

Staphylococcus aureus Magnitude order descriptor significance percentage (DSP)

| Physico-chemical property | Staphylococcus aureus QSAR_DSP |
|---|---|
| Jurs-RNCG | 0.000 |
| Jurs-TPSA | 0.000 |

TABLE 26

Mycobacterium ranae Magnitude order descriptor significance percentage (DSP)

| Physico-chemical property | Mycobacterium ranae QSAR_DSP |
|---|---|
| Density | −30.784 |
| Jurs-RASA | 16.827 |
| Jurs-PPSA-1 | −15.494 |
| Jurs-TPSA | 10.218 |
| Jurs-RPSA | −5.444 |
| Hbond donor | −3.905 |
| Hbond acceptor | 3.729 |
| Jurs-FPSA-1 | −3.409 |
| Fcharge | 2.892 |
| Jurs-PNSA-1 | −1.244 |
| RadOfGyration | 1.164 |
| Rotlbonds | −1.156 |
| Apol | 1.148 |
| Jurs-PPSA-2 | 1.016 |
| Jurs-PNSA-2 | −0.632 |
| Jurs-RNCG | 0.400 |
| Dipole-mag | 0.298 |
| Jurs-FNSA-3 | −0.127 |
| AlogP | 0.051 |
| Conformer Energy | 0.037 |
| Jurs-RPCG | −0.024 |
| Jurs-DPSA-2 | 0.00 |
| Jurs-DPSA-3 | 0.00 |
| Jurs-FPSA-3 | 0.00 |
| Jurs-RPCS | 0.00 |
| Jurs-SASA | 0.00 |
| Jurs-TASA | 0.00 |

QSAR Models Validation

Internal Validation Tests

Internal validation (cross-validation) tests of selected QSAR models (see Table 27) were performed at two levels. Both of the models showed $q^2_{LOO}>0.83$ for the leave-one-out cross-validation tests. For the leave-10%-out (leave-three-out) cross-validation tests, SA model showed $q^2_{L10O}$ of 0.875, whereas MR model showed $q^2_{L10O}$ values of 0.537.

TABLE 27

Statistical model validation data of Mycobacterium ranae (MR) and Staphylococcus aureus (SA) QSAR Model

| Internal Validation Tests Result | | | |
|---|---|---|---|
| Tests | Model | MR | SA |
| Leave-one-out | $q^2$ | 0.997 | 0.839 |
| | PRESS | 0.2405 | 22.9249 |

TABLE 27-continued

Statistical model validation data of Mycobacterium ranae (MR) and Staphylococcus aureus (SA) QSAR Model

| | | | |
|---|---|---|---|
| Leave-10%-out (100 trials) | $q^2$ | 0.537 | 0.875 |
| | PRESS | 33.6103 | 17.8572 |

| Randomization Tests 99 trails at 99% confidence level ((# Random r) >= (non-Random r)) = 0 | | |
|---|---|---|
| Model | MR | SA |
| r from non-Random | 0.9982 | 0.9877 |
| Mean value of r from Random trials | 0.61649 | 0.57241 |
| Std deviation of Random trial | 0.41594 | 0.39727 |

QSAR Model Validation by Randomization Tests

It is known that even with large number of observations and fewer terms, the QSAR models can be poorly predictive. Thus, with fewer observations (in this study twenty-five AMPs) and many more terms (in this study fifty descriptors and down selected to twenty-three), the QSAR models are prone to chance correlation. In the randomization test, the dependent variables (bioactivity values) are randomly reassigned to different compounds and new regression models are recomputed. This process is repeated several times. If the statistical data of these randomized models is comparable to the developed QSAR model, then the QSAR model developed is not predictive and the number of observations is insufficient. The inventors performed randomization tests of ninety-nine trials each at 99% confidence level for SA and MR QSAR models. The results of the randomization tests are presented in Table 27. The best mean random r value obtained for SA model is 0.572 ($r^2$=0.327), and MR model is 0.617 ($r^2$=0.380). The best random r value possible (based on the standard deviation) is about 0.730 ($r^2$=0.533) for the SA model and about 0.789 ($r^2$=0.622) for the MR model. These correlation coefficient values are far lower than the non-Random r values of 0.98 ($r^2$=0.96), thus indicating that the SA and MR QSAR models are not obtained by chance.

Analysis and Discussion

The two major structural variables in this study are 1) the Tic-Oic dipeptide and 2) the spacers A and B. The Tic-Oic dipeptide unit, which is critical for antibacterial activity, exhibits the greatest effect on the physicochemical properties via the following descriptors. A) Electrostatic potential: Dipole-mag, Jurs-FNSA-3, Jurs-PNSA-1, Jurs-PNSA-2; B) Molecular shape: H-bond donor, RadOfGyration, Rotlbonds; C) Amphipathicity: Jurs-RPSA, A log P . As previously stated, the physicochemical properties such as Dipole-mag, Fcharge, Jurs-FNSA-3, Jurs-RPSA, Jurs-FPSA-1, Jurs-PNSA-1, Jurs-PNSA-2, Jurs-PPSA-1, and Jurs-RPCG indicate the importance of electrostatics for the AMP bioactivity, while the physicochemical properties such as Density, H-bond acceptor, Jurs-RASA, H-bond donor, RadOfGyration, and Rotlbonds indicate the significance of the AMP molecular shape for bioactivity. The importance of amphipathicity is alluded to by the physicochemical properties such as Jurs-RASA, Jurs-RPSA, and A log P . The calculated values for these descriptors for each of the salient compounds are given in Table 28. Compound 25 was selected based on its broad spectrum activity (activity against Staphylococcus aureus ME/GM/TC resistant at 3 µM and Mycobacterium ranae at 10 µM concentration coupled with relatively low hemolytic activity at 14%) as the reference compound for this investigation. In addition the % deviation (Δ %) from the value for compound 25 and a % range (Δ % range) deviation for the series of compounds is also given. The effect of deleting either the Tic or Oic residue on the conformational flexibility of the resulting peptide is shown in FIG. 17.

The effect of Spacers A and B on the physicochemical properties via various descriptors maybe summarized as follows. A) Electrostatic potential: Dipole-mag, Jurs-FNSA-3, Jurs-RPSA, Jurs-PNSA-1, Jurs-PNSA-2, Jurs-PPSA-1; B) Molecular shape: Rotlbonds; C) Amphipathicity: Jurs-RPSA, A log P . The calculated values for these descriptors for each of the salient compounds are given in Table 29. The physicochemical properties and the descriptors most affected by Spacers A and B are clearly evident in the analogs shown in Table 30. The effect of varying the lengths of Spacers A and B on the conformational flexibility of the resulting peptide is shown in FIG. 18.

The 3D-QSAR also accurately predicts the effect of positive charge at both the C and N-terminus plays an effect on organism selectivity. Analysis of the data indicated that Compound 25 is significantly more active against SA than compound 28, while the activity of compounds 25 and 28 are identical against MR. Compound 28 has a free amine and thus a positive charge at the N-terminus while in compound 25 the amine is acetylated. The presence of a positive charge at the N-terminus reduces the activity from 3 μM (compound 25) to 10 μM (compound 28). Extending this logic to include compound 29 which differs from compound 25 by a having the free amine and a K residue (which introduces two positive charges at the N-terminus) reduces the activity even more to 30 μM. The effect of positive charge on bioactivity of SA QSAR model is about 34% {predominately from Jurs-FPSA-1 (29%), Jurs-DPSA-2 (3%) & Jurs-FPSA-3 (2%)}, whereas the effect of positive charge on bioactivity of MR QSAR model is only about 19% {predominately from Jurs-PPSA-1 (15%), Jurs-FPSA-1 (3%) & Jurs-PPSA-1 (1%)}.Thus, the effect a positive charge on bioactivity of SA is almost twice of the same on MR. This data and results explain the difference in activity of Compound 25 and Compounds 28 and 29 with respect to SA and the identical activity of the same compounds with respect to MR.

Increasing the number of Lys residues at the C-terminus also plays a role in organism selectivity. Compound 30 has four K residues at the C-terminus with a MR activity of 30 μM, compound 40, with six K residues at the C-terminus with a MR activity of 3 μM. The same trend holds true for compounds 31 and 42. Compound 31 has four K residues at the C-terminus with a MR activity of 10 μM and compound 42 has five K residues at the C-terminus with a MR activity of 3 μM. As can be seen from Table 30 the physicochemical properties Jurs-FPSA-1 and Density cause an increase in the SA bioactivity from compound 30 to compound 40, but physicochemical properties Jurs-TASA and Jurs-PNSA-1 cause a decrease in the SA bioactivity from compound 30 to compound 40. Thus, this cancellation effect is manifested in the equal activity of compound 30 and compound 40 against SA. As can be seen from the above Table 31 the physicochemical properties Density, Jurs-RASA and Jurs-TPSA-1 cause an increase in the MR bioactivity from compound 30 to compound 40, but physicochemical properties Jurs-PPSA-1 causes only a marginal decrease in the MR bioactivity from compound 30 to compound 40. Thus, the net effect is manifested in the increased bioactivity of compound 40 as compared to compound 30 against SA. In summary, even a small change such as addition of a single Lys has an effect on all the physicochemical properties of the peptide. The cumulative effect of this difference in physicochemical properties results in the large differences in observed bioactivity as shown by the example of compound 30 and compound 40.

Recently, Meroueh et al[88] reported the three-dimensional structure of bacterial cell wall peptidoglycan of SA, which concurs with the previously reported observations that the SA peptidoglycan outer layer is distinctly anionic[89]. Thus, for the electrostatic interactions occurring between the target (SA) cell's membrane and the peptide determines organism potency, and it is a necessary condition for any active AMP to provide a complimentary polar face for the initial electrostatic attraction. The ESP maps of the inner faces of the hexagonal units of SA cell membrane (FIGS. 19A, 19B and 19C) show that about half of the inner surface is distinctly polar, while the opposite half is distinctly non-polar. This figure illustrates two major points: 1) the peptidoglycan presents a highly charged polar face to the approaching AMP and 2) once bound to the surface, the peptidoglycan presents an amphipathic pore to the AMP which is very complimentary to its own amphipathic character. Also, it is known that SA outer cell membrane pore size measures ~70-100 Å[88] and we have found that the largest dimension of these bioactive AMPs is about 30-40 Å. Thus, one can rationally speculate that this amphipathic pore may play a role in transporting AMPs through the peptidoglycan layer to the lipid bilayer of the membrane propelled by the complementarity of electrostatics between AMPs and the SA peptidoglycan layer.

TABLE 28

Calculated Descriptor most Affected by the Tic-Oic dipeptide unit.

| Compound/ | Compound 25 FKAB-1G | | Compound 33 FKAB-1Gf | | Compound 36 FKAB-1Gf1 | | Compound 34 FKAB-1Gg | | Compound 35 FKAB-1Gg1 | | |
|---|---|---|---|---|---|---|---|---|---|---|---|
| Property | value | Δ % | value | Δ % | value | Δ % | value | Δ % | value | Δ % | Δ % |
| ELECTROSTATIC POTENTIAL | | | | | | | | | | | |
| Dipole-magnitude | 269.60 | 0 | 251.73 | −6.6 | 273.75 | +1.5 | 81.00 | −69.95 | 297.77 | +10.45 | 80.4 |
| F-Charge | 6.00 | 0 | 6.00 | 0 | 6.00 | 0 | 6.00 | 0 | 6.00 | 0 | 0% |
| Jurs-FNSA-3 | −0.05 | 0 | −0.06 | 20 | −0.04 | −20 | −0.03 | −40 | −0.04 | −20 | 60% |
| Jurs-RPSA | 0.27 | 0 | 0.33 | +22.2 | 0.30 | +11.1 | 0.26 | 3.7 | 0.27 | 0 | 22.20% |
| Jurs-FPSA-1 | 0.82 | 0 | 0.83 | +1.2 | 0.82 | 0 | 0.81 | −1.2 | 0.78 | 4.87 | 6.07% |
| Jurs-PNSA-1 | 576.30 | 0 | 446.76 | −22.47 | 565.76 | −1.8 | 503.61 | −12.6 | 713.07 | +23.7 | 46.17% |
| Jurs-PNSA-2 | −15950.51 | 0 | −9781.01 | −38.67 | −8051.80 | −49.52 | −6499.05 | −59.2 | −10525.42 | −34.0 | 59.20% |

TABLE 28-continued Calculated Descriptor most Affected by the Tic-Oic dipeptide unit.

| Compound/ Property | Compound 25 FKAB-1G value | Δ % | Compound 33 FKAB-1Gf value | Δ % | Compound 36 FKAB-1Gf1 value | Δ % | Compound 34 FKAB-1Gg value | Δ % | Compound 35 FKAB-1Gg1 value | Δ % | Δ % |
|---|---|---|---|---|---|---|---|---|---|---|---|
| Jurs-PPSA-1 | 2672.17 | 0 | 2225.44 | −16.7 | 2513.86 | −5.95 | 2136.09 | −20.06 | 2459.00 | −7.97 | 20.06% |
| Jurs-RPCG | 0.01 | 0 | 0.02 | 100 | 0.01 | 0 | 0.01 | 0 | 0.01 | 0 | 100% |
| MOLECULAR SHAPE | | | | | | | | | | | |
| Density | 1.05 | 0 | 1.03 | −1.9 | 1.05 | 0 | 1.06 | +0.95 | 1.07 | +1.9 | 3.80% |
| H-bond acceptor | 20.00 | 0 | 16.00 | −20 | 20.00 | 0 | 17.00 | −15 | 20.00 | 0 | 40% |
| Jurs-RASA | 0.73 | 0 | 0.67 | −8.2 | 0.70 | −4.1 | 0.74 | +1.4 | 0.73 | 0 | 9.60% |
| H-bond donor | 32.00 | 0 | 32.00 | 0 | 36.00 | +12.5 | 32.00 | 0 | 35.00 | +9.4 | 12.50% |
| Rad-Of-Gyration | 14.55 | 0 | 13.47 | −7.4 | 15.88 | +9.1 | 10.18 | −30.0 | 16.79 | +15.39 | 45.39% |
| Rotl-bonds | 78.00 | 0 | 70.00 | −10.25 | 82.00 | +5.1 | 72.00 | −7.69 | 81.00 | +3.85 | 15.35% |
| AMPHIPATHICITY | | | | | | | | | | | |
| Jurs-RASA | 0.73 | 0 | 0.67 | −8.2 | 0.70 | −4.1 | 0.74 | +1.4 | 0.73 | 0 | 9.60% |
| Jurs-RPSA | 0.27 | 0 | 0.33 | +22.2 | 0.30 | +11.1 | 0.26 | −3.7 | 0.27 | 0 | 25.90% |
| AlogP | −3.25 | 0 | −7.75 | 138 | −12.05 | 270.7 | −5.85 | 80 | −9.08 | 179.3 | 270% |

TABLE 29

Descriptors most Affected by Spacers A and B

| Compound/ Property | Compound 25 FKAB-1G Value | Δ % | Compound 31 FKAB-1Gd Value | Δ % | Compound 38 FKAB-1Gd1 Value | Δ % | Compound 39 FKAB-1Gd2 Value | Δ % | Compound 32 FKAB-1Ge Value | Δ % | Δ % range |
|---|---|---|---|---|---|---|---|---|---|---|---|
| ELECTROSTATIC POTENTIAL | | | | | | | | | | | |
| Dipole-magnitude | 269.596 | 0 | 222.841 | −17.35 | 256.579 | −4.82 | 220.357 | −18.25 | 145.619 | −45.99 | 45.99% |
| F-Charge | 6.000 | 0 | 6.000 | 0 | 6.000 | 0 | 6.000 | 0 | 6.000 | 0 | 0% |
| Jurs-FNSA-3 | −0.051 | 0 | −0.050 | −1.96 | −0.056 | +9.8 | −0.045 | −11.76 | −0.026 | −49.0 | 58.80% |
| Jurs-RPSA | 0.274 | 0 | 0.239 | −12.77 | 0.268 | −2.19 | 0.228 | −16.79 | 0.210 | −23.36 | 23.36% |
| Jurs-FPSA-1 | 0.823 | 0 | 0.827 | +0.49 | 0.805 | −2.2 | 0.829 | +0.73 | 0.834 | +1.33 | 3.53% |
| Jurs-PNSA-1 | 576.297 | 0 | 608.270 | +5.55 | 704.141 | +22.18 | 634.863 | +10.16 | 528.652 | −8.27 | 30.45% |
| Jurs-PNSA-2 | 15950.000 | 0 | −17351.269 | +8.78 | −19787.484 | +24.055 | −18648.209 | +16.91 | −6814.498 | −57.27 | 81.33% |
| Jurs-PPSA-1 | 2672.174 | 0 | 2911.683 | +8.94 | 2899.114 | +8.5 | 3086.010 | +15.5 | 2661.015 | −0.415 | 15.50% |
| Jurs-RPCG | 0.013 | 0 | 0.013 | 0 | 0.013 | 0 | 0.012 | 0 | 0.013 | 0 | 0% |
| MOLECULAR SHAPE | | | | | | | | | | | |
| Density | 1.054 | 0 | 1.043 | −1.0 | 1.047 | −0.66 | 1.031 | −2.18 | 1.042 | −1.13 | 2.18% |
| H-bond | 20.000 | 0 | 20.000 | 0 | 20.000 | 0 | 20.000 | 0 | 16.000 | −20 | 20% |
| Jurs-RASA | 0.726 | 0 | 0.761 | +4.8 | 0.732 | +0.83 | 0.772 | +6.33 | 0.790 | +8.8 | 8.80% |
| H-bond donor | 32.000 | 0 | 32.000 | 0 | 32.000 | 0 | 32.000 | 0 | 28.000 | −12.5 | 12.50% |
| Rad-Of-Gyration | 14.550 | 0 | 13.153 | −9.6 | 14.228 | −2.2 | 14.161 | −2.67 | 11.799 | −18.9 | 18.90% |
| Rotl-bonds | 78.000 | 0 | 86.000 | +10.25 | 82.000 | +5.13 | 94.000 | +20.52 | 66.000 | −15.38 | 35.90% |
| AMPHIPATHICITY | | | | | | | | | | | |
| Jurs-RASA | 0.726 | 0 | 0.761 | +4.8 | 0.732 | +0.83 | 0.772 | +6.33 | 0.790 | +8.8 | 8.80% |
| Jurs-RPSA | 0.274 | 0 | 0.239 | −12.77 | 0.268 | −2.12 | 0.228 | −16.79 | 0.210 | −23.36 | 23.36% |
| AlogP | −3.252 | 0 | −1.520 | 53.26 | −2.527 | 22.3 | 1.650 | 49.3 | 1.054 | 67.56 | 67.56% |

TABLE 30

Descriptors relating charge density with SA activity

| | | Percent Contribution | | | |
|---|---|---|---|---|---|
| Cmpd # | SA Activity | +29% Jurs-FPSA-1 | −16% Density | −15% Jurs-TASA | +11% Jurs-PNSA-1 |
| 30 | 3 | 0.834 | 1.042 | 2520 | 528 |
| 40 | 3 | 0.837 | 1.037 | 2761 | 564 |
| Effect on Bioactivity | | Increase BA | Increase BA | Decrease BA | Decrease BA |

TABLE 31

Descriptors relating charge density with MR activity

| | | Percent Contribution | | | |
|---|---|---|---|---|---|
| Cmpd # | MR Activity | −30% Density | +16% Jurs-RASA | −15% Jurs-PPSA-1 | +10% Jurs-TPSA-1 |
| 30 | 30 | 1.043 | 0.791 | 2668.13 | 670.01 |
| 40[90] | 3 | 1.037 | 0.794 | 2919.12 | 717.85 |
| Effect on Bioactivity | | Increase BA | Increase BA | Decrease BA | Increase BA |

The following references are cited above by number, and the entire contents of these and all references cited in this document are incorporated herein by reference.

References:
1. Yeaman, M. R.; Yount, N.Y., Mechanisms of antimicrobial peptide action and resistance. *Pharmacological Reviews* 2003, 55, (1), 27-55.
2. Dennison, S. R.; Wallace, J.; Harris, F.; Phoenix, D. A., Amphiphilic α-helical antimicrobial peptides and their structure/function relationships. *Protein and peptide Letters* 2005, 12, 31-39.
3. Toke, O., Antimicrobial peptides; new candidates in the fight against bacterial infections. *Biopolymers* 2005, 80, 717-735.
4. Ganz, T., Defensins: antimicrobial peptides of innate immunity. *Nature reviews, Immunology* 2003, 3, 710-720.
5. Simmaco, M.; Mignogna, G.; Barra, D., Antimicrobial peptides from amphibian skin: what do they tell us? *Biopolymers* 1999, 47, 435-450.
6. Hancock, R. E. W.; Lehrer, R., Cationic peptides: a new source of antibiotics. *Trends Biotechnol* 1998, 16, 82-88.
7. Zasloff, M., Antimicrobial peptides of multicellular organisms. *Nature* 2002, 415, 389-395.
8. Powers, J.-P. S.; Hancock, R. E. W., The relationship between peptide structure and antibacterial activity. *Peptides* 2003, 24, 1681-1691.
9. Blondelle, S. E.; Lohner, K.; Aguilar, M.-I., Lipid-induced conformation and lipid-binding properties of cytolytic and antimicrobial peptide: determination and biological specificity. *Biochimica et Biophysica Acta* 1999, 1462, 89-108.
10. Brogden, K. A., Antimicrobial peptides: pore formers or metabolic inhibitors of bacteria. *Nature Reviews Microbiol* 2005, 3, 238-250.
11. Pouny, Y.; Rapaport, D.; Mor, A.; Nicolas, P.; Shai, Y., Interaction of antimicrobial dermaseptin and fluorescently labeled analogues with phospholipid membranes. *Biochemistry* 1992, 31, 12416-12423.
12. Papo, N.; Shai, Y., Can we predict biological activity of antimicrobial peptides from their interaction with model phospholipid membranes? *Peptides* 2003, 24, 1693-1703.
13. Bechinger, B., The structure, dynamics and orientation of antimicrobial peptides in membranes by multidimensional solid-state NMR spectroscopy. *Biochim. et Biophys. Acta* 1999, 1462, 157-183.
14. Lee, M. T.; Chen, F. Y.; Haung, H. W., Energetics of pore formation induced by membrane active peptides. *Biochemistry* 2004, 43, 3590-3599.
15. Bechinger, B., Solid-state NMR investigations of the interaction contributions that determine the alignment of helical polypeptides in biological membranes. *FEBS Lett.* 2001, 504, 161-165.
16. Song, Y. M.; Park, Y.; Lim, S. S.; Yang, S.-T.; Woo, E.-R.; Park, S.; Lee, J. S.; Kim, J. I.; Hahm, K.-S.; Kim, Y.; Shin, S. Y., Cell selectivity and mechanism of action of antimicrobial model peptides containing peptoid residues. *Biochemistry* 2005, 44, 12094-12106.
17. Giangaspero, A.; Sandri, L.; Tossi, A., Amphipathic α-helical antimicrobial peptides. *Eur. J. Biochem.* 2001, 268, 5589-5600.
18. Glukhov, E.; Stark, M.; Burrows, L. L.; Deber, C. M., Basis for selectivity of cationic antimicrobial peptides for bacterial versus mammalian membranes. *J. Biol. Chem.* 2005, 280, 33960-33967.
19. White, S. H.; Wimley, W. C., Hydrophobic interactions of peptides with membrane interfaces. *Biochim. Biophys. Acta* 1998, 1376, (3), 339-352.
20. Situ, H.; Wei, G.; Smith, C. J.; Mashhoon, S.; Bobek, L. A., Human salivary MUC7 mucin peptides: effect of size, charge and cystine residues on antifungal activity. *Biochem. J.* 2003, 375, 175-182.
21. Moerman, L.; Bosteels, S.; Noppe, W.; Willems, J.; Clynen, E.; Schoofs, L.; Thevissen, K.; Tytgat, J.; Van Elder, J.; van der Walt, J.; Verdonck, F., Antibacterial and antifungal properties of helical cationic peptides in the venom of acorpions from southern Africa. *Eur. J. Biochem.* 2002, 269, 4799-4810.
22. Deslouches, B.; Phadke, S. M.; Lazarevic, V.; Cascio, M.; Islam, K.; Montelaro, R. C.; Mietzner, T. A., De novo generation of cationic antimicrobial peptides: influence of length and tryptophan substitution on antimicrobial activity. *Antimicrobial Agents and Chemotherapy* 2005, 49, 316-322.
23. Wareham, D. W.; Bean, D. C., In vitro activity of polymyxin B in combination with imipenem, rifampicin and azithromycin versus multidrug resistant strains of *Acinetobacter baumannii* producing OXA-23 carbapenemases. *Ann. Clin. Microbiol. Antimicrob.* 2006, 5, 10.
24. Zasloff, M., Antimicrobial peptides of multicellular organisms. *Nature* 2002, 415, 389-395.
25. Wenk, M. R.; Seelig, J., Magainin-2-amide interaction with lipid membranes: calorimetric detection of peptide binding and pore formation. *Biochemistry* 1998, 37, 3909-3916.
26. Yang, L.; Weiss, T. M.; Lehrer, R. I.; Huang, H. W., Crystallization of antimicrobial pores in membranes: magainin and protegrin. *Biochemical J.* 2000, 79, 2002-2009.
27. Hicks, R. P.; Mones, E.; Kim, H.; Koser, B. W.; Nichols, D. A.; Bhattacharjee, A. K., Comparison of the conformation and electrostatic surface properties of magainin peptides bound to SDS and DPC micelles: Insight into possible modes on antimicrobial activity. *Biopolymers* 2003, 68, 459-470.
28. Rozek, A.; Friedrich, C. L.; Hancock, R. E., Structure of the bovine antimicrobial peptide indolicidin bound to dodecylphosphocholine and sodium dodecyl sulfate micelles. *Biochemistry* 2000, 39, 15765-15774.
29. Whitehead, T. L.; Jones, L. M.; Hicks, R. P., Effects of the incorporation of CHAPS into SDS micelles on neuropeptide-micelle binding: separation of the role of electrostatic interactions from hydrophobic interactions. *Biopolymers* 2001, 58, (7), 593-605.
30. Whitehead, T. L.; Jones, L. M.; Hicks, R. P., PFG-NMR investigations of the binding of cationic neuropeptides to anionic and zwitterionic micelles. *J Biomol Struct Dyn* 2004, 21, (4), 567-576.
31. Kyle, D. J.; Blake, P. R.; Smithwick, D.; Green, L. M.; Martin, J. A.; Sinsko, J. A.; Summers, M. F., NMR and computational evidence that high-affinity bradykinin receptor antagonists adopt C-terminal beta-turns. *J Med Chem* 1993, 36, (10), 1450-60.
32. Hicks, R. P.; Bhonsle, J. B.; Venugopal, D.; Koser, B. W.; Magill, A. J., De Novo Design of Selective Antibiotic Peptides by Incorporation of Un-natural Amino Acids. *J. Med. Chem.* 2007, 50, (13), 3026-3036.
33. Giacometti, A.; Cirioni, O.; Del Prete, M. S.; Paggi, A. M.; D'Errico, M. M.; Scalise, G., Combination studies between polycationic peptides and clinically used antibiotics against Gram-positive and Gram-negative bacteria. *Peptides* 2000, 21, 1155-1160.
34. Grgurina, I.; Bensaci, M.; Pocsfalvi, G.; Mannina, L.; Cruciani, O.; Fiore, A.; Fogliano, V.; Sorensen, K. N.; Takemoto, J. Y., Novel cyclic lipodepsipeptide from

*Pseudomonas syringae* pv. *lachrymans* strain 508 and Syringopeptin antimicrobial activities. *Antimicrobial Agents and Chemotherapy* 2005, 49, (12), 5037-5045.

35. Lockwood, N. A.; Haseman, J. R.; Tirrell, M. V.; Mayo, K. H., Acylation of SC4 dodecapeptide increases bactericidal potency against Gram-positive bacteria, including drug-resistant strains. *Biochem. J.* 2004, 378, 93-103.

36. Giacometti, A.; Cirioni, O.; Del Prete, M. S.; Barchiesi, F.; Paggi, A. M.; Petrelli, E.; Scalise, G., Comparative activities of polycationic peptides and clinically used antimicrobial agents against multidrug-resistant nosocomial isolates of *Acinetobacter baumannii. J. Antimicrobial Chemotherapy* 2000, 46, 807-810.

37. Sklenar, M.; Piotto, M.; Leppik, R.; Saudek, V., Gradient-tailored water suppression for $^1$H-$^{15}$N HSQS experiments optimized to retain full sensitivity. *J. Magn. Res. Series A* 1993, 102, 241.

38. Di Modugno, E.; Erbetti, I.; Ferrari, L.; Galassi, G.; Hammond, S. M.; Xerri, L., In vitro activity of the tribactam GV 104326 against Gram-Positive, Gram-Negative and anaerobic bacteria. *Antimicrobial Agents and Chemotherapy* 1994, 38; 2362-2368.

39. Misiek, M.; Pursiano, T. A.; Leitner, F.; Price, K. E., Microbiological properties of a new cephalosporin, BL-S 339: 7-(phenylacetyimidoyl-aminoacetamido)-3-(2-methyl-1,3,4-thiadiazol-5-ylthiomethyl)ceph-3-em-4-carboxylic acid. *Antimicrobial Agents and Chemotherapy* 1973, 3, 40-48.

40. Edwards, J. R.; Turner, P. J.; Withnell, E. S.; Grindy, A. J.; Narin, K., In vitro antibacterial activity of SM-7338, a carbapenem antibiotic with stability to dehydropeptidase 1. *Antimicrobial Agents and Chemotherapy* 1989, 33, (2), 215-222.

41. Montesinos, M. C.; Gadangi, P.; Longaker, M.; Sung, J.; Levine, J.; Nilsen, D.; Reibman, J.; Li, M.; Jiang, C.-K.; Hirschhorn, R.; Recht, P. A.; Ostad, E.; Levin, R. I.; Cronstein, B. N., Wound healing is accelerated by agonists of adenosine A$_2$ (G$_{xs}$-linked) receptors. *J. Exp. Med.* 1997, 186, 1615-1620.

42. Grant, G. A., *Synthetic Peptides, A user's guide.* 2$^{nd}$ ed.; Oxford University Press: New York, N.Y., 2002.

43. Benoiton, N. L., *Chemistry of Peptide Synthesis.* Taylor and Francis (CRC Press): Boca-Raton, Fla., 2006.

44. Schmidt, J. J.; Stafford, R. G.; Millard, C. B., High-throughput assays for botulinum neurotoxin proteolytic activity: serotypes A, B, D, and F. *Anal Biochem* 2001, 296, (1), 130-7.

45. Ghose, A. K.; Crippen, G. M., Atomic physicochemical parameters for three-dimensional structure-directed quantitative structure-activity relationships. 2. Modeling dispersive and hydrophobic interactions. *Chem. Inf. Comput. Sci.* 1987, 27, 21.

46. Ghose, A. K.; Crippen, G. M., Atomic physicochemical parameters for three-dimensional structure-directed quantitative structure-activity relationships. 1. Partition coefficients as a measure of hydrophobicity. *J. Comput. Chem.* 1986, 7, 565.

47. Hansch, C., *Accounts of Chemical Research* 1969, 2, 232-239.

48. Cramer, R. D. I.; E., P. D.; Bunce, J. D., *J. Am. Chem. Soc.* 1988, 110, 5959-5967.

49. Hopfinger, A. J.; Burke, B. J., *Molecular shape analysis: a formation to quantitatively establish spatial molecular similarity.* Wiley: New York, 1990; p 173-209.

50. Klebe, G., *Perspectives in Drug Discovery and Design* 1998, 12/13/14, 87-104.

51. Jain, A. N.; Dietterich, T. G.; Lathrop, R. H.; Chapman, D.; Critchlow, R. E. J., *J. Computer-Aided Mol. Design* 1994, 8, 635-652.

52. Doweyko, A. M., *J. Math. Chem.* 1991, 7, 273-285.

53. Wiener, H., *J. Am. Chem. Soc.* 1947, 69, 17-20.

54. Bonchev, D., *Information theoretic indices for characterization of chemical structures.* 1983; Vol. 5, p 249.

55. Hosoya, H., *Bulletin of the Chemical Society of Japan* 1971, (44), 2332-2339.

56. Kier, L. B.; Hall, L. H., *Molecular connectivity in chemistry and drug research.* Academic Press: New York, 1976; Vol. 14, p 257.

57. Kier, L. B., *Quantitative Structure-Activity Relationships* 1985, 4, 109-116.

58. Kier, L. B.; Hall, L. H.; Frazer, J. W., *J. Math. Chem.* 1991, 7, 229-241.

59. Balaban, A. T., *Chem. Phys. Letts* 1982, 89, 399-404.

60. Bonchev, D.; Mekenyan, O.; Trinajstic, N., *J. Comp. Chem.* 1981, 2, 127-148.

61. Marsili, M.; Gasteiger, J., Fast calculation of atomic charges from molecular topology and orbital electronegativies. *Studies in Physical and Theoretical Chemistry* 1981, 16, 56-67.

62. Rohrbaugh, R. H.; Jurs, P. C., *Analytica Chimica Acta* 1987, 199, 99-109.

63. Stanton, D. T.; Jurs, P. C., *Anal. Chem.* 1990, 62, 2323-2329.

64. Kharkar, P. S.; Desai, B.; Gaveria, H.; Varu, B.; Loriya, R., *J. Med. Chem.* 2002, 45, 4858-4867.

65. Drew, M. G. B.; Wilden, G. R. H.; Spillane, W. J.; Walsh, R. M.; Ryder, C. A., *J. Agricultural and Food Chem.* 1998, 46, 3016-3026.

66. Hirashima, A.; Rafaeli, A.; Gileadi, C.; Kuwano, E., *Bioorg. Med. Chem.* 1999, 7, 2621-2628.

67. Hasegawa, K.; Arakawa, M.; Funatsu, K., Rational choice of bioactive conformations through use of conformation analysis and 3-way partial least squares modeling. *Chemometrics and Intelligent Lab. Sys.* 2000, 50, (2), 252-261.

68. Hopfinger, A. J.; Wang, S.; Tokarski, J. S.; Jin, B.; Albuquerque, M., *J. Am. Chem. Soc.* 1997, 119, 10509-10524.

69. Hasegawa, K.; Arakawa, M.; Funatsu, K., *Comput. Biol. Chem.* 2003, 27, 211-216.

70. Vedani, A.; McMasters, D. R.; Dobler, M., *Quantitative Structure-Activity Relationships* 2000, 19, 149-161.

71. Appell, M.; Dunn, W. J.; Reith, M. E. A.; Miller, L.; Flippen-Anderson, J. L., *Bioorganic & Med. Chem.* 2002, 10, 1197-1206.

72. Xiao, Y.-D.; Hammond, P. S.; Harris, R.; SCHMITT, J. D.; Klucik, J., *J. Med. Chem.* 2004, 47, 831-6839.

73. Sulea, T.; Kurunczi, L.; Oprea, T. L.; Simon, Z., *J. Computer-Aided Mol. Design* 1998, 12, 133-146.

74. Bhonsle, J. B.; Wang, Z. W.; Tamamura, H.; Fujii, N.; Peiper, S. C.; Trent, J. O., A simple, automated quasi-4D-QSAR, quasi-multi way PLS approach to develop highly predictive QSAR models for highly flexible CXCR4 inhibitor cyclic pentapeptide ligands using scripted common molecular modeling tools. *QSAR & Combinatorial Science* 2005, 24, (5), 620-630.

75. Accelrys INC, . . . , Cerius2 Version 4.10, 9685 Scranton Road San Diego, Calif. 92121-3752.

76. Bhonsle, J. B.; Bhattacharjee, A. K.; Gupta, R., Novel semi-automated methodology for developing highly predictive QSAR models: application for development of QSAR models for insect repellent amides. *J. Molecular Modeling* 2007, 13, (1), 179-208.

77. Marsili, M.; Gasteiger, J., Fast calculation of atomic charges from molecular topology and orbital electronegativies. *Studies in Physical and Theoretical Chemistry* 1981, 16, 56-67.
78. Mayo, S. L.; Olafson, B. D.; Goddard, W. A. I., DREIDING: A generic force field. *J. Phys. Chem.* 1990, 94, 8897-8909.
79. Levitt, M.; Lifson, S., Refinement of protein conformations using a macromolecular energy minimization procedure. *J. Mol. Biol.* 1969, 46, (2), 269-279.
80. Chang, G.; Guida, W. C.; Still, W. C., An internal-coordinate Monte Carlo method for searching conformational space. *J. Am. Chem. Soc.* 1989, 111, 4379-4386.
81. Bro, R., *J. Chemometrics* 1996, 10, 47-61.
82. Hasegawa, K.; Arakawa, M.; Funatsu, K., 3D-QSAR study of insecticidal neonicotinoid compounds based on 3-way partial least squares model. *Chemometrics and Intelligent Lab. Sys.* 1999, 47, 33-40.
83. Hill, T. L., An Introduction to statistical thermodynamics. In *An introduction to statistical thermodynamics*, Dover Publications: New York, 1960.
84. Dewar, M. J. S.; Thiel, W. J., *J. Am. Chem. Soc.* 1977, 99, 4907.
85. Richon, A. B.; Young, S. S., An introduction to QSAR Methodology. *Network Science Corporation* Saluda N.C. 1997.
86. Yao, S. W.; Lopes, V. H. C.; Fernandez, F.; Garcia-Mera, X.; Morales, M.; Rodriquez-Borges, J. E.; Corderio, M. N. D. S., Synthesis and QSAR study of the anticancer activity of some novel indane carbocyclic nucleosides. *Bioorganic & Med. Chem.* 2003, 11, (23), 4999-5006.
87. *Sybyl Molecular Modeling System Version 6.9.1*, St. Louis, 2003.
88. Meroueh, S. O.; Bencze, K. Z.; Hesek, D.; Lee, M.; Fisher, J. F.; TStemmler, T. L.; Mobashery, S., Three-dimensional structures of bacterial cell wall peptidoglycan. 2006, 103, (12), 4404-4409.
89. Hancock, R. E., Cationic antimicrobial peptides: toward clinical applications. *Expert Opin. Investig. Drugs* 2000, 8, 1723-1729.
90. Atrih, A.; Zollner, P.; Allmaier, G.; Williamson, M. P.; Foster, S. J., Peptidoglycan structural dynamics during germination of *Bacillus subtilis* 168 Endospores. *J. Bacteriology* 1998, 180, (17), 4603-4612.

The invention claimed is:

1. A synthetic antimicrobial peptide analog having a formula selected from the group consisting of:

Σ-Glycine-O-(Tic-Oic-X-J-Tic-Oic-X—Z)$_n$-Tic-Oic-Π-J-Tic-U$_m$—CONH$_2$

Σ-Glycine-O-(Tic-Oic-X—Z-Tic-Oic-X-J)$_n$-Tic-Oic-Π-Z-Tic-U$_m$—CONH$_2$

Σ-Glycine-B-(Tic-Oic-X—Z-Tic-Oic-X-J)$_n$-Tic-Oic-Π-Z-Tic-U$_m$—CONH$_2$

Σ-Glycine-O-(Tic-Oic-X-J-Tic-Oic-X—Z)$_n$-Tic-Oic-Π-J-Tic-U$_m$—CONH$_2$

Σ-Glycine-O-(Tic-Oic-X—Z-Tic-Oic-X-J)$_n$-Tic-Oic-Π-Z-Tic-U$_m$—CONH$_2$

Σ-Glycine-B-(Tic-Oic-X—Z-Tic-Oic-X-J)$_n$-Tic-Oic-Π-Z-Tic-U$_m$—CONH$_2$

Σ-Glycine-O-(Tic-Oic-X-J-Tic-Oic-X—Z)$_n$-Tic-Oic-Π-J-Tic-U$_m$—CONH—(CH$_2$)$_k$—NH$_2$ Σ-Glycine-O-(Tic-Oic-X-J-Tic-Oic-X—Z)$_n$-Tic-Π-U$_m$—CONH$_2$ Σ-Glycine-O-(Tic-Oic-X-J-Tic-Oic-X—Z)$_n$-Oic-Π-U$_m$—CONH$_2$ Σ-Glycine-O-(Tic-Oic-X—Z-Tic-Oic-X-J)$_n$-Tic-Π-U$_m$—CONH$_2$, Σ-Glycine-O-(Tic-Oic-X—Z-Tic-Oic-X-J)$_n$-Oic-Π-U$_m$—CONH$_2$ Σ-Glycine-O-(Tic-Oic-Z-Tic-Oic-J)$_n$-Tic-Oic-Z-Tic-U$_m$—CONH$_2$ Σ-Glycine-B-(Tic-Oic-Z-Tic-Oic-J)$_n$-Tic-Oic-Z-Tic-U$_m$—CONH$_2$ Σ-Glycine-O-(Tic-Tic-X-J-Tic-Tic-X—Z)$_n$-Tic-Tic-Π-J-Tic-U$_m$—CONH$_2$ Σ-Glycine-O-(Tic-Tic-X—Z-Tic-Tic-X-J)$_n$-Tic-Tic-Π-Z-Tic-U$_m$—CONH$_2$ Σ-Glycine-B-(Tic-Tic-X—Z-Tic-Tic-X-J)$_n$-Tic-Tic-Π-Z-Tic-U$_m$—CONH$_2$ Σ-Glycine-O-(Tic-Tic-X-J-Tic-Tic-X—Z)$_n$-Tic-Tic-Π-J-Tic-U$_m$—CONH$_2$ Σ-Glycine-O-(Tic-Tic-X—Z-Tic-Tic-X-J)$_n$-Tic-Tic-Π-Z-Tic-U$_m$—CONH$_2$ Σ-Glycine-B-(Tic-Tic-X—Z-Tic-Tic-X-J)$_n$-Tic-Tic-Π-Z-Tic-U$_m$—CONH$_2$ Σ-Glycine-O-(Tic-Tic-X-J-Tic-Tic-X—Z)$_n$-Tic-Tic-Π-J-Tic-U$_m$—CONH—(CH$_2$)$_k$—NH$_2$ Σ-Glycine-O-(Tic-Tic-X-J-Tic-Tic-X—Z)$_n$-Tic-Π-U$_m$—CONH$_2$ Σ-Glycine-O-(Tic-Tic-X-J-Tic-Tic-X—Z)$_n$-Tic-Π-U$_m$—CONH$_2$ Σ-Glycine-O-(Tic-Tic-X—Z-Tic-Tic-X-J)$_n$-Tic-Π-U$_m$—CONH$_2$, Σ-Glycine-O-(Tic-Tic-X—Z-Tic-Tic-X-J)$_n$-Tic-Π-U$_m$—CONH$_2$, Σ-Glycine-O-(Tic-Tic-Z-Tic-Tic-J)$_n$-Tic-Tic-Z-Tic-U$_m$—CONH$_2$ Σ-Glycine-B-(Tic-Tic-Z-Tic-tic-J)$_n$-Tic-Tic-Z-Tic-U$_m$—CONH$_2$ Σ-Glycine-O-(Oic-Tic-X-J-Oic-Tic-X—Z)$_n$-Oic-Tic-Π-J-Tic-U$_m$—CONH$_2$ Σ-Glycine-O-(Oic-Tic-X—Z-Oic-Tic-X-J)$_n$-Oic-Tic-Π-Z-Tic-U$_m$—CONH$_2$ Σ-Glycine-B-(Oic-Tic-X—Z-Oic-Tic-X-J)$_n$-Oic-Tic-Π-Z-Tic-U$_m$—CONH$_2$ Σ-Glycine-O-(Oic-Tic-X-J-Oic-Tic-X—Z)$_n$-Oic-Tic-Π-J-Tic-U$_m$—CONH$_2$ Σ-Glycine-O-(Oic-Tic-X—Z-Oic-Tic-X-J)$_n$-Oic-Tic-Π-Z-Tic-U$_m$—CONH$_2$ Σ-Glycine-B-(Oic-Tic-X—Z-Oic-Tic-X-J)$_n$-Oic-Tic-Π-Z-Tic-U$_m$—CONH$_2$ Σ-Glycine-O-(Oic-Tic-X-J-Tic-Tic-X—Z)$_n$-Tic-Tic-Π-J-Tic-U$_m$—CONH—(CH$_2$)$_k$—NH$_2$ Σ-Glycine-O-(Oic-Tic-X-J-Oic-Tic-X—Z)$_n$-Tic-Π-U$_m$—CONH$_2$ Σ-Glycine-O-(Oic-Tic-X-J-Oic-Tic-X—Z)$_n$-Tic-Π-U$_m$—CONH$_2$ Σ-Glycine-O-(Oic-Tic-X—Z-Oic-Tic-X-J)$_n$-Tic-Π-U$_m$—CONH$_2$, Σ-Glycine-O-(Oic-Tic-X—Z-Oic-Tic-X-J)$_n$-Tic-Π-U$_m$—CONH$_2$ Σ-Glycine-O-(Oic-Tic-Z-Oic-Tic-J)$_n$-Oic-Tic-Z-Tic-U$_m$—CONH$_2$ Σ-Glycine-B-(Oic-Tic-Z-Oic-tic-J)$_n$-Oic-Tic-Z-Tic-U$_m$—CONH$_2$ Σ-Glycine-O-(Oic-Oic-X-J-Oic-Oic-X—Z)$_n$-Oic-Oic-Π-J-Tic-U$_m$—CONH$_2$ Σ-Glycine-O-(Oic-Oic-X—Z-Oic-Oic-X-J)$_n$-Oic-Oic-Π-Z-Tic-U$_m$—CONH$_2$ Σ-Glycine-B-(Oic-Oic-X—Z-Oic-Oic-X-J)$_n$-Oic-Oic-Π-Z-Tic-U$_m$—CONH$_2$ Σ-Glycine-O-(Oic-Oic-X-J-Oic-Oic-X—Z)$_n$-Oic-Oic-Π-J-Tic-U$_m$—CONH$_2$ Σ-Glycine-O-(Oic-Oic-X—Z-Oic-Oic-X-J)$_n$-Oic-Oic-Π-Z-Tic-U$_m$—CONH$_2$ Σ-Glycine-B-(Oic-Oic-X—Z-Oic-Oic-X-J)$_n$-Oic-Oic-Π-Z-Tic-U$_m$—CONH$_2$ Σ-Glycine-O-(Oic-Oic-X-J-Oic-Oic-X—Z)$_n$-Oic-Oic-Π-J-Tic-U$_m$—CONH—(CH$_2$)$_k$—NH$_2$ Σ-Glycine-O-(Oic-Oic-X-J-Oic-Oic-X—Z)$_n$-Tic-Π-U$_m$—CONH$_2$ Σ-Glycine-O-(Oic-Oic-X-J-Oic-Oic-X—Z)$_n$-Tic-Π-U$_m$—CONH$_2$ Σ-Glycine-O-(Oic-Oic-X—Z-Oic-Oic-X-J)$_n$-Tic-Π-U$_m$—CONH$_2$, Σ-Glycine-O-(Oic-Oic-X—Z-Oic-Oic-X-J)$_n$-Tic-Π-U$_m$—CONH$_2$, Σ-Glycine-O-(Oic-Oic-Z-Oic-Oic-J)$_n$-Oic-Oic-Z-Tic-U$_m$—CONH$_2$ Σ-Glycine-B-(Oic-Oic-Z-Oic-tic-J)$_n$-Oic-Oic-Z-Tic-U$_m$—CONH$_2$ Σ-U$_m$-Glycine-O-(Tic-Oic-X-J-Tic-Oic-X—Z)$_n$-Tic-Oic-Π-J-Tic-CONH$_2$ Σ-U$_m$-Glycine-O-(Tic-Oic-X—Z-Tic-Oic-X-J)$_n$-Tic-Oic-Π-Z-Tic-CONH$_2$ Σ-U$_m$-Glycine-B-(Tic-Oic-X—Z-Tic-Oic-X-J)$_n$-Tic-Oic-Π-Z-Tic-CONH$_2$ Σ-U$_m$-Glycine-O-(Tic-Oic-X-J-Tic-Oic-X—Z)$_n$-Tic-Oic-Π-J-Tic-CONH$_2$ Σ-U$_m$-Glycine-O-(Tic-Oic-X—Z-Tic-Oic-X-J)$_n$-Tic-Oic-Π-Z-Tic-CONH$_2$ Σ-U$_m$-Glycine-B-(Tic-Oic-X—Z-Tic-Oic-X-J)$_n$-Tic-Oic-Π-Z-Tic-CONH$_2$ Σ-U$_m$-Glycine-O-(Tic-Oic-X-J-Tic-Oic-X—Z)$_n$-Tic-Oic-Π-J-Tic-CONH—(CH$_2$)$_k$—NH$_2$ Σ-U$_m$-Glycine-O-(Tic-Oic-X-J-Tic-Oic-X—Z)$_n$-Tic-Π-CONH$_2$ Σ-U$_m$-Glycine-O-(Tic-Oic-X-J-Tic-Oic-X—Z)$_n$-Oic-Π-CONH$_2$ Σ-U$_m$-Glycine-O-(Tic-Oic-X—Z-Tic-Oic-X-J)$_n$-Tic-Π-CONH$_2$ Σ-U$_m$-Glycine-O-(Tic-Oic-X—Z-Tic-Oic-X-J)$_n$-Oic-Π-CONH$_2$, Σ-U$_m$-Glycine-O-(Tic-Tic-X-J-Tic-Tic-X—Z)$_n$-Tic-Oic-Π-J-Tic-CONH$_2$ Σ-U$_m$-Glycine-O-(Tic-Tic-X—Z-Tic-Tic-X-J)$_n$-Tic-Oic-Π-Z-Tic-CONH$_2$ Σ-U$_m$-Glycine-B-(Tic-Tic-X—Z-Tic-Tic-X-J)$_n$-Tic-Oic-Π-Z-Tic-CONH$_2$ Σ-U$_m$-Glycine-O-(Tic-Tic-X-J-Tic-Tic-X—Z)$_n$-Tic-Oic-Π-J-Tic-CONH$_2$ Σ-U$_m$-Glycine-O-(Tic-Tic-X—Z-Tic-Tic-X-J)$_n$-Tic-Oic-Π-Z-Tic-CONH$_2$ Σ-U$_m$-Glycine-B-(Tic-Tic-X—Z-Tic-Tic-X-J)$_n$-Tic-Oic-Π-Z-Tic-CONH$_2$, Σ-U$_m$-Glycine-O-(Tic-Tic-X-J-Tic-Tic-X—Z)$_n$-Tic-Oic-Π-J-Tic-CONH—(CH$_2$)$_k$—NH$_2$ Σ-U$_m$-Glycine-O-(Tic-Tic-X-J-Tic-Tic-X—Z)$_n$-Tic-Π-CONH$_2$ Σ-U$_m$-Glycine-O-(Tic-Tic-X-J-Tic-Tic-X—Z)$_n$-Oic-Π-CONH$_2$ Σ-U$_m$-Glycine-O-(Tic-Tic-X—Z-Tic-Tic-X-J)$_n$-Tic-Π-CONH$_2$, and Σ-U$_m$-Glycine-O-(Tic-Tic-X—Z-Tic-Tic-X-J)$_n$-Oic-Π-CONH$_2$ wherein Tic stands for tetrahydroisoquinolinecarboxylic acid, Oic stands for octahydroindolecarboxylic acid, Σ is acetyl, NH$_2$, biotin, β-thienylalanine (Thi), cysteine, Keyhole Limpet Haemocyanin (KLH), or Bovine Serum Albumine (BSA), U is lysine, arginine, histidine, ornithine, 2,3-diaminopropionic acid (Dpr), diaminobutanoic acid (Dab), 4-aminopiperidine-4-carboxylic acid (Apc4), or 3-aminopiperidine-3-carboxylic acid (Apc3), X is glycine, alanine, β-alanine, gamma-aminobutyric acid (Gaba), ∈-aminohexanoic acid (Ahx), phenylglycine (Phg), 9-aminooctanoic acid (9-Aoa), 10-aminodecanoic acid (10Ada), 12-aminododecanoic acid (12-Adda), or 16-aminopalmitic acid (16-Apa), J is lysine, arginine, histidine, ornithine, 2,3-diaminopropionic acid (Dpr), or 2,4-diaminobutanoic acid (Dab), Z is phenylalanine, tyrosine, tryptophan, 4-fluorophenylalanine (Fpa), 4-chlorophenylalanine (Cph), 4-nitrophenylalanine (Nph), phenyl glycine (Phg), valine, isoleucine, norvaline, norleucine, norisoleucine, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, N-Ethylglycine, allo-Isoleucine, N-Methylglycine, N-Methylisoleucine, or N-Methylvaline, O is phenylalanine, leucine, valine or isoleucine, B is lysine, arginine, histidine, ornithine, 2,3-diaminopropionic acid (Dpr), 2,4-diaminobutanoic acid (Dab), 4-aminopiperidine-4-carboxylic acid (Apc4), or 3-aminopiperidine-3-carboxylic acid (Apc3), Π is glycine, alanine, β-alanine, gamma-aminobutyric acid (Gaba), or ∈-Aminohexanoic acid (Ahx), n is 1 to 4 repeating units, m is 1 to 5 repeating units, and k is 1 to 5 repeating units.

2. The antimicrobial peptide of claim 1, which in its secondary structure includes at least three β-turns and exhibits sufficient conformational flexibility to bind to the membrane of at least one of Gram positive bacteria, Gram negative bacteria or *Mycobacterium*.

3. The antimicrobial peptide of claim 1, which exhibits less hemolytic activity than naturally occurring non-selective antimicrobial peptides.

4. The antimicrobial peptide of claim 1, which is selected from the group consisting of NH$_2$-GKGL-Tic-Oic-GK-Tic-Oic-GF-Tic-Oic-GK-Tic-Oic-GF-Tic-Oic-GK-Tic-Oic-GKR—CONH$_2$ (SEQ ID NO:4)

NH$_2$-GKGL-Tic-Oic-GR-Tic-Oic-GF-Tic-Oic-GR-Tic-Oic-GF-Tic-Oic-GR-Tic-Oic-GKR—CONH$_2$ (SEQ ID NO:5)

NH$_2$-GKGL-Tic-Oic-GL-Tic-Oic-GK-Tic-Oic-GL-Tic-Oic-GK-Tic-Oic-GL-Tic-Oic-GLR—CONH$_2$ (SEQ ID NO:6)

NH$_2$-GKGL-Tic-Oic-GK-Tic-Oic-GL-Tic-Oic-GK-Tic-Oic-GL-Tic-Oic-GK-Tic-Oic-GK LR—CONH$_2$ (SEQ ID NO:7)

NH$_2$-GKGL-Tic-Oic-FK-Tic-Oic-KF-Tic-Oic-FK-Tic-Oic-KF-Tic-Oic-FK-Tic-Oic-FKR—CONH$_2$ (SEQ ID NO:8)

NH$_2$—KL-Tic-Oic-K-Tic-Oic-F-Tic-Oic-K-Tic-Oic-F-Tic-Oic-K-Tic-Oic-KR—CONH$_2$ (SEQ ID NO:9)

Ac-GF-Tic-Oic-GK-Tic-Oic-GF-Tic-Oic-GK-Tic-KKKK—CONH$_2$ (SEQ ID NO:10)

Ac-GF-Tic-Oic-GK-Tic-Oic-GF-Tic-Oic-GK-Tic-KKKK—CONH—CH2-CH2-NH$_2$ (SEQ ID NO:11)

Ac-GF-Tic-Oic-GK-Tic-Oic-GF-Tic-Oic-GK-Tic-KKKK—CONH—CH$_2$—CH$_2$—CH$_2$—NH$_2$ (SEQ ID NO:12)

NH$_2$-GF-Tic-Oic-GK-Tic-Oic-GF-Tic-Oic-GK-Tic-KKKK—CONH$_2$ (SEQ ID NO:13)

NH$_2$—KL-Tic-Oic-GK-Tic-Oic-GF-Tic-Oic-GK-Tic-KKKK—CONH$_2$ (SEQ ID NO:14)

Ac-F-Tic-Oic-K-Tic-Oic-F-Tic-Oic-K-Tic-KKKK—CONH$_2$ (SEQ ID NO:15)

Ac-Gaba-F-Tic-Oic-Gaba-K-Tic-Oic-Gaba-F-Tic-Oic-Gaba-K-Tic-KKKK—CONH$_2$ (SEQ ID NO:16)

Ac-G-Tic-Oic-K-Tic-Oic-G-Tic-Oic-K-Tic-KKKK—CONH$_2$ (SEQ ID NO:17)

Ac-GF-Oic-GK-Oic-GF-Oic-GKKKKK—CONH$_2$ (SEQ ID NO:18)

Ac-GF-Tic-GK-Tic-GF-Tic-GK-Tic-KKKK—CONH$_2$ (SEQ ID NO:19)

Ac-GF-Tic-Oic-G-GK-Tic-G-GF-Tic-G-GK-Tic-KKKK—CONH$_2$ (SEQ ID NO:20)

Ac-GF-G-Oic-GK-G-Oic-GF-G-Oic-GK-G-KKKK—CONH$_2$ (SEQ ID NO:21)

Ac-GF-F-Oic-GK-F-Oic-GF-F-Oic-GK-F-KKKK—CONH$_2$ (SEQ ID NO:22)

Ac-βAla-F-Tic-Oic-βAla-K-Tic-Oic-βAla-F-Tic-Oic-βAla-K-Tic-KKKK—CONH$_2$ (SEQ ID NO:23)

Ac-Alix-F-Tic-Oic-Ahx-K-Tic-Oic-Ahx-F-Tic-Oic-Ahx-K-Tic-KKKK—CONH$_2$ (SEQ ID NO:24)

Ac-F-Tic-Oic-K-Tic-Oic-F-Tic-Oic-K-Tic-KKKKKK—CONH$_2$ (SEQ ID NO:25)

Ac-GF-Tic-Oic-GK-Tic-Oic-GF-Tic-Oic-GK-Tic-KKKKK—CONH$_2$ (SEQ ID NO:26)

Ac-Gaba-F-Tic-Oic-Gaba-K-Tic-Oic-Gaba-F-Tic-Oic-Gaba-K-Tic-KKKKK—CONH$_2$ (SEQ ID NO:27)

Ac-GF-Tic-Oic-GK-Tic-Oic-GF-Tic-Oic-GK-Tic-Orn-Orn-Orn-Orn-CONH$_2$ (SEQ ID NO:28)

Ac-G-Fpa-Tic-Oic-GK-Tic-Oic-G-Fpa-Tic-Oic-GK-Tic-KKKK—CONH$_2$ (SEQ ID NO:29)

Ac-GF-Tic-Oic-G-Orn-Tic-Oic-GF-Tic-Oic-G-Orn-Tic-Orn-Orn-Orn-Orn-CONH$_2$ (SEQ ID NO:30)

Biotin-GF-Tic-Oic-GK-Tic-Oic-GF-Tic-Oic-GK-Tic-KKKK—CONH$_2$ (SEQ ID NO:31)

Ac-GF-Tic-Oic-G-Dpr-Tic-Oic-GF-Tic-Oic-G-Dpr-Tic-Dpr-DprDpr-Dpr-CONH$_2$ (SEQ ID NO:32)

Ac-βAla-Fpa-Tic-Oic-βAla-Dpr-Tic-Oic-βAla-Fpa-Tic-Oic-βAla-Dpr-Tic-Dpr-Dpr-Dpr-CONH$_2$ (SEQ ID NO:33)

Ac-G-dF-Tic-Oic-GK-Tic-Oic-G  dF-Tic-Oic-GK-Tic-KKKK—CONH$_2$

Ac-GF-Tic-Oic-G-dK-Tic-Oic-GF-Tic-Oic-G-dK-Tic-KKKK—CONH$_2$

Ac-GF-Tic-Oic-GK-Tic-Oic-GF-Tic-Oic-GK-Tic-Dpr-Dpr-Dpr-Dpr-CONH$_2$ (SEQ ID NO:46)

(NH$_2$)$_4$—(K)$_2$—K-Tic-Oic-GK-Tic-Oic-GF-Tic-Oic-GK-Tic-Oic-GF-Tic-Oic-GK-Tic-CONH$_2$ (SEQ ID NO:47)

Ac-G-Fpa-Tic-Oic-G-Dpr-Tic-Oic-G-Fpa-Tic-Oic-G-Dpr-Tic-Dpr-Dpr-Dpr-CONH$_2$ (SEQ ID NO:48)

Ac-GF-Tic-Oic-GK-Tic-Oic-GF-Tic-Oic-GK-Tic-βA-KKKK—CONH$_2$ (SEQ ID NO:35)

Ac-GF-Tic-Oic-GK-Tic-Oic-GF-Tic-Oic-GK-Tic-Gaba-KKKK—CONH$_2$ (SEQ ID NO:36)

Ac-GF-Tic-Oic-GK-Tic-Oic-GF-Tic-Oic-GK-Tic-Ahx-KKKK—CONH$_2$ (SEQ ID NO:37)

Ac-GF-Tic-Oic-G-Dab-Tic-Oic-GF-Tic-Oic-G-Dab-Tic-Dab-Dab-Dab-Dab-CONH$_2$ (SEQ ID NO:38)

Ac-GF-Tic-Oic-G-Tic-Oic-GF-Tic-Oic-G-Tic-G-KKKK—CONH$_2$ (SEQ ID NO:49)

Ac-GF-Tic-Oic-GK-Tic-Oic-GF-Tic-Oic-GK-Tic-Dab-Dab-Dab-Dab-CONH$_2$ (SEQ ID NO:50)

(NH$_2$)$_4$-(Orn)$_2$-Orn-Tic-Oic-G-Orn-Tic-Oic-GF-Tic-Oic-G-Orn-Tic-Oic-GF-Tic-Oic-G-Orn-Tic-CONH$_2$ (SEQ ID NO:51)

Thi-GF-Tic-Oic-GK-Tic-Oic-GF-Tic-Oic-GK-Tic-G-KKKK—CONH$_2$ (SEQ ID NO:52)

Ac-GF-Tic-Oic-GR-Tic-Oic-GF-Tic-Oic-GR-Tic-RRRR—CONH$_2$ (SEQ ID NO:41)

Ac-GF-Tic-Tic-GK-Tic-Tic-GF-Tic-Tic-GK-Tic-KKKK—CONH$_2$ (SEQ ID NO:42)

Ac-GF-Oic-Oic-GK-Oic-Oic-GF-Oic-Oic-GK-Oic-KKKK—CONH$_2$ (SEQ ID NO:53)

Cys-GF-Tic-Oic-GK-Tic-Oic-GF-Tic-Oic-GK-Tic-G-KKKK—CONH$_2$ (SEQ ID NO:54)

(NH$_2$)$_4$-(Dpr)$_2$-Dpr-Tic-Oic-G-Dpr-Tic-Oic-GF-Tic-Oic-G-Dpr-Tic-Oic-GF-Tic-Oic-G-Dpr-Tic-CONH$_2$ (SEQ ID NO:55)

(NH$_2$)$_4$-(Dab)$_2$-Dab-Tic-Oic-G-Dab-Tic-Oic-GF-Tic-Oic-G-Dab-Tic-Oic-GF-Tic-Oic-G-Dab-Tic-CONH$_2$ (SEQ ID NO:56)
Ac-G-Nph-Tic-Oic-GK-Tic-Oic-G-Nph-Tic-Oic-GK-Tic-KKKK—CONH$_2$ (SEQ ID NO:34)
Thi-GF-Tic-Oic-GK-Tic-Oic-GF-Tic-Oic-GK-Tic-KKKK—CONH$_2$ (SEQ ID NO:39)
Ac-GF-Tic-Oic-GW-Tic-Oic-GF-Tic-Oic-GW-Tic-KKKK—CONH$_2$ (SEQ ID NO:40)
Ac-G-Cph-Tic-Oic-GK-Tic-Oic-G-Cph-Tic-Oic-GK-Tic-KKKK—CONH$_2$ (SEQ ID NO:43)
Ac-GF-Oic-Tic-GK-Oic-Tic-GF-Oic-Tic-GK-Tic-KKKK—CONH$_2$ (SEQ ID NO:44)
Ac-βAla-Fpa-Tic-Oic-βAla-K-Tic-Oic-βAla-Fpa-Tic-Oic-βAla-K-Tic-Dpr-Dpr-Dpr-Dpr-CONH$_2$, (SEQ ID NO:45)
Ac-KKKK-GF-Tic-Oic-GK-Tic-Oic-GF-Tic-Oic-GK-Tic-CONH$_2$ (SEQ ID NO:1), and
Ac-KKKK-GF-Tic-Tic-GK-Tic-Tic-GF-Tic-Tic-GK-Tic-CONH$_2$ (SEQ ID NO:57).

5. The antimicrobial peptide of claim 1, which is stably in association with a pharmaceutically acceptable adjuvant.

6. A method for treating at least one of Gram positive bacteria, Gram negative bacteria, *Mycobacterium*, *Plasmodium falciparum*, *Candida albicans* *Cryptococcus neoformans*, *Botrytis cinerea*, *Fusarium culmorum* or *Neurospora crassa*, comprising the step of administering to a mammal suspected of infection by at least one of Gram positive bacteria, Gram negative bacteria or *Mycobacterium* a pharmaceutically effective amount of at least one of the synthetic antimicrobial peptide analogs having a formula selected from the group consisting of:

Σ-Glycine-O-(Tic-Oic-X-J-Tic-Oic-X—Z)$_n$-Tic-Oic-Π-J-Tic-U$_m$—CONH$_2$
Σ-Glycine-O-(Tic-Oic-X—Z-Tic-Oic-X-J)$_n$-Tic-Oic-Π-Z-Tic-U$_m$—CONH$_2$
Σ-Glycine-B-(Tic-Oic-X—Z-Tic-Oic-X-J)$_n$-Tic-Oic-Π-Z-Tic-U$_m$—CONH$_2$
Σ-Glycine-O-(Tic-Oic-X-J-Tic-Oic-X—Z)$_n$-Tic-Oic-Π-J-Tic-U$_m$—CONH$_2$
Σ-Glycine-O-(Tic-Oic-X—Z-Tic-Oic-X-J)$_n$-Tic-Oic-Π-Z-Tic-U$_m$—CONH$_2$
Σ-Glycine-B-(Tic-Oic-X—Z-Tic-Oic-X-J)$_n$-Tic-Oic-Π-Z-Tic-U$_m$—CONH$_2$
Σ-Glycine-O-(Tic-Oic-X-J-Tic-Oic-X—Z)$_n$-Tic-Oic-Π-J-Tic-U$_m$—CONH—(CH$_2$)$_k$—NH$_2$
Σ-Glycine-O-(Tic-Oic-X-J-Tic-Oic-X—Z)$_n$-Tic-Π-U$_m$—CONH$_2$
Σ-Glycine-O-(Tic-Oic-X-J-Tic-Oic-X—Z)$_n$-Oic-Π-U$_m$—CONH$_2$
Σ-Glycine-O-(Tic-Oic-X—Z-Tic-Oic-X-J)$_n$-Tic-Π-U$_m$—CONH$_2$,
Σ-Glycine-O-(Tic-Oic-X—Z-Tic-Oic-X-J)$_n$-Oic-Π-U$_m$—CONH$_2$
Σ-Glycine-O-(Tic-Oic-Z-Tic-Oic-J)$_n$-Tic-Oic-Z-Tic-U$_m$—CONH$_2$
Σ-Glycine-B-(Tic-Oic-Z-Tic-Oic-J)$_n$-Tic-Oic-Z-Tic-U$_m$—CONH$_2$
Σ-Glycine-O-(Tic-Tic-X-J-Tic-Tic-X—Z)$_n$-Tic-Tic-Π-J-Tic-U$_m$—CONH$_2$
Σ-Glycine-O-(Tic-Tic-X—Z-Tic-Tic-X-J)$_n$-Tic-Tic-Π-Z-Tic-U$_m$—CONH$_2$
Σ-Glycine-B-(Tic-Tic-X—Z-Tic-Tic-X-J)$_n$-Tic-Tic-Π-Z-Tic-U$_m$—CONH$_2$
Σ-Glycine-O-(Tic-Tic-X-J-Tic-Tic-X—Z)$_n$-Tic-Tic-Π-J-Tic-U$_m$—CONH$_2$
Σ-Glycine-O-(Tic-Tic-X—Z-Tic-Tic-X-J)$_n$-Tic-Tic-Π-Z-Tic-U$_m$—CONH$_2$
Σ-Glycine-B-(Tic-Tic-X—Z-Tic-Tic-X-J)$_n$-Tic-Tic-Π-Z-Tic-U$_m$—CONH$_2$
Σ-Glycine-O-(Tic-Tic-X-J-Tic-Tic-X—Z)$_n$-Tic-Tic-Π-J-Tic-U$_m$—CONH—(CH$_2$)$_k$—NH$_2$
Σ-Glycine-O-(Tic-Tic-X-J-Tic-Tic-X—Z)$_n$-Tic-Π-U$_m$—CONH$_2$
Σ-Glycine-O-(Tic-Tic-X-J-Tic-Tic-X—Z)$_n$-Tic-Π-U$_m$—CONH$_2$
Σ-Glycine-O-(Tic-Tic-X—Z-Tic-Tic-X-J)$_n$-Tic-Π-U$_m$—CONH$_2$,
Σ-Glycine-O-(Tic-Tic-X—Z-Tic-Tic-X-J)$_n$-Tic-Π-U$_m$—CONH$_2$,
Σ-Glycine-O-(Tic-Tic-Z-Tic-Tic-J)$_n$-Tic-Tic-Z-Tic-U$_m$—CONH$_2$
Σ-Glycine-B-(Tic-Tic-Z-Tic-tic-J)$_n$-Tic-Tic-Z-Tic-U$_m$—CONH$_2$
Σ-Glycine-O-(Oic-Tic-X-J-Oic-Tic-X—Z)$_n$-Oic-Tic-Π-J-Tic-U$_m$—CONH$_2$
Σ-Glycine-O-(Oic-Tic-X—Z-Oic-Tic-X-J)$_n$-Oic-Tic-Π-Z-Tic-U$_m$—CONH$_2$
Σ-Glycine-O-(Oic-Tic-X—Z-Oic-Tic-X-J)$_n$-Oic-Tic-Π-Z-Tic-U$_m$—CONH$_2$
Σ-Glycine-O-(Oic-Tic-X-J-Oic-Tic-X—Z)$_n$-Oic-Tic-Π-J-Tic-U$_m$—CONH$_2$
Σ-Glycine-O-(Oic-Tic-X—Z-Oic-Tic-X-J)$_n$-Oic-Tic-Π-Z-Tic-U$_m$—CONH$_2$
Σ-Glycine-B-(Oic-Tic-X—Z-Oic-Tic-X-J)$_n$-Oic-Tic-Π-Z-Tic-U$_m$—CONH$_2$
Σ-Glycine-O-(Oic-Tic-X-J-Tic-Tic-X—Z)$_n$-Tic-Tic-Π-J-Tic-U$_m$—CONH—(CH$_2$)$_k$—NH$_2$
Σ-Glycine-O-(Oic-Tic-X-J-Oic-Tic-X—Z)$_n$-Tic-Π-U$_m$—CONH$_2$
Σ-Glycine-O-(Oic-Tic-X-J-Oic-Tic-X—Z)$_n$-Tic-Π-U$_m$—CONH$_2$
Σ-Glycine-O-(Oic-Tic-X—Z-Oic-Tic-X-J)$_n$-Tic-Π-U$_m$—CONH$_2$,
Σ-Glycine-O-(Oic-Tic-X—Z-Oic-Tic-X-J)$_n$-Tic-Π-U$_m$—CONH$_2$
Σ-Glycine-O-(Oic-Tic-Z-Oic-Tic-J)$_n$-Oic-Tic-Z-Tic-U$_m$—CONH$_2$
Σ-Glycine-B-(Oic-Tic-Z-Oic-tic-J)$_n$-Oic-Tic-Z-Tic-U$_m$—CONH$_2$
Σ-Glycine-O-(Oic-Oic-X-J-Oic-Oic-X—Z)$_n$-Oic-Oic-Π-J-Tic-U$_m$—CONH$_2$
Σ-Glycine-O-(Oic-Oic-X—Z-Oic-Oic-X-J)$_n$-Oic-Oic-Π-Z-Tic-U$_m$—CONH$_2$
Σ-Glycine-B-(Oic-Oic-X—Z-Oic-Oic-X-J)$_n$-Oic-Oic-Π-Z-Tic-U$_m$—CONH$_2$
Σ-Glycine-O-(Oic-Oic-X-J-Oic-Oic-X—Z)$_n$-Oic-Oic-Π-J-Tic-U$_m$—CONH$_2$
Σ-Glycine-O-(Oic-Oic-X—Z-Oic-Oic-X-J)$_n$-Oic-Oic-Π-Z-Tic-U$_m$—CONH$_2$
Σ-Glycine-B-(Oic-Oic-X—Z-Oic-Oic-X-J)$_n$-Oic-Oic-Π-Z-Tic-U$_m$—CONH$_2$
Σ-Glycine-O-(Oic-Oic-X-J-Oic-Oic-X—Z)$_n$-Oic-Oic-Π-J-Tic-U$_m$—CONH—(CH$_2$)$_k$—NH$_2$
Σ-Glycine-O-(Oic-Oic-X-J-Oic-Oic-X—Z)$_n$-Tic-Π-U$_m$—CONH$_2$
Σ-Glycine-O-(Oic-Oic-X-J-Oic-Oic-X—Z)$_n$-Tic-Π-U$_m$—CONH$_2$
Σ-Glycine-O-(Oic-Oic-X—Z-Oic-Oic-X-J)$_n$-Tic-Π-U$_m$—CONH$_2$,
Σ-Glycine-O-(Oic-Oic-X—Z-Oic-Oic-X-J)$_n$-Tic-Π-U$_m$—CONH$_2$, Σ-Glycine-O-(Oic-Oic-Z-Oic-Oic-J)$_n$-Oic-Oic-Z-Tic-U$_m$—CONH$_2$ Σ-Glycine-B-(Oic-Oic-Z-Oic-tic-J)$_n$-Oic-Oic-Z-Tic-U$_m$—CONH$_2$ Σ-U$_m$-Glycine-O-(Tic-Oic-X-J-Tic-Oic-X—Z)$_n$-Tic-Oic-Π-J-Tic-CONH$_2$ Σ-U$_m$-Glycine-O-(Tic-Oic-X—Z-Tic-Oic-X-J)$_n$-Tic-Oic-Π-Z-Tic-CONH$_2$ Σ-U$_m$-Glycine-B-(Tic-Oic-X—Z-Tic-Oic-X-J)$_n$-Tic-Oic-Π-Z-Tic-CONH$_2$ Σ-U$_m$Glycine-O-(Tic-Oic-X-J-Tic-Oic-X—Z)$_n$-Tic-Oic-Π-J-Tic-CONH$_2$ Σ-U$_m$-Glycine-O-(Tic-Oic-X—Z-Tic-Oic-X-J)$_n$-Tic-Oic-Π-Z-Tic-CONH$_2$ Σ-U$_m$-Glycine-B-(Tic-Oic-X—Z-Tic-Oic-X-J)$_n$-Tic-Oic-Π-Z-Tic-CONH$_2$, Σ-U$_m$-Glycine-O-(Tic-Oic-X-J-Tic-Oic-X—Z)$_n$-Tic-Oic-Π-J-Tic-CONH—(CH$_2$)$_k$—NH$_2$ Σ-U$_m$-Glycine-O-(Tic-Oic-X-J-Tic-Oic-X—Z)$_n$-Tic-Π-CONH$_2$ Σ-U$_m$-Glycine-O-(Tic-Oic-X-J-Tic-Oic-X—Z)$_n$-Oic-Π-CONH$_2$ Σ-U$_m$-Glycine-O-(Tic-Oic-X—Z-Tic-Oic-X-J)$_n$-Tic-Π-CONH$_2$ Σ-U$_m$-Glycine-O-(Tic-Oic-X—Z-Tic-Oic-X-J)$_n$-Oic-Π-CONH$_2$ Σ-U$_m$-Glycine-O-(Tic-Tic-X-J-Tic-Tic-X—Z)$_n$-Tic-Oic-Π-J-Tic-CONH$_2$ Σ-U$_m$-Glycine-O-(Tic-Tic-X—Z-Tic-Tic-X-J)$_n$-Tic-Oic-Π-Z-Tic-CONH$_2$ Σ-U$_m$-Glycine-B-(Tic-Tic-X—Z-Tic-Tic-X-J)$_n$-Tic-Oic-Π-Z-Tic-CONH$_2$ Σ-U$_m$Glycine-O-(Tic-Tic-X-J-Tic-Tic-X—Z)$_n$-Tic-Oic-Π-J-Tic-CONH$_2$ Σ-U$_m$-Glycine-O-(Tic-Tic-X—Z-Tic-Tic-X-J)$_n$-Tic-Oic-Π-Z-Tic-CONH$_2$ Σ-U$_m$-Glycine-B-(Tic-Tic-X—Z-Tic-Tic-X-J)$_n$-Tic-Oic-Π-Z-Tic-CONH$_2$, Σ-U$_m$-Glycine-O-(Tic-Tic-X-J-Tic-Tic-X—Z)$_n$-Tic-Oic-Π-J-Tic-CONH—(CH$_2$)$_k$—NH$_2$ Σ-U$_m$-Glycine-O-(Tic-Tic-X-J-Tic-Tic-X—Z)$_n$-Tic-Π-CONH$_2$ Σ-U$_m$-Glycine-O-(Tic-Tic-X-J-Tic-Tic-X—Z)$_n$-Oic-Π-CONH$_2$ Σ-U$_m$-Glycine-O-(Tic-Tic-X—Z-Tic-Tic-X-J)$_n$-Tic-Π-CONH$_2$ and Σ-U$_m$-Glycine-O-(Tic-Tic-X—Z-Tic-Tic-X-J)$_n$-Oic-Π-CONH$_2$, wherein Tic stands for tetrahydroisoquinolinecarboxylic acid, Oic stands for octahydroindolecarboxylic acid, Σ is acetyl, NH$_2$, biotin, β-thienylalanine (Thi), cysteine, Keyhole Limpet Haemocyanin (KLH), or Bovine Serum Albumine (BSA), U is lysine, arginine, histidine, ornithine, 2,3-diaminopropionic acid (Dpr), diaminobutanoic acid (Dab), 4-aminopiperidine-4-carboxylic acid (Apc4), or 3-aminopiperidine-3-carboxylic acid (Apc3), X is glycine, alanine, β-alanine, gamma-aminobutyric acid (Gaba), ∈-aminohexanoic acid (Ahx), phenylglycine (Phg), 9-aminooctanoic acid (9-Aoa), 10-aminodecanoic acid (10Ada), 12-aminododecanoic acid (12-Adda), or 16-aminopalmitic acid (16-Apa), J is lysine, arginine, histidine, ornithine, 2,3-diaminopropionic acid (Dpr), or 2,4-diaminobutanoic acid (Dab), Z is phenylalanine, tyrosine, tryptophan, 4-fluorophenylalanine (Fpa), 4-chlorophenylalanine (Cph), 4-nitrophenylalanine (Nph), phenyl glycine (Phg), valine, isoleucine, norvaline, norleucine, norisoleucine, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, N-Ethylglycine, allo-Isoleucine, N-Methylglycine, N-Methylisoleucine, or N-Methylvaline, O is phenylalanine, leucine, valine or isoleucine, B is lysine, arginine, histidine, ornithine, 2,3-diaminopropionic acid (Dpr), 2,4-diaminobutanoic acid (Dab), 4-aminopiperidine-4-carboxylic acid (Apc4), or 3-aminopiperidine-3-carboxylic acid (Apc3), Π is glycine, alanine, β-alanine, gamma-aminobutyric acid (Gaba), or ∈-Aminohexanoic acid (Ahx), n is 1 to 4 repeating units, m is 1 to 5 repeating units, and k is 1 to 5 repeating units, and a pharmaceutically acceptable adjuvant.

7. The method of claim 6 wherein the antimicrobial peptide in its secondary structure includes at least three β-turns and exhibits sufficient conformational flexibility to bind to the membrane of at least one of Gram positive bacteria, Gram negative bacteria or *Mycobacterium*.

8. The method of claim 6, wherein the antimicrobial peptide exhibits less hemolytic activity than naturally occurring non-selective antimicrobial peptides.

9. The method of claim 6, wherein the at least one antimicrobial peptide is selected from the group consisting of NH$_2$-GKGL-Tic-Oic-GK-Tic-Oic-GF-Tic-Oic-GK-Tic-Oic-GF-Tic-Oic-GK-Tic-Oic-GKR—CONH$_2$ (SEQ ID NO:4)

NH$_2$-GKGL-Tic-Oic-GR-Tic-Oic-GF-Tic-Oic-GR-Tic-Oic-GF-Tic-Oic-GR-Tic-Oic-GKR—CONH$_2$ (SEQ ID NO:5)

NH$_2$-GKGL-Tic-Oic-GL-Tic-Oic-GK-Tic-Oic-GL-Tic-Oic-GK-Tic-Oic-GL-Tic-Oic-GLR—CONH$_2$ (SEQ ID NO:6)

NH$_2$-GKGL-Tic-Oic-GK-Tic-Oic-GL-Tic-Oic-GK-Tic-Oic-GL-Tic-Oic-GK-Tic-Oic-GK LR—CONH$_2$ (SEQ ID NO:7)

NH$_2$-GKGL-Tic-Oic-FK-Tic-Oic-KF-Tic-Oic-FK-Tic-Oic-KF-Tic-Oic-FK-Tic-Oic-FKR—CONH$_2$ (SEQ ID NO:8)

NH$_2$—KL-Tic-Oic-K-Tic-Oic-F-Tic-Oic-K-Tic-Oic-F-Tic-Oic-K-Tic-Oic-KR—CONH$_2$ (SEQ ID NO:9)

Ac-GF-Tic-Oic-GK-Tic-Oic-GF-Tic-Oic-GK-Tic-KKKK—CONH$_2$ (SEQ ID NO:10)

Ac-GF-Tic-Oic-GK-Tic-Oic-GF-Tic-Oic-GK-Tic-KKKK—CONH—CH2—CH2—NH$_2$ (SEQ ID NO:11)

Ac-GF-Tic-Oic-GK-Tic-Oic-GF-Tic-Oic-GK-Tic-KKKK—CONH—CH$_2$—CH$_2$—CH$_2$—NH$_2$ (SEQ ID NO:12)

NH$_2$-GF-Tic-Oic-GK-Tic-Oic-GF-Tic-Oic-GK-Tic-KKKK—CONH$_2$ (SEQ ID NO:13)

NH$_2$—KL-Tic-Oic-GK-Tic-Oic-GF-Tic-Oic-GK-Tic-KKKK—CONH$_2$ (SEQ ID NO:14)

Ac—F-Tic-Oic-K-Tic-Oic-F-Tic-Oic-K-Tic-KKKK—CONH$_2$ (SEQ ID NO:15)

Ac-Gaba-F-Tic-Oic-Gaba-K-Tic-Oic-Gaba-F-Tic-Oic-Gaba-K-Tic-KKKK—CONH$_2$ (SEQ ID NO:16)

Ac-G-Tic-Oic-K-Tic-Oic-G-Tic-Oic-K-Tic-KKKK—CONH$_2$ (SEQ ID NO:17)

Ac-GF-Oic-GK-Oic-GF-Oic-GKKKKK—CONH$_2$ (SEQ ID NO:18)

Ac-GF-Tic-GK-Tic-GF-Tic-GK-Tic-KKKK—CONH$_2$ (SEQ ID NO:19)
Ac-GF-Tic-G-GK-Tic-G-GF-Tic-G-GK-Tic-KKKK—CONH$_2$ (SEQ ID NO:20)
Ac-GF-G-Oic-GK-G-Oic-GF-G-Oic-GK-G-KKKK—CONH$_2$ (SEQ ID NO:21)
Ac-GF-F-Oic-GK-F-Oic-GF-F-Oic-GK-F-KKKK—CONH$_2$ (SEQ ID NO:22)
Ac-βAla-F-Tic-Oic-βAla-K-Tic-Oic-βAla-F-Tic-Oic-βAla-K-Tic-KKKK—CONH$_2$ (SEQ ID NO:23)
Ac-Ahx-F-Tic-Oic-Ahx-K-Tic-Oic-Ahx-F-Tic-Oic-Ahx-K-Tic-KKKK—CONH$_2$ (SEQ ID NO:24)
Ac—F-Tic-Oic-K-Tic-Oic-F-Tic-Oic-K-Tic-KKKKKK—CONH$_2$ (SEQ ID NO:25)
Ac-GF-Tic-Oic-GK-Tic-Oic-GF-Tic-Oic-GK-Tic-KKKKK—CONH$_2$ (SEQ ID NO:26)
Ac-Gaba-F-Tic-Oic-Gaba-K-Tic-Oic-Gaba-F-Tic-Oic-Gaba-K-Tic-KKKKK—CONH$_2$ (SEQ ID NO:27)
Ac-GF-Tic-Oic-GK-Tic-Oic-GF-Tic-Oic-GK-Tic-Orn-Orn-Orn-Orn-CONH$_2$(SEQ ID NO:28)
Ac-G-Fpa-Tic-Oic-GK-Tic-Oic-G-Fpa-Tic-Oic-GK-Tic-KKKK—CONH$_2$ (SEQ ID NO:29)
Ac-GF-Tic-Oic-G-Orn-Tic-Oic-GF-Tic-Oic-G-Orn-Tic-Orn-Orn-Orn-Orn-CONH$_2$ (SEQ ID NO:30)
Biotin-GF-Tic-Oic-GK-Tic-Oic-GF-Tic-Oic-GK-Tic-KKKK—CONH$_2$ (SEQ ID NO:31)
Ac-GF-Tic-Oic-G-Dpr-Tic-Oic-GF-Tic-Oic-G-Dpr-Tic-Dpr-DprDpr-Dpr-CONH$_2$ (SEQ ID NO:32)
Ac-βAla-Fpa-Tic-Oic-βAla-Dpr-Tic-Oic-βAla-Fpa-Tic-Oic-βAla-Dpr-Tic-Dpr-Dpr-Dpr-Dpr-CONH$_2$ (SEQ ID NO:33)
Ac-G-dF-Tic-Oic-GK-Tic-Oic-G    dF-Tic-Oic-GK-Tic-KKKK—CONH$_2$
Ac-GF-Tic-Oic-G-dK-Tic-Oic-GF-Tic-Oic-G-dK-Tic-KKKK—CONH$_2$
Ac-GF-Tic-Oic-GK-Tic-Oic-GF-Tic-Oic-GK-Tic-Dpr-Dpr-Dpr-Dpr-CONH$_2$ (SEQ ID NO:46)
(NH$_2$)$_4$—(K)$_2$—K-Tic-Oic-GK-Tic-Oic-GF-Tic-Oic-GK-Tic-Oic-GF-Tic-Oic-GK-Tic-CONH$_2$ (SEQ ID NO:47)
Ac-G-Fpa-Tic-Oic-G-Dpr-Tic-Oic-G-Fpa-Tic-Oic-G-Dpr-Tic-Dpr-Dpr-Dpr-Dpr-CONH$_2$ (SEQ ID NO:48)
Ac-GF-Tic-Oic-GK-Tic-Oic-GF-Tic-Oic-GK-Tic-βA-KKKK—CONH$_2$ (SEQ ID NO:35)
Ac-GF-Tic-Oic-GK-Tic-Oic-GF-Tic-Oic-GK-Tic-Gaba-KKKK—CONH$_2$ (SEQ ID NO:36)
Ac-GF-Tic-Oic-GK-Tic-Oic-GF-Tic-Oic-GK-Tic-Ahx-KKKK—CONH$_2$ (SEQ ID NO:37)
Ac-GF-Tic-Oic-G-Dab-Tic-Oic-GF-Tic-Oic-G-Dab-Tic-Dab-Dab-Dab-Dab-CONH$_2$ (SEQ ID NO:38)
Ac-GF-Tic-Oic-G-Tic-Oic-GF-Tic-Oic-G-Tic-G-KKKK—CONH$_2$ (SEQ ID NO:49)
Ac-GF-Tic-Oic-GK-Tic-Oic-GF-Tic-Oic-GK-Tic-Dab-Dab-Dab-Dab-CONH$_2$ (SEQ ID NO:50)
(NH$_2$)$_4$-(Orn)$_2$-Orn-Tic-Oic-G-Orn-Tic-Oic-GF-Tic-Oic-G-Orn-Tic-Oic-GF-Tic-Oic-G-Orn-Tic-CONH$_2$ (SEQ ID NO:51)
Thi-GF-Tic-Oic-GK-Tic-Oic-GF-Tic-Oic-GK-Tic-G-KKKK—CONH$_2$ (SEQ ID NO:52)
Ac-GF-Tic-Oic-GR-Tic-Oic-GF-Tic-Oic-GR-Tic-RRRR—CONH$_2$ (SEQ ID NO:41)
Ac-GF-Tic-Tic-GK-Tic-Tic-GF-Tic-Tic-GK-Tic-KKKK—CONH$_2$ (SEQ ID NO:42)
Ac-GF-Oic-Oic-GK-Oic-Oic-GF-Oic-Oic-GK-Oic-KKKK—CONH$_2$ (SEQ ID NO:53)
Cys-GF-Tic-Oic-GK-Tic-Oic-GF-Tic-Oic-GK-Tic-G-KKKK—CONH$_2$ (SEQ ID NO:54)
(NH$_2$)$_4$-(Dpr)$_2$-Dpr-Tic-Oic-G-Dpr-Tic-Oic-GF-Tic-Oic-G-Dpr-Tic-Oic-GF-Tic-Oic-G-Dpr-Tic-CONH$_2$ (SEQ ID NO:55)
(NH$_2$)$_4$-(Dab)$_2$-Dab-Tic-Oic-G-Dab-Tic-Oic-GF-Tic-Oic-G-Dab-Tic-Oic-GF-Tic-Oic-G-Dab-Tic-CONH$_2$ (SEQ ID NO:56)
Ac-G-Nph-Tic-Oic-GK-Tic-Oic-G-Nph-Tic-Oic-GK-Tic-KKKK—CONH$_2$ (SEQ ID NO:34)
Thi-GF-Tic-Oic-GK-Tic-Oic-GF-Tic-Oic-GK-Tic-KKKK—CONH$_2$ (SEQ ID NO:39)
Ac-GF-Tic-Oic-GW-Tic-Oic-GF-Tic-Oic-GW-Tic-KKKK—CONH$_2$ (SEQ ID NO:40)
Ac-G-Cph-Tic-Oic-GK-Tic-Oic-G-Cph-Tic-Oic-GK-Tic-KKKK—CONH$_2$(SEQ ID NO:43)
Ac-GF-Oic-Tic-GK-Oic-Tic-GF-Oic-Tic-GK-Tic-KKKK—CONH$_2$(SEQ ID NO:44)
Ac-βAla-Fpa-Tic-Oic-βAla-K-Tic-Oic-βAla-Fpa-Tic-Oic-βAla-K-Tic-Dpr-Dpr-Dpr-Dpr-CONH$_2$, (SEQ ID NO:45)
Ac-KKKK-GF-Tic-Oic-GK-Tic-Oic-GF-Tic-Oic-GK-Tic-CONH$_2$ (SEQ ID NO:1), and
Ac-KKKK-GF-Tic-Tic-GK-Tic-Tic-GF-Tic-Tic-GK-Tic-CONH$_2$ (SEQ ID NO:57).

10. The method of claim 6 wherein the antimicrobial peptide is administered by topical, intravenous, infusion, and oral administration.

11. The method of claim 6, wherein the synthetic antimicrobial peptide analog is administered in conjunction with an antibiotic.

12. The method of claim 6, wherein the antibiotic is selected from the group consisting of ciprofloxacin, carbenicillin, nalidixic acid, amoxicillin, levofloxacin, cefuroxime and erythromycin, imipenem, rifampicin and azithromycin.

13. The method of claim 6, wherein the infection is by *Mycobacterium*, and the at least one synthetic antimicrobial peptide analog has the formula selected from the group consisting of Σ-Glycine-O-(Tic-Tic-X-J-Tic-Tic-X—Z)$_n$-Tic-Tic-Π-J-Tic-U$_m$—CONH$_2$
Σ-Glycine-O-(Tic-Tic-X—Z-Tic-Tic-X-J)$_n$-Tic-Tic-Π-Z-Tic-U$_m$—CONH$_2$
Σ-Glycine-B-(Tic-Tic-X—Z-Tic-Tic-X-J)$_n$-Tic-Tic-Π-Z-Tic-U$_m$—CONH$_2$
Σ-Glycine-O-(Tic-Tic-X-J-Tic-Tic-X—Z)$_n$-Tic-Tic-Π-J-Tic-U$_m$—CONH$_2$
Σ-Glycine-O-(Tic-Tic-X—Z-Tic-Tic-X-J)$_n$-Tic-Tic-Π-Z-Tic-U$_m$—CONH$_2$
Σ-Glycine-B-(Tic-Tic-X—Z-Tic-Tic-X-J)$_n$-Tic-Tic-Π-Z-Tic-U$_m$—CONH$_2$
Σ-Glycine-O-(Tic-Tic-X-J-Tic-Tic-X—Z)$_n$-Tic-Tic-Π-J-Tic-U$_m$—CONH—(CH$_2$)$_k$—NH$_2$
Σ-Glycine-O-(Tic-Tic-X-J-Tic-Tic-X—Z)$_n$-Tic-Π-U$_m$—CONH$_2$
Σ-Glycine-O-(Tic-Tic-X-J-Tic-Tic-X—Z)$_n$-Tic-Π-U$_m$—CONH$_2$
Σ-Glycine-O-(Tic-Tic-X—Z-Tic-Tic-X-J)$_n$-Tic-Π-U$_m$—CONH$_2$,
Σ-Glycine-O-(Tic-Tic-X—Z-Tic-Tic-X-J)$_n$-Tic-Π-U$_m$—CONH$_2$,
Σ-Glycine-O-(Tic-Tic-Z-Tic-Tic-J)$_n$-Tic-Tic-Z-Tic-U$_m$—CONH$_2$
Σ-Glycine-B-(Tic-Tic-Z-Tic-tic-J)$_n$-Tic-Tic-Z-Tic-U$_m$—CONH$_2$
Σ-Glycine-O-(Oic-Tic-X-J-Oic-Tic-X—Z)$_n$-Oic-Tic-Π-J-Tic-U$_m$—CONH$_2$
Σ-Glycine-O-(Oic-Tic-X—Z-Oic-Tic-X-J)$_n$-Oic-Tic-Π-Z-Tic-U$_m$—CONH$_2$ Σ-Glycine-B-(Oic-Tic-X—Z-Oic-Tic-X-J)$_n$-Oic-Tic-Π-Z-Tic-U$_m$—CONH$_2$ Σ-Glycine-O-(Oic-Tic-X-J-Oic-Tic-X—Z)$_n$-Oic-Tic-Π-J-Tic-U$_m$—CONH$_2$ Σ-Glycine-O-(Oic-Tic-X—Z-Oic-Tic-X-J)$_n$-Oic-Tic-Π-Z-Tic-U$_m$—CONH$_2$ Σ-Glycine-B-(Oic-Tic-X—Z-Oic-Tic-X-J)$_n$-Oic-Tic-Π-Z-Tic-U$_m$—CONH$_2$ Σ-Glycine-O-(Oic-Tic-X-J-Tic-Tic-X—Z)$_n$-Tic-Tic-Π-J-Tic-U$_m$—CONH—(CH$_2$)$_k$—NH$_2$ Σ-Glycine-O-(Oic-Tic-X-J-Oic-Tic-X—Z)$_n$-Tic-Π-U$_m$—CONH$_2$ Σ-Glycine-O-(Oic-Tic-X-J-Oic-Tic-X—Z)$_n$-Tic-Π-U$_m$—CONH$_2$ Σ-Glycine-O-(Oic-Tic-X—Z-Oic-Tic-X-J)$_n$-Tic-Π-U$_m$—CONH$_2$, Σ-Glycine-O-(Oic-Tic-X—Z-Oic-Tic-X-J)$_n$-Tic-Π-U$_m$—CONH$_2$, Σ-Glycine-O-(Oic-Tic-Z-Oic-Tic-X-J)$_n$-Oic-Tic-Z-Tic-U$_m$—CONH$_2$ Σ-Glycine-B-(Oic-Tic-Z-Oic-tic-J)$_n$-Oic-Tic-Z-Tic-U$_m$—CONH$_2$ Σ-Glycine-O-(Oic-Oic-X-J-Oic-Oic-X—Z)$_n$-Oic-Oic-Π-J-Tic-U$_m$—CONH$_2$ Σ-Glycine-O-(Oic-Oic-X—Z-Oic-Oic-X-J)$_n$-Oic-Oic-Π-Z-Tic-U$_m$—CONH$_2$ Σ-Glycine-B-(Oic-Oic-X—Z-Oic-Oic-X-J)$_n$-Oic-Oic-Π-Z-Tic-U$_m$—CONH$_2$ Σ-Glycine-O-(Oic-Oic-X-J-Oic-Oic-X—Z)$_n$-Oic-Oic-Π-J-Tic-U$_m$—CONH$_2$ Σ-Glycine-O-(Oic-Oic-X—Z-Oic-Oic-X-J)$_n$-Oic-Oic-Π-Z-Tic-U$_m$—CONH$_2$ Σ-Glycine-B-(Oic-Oic-X—Z-Oic-Oic-X-J)$_n$-Oic-Oic-Π-Z-Tic-U$_m$—CONH$_2$ Σ-Glycine-O-(Oic-Oic-X-J-Oic-Oic-X—Z)$_n$-Oic-Oic-Π-J-Tic-U$_m$—CONH—(CH$_2$)$_k$—NH$_2$ Glycine-O-(Oic-Oic-X-J-Oic-Oic-X—Z)$_n$-Tic-Π-U$_m$—CONH$_2$ Σ-Glycine-O-(Oic-Oic-X-J-Oic-Oic-X—Z)$_n$-Tic-Π-U$_m$—CONH$_2$ Σ-Glycine-O-(Oic-Oic-X—Z-Oic-Oic-X-J)$_n$-Tic-Π-U$_m$—CONH$_2$, Σ-Glycine-O-(Oic-Oic-X—Z-Oic-Oic-X-J)$_n$-Tic-Π-U$_m$—CONH$_2$, Σ-Glycine-O-(Oic-Oic-Z-Oic-Oic-J)$_n$-Oic-Oic-Z-Tic-U$_m$—CONH$_2$ Σ-Glycine-B-(Oic-Oic-Z-Oic-tic-J)$_n$-Oic-Oic-Z-Tic-U$_m$—CONH$_2$ Σ-U$_m$-Glycine-O-(Tic-Tic-X-J-Tic-Tic-X—Z)$_n$-Tic-Oic-Π-J-Tic-CONH$_2$ Σ-U$_m$-Glycine-O-(Tic-Tic-X—Z-Tic-Tic-X-J)$_n$-Tic-Oic-Π-Z-Tic-CONH$_2$ Σ-U$_m$-Glycine-B-(Tic-Tic-X—Z-Tic-Tic-X-J)$_n$-Tic-Oic-Π-Z-Tic-CONH$_2$ Σ-U$_m$-Glycine-O-(Tic-Tic-X-J-Tic-Tic-X—Z)$_n$-Tic-Oic-Π-J-Tic-CONH$_2$ Σ-U$_m$-Glycine-O-(Tic-Tic-X—Z-Tic-Tic-X-J)$_n$-Tic-Oic-Π-Z-Tic-CONH$_2$ Σ-U$_m$-Glycine-B-(Tic-Tic-X—Z-Tic-Tic-X-J)$_n$-Tic-Oic-Π-Z-Tic-CONH$_2$, Σ-U$_m$-Glycine-O-(Tic-Tic-X-J-Tic-Tic-X—Z)$_n$-Tic-Oic-Π-J-Tic-CONH—(CH$_2$)$_k$—NH$_2$ Σ-U$_m$-Glycine-O-(Tic-Tic-X-J-Tic-Tic-X—Z)$_n$-Tic-Π-CONH$_2$ Σ-U$_m$-Glycine-O-(Tic-Tic-X-J-Tic-Tic-X—Z)$_n$-Oic-Π-CONH$_2$ Σ-U$_m$-Glycine-O-(Tic-Tic-X—Z-Tic-Tic-X-J)$_n$-Tic-Π-CONH$_2$ and Σ-U$_m$-Glycine-O-(Tic-Tic-X—Z-Tic-Tic-X-J)$_n$-Oic-Π-CONH$_2$.

14. The method of claim 13, wherein the at least one synthetic antimicrobial peptide is Ac-GF-Tic-Tic-GK-Tic-Tic-GF-Tic-Tic-GK-Tic-KKKK—CONH$_2$ (SEQ ID NO:42) or Ac-GF-Oic-Tic-GK-Oic-Tic-GF-Oic-Tic-GK-Tic-KKKK—CONH$_2$ (SEQ ID NO:44) or Ac-KKKK-GF-Tic-Tic-GK-Tic-Tic-GF-Tic-Tic-GK-Tic-CONH$_2$ (SEQ ID NO:57), or a combination of these.

15. A method for treating infection by *Bacillus anthracis* or *Yersinia pestis* (plague), comprising the step of administering to a mammal suspected of infection by *Bacillus anthracis* or *Yersinia pestis* (plague), a pharmaceutically effective amount of one of the synthetic antimicrobial peptides NH$_2$—KL-Tic-Oic-K-Tic-Oic-F-Tic-Oic-K-Tic-Oic-F-Tic-Oic-K-Tic-Oic-KR—CONH$_2$, (SEQ ID NO:9)

Ac-GF-Tic-GK-Tic-GF-Tic-GK-Tic-KKKK—CONH$_2$, (SEQ ID NO:19)

Ac-βAla-F-Tic-Oic-βAla-K-Tic-Oic-βAla-F-Tic-Oic-βAla-K-Tic-KKKK—CONH$_2$, SEQ ID NO:23)

Ac-G-Fpa-Tic-Oic-GK-Tic-Oic-G-Fpa-Tic-Oic-GK-Tic-KKKK—CONH$_2$, (SEQ ID NO:29)

Ac-GF-Tic-Oic-G-Orn-Tic-Oic-GF-Tic-Oic-G-Orn-Tic-Orn-Orn-Orn-Orn-CONH$_2$, (SEQ ID NO:30)

Ac-GF-Tic-Oic-GK-Tic-Oic-GF-Tic-Oic-GK-Tic-βA-KKKK—CONH$_2$, (SEQ ID NO:35)

Ac-GF-Tic-Oic-GK-Tic-Oic-GF-Tic-Oic-GK-Tic-Gaba-KKKK—CONH$_2$, (SEQ ID NO:36)

Ac-GF-Tic-Oic-GK-Tic-Oic-GF-Tic-Oic-GK-Tic-Ahx-KKKK—CONH$_2$, (SEQ ID NO:37)

Ac-GF-Tic-Oic-G-Dab-Tic-Oic-GF-Tic-Oic-G-Dab-Tic-Dab-Dab-Dab-Dab-CONH$_2$, (SEQ ID NO:38)

Thi-GF-Tic-Oic-GK-Tic-Oic-GF-Tic-Oic-GK-Tic-KKKK—CONH$_2$, (SEQ ID NO:39)

Ac-GF-Tic-Oic-GW-Tic-Oic-GF-Tic-Oic-GW-Tic-KKKK—CONH$_2$, (SEQ ID NO:40)

Ac-GF-Tic-Tic-GK-Tic-Tic-GF-Tic-Tic-GK-Tic-KKKK—CONH$_2$, (SEQ ID NO:42)

Ac-G-Cph-Tic-Oic-GK-Tic-Oic-G-Cph-Tic-Oic-GK-Tic-KKKK—CONH$_2$, (SEQ ID NO:43)

or a combination of these.

16. The method of claim 15, wherein the antimicrobial peptide exhibits less hemolytic activity than naturally occurring non-selective antimicrobial peptides.

* * * * *

SEQUENCE LISTING

<160> NUMBER OF SEQ ID NOS: 57

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(16)
<223> OTHER INFORMATION: Oic
<220> FEATURE:
<221> NAME/KEY: MOD_RES
<222> LOCATION: (19)..(19)
<223> OTHER INFORMATION: Tic

<400> SEQUENCE: 1

Lys Lys Lys Lys Gly Phe Xaa Xaa Gly Lys Xaa Xaa Gly Phe Xaa Xaa
1               5                   10                  15

Gly Lys Xaa

<210> SEQ ID NO 2
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Lys Lys
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Leu Met Asn Ser
1               5

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: Oic
<220> FEATURE:
<221> NAME/KEY: MOD_RES
<222> LOCATION: (13)..(13)
<223> OTHER INFORMATION: Tic
<220> FEATURE:
<221> NAME/KEY: MOD_RES
<222> LOCATION: (14)..(14)
<223> OTHER INFORMATION: Oic
<220> FEATURE:
<221> NAME/KEY: MOD_RES
<222> LOCATION: (17)..(17)
<223> OTHER INFORMATION: Tic
<220> FEATURE:
<221> NAME/KEY: MOD_RES
<222> LOCATION: (18)..(18)
<223> OTHER INFORMATION: Oic
<220> FEATURE:
<221> NAME/KEY: MOD_RES
<222> LOCATION: (21)..(21)
<223> OTHER INFORMATION: Tic
<220> FEATURE:
<221> NAME/KEY: MOD_RES
<222> LOCATION: (22)..(22)
<223> OTHER INFORMATION: Oic
<220> FEATURE:
<221> NAME/KEY: MOD_RES
<222> LOCATION: (25)..(25)
<223> OTHER INFORMATION: Tic
<220> FEATURE:
<221> NAME/KEY: MOD_RES
<222> LOCATION: (26)..(26)
```

-continued

```
<223> OTHER INFORMATION: Oic

<400> SEQUENCE: 4

Gly Lys Gly Leu Xaa Xaa Gly Lys Xaa Xaa Gly Phe Xaa Xaa Gly Lys
1               5                   10                  15

Xaa Xaa Gly Phe Xaa Xaa Gly Lys Xaa Xaa Gly Lys Arg
            20                  25

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: Oic
<220> FEATURE:
<221> NAME/KEY: MOD_RES
<222> LOCATION: (13)..(13)
<223> OTHER INFORMATION: Tic
<220> FEATURE:
<221> NAME/KEY: MOD_RES
<222> LOCATION: (14)..(14)
<223> OTHER INFORMATION: Oic
<220> FEATURE:
<221> NAME/KEY: MOD_RES
<222> LOCATION: (17)..(17)
<223> OTHER INFORMATION: Tic
<220> FEATURE:
<221> NAME/KEY: MOD_RES
<222> LOCATION: (18)..(18)
<223> OTHER INFORMATION: Oic
<220> FEATURE:
<221> NAME/KEY: MOD_RES
<222> LOCATION: (21)..(21)
<223> OTHER INFORMATION: Tic
<220> FEATURE:
<221> NAME/KEY: MOD_RES
<222> LOCATION: (22)..(22)
<223> OTHER INFORMATION: Oic
<220> FEATURE:
<221> NAME/KEY: MOD_RES
<222> LOCATION: (25)..(25)
<223> OTHER INFORMATION: Tic
<220> FEATURE:
<221> NAME/KEY: MOD_RES
<222> LOCATION: (26)..(26)
<223> OTHER INFORMATION: Oic

<400> SEQUENCE: 5

Gly Lys Gly Leu Xaa Xaa Gly Arg Xaa Xaa Gly Phe Xaa Xaa Gly Arg
1               5                   10                  15

Xaa Xaa Gly Phe Xaa Xaa Gly Arg Xaa Xaa Gly Lys Arg
            20                  25

<210> SEQ ID NO 6
<211> LENGTH: 29
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: Oic
<220> FEATURE:
<221> NAME/KEY: MOD_RES
<222> LOCATION: (13)..(13)
<223> OTHER INFORMATION: Tic
<220> FEATURE:
<221> NAME/KEY: MOD_RES
<222> LOCATION: (14)..(14)
<223> OTHER INFORMATION: Oic
<220> FEATURE:
<221> NAME/KEY: MOD_RES
<222> LOCATION: (17)..(17)
<223> OTHER INFORMATION: Tic
<220> FEATURE:
<221> NAME/KEY: MOD_RES
<222> LOCATION: (18)..(18)
<223> OTHER INFORMATION: Oic
<220> FEATURE:
<221> NAME/KEY: MOD_RES
<222> LOCATION: (21)..(21)
<223> OTHER INFORMATION: Tic
<220> FEATURE:
<221> NAME/KEY: MOD_RES
<222> LOCATION: (22)..(22)
<223> OTHER INFORMATION: Oic
<220> FEATURE:
<221> NAME/KEY: MOD_RES
<222> LOCATION: (25)..(25)
<223> OTHER INFORMATION: Tic
<220> FEATURE:
<221> NAME/KEY: MOD_RES
<222> LOCATION: (26)..(26)
<223> OTHER INFORMATION: Oic

<400> SEQUENCE: 6

Gly Lys Gly Leu Xaa Xaa Gly Leu Xaa Xaa Gly Lys Xaa Xaa Gly Leu
1               5                   10                  15

Xaa Xaa Gly Lys Xaa Xaa Gly Leu Xaa Xaa Gly Leu Arg
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (9)..(9)
<223> OTHER INFORMATION: Tic
```

```
<220> FEATURE:
<221> NAME/KEY: MOD_RES
<222> LOCATION: (10)..(10)
<223> OTHER INFORMATION: Oic
<220> FEATURE:
<221> NAME/KEY: MOD_RES
<222> LOCATION: (13)..(13)
<223> OTHER INFORMATION: Tic
<220> FEATURE:
<221> NAME/KEY: MOD_RES
<222> LOCATION: (14)..(14)
<223> OTHER INFORMATION: Oic
<220> FEATURE:
<221> NAME/KEY: MOD_RES
<222> LOCATION: (17)..(17)
<223> OTHER INFORMATION: Tic
<220> FEATURE:
<221> NAME/KEY: MOD_RES
<222> LOCATION: (18)..(18)
<223> OTHER INFORMATION: Oic
<220> FEATURE:
<221> NAME/KEY: MOD_RES
<222> LOCATION: (21)..(21)
<223> OTHER INFORMATION: Tic
<220> FEATURE:
<221> NAME/KEY: MOD_RES
<222> LOCATION: (22)..(22)
<223> OTHER INFORMATION: Oic
<220> FEATURE:
<221> NAME/KEY: MOD_RES
<222> LOCATION: (25)..(25)
<223> OTHER INFORMATION: Tic
<220> FEATURE:
<221> NAME/KEY: MOD_RES
<222> LOCATION: (26)..(26)
<223> OTHER INFORMATION: Oic

<400> SEQUENCE: 7

Gly Lys Gly Leu Xaa Xaa Gly Lys Xaa Xaa Gly Leu Xaa Xaa Gly Lys
1               5                   10                  15

Xaa Xaa Gly Leu Xaa Xaa Gly Lys Xaa Xaa Gly Lys Arg
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: Oic
<220> FEATURE:
<221> NAME/KEY: MOD_RES
<222> LOCATION: (13)..(13)
<223> OTHER INFORMATION: Tic
<220> FEATURE:
<221> NAME/KEY: MOD_RES
<222> LOCATION: (14)..(14)
<223> OTHER INFORMATION: Oic
<220> FEATURE:
<221> NAME/KEY: MOD_RES
<222> LOCATION: (17)..(17)
```

-continued

```
<223> OTHER INFORMATION: Tic
<220> FEATURE:
<221> NAME/KEY: MOD_RES
<222> LOCATION: (18)..(18)
<223> OTHER INFORMATION: Oic
<220> FEATURE:
<221> NAME/KEY: MOD_RES
<222> LOCATION: (21)..(21)
<223> OTHER INFORMATION: Tic
<220> FEATURE:
<221> NAME/KEY: MOD_RES
<222> LOCATION: (22)..(22)
<223> OTHER INFORMATION: Oic
<220> FEATURE:
<221> NAME/KEY: MOD_RES
<222> LOCATION: (25)..(25)
<223> OTHER INFORMATION: Tic
<220> FEATURE:
<221> NAME/KEY: MOD_RES
<222> LOCATION: (26)..(26)
<223> OTHER INFORMATION: Oic

<400> SEQUENCE: 8

Gly Lys Gly Leu Xaa Xaa Phe Lys Xaa Xaa Lys Phe Xaa Xaa Phe Lys
1               5                  10                  15

Xaa Xaa Lys Phe Xaa Xaa Phe Lys Xaa Xaa Phe Lys Arg
            20                  25

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (10)..(10)
<223> OTHER INFORMATION: Oic
<220> FEATURE:
<221> NAME/KEY: MOD_RES
<222> LOCATION: (12)..(12)
<223> OTHER INFORMATION: Tic
<220> FEATURE:
<221> NAME/KEY: MOD_RES
<222> LOCATION: (13)..(13)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(16)
<223> OTHER INFORMATION: Oic
<220> FEATURE:
<221> NAME/KEY: MOD_RES
```

```
<222> LOCATION: (18)..(18)
<223> OTHER INFORMATION: Tic
<220> FEATURE:
<221> NAME/KEY: MOD_RES
<222> LOCATION: (19)..(19)
<223> OTHER INFORMATION: Oic

<400> SEQUENCE: 9

Lys Leu Xaa Xaa Lys Xaa Xaa Phe Xaa Xaa Lys Xaa Xaa Phe Xaa Xaa
1               5                   10                  15

Lys Xaa Xaa Lys Arg
            20

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 10

Gly Phe Xaa Xaa Gly Lys Xaa Xaa Gly Phe Xaa Xaa Gly Lys Xaa Lys
1               5                   10                  15

Lys Lys Lys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
```

```
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 11

Gly Phe Xaa Xaa Gly Lys Xaa Xaa Gly Phe Xaa Xaa Gly Lys Xaa Lys
1               5                   10                  15

Lys Lys Lys

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 12

Gly Phe Xaa Xaa Gly Lys Xaa Xaa Gly Phe Xaa Xaa Gly Lys Xaa Lys
1               5                   10                  15

Lys Lys Lys

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
```

```
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 13

Gly Phe Xaa Xaa Gly Lys Xaa Xaa Gly Phe Xaa Xaa Gly Lys Xaa Lys
1               5                   10                  15

Lys Lys Lys

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 14

Lys Leu Xaa Xaa Gly Lys Xaa Xaa Gly Phe Xaa Xaa Gly Lys Xaa Lys
1               5                   10                  15

Lys Lys Lys

<210> SEQ ID NO 15
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Oic
<220> FEATURE:
<221> NAME/KEY: MOD_RES
<222> LOCATION: (11)..(11)
<223> OTHER INFORMATION: Tic

<400> SEQUENCE: 15

Phe Xaa Xaa Lys Xaa Xaa Phe Xaa Xaa Lys Xaa Lys Lys Lys Lys
1               5                   10                  15

<210> SEQ ID NO 16
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gaba
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (5)..(5)
<223> OTHER INFORMATION: Gaba
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (9)..(9)
<223> OTHER INFORMATION: Gaba
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
```

```
<223> OTHER INFORMATION: Oic
<220> FEATURE:
<221> NAME/KEY: MOD_RES
<222> LOCATION: (13)..(13)
<223> OTHER INFORMATION: Gaba
<220> FEATURE:
<221> NAME/KEY: MOD_RES
<222> LOCATION: (15)..(15)
<223> OTHER INFORMATION: Tic

<400> SEQUENCE: 16

Xaa Phe Xaa Xaa Xaa Lys Xaa Xaa Xaa Phe Xaa Xaa Xaa Lys Xaa Lys
1               5                   10                  15

Lys Lys Lys

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Oic
<220> FEATURE:
<221> NAME/KEY: MOD_RES
<222> LOCATION: (11)..(11)
<223> OTHER INFORMATION: Tic

<400> SEQUENCE: 17

Gly Xaa Xaa Lys Xaa Xaa Gly Xaa Xaa Lys Xaa Lys Lys Lys Lys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (9)..(9)
<223> OTHER INFORMATION: Oic
```

```
<400> SEQUENCE: 18

Gly Phe Xaa Gly Lys Xaa Gly Phe Xaa Gly Lys Lys Lys Lys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (9)..(9)
<223> OTHER INFORMATION: Tic
<220> FEATURE:
<221> NAME/KEY: MOD_RES
<222> LOCATION: (12)..(12)
<223> OTHER INFORMATION: Tic

<400> SEQUENCE: 19

Gly Phe Xaa Gly Lys Xaa Gly Phe Xaa Gly Lys Xaa Lys Lys Lys Lys
1               5                   10                  15

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (15)..(15)
<223> OTHER INFORMATION: Tic

<400> SEQUENCE: 20

Gly Phe Xaa Gly Gly Lys Xaa Gly Gly Phe Xaa Gly Lys Xaa Lys
1               5                   10                  15

Lys Lys Lys

<210> SEQ ID NO 21
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Oic
<220> FEATURE:
```

```
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (12)..(12)
<223> OTHER INFORMATION: Oic

<400> SEQUENCE: 21

Gly Phe Gly Xaa Gly Lys Gly Xaa Gly Phe Gly Xaa Gly Lys Gly Lys
1               5                   10                  15

Lys Lys Lys

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (12)..(12)
<223> OTHER INFORMATION: Oic

<400> SEQUENCE: 22

Gly Phe Phe Xaa Gly Lys Phe Xaa Gly Phe Phe Xaa Gly Lys Phe Lys
1               5                   10                  15

Lys Lys Lys

<210> SEQ ID NO 23
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (9)..(9)
<223> OTHER INFORMATION: Beta-Ala
<220> FEATURE:
```

```
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (15)..(15)
<223> OTHER INFORMATION: Tic

<400> SEQUENCE: 23

Xaa Phe Xaa Xaa Xaa Lys Xaa Xaa Xaa Phe Xaa Xaa Xaa Lys Xaa Lys
1               5                   10                  15

Lys Lys Lys

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (5)..(5)
<223> OTHER INFORMATION: Ahx
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (9)..(9)
<223> OTHER INFORMATION: Ahx
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (13)..(13)
<223> OTHER INFORMATION: Ahx
<220> FEATURE:
<221> NAME/KEY: MOD_RES
<222> LOCATION: (15)..(15)
<223> OTHER INFORMATION: Tic

<400> SEQUENCE: 24

Xaa Phe Xaa Xaa Xaa Lys Xaa Xaa Xaa Phe Xaa Xaa Xaa Lys Xaa Lys
1               5                   10                  15
```

Lys Lys Lys

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (5)..(5)
<223> OTHER INFORMATION: Tic
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Oic
<220> FEATURE:
<221> NAME/KEY: MOD_RES
<222> LOCATION: (11)..(11)
<223> OTHER INFORMATION: Tic

<400> SEQUENCE: 25

Phe Xaa Xaa Lys Xaa Xaa Phe Xaa Xaa Lys Xaa Lys Lys Lys Lys
1               5                   10                  15

Lys

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:

```
<221> NAME/KEY: MOD_RES
<222> LOCATION: (15)..(15)
<223> OTHER INFORMATION: Tic

<400> SEQUENCE: 26

Gly Phe Xaa Xaa Gly Lys Xaa Xaa Gly Phe Xaa Xaa Gly Lys Xaa Lys
1               5                   10                  15

Lys Lys Lys Lys
            20

<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gaba
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (5)..(5)
<223> OTHER INFORMATION: Gaba
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (9)..(9)
<223> OTHER INFORMATION: Gaba
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (13)..(13)
<223> OTHER INFORMATION: Gaba
<220> FEATURE:
<221> NAME/KEY: MOD_RES
<222> LOCATION: (15)..(15)
<223> OTHER INFORMATION: Tic

<400> SEQUENCE: 27

Xaa Phe Xaa Xaa Xaa Lys Xaa Xaa Xaa Phe Xaa Xaa Xaa Lys Xaa Lys
1               5                   10                  15

Lys Lys Lys Lys
            20

<210> SEQ ID NO 28
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
<223> OTHER INFORMATION: Orn

<400> SEQUENCE: 28

Gly Phe Xaa Xaa Gly Lys Xaa Xaa Gly Phe Xaa Xaa Gly Lys Xaa Xaa
1               5                   10                  15

Xaa Xaa Xaa

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Fpa
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (10)..(10)
<223> OTHER INFORMATION: Fpa
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
```

```
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 29

Gly Xaa Xaa Xaa Gly Lys Xaa Xaa Gly Xaa Xaa Xaa Gly Lys Xaa Lys
1               5                   10                  15

Lys Lys Lys

<210> SEQ ID NO 30
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (14)..(14)
<223> OTHER INFORMATION: Orn
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
<223> OTHER INFORMATION: Orn

<400> SEQUENCE: 30

Gly Phe Xaa Xaa Gly Xaa Xaa Xaa Gly Phe Xaa Xaa Gly Xaa Xaa Xaa
1               5                   10                  15

Xaa Xaa Xaa

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
```

```
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 31

Gly Phe Xaa Xaa Gly Lys Xaa Xaa Gly Phe Xaa Xaa Gly Lys Xaa Lys
1               5                   10                  15

Lys Lys Lys

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (6)..(6)
<223> OTHER INFORMATION: Dpr
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (14)..(14)
<223> OTHER INFORMATION: Dpr
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
```

```
<223> OTHER INFORMATION: Dpr

<400> SEQUENCE: 32

Gly Phe Xaa Xaa Gly Xaa Xaa Xaa Gly Phe Xaa Xaa Gly Xaa Xaa Xaa
1               5                   10                  15

Xaa Xaa Xaa

<210> SEQ ID NO 33
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Fpa
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (6)..(6)
<223> OTHER INFORMATION: Dpr
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Fpa
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (14)..(14)
<223> OTHER INFORMATION: Dpr
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
```

<223> OTHER INFORMATION: Dpr

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 34
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nph
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (10)..(10)
<223> OTHER INFORMATION: Nph
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 34

Gly Xaa Xaa Xaa Gly Lys Xaa Xaa Gly Xaa Xaa Xaa Gly Lys Xaa Lys
1               5                   10                  15

Lys Lys Lys

<210> SEQ ID NO 35
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)

```
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(16)
<223> OTHER INFORMATION: Beta-Ala

<400> SEQUENCE: 35

Gly Phe Xaa Xaa Gly Lys Xaa Xaa Gly Phe Xaa Xaa Gly Lys Xaa Xaa
1               5                   10                  15

Lys Lys Lys Lys
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(16)
<223> OTHER INFORMATION: Gaba

<400> SEQUENCE: 36

Gly Phe Xaa Xaa Gly Lys Xaa Xaa Gly Phe Xaa Xaa Gly Lys Xaa Xaa
1               5                   10                  15

Lys Lys Lys Lys
            20
```

```
<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(16)
<223> OTHER INFORMATION: Ahx

<400> SEQUENCE: 37

Gly Phe Xaa Xaa Gly Lys Xaa Xaa Gly Phe Xaa Xaa Gly Lys Xaa Xaa
1               5                   10                  15

Lys Lys Lys Lys
            20

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (6)..(6)
<223> OTHER INFORMATION: Dab
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
```

```
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (14)..(14)
<223> OTHER INFORMATION: Dab
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
<223> OTHER INFORMATION: Dab

<400> SEQUENCE: 38

Gly Phe Xaa Xaa Gly Xaa Xaa Xaa Gly Phe Xaa Xaa Gly Xaa Xaa Xaa
1               5                   10                  15

Xaa Xaa Xaa

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thi
<220> FEATURE:
<221> NAME/KEY: MOD_RES
<222> LOCATION: (4)..(4)
<223> OTHER INFORMATION: Tic
<220> FEATURE:
<221> NAME/KEY: MOD_RES
<222> LOCATION: (5)..(5)
<223> OTHER INFORMATION: Oic
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Oic
<220> FEATURE:
<221> NAME/KEY: MOD_RES
<222> LOCATION: (12)..(12)
<223> OTHER INFORMATION: Tic
<220> FEATURE:
<221> NAME/KEY: MOD_RES
<222> LOCATION: (13)..(13)
<223> OTHER INFORMATION: Oic
<220> FEATURE:
<221> NAME/KEY: MOD_RES
<222> LOCATION: (16)..(16)
<223> OTHER INFORMATION: Tic

<400> SEQUENCE: 39

Xaa Gly Phe Xaa Xaa Gly Lys Xaa Xaa Gly Phe Xaa Xaa Gly Lys Xaa
1               5                   10                  15

Lys Lys Lys Lys
            20

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 40

Gly Phe Xaa Xaa Gly Trp Xaa Xaa Gly Phe Xaa Xaa Gly Trp Xaa Lys
1               5                   10                  15

Lys Lys Lys

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 41

Gly Phe Xaa Xaa Gly Arg Xaa Xaa Gly Phe Xaa Xaa Gly Arg Xaa Arg
1               5                   10                  15

Arg Arg Arg
```

```
<210> SEQ ID NO 42
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Tic
<220> FEATURE:
<221> NAME/KEY: MOD_RES
<222> LOCATION: (7)..(8)
<223> OTHER INFORMATION: Tic
<220> FEATURE:
<221> NAME/KEY: MOD_RES
<222> LOCATION: (11)..(12)
<223> OTHER INFORMATION: Tic
<220> FEATURE:
<221> NAME/KEY: MOD_RES
<222> LOCATION: (15)..(15)
<223> OTHER INFORMATION: Tic

<400> SEQUENCE: 42

Gly Phe Xaa Xaa Gly Lys Xaa Xaa Gly Phe Xaa Xaa Gly Lys Xaa Lys
1               5                   10                  15

Lys Lys Lys

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cph
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (10)..(10)
<223> OTHER INFORMATION: Cph
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic

<400> SEQUENCE: 43
```

```
Gly Xaa Xaa Xaa Gly Lys Xaa Xaa Gly Xaa Xaa Xaa Gly Lys Xaa Lys
1               5                   10                  15

Lys Lys Lys
```

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (4)..(4)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (11)..(11)
<223> OTHER INFORMATION: Oic
<220> FEATURE:
<221> NAME/KEY: MOD_RES
<222> LOCATION: (12)..(12)
<223> OTHER INFORMATION: Tic
<220> FEATURE:
<221> NAME/KEY: MOD_RES
<222> LOCATION: (15)..(15)
<223> OTHER INFORMATION: Tic

<400> SEQUENCE: 44

```
Gly Phe Xaa Xaa Gly Lys Xaa Xaa Gly Phe Xaa Xaa Gly Lys Xaa Lys
1               5                   10                  15

Lys Lys Lys
```

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Fpa
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (5)..(5)
<223> OTHER INFORMATION: Beta-Ala
<220> FEATURE:
<221> NAME/KEY: MOD_RES
<222> LOCATION: (7)..(7)

```
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (9)..(9)
<223> OTHER INFORMATION: Beta-Ala
<220> FEATURE:
<221> NAME/KEY: MOD_RES
<222> LOCATION: (10)..(10)
<223> OTHER INFORMATION: Fpa
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (13)..(13)
<223> OTHER INFORMATION: Beta-Ala
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
<223> OTHER INFORMATION: Dpr

<400> SEQUENCE: 45

Xaa Xaa Xaa Xaa Xaa Lys Xaa Xaa Xaa Xaa Xaa Xaa Xaa Lys Xaa Xaa
1               5                   10                  15

Xaa Xaa Xaa

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
```

<223> OTHER INFORMATION: Dpr

<400> SEQUENCE: 46

Gly Phe Xaa Xaa Gly Lys Xaa Xaa Gly Phe Xaa Xaa Gly Lys Xaa Xaa
1               5                   10                  15

Xaa Xaa Xaa

<210> SEQ ID NO 47
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
<222> LOCATION: (10)..(10)
<223> OTHER INFORMATION: Tic
<220> FEATURE:
<221> NAME/KEY: MOD_RES
<222> LOCATION: (11)..(11)
<223> OTHER INFORMATION: Oic
<220> FEATURE:
<221> NAME/KEY: MOD_RES
<222> LOCATION: (14)..(14)
<223> OTHER INFORMATION: Tic
<220> FEATURE:
<221> NAME/KEY: MOD_RES
<222> LOCATION: (15)..(15)
<223> OTHER INFORMATION: Oic
<220> FEATURE:
<221> NAME/KEY: MOD_RES
<222> LOCATION: (18)..(18)
<223> OTHER INFORMATION: Tic
<220> FEATURE:
<221> NAME/KEY: MOD_RES
<222> LOCATION: (19)..(19)
<223> OTHER INFORMATION: Oic
<220> FEATURE:
<221> NAME/KEY: MOD_RES
<222> LOCATION: (22)..(22)
<223> OTHER INFORMATION: Tic

<400> SEQUENCE: 47

Lys Xaa Xaa Gly Lys Xaa Xaa Gly Phe Xaa Xaa Gly Lys Xaa Xaa Gly
1               5                   10                  15

Phe Xaa Xaa Gly Lys Xaa
            20

<210> SEQ ID NO 48
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (2)..(2)
<223> OTHER INFORMATION: Fpa
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (6)..(6)
<223> OTHER INFORMATION: Dpr
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (10)..(10)
<223> OTHER INFORMATION: Fpa
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (14)..(14)
<223> OTHER INFORMATION: Dpr
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
<223> OTHER INFORMATION: Dpr

<400> SEQUENCE: 48

Gly Xaa Xaa Xaa Gly Xaa Xaa Xaa Gly Xaa Xaa Xaa Gly Xaa Xaa Xaa
1               5                   10                  15

Xaa Xaa Xaa

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
```

```
<222> LOCATION: (10)..(10)
<223> OTHER INFORMATION: Tic
<220> FEATURE:
<221> NAME/KEY: MOD_RES
<222> LOCATION: (11)..(11)
<223> OTHER INFORMATION: Oic
<220> FEATURE:
<221> NAME/KEY: MOD_RES
<222> LOCATION: (13)..(13)
<223> OTHER INFORMATION: Tic

<400> SEQUENCE: 49

Gly Phe Xaa Xaa Gly Xaa Xaa Gly Phe Xaa Xaa Gly Xaa Gly Lys Lys
1               5                   10                  15

Lys Lys

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tic
<220> FEATURE:
<221> NAME/KEY: MOD_RES
<222> LOCATION: (4)..(4)
<223> OTHER INFORMATION: Oic
<220> FEATURE:
<221> NAME/KEY: MOD_RES
<222> LOCATION: (7)..(7)
<223> OTHER INFORMATION: Tic
<220> FEATURE:
<221> NAME/KEY: MOD_RES
<222> LOCATION: (8)..(8)
<223> OTHER INFORMATION: Oic
<220> FEATURE:
<221> NAME/KEY: MOD_RES
<222> LOCATION: (11)..(11)
<223> OTHER INFORMATION: Tic
<220> FEATURE:
<221> NAME/KEY: MOD_RES
<222> LOCATION: (12)..(12)
<223> OTHER INFORMATION: Oic
<220> FEATURE:
<221> NAME/KEY: MOD_RES
<222> LOCATION: (15)..(15)
<223> OTHER INFORMATION: Tic
<220> FEATURE:
<221> NAME/KEY: MOD_RES
<222> LOCATION: (16)..(19)
<223> OTHER INFORMATION: Dab

<400> SEQUENCE: 50

Gly Phe Xaa Xaa Gly Lys Xaa Xaa Gly Phe Xaa Xaa Gly Lys Xaa Xaa
1               5                   10                  15

Xaa Xaa Xaa

<210> SEQ ID NO 51
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
```

```
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
<222> LOCATION: (10)..(10)
<223> OTHER INFORMATION: Tic
<220> FEATURE:
<221> NAME/KEY: MOD_RES
<222> LOCATION: (11)..(11)
<223> OTHER INFORMATION: Oic
<220> FEATURE:
<221> NAME/KEY: MOD_RES
<222> LOCATION: (13)..(13)
<223> OTHER INFORMATION: Orn
<220> FEATURE:
<221> NAME/KEY: MOD_RES
<222> LOCATION: (14)..(14)
<223> OTHER INFORMATION: Tic
<220> FEATURE:
<221> NAME/KEY: MOD_RES
<222> LOCATION: (15)..(15)
<223> OTHER INFORMATION: Oic
<220> FEATURE:
<221> NAME/KEY: MOD_RES
<222> LOCATION: (18)..(18)
<223> OTHER INFORMATION: Tic
<220> FEATURE:
<221> NAME/KEY: MOD_RES
<222> LOCATION: (19)..(19)
<223> OTHER INFORMATION: Oic
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (22)..(22)
<223> OTHER INFORMATION: Tic

<400> SEQUENCE: 51

Xaa Xaa Xaa Gly Xaa Xaa Xaa Gly Phe Xaa Xaa Gly Xaa Xaa Xaa Gly
1               5                   10                  15

Phe Xaa Xaa Gly Xaa Xaa
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thi
<220> FEATURE:
<221> NAME/KEY: MOD_RES
<222> LOCATION: (4)..(4)
<223> OTHER INFORMATION: Tic
<220> FEATURE:
```

```
<221> NAME/KEY: MOD_RES
<222> LOCATION: (5)..(5)
<223> OTHER INFORMATION: Oic
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Oic
<220> FEATURE:
<221> NAME/KEY: MOD_RES
<222> LOCATION: (12)..(12)
<223> OTHER INFORMATION: Tic
<220> FEATURE:
<221> NAME/KEY: MOD_RES
<222> LOCATION: (13)..(13)
<223> OTHER INFORMATION: Oic
<220> FEATURE:
<221> NAME/KEY: MOD_RES
<222> LOCATION: (16)..(16)
<223> OTHER INFORMATION: Tic

<400> SEQUENCE: 52

Xaa Gly Phe Xaa Xaa Gly Lys Xaa Xaa Gly Phe Xaa Xaa Gly Lys Xaa
1               5                   10                  15

Gly Lys Lys Lys Lys
            20

<210> SEQ ID NO 53
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Oic
<220> FEATURE:
<221> NAME/KEY: MOD_RES
<222> LOCATION: (7)..(8)
<223> OTHER INFORMATION: Oic
<220> FEATURE:
<221> NAME/KEY: MOD_RES
<222> LOCATION: (11)..(12)
<223> OTHER INFORMATION: Oic
<220> FEATURE:
<221> NAME/KEY: MOD_RES
<222> LOCATION: (15)..(15)
<223> OTHER INFORMATION: Oic

<400> SEQUENCE: 53

Gly Phe Xaa Xaa Gly Lys Xaa Xaa Gly Phe Xaa Xaa Gly Lys Xaa Lys
1               5                   10                  15

Lys Lys Lys

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Tic
<220> FEATURE:
<221> NAME/KEY: MOD_RES
<222> LOCATION: (5)..(5)
<223> OTHER INFORMATION: Oic
```

-continued

```
<220> FEATURE:
<221> NAME/KEY: MOD_RES
<222> LOCATION: (8)..(8)
<223> OTHER INFORMATION: Tic
<220> FEATURE:
<221> NAME/KEY: MOD_RES
<222> LOCATION: (9)..(9)
<223> OTHER INFORMATION: Oic
<220> FEATURE:
<221> NAME/KEY: MOD_RES
<222> LOCATION: (12)..(12)
<223> OTHER INFORMATION: Tic
<220> FEATURE:
<221> NAME/KEY: MOD_RES
<222> LOCATION: (13)..(13)
<223> OTHER INFORMATION: Oic
<220> FEATURE:
<221> NAME/KEY: MOD_RES
<222> LOCATION: (16)..(16)
<223> OTHER INFORMATION: Tic

<400> SEQUENCE: 54

Cys Gly Phe Xaa Xaa Gly Lys Xaa Xaa Gly Phe Xaa Xaa Gly Lys Xaa
1               5                   10                  15

Gly Lys Lys Lys Lys
            20

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dpr
<220> FEATURE:
<221> NAME/KEY: MOD_RES
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (5)..(5)
<223> OTHER INFORMATION: Dpr
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
<222> LOCATION: (10)..(10)
<223> OTHER INFORMATION: Tic
<220> FEATURE:
<221> NAME/KEY: MOD_RES
<222> LOCATION: (11)..(11)
<223> OTHER INFORMATION: Oic
<220> FEATURE:
<221> NAME/KEY: MOD_RES
<222> LOCATION: (13)..(13)
<223> OTHER INFORMATION: Dpr
<220> FEATURE:
<221> NAME/KEY: MOD_RES
<222> LOCATION: (14)..(14)
<223> OTHER INFORMATION: Tic
<220> FEATURE:
<221> NAME/KEY: MOD_RES
<222> LOCATION: (15)..(15)
```

```
<223> OTHER INFORMATION: Oic
<220> FEATURE:
<221> NAME/KEY: MOD_RES
<222> LOCATION: (18)..(18)
<223> OTHER INFORMATION: Tic
<220> FEATURE:
<221> NAME/KEY: MOD_RES
<222> LOCATION: (19)..(19)
<223> OTHER INFORMATION: Oic
<220> FEATURE:
<221> NAME/KEY: MOD_RES
<222> LOCATION: (21)..(21)
<223> OTHER INFORMATION: Dpr
<220> FEATURE:
<221> NAME/KEY: MOD_RES
<222> LOCATION: (22)..(22)
<223> OTHER INFORMATION: Tic

<400> SEQUENCE: 55

Xaa Xaa Xaa Gly Xaa Xaa Xaa Gly Phe Xaa Xaa Gly Xaa Xaa Xaa Gly
1               5                   10                  15

Phe Xaa Xaa Gly Xaa Xaa
            20

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Dab
<220> FEATURE:
<221> NAME/KEY: MOD_RES
<222> LOCATION: (2)..(2)
<223> OTHER INFORMATION: Tic
<220> FEATURE:
<221> NAME/KEY: MOD_RES
<222> LOCATION: (3)..(3)
<223> OTHER INFORMATION: Oic
<220> FEATURE:
<221> NAME/KEY: MOD_RES
<222> LOCATION: (5)..(5)
<223> OTHER INFORMATION: Dab
<220> FEATURE:
<221> NAME/KEY: MOD_RES
<222> LOCATION: (6)..(6)
<223> OTHER INFORMATION: Tic
<220> FEATURE:
<221> NAME/KEY: MOD_RES
<222> LOCATION: (7)..(7)
<223> OTHER INFORMATION: Oic
<220> FEATURE:
<221> NAME/KEY: MOD_RES
<222> LOCATION: (10)..(10)
<223> OTHER INFORMATION: Tic
<220> FEATURE:
<221> NAME/KEY: MOD_RES
<222> LOCATION: (11)..(11)
<223> OTHER INFORMATION: Oic
<220> FEATURE:
<221> NAME/KEY: MOD_RES
<222> LOCATION: (13)..(13)
<223> OTHER INFORMATION: Dab
<220> FEATURE:
<221> NAME/KEY: MOD_RES
<222> LOCATION: (14)..(14)
<223> OTHER INFORMATION: Tic
<220> FEATURE:
<221> NAME/KEY: MOD_RES
<222> LOCATION: (15)..(15)
<223> OTHER INFORMATION: Oic
<220> FEATURE:
<221> NAME/KEY: MOD_RES
```

```
<222> LOCATION: (18)..(18)
<223> OTHER INFORMATION: Tic
<220> FEATURE:
<221> NAME/KEY: MOD_RES
<222> LOCATION: (19)..(19)
<223> OTHER INFORMATION: Oic
<220> FEATURE:
<221> NAME/KEY: MOD_RES
<222> LOCATION: (21)..(21)
<223> OTHER INFORMATION: Dab
<220> FEATURE:
<221> NAME/KEY: MOD_RES
<222> LOCATION: (22)..(22)
<223> OTHER INFORMATION: Tic

<400> SEQUENCE: 56

Xaa Xaa Xaa Gly Xaa Xaa Xaa Gly Phe Xaa Xaa Gly Xaa Xaa Xaa Gly
1               5                   10                  15

Phe Xaa Xaa Gly Xaa Xaa
            20

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Tic
<220> FEATURE:
<221> NAME/KEY: MOD_RES
<222> LOCATION: (11)..(12)
<223> OTHER INFORMATION: Tic
<220> FEATURE:
<221> NAME/KEY: MOD_RES
<222> LOCATION: (15)..(16)
<223> OTHER INFORMATION: Tic
<220> FEATURE:
<221> NAME/KEY: MOD_RES
<222> LOCATION: (19)..(19)
<223> OTHER INFORMATION: Tic

<400> SEQUENCE: 57

Lys Lys Lys Lys Gly Phe Xaa Xaa Gly Lys Xaa Xaa Gly Phe Xaa Xaa
1               5                   10                  15

Gly Lys Xaa
```